US010697976B2

(12) United States Patent
Thompson et al.

(10) Patent No.: US 10,697,976 B2
(45) Date of Patent: Jun. 30, 2020

(54) MASS LABELS

(71) Applicant: ELECTROPHORETICS LIMITED, Surrey (GB)

(72) Inventors: Andrew Hugin Thompson, Surrey (GB); Karsten Kuhn, Frankfurt (DE); Gitte Böhm, Frankfurt (DE)

(73) Assignee: ELECTROPHORETICS LIMITED, Surrey (GB)

( * ) Notice: Subject to any disclaimer, the term of this patent is extended or adjusted under 35 U.S.C. 154(b) by 161 days.

(21) Appl. No.: 15/106,649

(22) PCT Filed: Dec. 18, 2014

(86) PCT No.: PCT/EP2014/078602
§ 371 (c)(1),
(2) Date: Jun. 20, 2016

(87) PCT Pub. No.: WO2015/091876
PCT Pub. Date: Jun. 25, 2015

(65) Prior Publication Data
US 2017/0045526 A1    Feb. 16, 2017

(30) Foreign Application Priority Data
Dec. 19, 2013  (GB) .................................. 1322567.7

(51) Int. Cl.
*G01N 33/68*    (2006.01)

(52) U.S. Cl.
CPC ................................ *G01N 33/6848* (2013.01)

(58) Field of Classification Search
CPC .................................................. G01N 33/6848
See application file for complete search history.

(56) References Cited

U.S. PATENT DOCUMENTS

| | | | |
|---|---|---|---|
| 6,824,981 B2 | 11/2004 | Chait et al. | |
| 7,332,355 B2 | 2/2008 | Hsieh-Wilson et al. | |
| 7,556,969 B2 | 7/2009 | Wang et al. | |

FOREIGN PATENT DOCUMENTS

| | | |
|---|---|---|
| EP | 1695717 | 8/2006 |
| WO | 1997/27325 | 7/1997 |
| WO | 1997/27327 | 7/1997 |
| WO | 1997/27331 | 7/1997 |
| WO | 2000/02895 | 1/2000 |
| WO | 2001/68664 A2 | 9/2001 |
| WO | 2003/025576 A2 | 3/2003 |
| WO | 2007/012849 A2 | 2/2007 |
| WO | 2008/147481 A1 | 12/2008 |
| WO | 2009/153577 A1 | 12/2009 |
| WO | 2011/036059 A1 | 3/2011 |
| WO | 2012/006603 A2 | 1/2012 |

OTHER PUBLICATIONS

Dolusic et al. "Biotinylated Indoles as Probes for Indole-Binding Proteins" Bioconjugate Chemistry, 2001, vol. 12, No. 2, pp. 152-162.*
Dayon et al. "Relative Quantification of Proteins in Human Cerebrospinal Fluids by MS/MS Using 6-Plex Isobaric Tags" Anal. Chem. 2008, vol. 80, No. 8, pp. 2921-2931.*
Nika, H. et al., "Phosphopeptide Characterization by Mass Spectrometry Using Reversed-Phase Supports for Solid-Phase Beta-Elimination/Michael Addition", Journal of Biomolecular Techniques, vol. 23, Issue 2, Jul. 2012, pp. 51-68.
Jones, J., "The Chemical Synthesis of Peptides", Clarendon Press, Oxford, 1994, 230 pages.
Fields, G.B. et al., "Solid phase peptide sythesis utilizing 9-fluorenylmethoxycarbonyl amino acids", International Journal of Peptide & Protein Research, vol. 35, No. 3, Mar. 1990, pp. 161-214.
Albericio, F., "Orthogonal Protecting Groups for Na-Amino and C-Terminal Carboxyl Functions in Solid-Phase Peptide Synthesis", Biopolymers (Peptide Science), vol. 55, 2000, pp. 123-139.
Arar, K. et al., "Synthesis and Antiviral Activity of Peptide-Oligonucleotide Conjugates Prepared by Using Nalpha—(Bromoacetyl)peptides", Bioconjugate Chemistry, vol. 6, No. 5, 1995, pp. 573-577.
Ustinov, A.V. et al., "Reactive trityl derivatives: stabilised carbocation mass-tags for life sciences applications", Organic & Biomolecular Chemistry, vol. 6, 2008, pp. 4593-4608.
Shchepinov, M.S. et al., "Trityl mass-tags for encoding in combinatorial oligonucleotide synthesis", Nucleic Acids Symposium Series, No. 42, 1999, pp. 107-108.
Bernad, P.L. Jr. et al., "S(O)-Pixyl protecting group as efficient mass-tag", Chemical Communications (Camb), Issue 27, 2005, pp. 3466-3468.
Shao, G. et al., "Trace Detection of Glycolic Acid by Electrophore Labeling Gas Chromatography-Electron Capture Mass Spectrometry", Analytical Chemistry, vol. 76, No. 11, Jun. 1, 2004, pp. 3049-3054.
Zhang, X. et al., "Synthesis of Releasable Electrophore Tags for Applications in Mass Spectrometry", Bioconjugate Chemistry, vol. 13, No. 5, 2002, pp. 1002-1012.
Giese, R.W., "Electron-capture mass spectrometry: recent advances", Journal of Chromatography A, vol. 892, 2000, pp. 329-346.
Arlinghaus, H.F. et al., "Multiplexed DNA Sequencing and Diagnostics by Hybridization with Enriched Stable Isotope Labels", Analytical Chemistry, vol. 69, No. 8, Apr. 15, 1997, pp. 1510-1517.

(Continued)

*Primary Examiner* — Joseph R Kosack
(74) *Attorney, Agent, or Firm* — Arent Fox LLP

(57) ABSTRACT

The present invention provides a method for labelling one or more analytes in a sample, the method comprising: a) contacting the sample with one or more bifunctional linker reagents having the general formula $Re^1$-$L^1$-$Re^2$, wherein $Re^1$ is a first reactive group, $L^1$ is a linker moiety and $Re^2$ is a second reactive group, wherein $Re^1$ reacts with an analyte to form a modified analyte; and b) contacting the sample with one or more mass labels, wherein $Re^2$ of the bifunctional linker attached to the analyte reacts with a mass label to form a labelled analyte, wherein each mass label is relatable to an analyte by mass spectrometry.

20 Claims, 29 Drawing Sheets

(56) References Cited

OTHER PUBLICATIONS

Sachleben, R.A. et al., "Resonance Ionization Spectroscopy for Multiplex Sequencing of Tin-Labeled DNA", Genetic Analysis Techniques and Applications, vol. 8, Issue 6, 1991, pp. 167-170.
Thompson, A. et al., "Tandem Mass Tags: A Novel Quantification Strategy for Comparative Analysis of Complex Protein Mixtures by MS/MS", Analytical Chemistry, vol. 75, No. 8, Apr. 15, 2003, pp. 1895-1904.
Pappin, D.J., "Multiplexed Protein Quantitation in *Saccharomyces cerevisiae* Using Amine-Reactive Isobaric Tagging Reagents," MCP Papers in Press, published on Sep. 28, 2004 as Manuscript M400129-MCP200, pp. 1-74.
Lloyd-Williams, P. et al., "Convergent Solid-Phase Peptide Synthesis", Tetrahedron, vol. 49, No. 48, 1993, pp 11065-11133.
Geahlen, R.L. et al., "A General Method for Preparation of Peptides Biotinylated at the Carboxy Terminus", Analytical Biochemistry, vol. 202, 1992, pp. 68-70.
Sawutz, D.G. et al., "Synthesis and Molecular Characterization of a Biotinylated Analog of [Lys]Bradykinin", Peptides, vol. 12, 1991, pp. 1019-1024.
Natarajan, S. et al., "Site-specific biotinylation a novel approach and its application to Endothelin-1 analogs and PTH-analog", International Journal of Peptide and Protein Research, vol. 40, 1992, pp. 567-574.
Wasinger, V.C. et al., "Progress with gene-product mapping of the Mollicutes: Mycoplasma genitalium", Electrophoresis, vol. 16, 1995, pp. 1090-1094.
Patterson, S.D., "Proteomics: the industrialization of protein chemistry", Current Opinion in Biotechnology, vol. 11, 2000, pp. 413-418.
Vanmechelen, E. et al., "Quantification of tau phosphorylated at threonine 181 in human cerebrospinal fluid: a sandwich ELISA with a synthetic phosphopeptide for standardization", Neuroscience Letters, vol. 285, 2000, pp. 49-52.
Nakayama, K. et al., "Expression and phosphorylation status of retinoblastoma protein in adult T-cell leukemia/ lymphoma", Leukemia Research, vol. 24, 2000, pp. 299-305.
Ignatoski, K.M.W., "Immunoprecipitation and Western Blotting of Phosphotyrosine-Containing Proteins", Methods in Molecular Biology, vol. 124, pp. 39-48.
Nakanishi, T. et al., "Direct on-membrane peptide mass fingerprinting with MALDI-MS of tyrosine-phosphorylated proteins detected by immunostaining", Journal of Chromatography B, vol. 847, 2007, pp. 24-29.
Cantin, G.T. et al., "Quantitative phosphoproteomic analysis of the tumor necrosis factor pathway", Journal of Proteome Research, vol. 5, Jan. 2006, pp. 127-134.
Adamcyzk, M. et al., "Identification of phosphopeptides by chemical modification with an isotopic tag and ion trap mass spectrometry", Rapid Communications in Mass Spectrometry, vol. 16, 2002, pp. 999-1001.
Adamcyzk, M. et al., "Selective analysis of phosphopeptides within a protein mixture by chemical modification, reversible biotinylation and mass spectrometry", Rapid Communications in Mass Spectrometry, vol. 15, 2001, pp. 1481-1488.
Goshe, M.B. et al., "Phosphoprotein Isotope-Coded Affinity Tag Approach for Isolating and Quantitating Phosphopeptides in Proteome-Wide Analyses", Analytical Chemistry, vol. 73, No. 11, Jun. 1, 2001, pp. 2578-2586.
Kota, U. et al., "Isotope-Labeling and Affinity Enrichment of Phosphopeptides for Proteomic Analysis Using Liquid Chromatography-Tandem Mass Spectrometry", Methods Molecular Biology, vol. 564, 2009, pp. 303-321.
Qian, W.J. et al., "Phosphoprotein Isotope-Coded Solid-Phase Tag Approach for Enrichment and Quantitative Analysis of Phosphopeptides from Complex Mixtures", Analytic Chemistry, vol. 75, 2003, pp. 5441-5450.

Gygi, S.P. et al., "Quantitative analysis of complex protein mixtures using isotope-coded affinity tags", Nature Biotechnology, vol. 17, Oct. 1999, pp. 994-999.
Zhou, H. et al., "Quantitative proteome analysis by solid-phase isotope tagging and mass spectrometry", Nature Biotechnology, vol. 19, May 2002, pp. 512-515.
Wu, J. et al., "Integrating titania enrichment, iTRAQ labeling, and Orbitrap CID-HCD for global identification and quantitative analysis of phosphopeptides", Proteomics, vol. 10, 2010, pp. 2224-2234.
Arrigoni, G. et al., "Chemical derivatization of phosphoserine and phosphothreonine containing peptides to increase sensitivity for MALDI-based analysis and for selectivity of MS/MS analysis", Proteomics, vol. 6, 2006, pp. 757-766.
Jaffe, H. et al., "Characterization of Serine and Threonine Phosphorylation Sites in Beta-Elimination/Ethanethiol Addition-Modified Proteins by Electrospray Tandem Mass Spectrometry and Database Searching", Biochemistry, vol. 37, No. 46, 1998, pp. 16211-16224.
Beausoleil, S.A. et al., "Large-scale characterization of HeLa cell nuclear phosphoproteins", Proceedings of the National Academy of Science USA, vol. 101, No. 33, Aug. 17, 2004, pp. 12130-12135.
Ficarro, S.B. et al., "Online Nanoflow Multidimensional Fractionation for High Efficiency Phosphopeptide Analysis", Molecular & Cellular Proteomics, vol. 10, 2011, 19 pages.
Hennrich, M.L. et al., "Improving Depth in Phosphoproteomics by Using a Strong Cation Exchange-Weak Anion Exchange-Reversed Phase Multidimensional Separation Approach", Analytical Chemistry, vol. 83, 2011, pp. 7137-7143.
McNulty, D.E. et al., "Hydrophilic Interaction Chromatography Reduces the Complexity of the Phosphoproteome and Improves Global Phosphopeptide Isolation and Detection", Molecular & Cellular Proteomics, vol. 7, 2008, pp. 971-980.
Byford, M.F., "Rapid and selective modification of phosphoserine residues catalysed by Ba2+ ions for their detection during peptide microsequencing", Biochemistry Journal, vol. 280, 1991, pp. 261-265.
Fadden, P. et al., "Quantitative and Selective Fluorophore Labeling of Phosphoserine on Peptides and Proteins: Characterization at the Attomole Level by Capillary Electrophoresis and Laser-Induced Fluorescence", Analytical Biochemistry, vol. 225, 1995, pp. 81-88.
Klemm, C. et al., "Derivatization of phosphorylated peptides with S- and N-nucleophiles for enhanced ionization efficiency in matrix-assisted laser desorption/ionization mass spectrometry", Rapid Communications in Mass Spectrometry, vol. 18, 2004, pp. 2697-2705.
Ahn, Y.H. et al., "Arginine-mimic labeling with guanidinoethanethiol to increase mass sensitivity of lysine-terminated phosphopeptides by matrix-assisted laser desorption/ionization time-of-flight mass spectrometry", Rapid Communications in Mass Spectrometry, vol. 21, 2007, pp. 2204-2210.
Molloy, M.P. et al., "Phosphopeptide Derivatization Signatures to Identify Serine and Threonine Phosphorylated Peptides by Mass Spectrometry", Analytical Chemistry, vol. 73, No. 22, Nov. 15, 2001, pp. 5387-5394.
Cindric, M. et al., "Accelerated on-column lysine derivatization and cysteine methylation by imidazole reaction in a deuterated environment for enhanced product ion analysis", Rapid Communications in Mass Spectrometry, vol. 20, 2006, pp. 694-702.
Conrotto, P. et al., "Sulfonation Chemistry as a Powerful Tool for MALDI TOF/TOF de Novo Sequencing and Post-Translational Modification Analysis", Journal of Biomolecular Techniques, vol. 16, Issue 4, Dec. 2005, pp. 441-452.
Pfleiderer, W. et al., "Recent progress in oligonucleotide synthesis", Acta Biochimica Polonica, vol. 43, No. 1, 1996, pp. 37-44.
Stawikowski, M. et al., "Introduction to Peptide Synthesis", Current Protocols of Protein Sciences, Chapter 18, Unit 1, Feb. 2002, 17 pages.
Thompson, A.J. et al., "Characterization of Protein Phosphorylation by Mass Spectrometry Using Immobilized Metal Ion Affinity Chromatography with On-Resin Beta-Elimination and Michael Addition", Analytical Chemistry, vol. 75, No. 13, Jul. 1, 2003, pp. 3232-3243.
Lee, H.S. et al., "Effects of Alkali on Glycoproteins. Beta-Elimination and nucleophilic Addition Reactions of Substituted

(56) References Cited

OTHER PUBLICATIONS

Threonyl Residues of Antifreeze Glycoprotein", Journal of Agricultural and Food Chemistry, vol. 25, No. 5, 1977, pp. 1153-1158.
Mega, T. et al., "Modifications of Substituted Seryl and Threonyl Residues in Phosphopeptides and a Polysialoglycoprotein by Beta-Elimination and Nucleophile Additions", Journal of Biochemistry, vol. 107, 1990, pp. 68-72.
Ndassa, Y.M. et al., "Improved Immobilized Metal Affinity Chromatography for Large-Scale Phosphoproteomics Applications", Journal of Proteome Research, vol. 5, 2006, pp. 2789-2799.
Wells, L. et al., "Mapping Sites of O-GlcNAc Modification Using Affinity Tags for Serine and Threonine Post Translational Modifications", Molecular & Cellular Proteomics, vol. 1, 2002, pp. 791-804.
Czeszak, X. et al., "Identification of substituted sites on Mucsac mucin motif peptides after enzymatic O-glycosylation combining beta-elimination and fixed-charge derivatization", Rapid Communications in Mass Spectrometry, vol. 16, 2002, pp. 27-34.
Czeszak, X. et al., "Localization of the O-Glycosylated Sites in Peptides by Fixed-Charge Derivatization with a Phosphonium Group", Analytical Chemistry, vol. 76, No. 15, Aug. 1, 2004, pp. 4320-4324.
Butkinaree, C. et al., "O-Linked Beta-N-Acetylglucosamine (O-GlcNAc): Extensive Crosstalk with Phosphorylation to Regulate Signaling and Transcription in Response to Nutrients and Stress", Biochimica et Biophysica Acta, vol. 1800, No. 2, Feb. 2010, pp. 96-106.
Hu, P. et al., "Site-specific interplay between O-GlcNAcylation and phosphorylation in cellular regulation", FEBS Letters, vol. 584, 2010, pp. 2526-2538.
Copeland, R.J. et al., "Cross-talk between GlcNAcylation and phosphorylation: roles in insulin resistance and glucose toxicity", American Journal of Physiology, Endocrinology and Metabolism, vol. 295, Apr. 29, 2008, pp. E17-E28.
Love, D.C. et al., "The Hexosamine Signaling Pathway: Deciphering the O-GlcNAc Code", Science's STKE, vol. 312, Nov. 22, 2005, re13.
Ficarro, S.B. et al., "Phosphoproteome analysis by mass spectrometry and its application to *Saccharomyces cerevisiae*", Nature Biotechnology, vol. 20, Mar. 2002, pp. 301-305.
Kinoshita, E. et al., "Novel immobilized zinc(II) affinity chromatography for phosphopeptides and phosphorylated proteins", Journal of Separation Science, vol. 28, 2005, pp. 155-162.
Zhou, H. et al., "Enhancing the Identification of Phosphopeptides from Putative Basophilic Kinase Substrates Using Ti (IV) Based IMAC Enrichment", Molecular & Cellular Proteomics, vol. 10, 2011, 14 pages.
Zhou, H. et al., "Zirconium Phosphonate-Modified Porous Silicon for Highly Specific Capture of Phosphopeptides and MALDI-TOF MS Analysis", Journal of Proteome Research, vol. 5, No. 9, 2006, pp. 2431-2437.
Zhou, H. et al., "Robust phosphoproteome enrichment using monodisperse microsphere-based immobilized titanium (IV) ion affinity chromatography", Nature Protocols, vol. 8, No. 3, 2013, pp. 461-480.
Tsunehiro, M. et al., "A Phos-tag-based magnetic-bead method for rapid and selective separation of phosphorylated biomolecules", Journal of Chromatography B, vol. 925, 2013, pp. 86-94.
Kinoshita, E. et al., "Highly sensitive detection of protein phosphorylation by using improved Phostag Biotin", Proteomics, vol. 12, 2012, pp. 932-937.
Zhang, X. et al., "Highly Efficient Phosphopeptide Enrichment by Calcium Phosphate Precipitation Combined with Subsequent IMAC Enrichment", Molecular & Cellular Proteomics, vol. 6, 2007, pp. 2032-2042.
Kuhn, K. et al., "TMT Labelling for the Quantitative Analysis of Adaptive Responses in the Meningococcal Proteome", Methods in Moleclular Biology, vol. 799, 2012, pp. 127-141.
Li, W. et al., "Susceptibility of the hydroxyl groups in serine and threonine to beta-elimination/Michael addition under commonly used moderately high-temperature conditions", Analytical Biochemistry, vol. 323, 2003, pp. 94-102.
McLachlin, D.T. et al., "Improved beta-Elimination-Based Affinity Purification Strategy for Enrichment of Phosphopeptides", Analytical Chemistry, vol. 75, No. 24, Dec. 15, 2003, pp. 6826-6836.
Jentoft, N. et al., "Labeling of Proteins by Reductive Methylation Using Sodium Cyanoborohydride", Journal of Biological Chemistry, vol. 254, No. 11, Jun. 10, 1979, pp. 4359-4365.
Wong, W.S.D. et al., "Pyridine Borane as a Reducing Agent for Proteins", Analytical Biochemistry, vol. 139, 1984, pp. 58-67.
Dirksen, A. et al., "Rapid Oxime and Hydrazone Ligations with Aromatic Aldehydes for Biomolecular Labeling", Bioconjugate Chemistry, vol. 19, 2008, pp. 2543-2548.
Dirksen, A. et al., "Nucleophilic Catalysis of Hydrazone Formation and Transimination: Implications for Dynamic Covalent Chemistry", Journal of Americal Chemical Society, vol. 128, 2006, pp. 15602-15603.
Byeon, J.Y. et al., "Efficient Bioconjugation of Protein Capture Agents to Biosensor Surfaces Using Aniline-Catalyzed Hydrazone Ligation", Langmuir, vol. 26, No. 19, 2010, pp. 15430-15435.
Li, X., "Click to Join Peptides/Proteins Together", Chemistry an Asian Journal, vol. 6, 2011, pp. 2606-2616.
Klement, E. et al., "Enrichment of O-GlcNAc Modified Proteins by the Periodate Oxidation-Hydrazide Resin Capture Approach", Journal of Proteome Research, vol. 9, No. 5, 2010, pp. 2200-2206.
Boeggeman, E. et al., "Direct Identification of Nonreducing GlcNAc Residues on N-Glycans of Glycoproteins Using a Novel Chemoenzymatic Method", Bioconjugate Chemistry, vol. 18, No. 3, 2007, pp. 806-814.
Sihlbom, C. et al., "Localization of 0-glycans in MUC1 glycoproteins using electron-capture dissociation fragmentation mass spectrometry", Glycobiology, vol. 19, No. 4, 2009, pp. 375-381.
Mechref, Y., "Use of CID/ETD Mass Spectrometry to Analyze Glycopeptides", Current Protocols in Protein Science, Chapter 12, Unit 12.1111, Apr. 2012, 14 pages.
Han, H. et al., "Rapidly Alternating Transmission Mode Electron-Transfer Dissociation and Collisional Activation for the Characterization of Polypeptide Ions", Analytical Chemistry, vol. 80, No. 9, May 1, 2008, pp. 3492-3497.
Yang, S. et al., "Solid-phase glycan isolation for glycomics analysis", Proteomics Clinical Applications, vol. 6, Dec. 2012, pp. 596-608.
Yang, S.J. et al., "Glycan Analysis by Reversible Reaction to Hydrazide Beads and Mass Spectrometry", Analytical Chemistry, vol. 84, 2012, pp. 2232-2238.
Li, B. et al., "Aqueous Phosphoric Acid as a Mild Reagent for Deprotection of Tert-Butyl Carbamates, Esters, and Ethers", Journal of Organic Chemistry, vol. 71, No. 24, 2006, pp. 9045-9050.
Pothukanuri, S. et al., "A Highly Efficient Azide-Based Protecting Group for Amines and Alcohols", Organic Letters, vol. 9, No. 11, 2007, pp. 2223-2225.
Goddard-Borger, E.D. et al., "An Efficient, Inexpensive, and Shelf-Stable Diazotransfer Reagent: Imidazole-1-sulfonyl Azide Hydrochloride", Organic Letters, vol. 9, No. 19, 2007, pp. 3797-3800.
Dephoure, N. et al., "Hyperplexing: A Method for Higher-Order Multiplexed Quantitative Proteomics Provides a Map of the Dynamic Response to Rapamycin in Yeast", Science Signaling, vol. 5, Mar. 27, 2012, rs2, 8 pages.
Everley, R.A. et al., "Increasing Throughput in Targeted Proteomics Assays: 54-Plex Quantitation in a Single Mass Spectrometry Run", Analytical Chemistry, vol. 85, 2013, pp. 5340-5346.
Zhang, X. et al., "N-Terminal peptide labeling strategy for incorporation of isotopic tags: a method for the determination of site-specific absolute phosphorylation stoichiometry", Rapid Communications in Mass Spectrometry, vol. 16, 2002, pp. 2325-2332.
Tan, F. et al., "An efficient method for dephosphorylation of phosphopeptides by cerium oxide", Journal of Mass Spectrometry, vol. 43, 2008, pp. 628-632.

(56) References Cited

OTHER PUBLICATIONS

Jia, W. et al., "Novel Mass Spectrometric Method for Phosphorylation Quantification Using Cerium Oxide Nanoparticles and Tandem Mass Tags", Analytical Chemistry, vol. 84, No. 5, Mar. 2012, pp. 2466-2473.

Wu, H.Y., et al., "Combining Alkaline Phosphatase Treatment and Hybrid Linear Ion Trap/Orbitrap High Mass Accuracy Liquid Chromatography-Mass Spectrometry Data for the Efficient and Confident Identification of Protein Phosphorylation", Analytical Chemistry, vol. 81, No. 18, Sep. 15, 2009, pp. 7778-7787.

Isidro-Llobet, A. et al., "Amino Acid-Protecting Groups", Chemical Reviews, vol. 109, No. 6, 2009, pp 2455-2504.

Brandes, N. et al., "Using Quantitative Redox Proteomics to Dissect the Yeast Redoxome", The Journal of Biological Chemistry, vol. 286, No. 48, Dec. 2, 2011, pp. 41893-41903.

Kumsta, C. et al., "Effects of Oxidative Stress on Behavior, Physiology, and the Redox Thiol Proteome of Caenorhabditis elegans", Antioxidants & Redox Signaling, vol. 14, No. 6, 2011, pp. 1023-1037.

Brennan, J.P. et al., "Detection and Mapping of Widespread Intermolecular Protein Disulfide Formation during Cardiac Oxidative Stress Using Proteomics with Diagonal Electrophoresis", The Journal of Biological Chemistry, vol. 279, No. 40, Oct. 1, 2004, pp. 41352-41360.

Leichert, L.I. et al., "Protein Thiol Modifications Visualized In Vivo", PLoS Biology, vol. 2, Issue 11, Nov. 2004, e333, pp. 1723-1737.

Boersema, P.J., et al., "Multiplex peptide stable isotope dimethyl labeling for quantitative proteomics", Nature Protocols, vol. 4, No. 4, 2009, pp. 484-494.

Derakhshan, B. et al., "Unbiased identification of cysteine S-nitrosylation sites on proteins", Nature Protocols, vol. 2, No. 7, 2007, pp. 1685-1691.

Lind, C. et al., "Identification of S-glutathionylated cellular proteins during oxidative stress and constitutive metabolism by affinity purification and proteomic analysis", Archives of Biochemistry and Biophysics, vol. 406, 2002, pp. 229-240.

Requejo, R. et al., "Quantification and identification of mitochondrial proteins containing vicinal dithiols", Archives of Biochemistry and Biophysics, vol. 504, 2010, pp. 228-235.

Garcia, L., International Search Report, PCT/EP/2014/078602, dated Jul. 14, 2015, 6 pages.

Shuanglong, L. et al., "Efficient 18F labeling of cysteine containing peptides and proteins using tetrazine-trans-cyclooctene ligation", Molecular Imaging, vol. 12, No. 2, 2013, pp. 121-128.

Communication pursuant to Article 94(3) EPC received from European Patent Office, for EP Application 14 321 612.0, dated Jul. 29, 2019, 4 pages.

\* cited by examiner

Load peptides onto C18 Resin

Reaction on C18 Solid phase increases local concentration of target and drives reaction to completion Barium Hydroxide Catalysed Beta-Elimination Thiol-TMT coupling Enrich with anti-TMT Antibody Thiol-TMT to be generated from Dithiopyridyl-TMT:

MASS LABELS

CROSS-REFERENCE TO RELATED APPLICATIONS

This application is the U.S. National Stage Application of International Patent Application No. PCT/EP2014/078602, filed on Dec. 18, 2014, which claims priority to GB Application No. 1322567.7, filed on Dec. 19, 2013, the contents of each of which is incorporated herein by reference in its entirety.

FIELD OF THE INVENTION

The present invention relates to methods, mass labels and kits for efficient labelling of biomolecules for analysis by mass spectrometry.

BACKGROUND OF THE INVENTION

The ability to quantitatively detect biomolecules using mass spectrometers has provided considerable advances in their study and application to human and veterinary disease, in environmental analysis and monitoring, and in food and beverage manufacturing.

Recently a range of chemical mass tags bearing heavy isotope substitutions have been developed to improve the quantitative analysis of biomolecules by mass spectrometry. Since their introduction in 2000, isobaric mass tags have provided improved means of proteomic expression profiling by universal labelling of amine functions in proteins and peptides prior to mixing and simultaneous analysis of multiple samples. Because the tags are isobaric, having the same mass, they do not increase the complexity of the mass spectrum since all precursors of the same peptide will appear at exactly the same point in the chromatographic separation and have the same aggregate mass. Only when the molecules are fragmented prior to tandem mass spectrometry are unique mass reporters released, thereby allowing the relative or absolute amount of the peptide present in each of the original samples to be calculated.

WO01/68664 sets out the underlying principles of isobaric mass tags and provides specific examples of suitable tags wherein different specific atoms within the molecules are substituted with heavy isotope forms including 13C and 15N. The limitation on the multiplexing rate for a single isobaric mass tag set can be overcome by providing multiple sets each carrying a unique additional mass. The additional mass is provided by the mass series modifying group. WO01/68664 describes the use of offset masses to make multiple isobaric sets to increase the overall plexing rates available without unduly increasing the size of the individual tags.

In patents WO 01/68664, WO 03/25576, WO 07/012849 and WO 11/036059 the concept of 'mass series modifiers', is discussed. In these patents, different chemistries are described by which sets of isobaric tags may be modified. A mass-series modifier is a linker that changes the overall mass of each of the members in a set of isobaric tags to give a new set of isobaric mass tags. In patents WO 01/68664, WO 03/25576, WO 07/012849 and WO 11/036059, a mass-series modifier is introduced as a linker between the mass tag and the reactive function used to couple to tag to a molecule of interest:

Mass Tag-Mass Series Modifier-Reactive Function

This means that starting from a set of 10 mass tags and 3 Mass Series Modifiers, 30 tags (3×10) can be constructed in three offset isobaric sets. For example, consider the amine-reactive isobaric tag pair below:

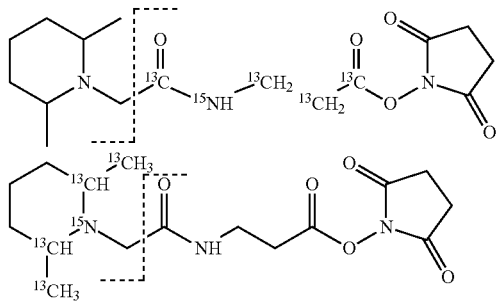

With three mass series modifiers comprising isotopes of beta-alanine, 3 pairs of isobaric tags can be created as shown below:

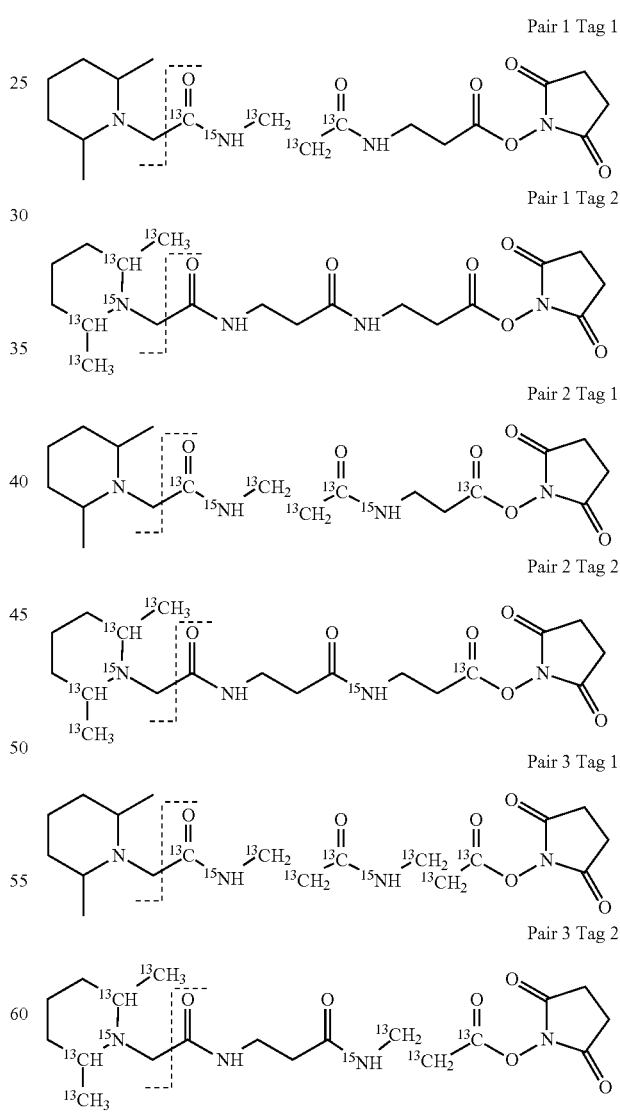

Note in the 6 tags above that the beta-alanine linker is introduced between the tag structure and the N-hydroxysuccinimide ester amine-reactive group. Pair 2 is approximately 2 daltons heavier than Pair 1. Similarly, Pair 3 is 4 approximately daltons heavier than Pair 1 and approximately 2 daltons heavier than Pair 2.

While this approach works well, it does mean that each of the 6 tags shown above must be synthesised individually prior to use.

Despite the significant benefits of previously disclosed isobaric mass tags there remains a need for further improvements to enable easy synthesis of mass labels whilst at the same time achieving high levels of multiplex analysis.

Solid phase chemistry has been used in many contexts to simplify reaction schemes. Solid phase reactions facilitate multi-step labelling protocols, which are challenging to complete efficiently using solution phase coupling protocols. Applications of such multi-step solid phase labelling reactions include labelling of large protein samples and profiling of post-translational modifications including the phosphorylation states of proteins, i.e. identification and/or quantitation of phosphorylated proteins and analysis of glycosylation of proteins. Proteins may be post-transcriptionally modified such that they contain phosphate groups at either some or all of their serine, threonine and tyrosine amino acid residues. In many cases the extent to which a protein is phosphorylated determines it bioactivity, i.e., its ability to effect cell functions such as differentiation, division, and metabolism. Similarly, many proteins are regulated at serine, threonine and tyrosine by modification with N-acetylglucosamine. Hence, a powerful tool for diagnosing various diseases and for furthering the understanding of protein/protein interactions is provided. Similarly, many new drugs are either antagonists or agonists of kinase proteins and detailed analysis of phosphoprotein activity is a powerful tool for characterisation of the activity of drugs that interfere with phosphorylation pathways. Glycoproteins are also key mediators of cell signalling pathways and clear understanding of patterns of glycosylation is also a critical tool in understanding cellular systems.

Whole genome sequencing has moved biological research to a stage where cellular systems are analyzed as a whole rather than analyzing the individual components. This is referred to as Systems Biology. However, whole genome analysis and global gene expression measurements at the mRNA level does not provide a complete understanding of cellular systems since genome technology typically does not provide protein level information which requires the use of proteomic techniques (1). Proteomics, the analysis of the entire complement of proteins expressed by a cell, tissue type, or organ, provides the most informative characterization of the cell because proteins are the primary players that carry out nearly all processes within the cell. A key aspect to successful proteomic measurements is the ability to precisely measure protein abundance changes in a high throughput manner so as to allow the effects of many "perturbations" upon, or changes to, a cell type, tissue type or organ, to be determined in a rapid fashion (2). A key goal of proteomic studies is to provide a greater understanding of the function of proteins in a global, cellular context, along with their basic molecular function. However, a complete understanding of cellular systems requires not only the identity and quantity of proteins in the system but also their 'post-translational state'. The post-translational state of a protein refers to the level and/or type of post-translational modifications that are displayed by the functional protein and may be referred to as 'epiproteomics'. For example many proteins are initially translated in an inactive form and upon subsequent proteolysis, the addition of sugar moieties, phosphate groups, lipid groups, methyl groups, carboxyl groups, and/or other additional groups, they gain biological function.

Conversely, proteins may be released in an active form and may be inactivated by post-translational modification. Information relating to the post-translational modifications of a given protein is necessary and, hence, methods of detecting the 'post-translational state' of proteins are important for furthering the understanding of intercellular signalling and for developing new and useful interventions and therapeutics. Key post-translational modifications of proteins include cleavage, phosphorylation, glycosylation and lipid modification. A complete understanding of all of these modifications of the protein complement of a cell will provide a stronger basis for understanding complex biological pathways and the nature of diseases as well as providing better tools for drug development and validation. This invention focuses in particular on the analysis of protein phosphorylation and glycosylation as phosphorylation and glycosylation are key post-translational modifications regulating the activity of numerous proteins and is central to many cellular signalling and regulation pathways.

The reversible phosphorylation of proteins plays a key role in transducing extracellular signals into the cell. Many proteins that participate in cell signaling pathways are phosphorylated via enzymes known as kinases and dephosphorylated via phosphatases. Phosphate groups are added to, for example, tyrosine, serine, threonine, histidine, and/or lysine amino acid residues depending on the specificity of the kinase acting upon the target protein. To date several disease states have been linked to the abnormal phosphorylation/dephosphorylation of specific proteins. For example, the polymerization of phosphorylated tau protein allows for the formation of paired helical filaments that are characteristic of Alzheimer's disease (3), and the hyperphosphorylation of retinoblastoma protein (pRB) has been reported to progress various tumours (4).

Various methods for analyzing phosphate groups on proteins have been developed, including gel separation of proteins followed by Western Blotting with anti-phosphate antibodies (5). More recently, mass spectrometric approaches have become of interest as mass spectrometry offers more information about proteins that have been modified than western blotting approaches. The first mass spectrometry approaches used mass spectrometry to characterise in detail proteins separated by gel electrophoresis and identified by Western Blots (6). With increasing sequencing capability on mass spectrometers, methods that attempt to achieve global analysis of protein phosphorylation have been developed in which large numbers of phosphorylated peptides are analysed (7-9). Global analysis is desirable as a more complete understanding of cellular systems can be achieved if all the protein phosphorylation states in a cell can be determined. Ideally, quantitative global analysis of protein phosphorylation in which two or more different cellular states can be compared is desirable and this is best achieved using mass spectrometry.

Two related mass spectrometry-based methods called Phosphoprotein Isotope-coded Affinity Tags (PhIAT)(10) and Phosphoprotein Isotope-coded Solid-phase Tags (PhIST)(11,12) employs hydroxide-catalysed beta elimination of phosphates from phosphoserine and phosphothreonine follow by reaction of 1,2-ethanedithiol (EDT) with the resulting Michael centres. The 1,2-ethanedithiol (EDT) coupling leaves a free thiol in the reacted peptides that can be coupled to either thiol reactive biotin such as ICAT biotin reagents (13) or ICAT solid phase reagents (14) respectively, superficially enabling global analysis of phosphoproteins in complex biological samples.

Isobaric mass tags have been used for global quantification of phosphopeptides in complex samples (15).

However, phosphopeptides do not behave in a helpful fashion for analysis by mass spectrometry. Phosphate groups introduce a relatively strong negative charge into peptides but analysis of peptides, particularly for sequencing of peptides, is typically carried out in the positive ion mode and thus, the presence of a phosphate group on a peptide typically reduces the sensitivity of detection of the peptide compared to the unphosphorylated analogue (16,17). In addition, the phosphate group is prone to neutral loss during ionisation reducing signal further as the peptide signal is split between peptide retaining the phosphate and peptide that has lost the phosphate. With multiply phosphorylated peptides, the issue is compounded as the phosphate can be lost independently from multiple sites producing a population of different combinations of retained or lost phosphate. In addition, for the analysis of complex samples or for global profiling of a cell or tissue sample, it is usual to fractionate either the peptides digested from the proteins in the sample and typically this may involve ion exchange chromatography as well as reverse phase chromatography. Since peptides are typically analysed in an acidic solvent or buffer, they are typically protonated and can be separated by strong cation exchange chromatography. Since phosphates introduce a strong negative charge, they do not separate well in Strong Cation eXchange (SCX) chromatography as phosphopeptides typically co-elute in one or two fractions, which means SCX can be used for crude enrichment of phosphopeptides but not for meaningful separation (18). Other fractionation methods have been proposed such as Strong and/or Weak Anion Exchange Chromatography (19,20) and Hydrophilic Interaction Chromatography (HILIC) (21) but it would be preferable to be able to analyse phosphopeptides using the same separation protocols as unmodified peptides.

The Barium Hydroxide catalysed Beta-Elimination reaction of phosphates with subsequent reaction of the resulting Michael centre has been known for many years as a way to label serine and threonine phosphates (22,23). The Beta-Elimination Michael Addition (BEMA) reactions can be used to exchange a phosphate group for an alternative group that can be beneficial for mass spectrometry. Replacement of the phosphate in serine and threonine with an aliphatic group means the phosphopeptide can be separated using standard Cation Exchange and/or Reverse Phase Chromatography methods as used for unmodified peptides (refs). Replacement of the phosphate group in phosphopeptides is also reported to enhance the detection of phosphopeptides particularly in Matrix Assisted Laser Desorption Ionisation (MALDI) analysis of phosphopeptides (16, 24-26).

However, Barium-catalyzed BEMA has not been very widely used for global analysis of phosphopeptides as the beta-elimination reaction, particularly of threonine phosphates, results in a relatively unreactive Michael centre and getting the reaction to go to completion is challenging particularly in a complex sample comprising many proteins in different concentrations. It is also a multi-step process and sample losses have meant that it is not normally suitable for small samples or complex samples where some of the targets of interest are present only in small quantities.

However, it has been shown that chemical reactions on peptides reversibly immobilised on hydrophobic solid supports can be more easily driven to completion perhaps due to the increase in local concentration of target peptide. In addition, the ease of removing contaminating reactants and high recovery rates are all likely factors in the effectiveness of solid phase reactions. Improved solid phase reaction protocols for guanidination (27) and sulphonation (28) have been demonstrated. In addition, the use of hydrophobic solid supports for the Barium Catalysed BEMA reactions has also been demonstrated (Nika et al. (29)). In this method C18 ZipTips were used and in the published protocol, a peptide sample with phosphopeptides, i.e. post digestion, is loaded onto a C18 ZipTip thus reversibly immobilizing the peptides. This has the effect of greatly increasing the local concentration of the Michael centre, after beta-elimination, increasing reaction rates significantly and the authors claim this results in substantially complete conversion of phosphate to the labeled form particularly for threonine phosphates, which are less reactive. In this publication, the dehydroalanyl and methyldehydroalanyl centres that result from beta-elimination of phosphates are reacted with 2-aminoethanethiol, thus converting the phosphate to an amino group (FIG. 1). The authors report that the amino group improves sensitivity of detection of the modified peptides. In addition, since changing reagents on solid support is relatively trivial, solid phase reactions also lend themselves to automation, as in the case of solid phase DNA and Peptide synthesis (30,31).

A related solid phase Barium-catalysed BEMA reaction method has also been published in which phosphopeptides captured on Immobilized Metal Affinity Chromatography (IMAC) columns were beta-eliminated on resin (32) to release phosphopeptides from the IMAC column. Thompson et al. (32) report that this approach has many of the same advantages as the use of a C18 resin but with the additional advantage of significant enrichment of the phosphopeptides prior to beta-elimination. The IMAC approach also removes the issue that some glycopeptides can beta-eliminate too (33,34) as these can be washed away prior to elution of phosphopeptides by beta-elimination. This approach should also cope with larger amounts of material than the C18 approach as it is primarily phosphopeptides that are retained on IMAC resins whereas the C18 approach retains all peptides although the issue of scale of samples needs to be considered carefully as discussed in the literature (35).

The ability to quickly screen for irregularities in the phosphorylation state of proteins will further the understanding of intra and inter cellular signaling and lead to the development of improved diagnostics for the detection of various disease states.

As noted above, O-linked glycopeptides are also able to undergo beta-elimination (34) to produce a Michael acceptor. This feature of glycopeptides has been exploited enable O-linked glycosylation sites to be labelled by substitution of the sugar function with biotin or (36) with charged groups for mass spectrometry (37,38). In addition, periodate oxidised sugars on glycopeptides can be reacted with hydrazide-functionalized or aminooxy-functionalized affinity tags enabling glycopeptide enrichment for analysis by mass spectrometry. These labelling reactions are typically multi-step labelling reactions that require addition and removal of several reagents. It would be highly beneficial to use solid supports to facilitate the addition or removal of these reagents for glycopeptide analysis.

The sugar O—N-acetylglucosamine (O-GlcNAc) is added to serines or threonines by O-GlcNAc transferase (OGT). O-GlcNAc appears to occur on serines and threonines that would otherwise be phosphorylated by serine/threonine kinases. Thus, if phosphorylation occurs, O-GlcNAc does not, and vice versa (39,40). This apparently competitive modification of certain sites may have significant consequences for signalling research particularly in cancer and metabolic research. Much cancer research is focused on phosphorylation, because of its important role in cell signalling pathways. As competitive or variable glycosylation occurs at the same sites, there is a risk that phosphorylation research has overlooked important roles that these modification sites play when glycosylated. O-GlcNAc addition and removal also appears to be a key regulator of the pathways that are disrupted in diabetes mellitus (41). The gene encoding the O-GlcNAcase (OGA) enzyme has been linked to non-insulin dependent diabetes mellitus (42).

Accordingly, it is an aim of the present invention to provide a range of novel labelling reagents, and labelling and MS analysis methodologies that specifically address the limitations of previously disclosed molecules and methods.

It is an object of this invention to provide labelling reagents which are easier to synthesize than known mass labels, whilst at the same time achieving high levels of multiplex analysis.

It is a further object of this invention to provide methods to simplify and automate multi-step labelling reactions of mass tags using reversible immobilisation of peptides on solid phase supports to allow facile addition and removal of reagents during these multi-step processes. This invention also provides novel labelling procedures for the enrichment, detection and quantification of peptides, particularly peptides with post-translational modifications such as phosphorylation and glycosylation with analysis by mass spectrometry.

SUMMARY OF THE INVENTION

The present invention provides a method for labelling one or more analytes in a sample, the method comprising:
  a) contacting the sample with one or more bifunctional linker reagents having the general formula $Re^1$-$L^1$-$Re^2$, wherein $Re^1$ is a first reactive group, $L^1$ is a linker moiety and $Re^2$ is a second reactive group, wherein $Re^1$ reacts with an analyte to form a modified analyte; and
  b) contacting the sample with one or more mass labels, wherein $Re^2$ of the bifunctional linker attached to the analyte reacts with a mass label to form a labelled analyte, wherein each mass label is relatable to the analyte by mass spectrometry.

By combining separate bifunctional linker and mass labelling reagents in a two-step reaction, multiple samples can be labelled without the need to synthesize large numbers of complex mass labelling reagents incorporating offset masses. This makes high-level multiplexing much more cost effective. This method also works well with solid phase methodologies.

$Re^1$ may be any reactive group which is capable of reacting with an analyte to form a modified, i.e. linker-labelled analyte:
Analyte-$L^1$-$Re^2$ $Re^2$ may be any reactive group which is capable of reacting with a mass label to form a labelled analyte:
Analyte-$L^1$-Mass label The linker moiety $L^1$ is not especially limited provided it attaches $Re^1$ to $Re^2$, and does not hinder the reaction of $Re^1$ with the analyte and the reaction of $Re^2$ with the mass label.

In a preferred embodiment the method comprises a further step prior to step a) of reversibly capturing the one or more analytes onto a solid phase support, and optionally eluting the labelled analyte from the solid phase support after step b), wherein each mass label is relatable to an analyte.

Preferably the solid phase support is a hydrophobic solid phase support, optionally wherein the solid phase support comprises a resin derivatized with an aliphatic hydrocarbon chain or a tolyl group, typically a saturated linear hydrocarbon chain consisting of 18 carbon atoms.

In another aspect, provided is a method for the mass spectrometric analysis of one or more analytes in a sample, the method comprising:
  a) contacting the sample with one or more bifunctional linker reagents having the general formula $Re^1$-$L^1$-$Re^2$, wherein $Re^1$ is a first reactive group, $L^1$ is a linker moiety and $Re^2$ is a second reactive group, wherein $Re^1$ reacts with an analyte to form a modified analyte;
  b) contacting the sample with one or more mass labels, wherein $Re^2$ of the bifunctional linker attached to the analyte reacts with a mass label to form a labelled analyte, wherein each mass label is relatable to an analyte by mass spectrometry; and
  c) analysing the labelled analytes by mass spectrometry Steps a) and b) may be consecutive or concurrent.

In a preferred embodiment, this method comprises a further step prior to step a) of reversibly capturing the one or more analytes onto a solid phase support and eluting the labelled analyte from the solid phase support after step b) and prior to step c).

In the above methods, where the reactive groups to be coupled are amino groups and active esters, then typically a buffer solution is contacted with the solid phase support bearing the one or more analytes to provide the correct pH for the coupling reaction. It is preferable that the solution has a pH of less than 7, optionally a pH of from 3 to 6, more preferably from 3.5 to 5. The use of low pH reaction conditions is advantageous because cleaner mass spectra are produced, and the problem of over-labelling of analytes is reduced.

The step of eluting the modified analyte(s) from the solid phase support usually comprises contacting the solid phase support with an organic solvent, preferably an organic solvent compatible with mass spectrometry.

Typically the mass label has the general formula:

$$V\text{-}L^2\text{-}M$$

wherein V is a mass marker moiety, $L^2$ is a linker cleavable by dissociation in a mass spectrometer and M is a mass normalisation moiety which ensures that the mass label has a desired aggregate mass, and the mass label further comprises a reactive group $Re^3$ which reacts with $Re^2$ of the bifunctional linker.

In one embodiment, $Re^2$ is a protected reactive group that is deprotected after step a) and prior to step (b).

In a preferred embodiment, prior to step a) a reactive modifier causes the beta elimination of a functional group of an analyte and in step a) $Re^1$ undergoes a Michael addition reaction with the double bond formed by the beta elimination. Beta elimination refers to the elimination of a substituent attached to the carbon at a position beta to a carbonyl group, for example the C=O of a peptide bond.

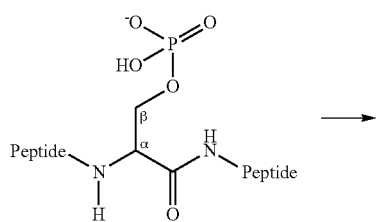

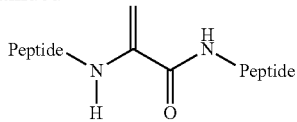

Michael addition refers to the addition, typically of a nucleophile, to the double bond formed by the beta elimination reaction (see for example the "thiol-TMT coupling" step shown in FIG. 2.

The functional group is not especially limited, although preferably is a post-translational modification of a biological molecule, most preferably the functional group is selected from a phosphate group and a saccharide group, preferably an O-linked saccharide group. The phosphate or O-linked saccharide group may be modifications of the hydroxyl group of the side chain of a serine or threonine residue. They may also be modifications of the tyrosine hydroxyl.

The reactive modifier may comprise a basic group. Preferably the reactive modifier comprises a hydroxide ion, typically an alkaline metal hydroxide, preferably barium, lithium, sodium, or potassium hydroxide, most preferably barium hydroxide. $Re^1$ typically comprises a nucleophilic group. Preferably the nucleophilic group is a thiol group or an amine group.

In one embodiment, the method comprises a further step prior to step a) of enriching the sample for analytes comprising one type of functional group. The sample may be enriched for analytes comprising phosphate functional groups. In this case, the enrichment step typically comprises reacting the analytes with immobilised antibodies against phosphopeptides or using immobilized metal oxide chromatography or immobilised metal ion affinity chromatography.

The solid phase support typically comprises titanium dioxide or is an immobilised metal ion solid phase support, preferably nitrilotriacetic acid (NTA), imino diacetic acid (IDA) or phosphonic acid (PhA) solid phase support, most preferably wherein the NTA or IDA solid phase supports are loaded with Fe2+ or Ga2+ ions or the PhA solid phase support is loaded with Ti4+ ions.

In another method of the invention the sample is enriched for analytes comprising O-linked saccharide functional groups. In this embodiment the enrichment step may comprise reacting the sample with affinity reagents bound to a solid phase support, preferably lectins or specific anti-carbohydrate antibodies.

The method of the invention may also comprise a step prior to step a) of depleting the sample of analytes comprising one type of functional group. In one embodiment, the method comprises a step prior to step a) of depleting the sample of analytes comprising saccharide groups by reacting the sample with affinity reagents bound to a solid phase support, preferably lectins or specific anti-carbohydrate antibodies, such that analytes comprising saccharide groups are captured on the solid phase support, and eluting the sample from the solid phase support under conditions in which the analytes comprising saccharide groups remain bound on the solid phase support.

In another embodiment, the method may also comprise a step prior to step a) of depleting the sample of analytes comprising phosphate groups by reacting the sample with immobilised antibodies against phosphopeptides or using immobilized metal oxide chromatography or immobilised metal ion affinity chromatography, and eluting the sample from the solid phase support under conditions in which the analytes comprising phosphate groups remain bound on the solid phase support.

In one embodiment, prior to step a) the one or more analytes are attached to the solid phase support by means of a functional group, and beta elimination of the functional group cleaves the analyte(s) from the solid phase support; and in a further step the released analytes(s) are isolated and reversibly captured onto a further solid phase support.

In one embodiment, the analyte comprises an O-linked saccharide; and prior to step a) the O-linked saccharide is reacted with an oxidising agent to form an aldehyde or a ketone; and $Re^1$ of the bifunctional linker reacts with the aldehyde or ketone. In this method the bifunctional linker preferably comprises a hydrazide or aminoxy reactive group. Typically the oxidising agent is periodate or galactose oxidase.

The method may comprise one or more wash steps, preferably to wash away unreacted bifunctional linker, mass label or reactive modifier. Preferably the one or more wash steps are carried out with a polar solvent, most preferably an aqueous solvent.

The methods of the invention are typically for the labelling or mass spectrometric analysis of a plurality of analytes.

In a preferred embodiment, in step a) each analyte is reacted with a bifunctional linker from a set of two or more bifunctional linkers, wherein each bifunctional linker in the set has a different mass.

In one embodiment each label in the set of two or more bifunctional linkers has the following structure:

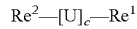

wherein $Re^1$ is a first reactive group, $Re^2$ is a second reactive group, U is a linker repeat unit and c is an integer from 1 to 10.

In one embodiment each bifunctional linker in the set of two or more bifunctional linkers has a different integer value of c.

In one embodiment U has the formula $U(D)_k$; wherein D is a mass adjuster moiety, k is an integer of 0 or greater, and each bifunctional linker in the set of two or more bifunctional linkers has a different value of k, and preferably the same value of c. Typically the mass adjuster moiety is selected from an isotopic substituent or substituent atoms or groups attached to the bifunctional linker. Preferably the mass adjuster moiety is selected from a halogen atom substituent, a methyl group substituent, and $^2H$, $^{15}N$, $^{13}C$ or 18O isotopic substituents.

In a preferred embodiment, $Re^1$ and $Re^2$ of each bifunctional linker are each independently selected from:

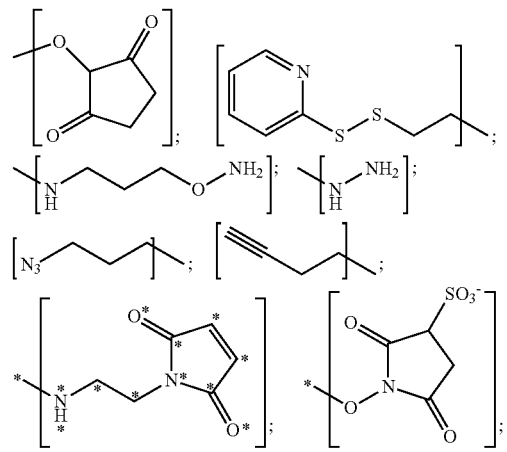

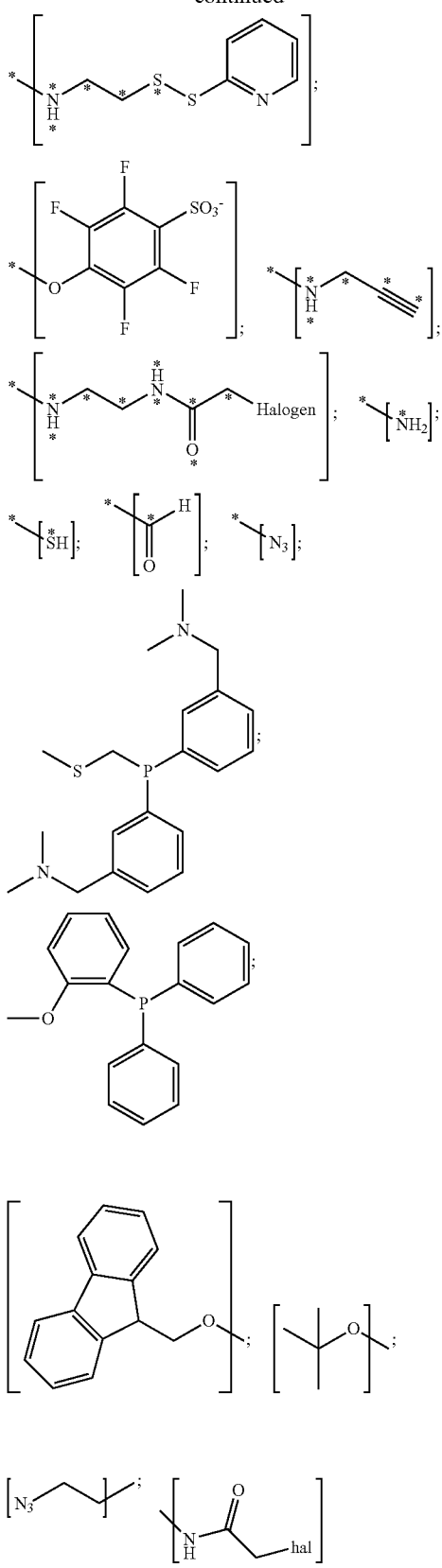

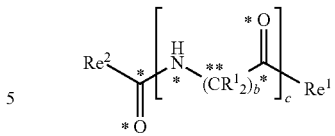

wherein Re¹ is the first reactive group, Re² is the second reactive group, each R¹ is independently H, a substituted or unsubstituted straight or branched $C_1$-$C_6$ alkyl group, a substituted or unsubstituted aliphatic cyclic group, a substituted or unsubstituted aromatic group or a substituted or unsubstituted heterocyclic group or an amino acid side chain; and b is an integer from 1-10 and c is an integer from 1 to 10; and wherein each * is an isotopic mass adjuster moiety which may be present or absent and * represents that oxygen is $^{18}O$, carbon is $^{13}C$ or nitrogen is $^{15}N$ or hydrogen is $^{2}H$.

The bifunctional linker may be selected from the following compounds:

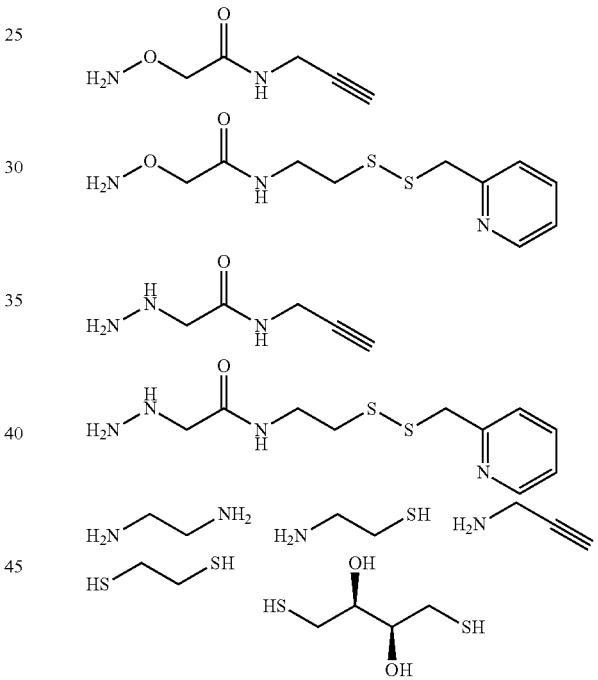

The bifunctional linker is preferably selected from the following compounds:

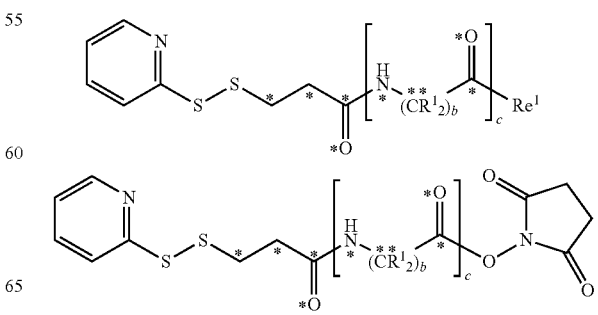

In a preferable embodiment the bifunctional linker has the general formula:

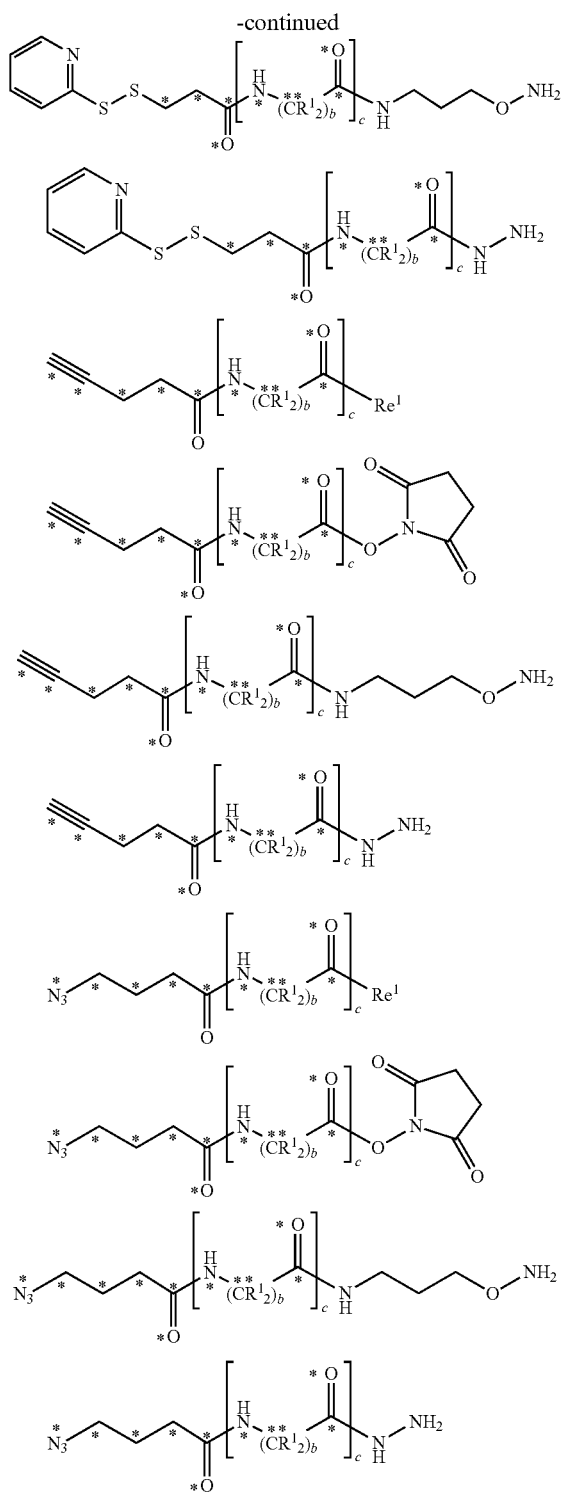

In a preferred embodiment, in step b) each modified analyte is labelled with a mass label from a set of two or more mass labels, wherein each label in the set is as defined above, and wherein the set comprises:
a group of labels having a mass marker moiety of common mass, each label in the group having a unique aggregate mass; or
a group of labels having a mass marker moiety, each mass marker moiety having a mass different from that of all other mass marker moieties in that group, and each label in the group having a common aggregate mass;
and wherein all the mass labels in the set are distinguishable from each other by mass spectrometry.

Typically the mass marker moiety V comprises the following group:

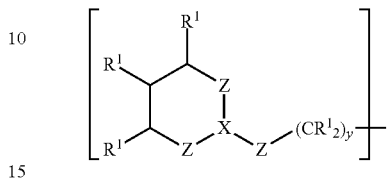

wherein the cyclic unit is aromatic or aliphatic and comprises from 0-3 double bonds independently between any two adjacent atoms; each Z is independently N, $N(R^1)$, $C(R^1)$, CO, $CO(R^1)$, $C(R^1)_2$, O or S; X is N, C or $C(R^1)$; each $R^1$ is independently H, a substituted or unsubstituted straight or branched $C_1$-$C_6$ alkyl group, a substituted or unsubstituted aliphatic cyclic group, a substituted or unsubstituted aromatic group or a substituted or unsubstituted heterocyclic group; and y is an integer from 0-10. $L^2$ preferably comprises an amide bond.

$Re^3$ of the mass label usually comprises a nucleophilic group, preferably an amino group or a thiol group, typically a protected thiol group.

Preferably $Re^3$ is selected from the following:

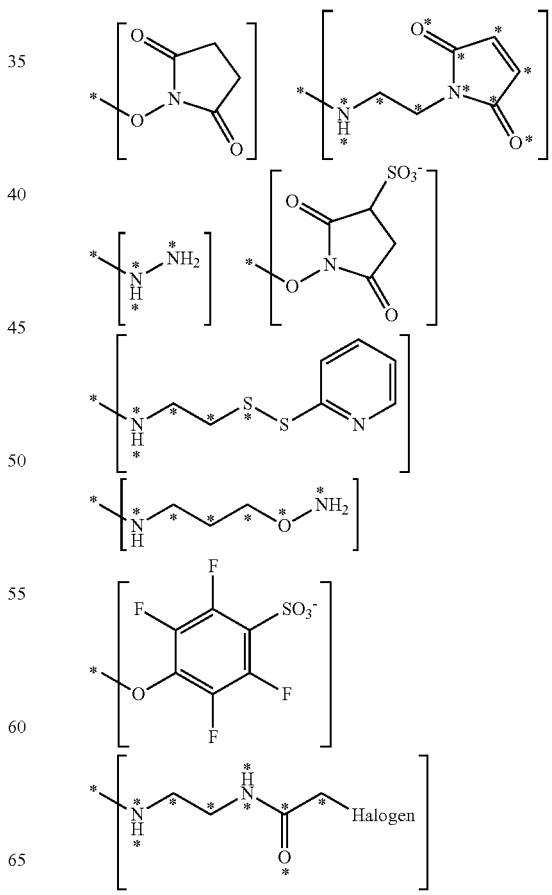

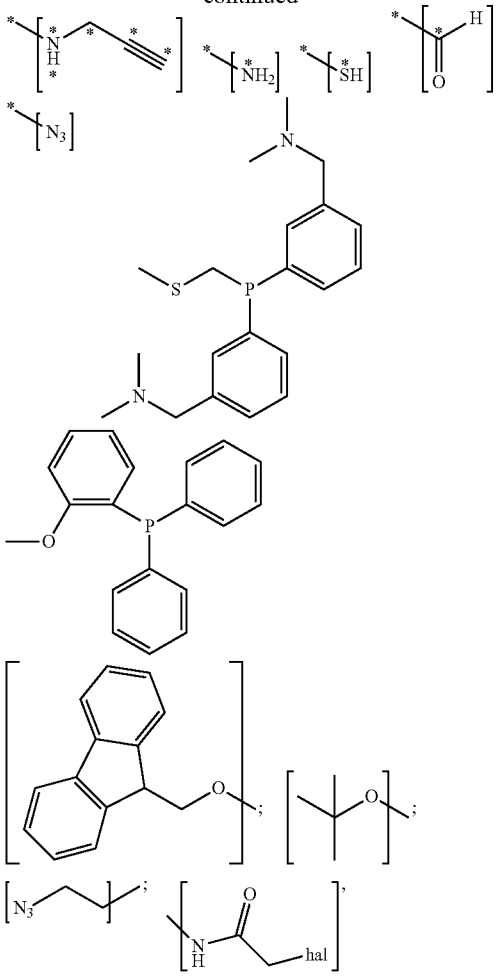

wherein hal is a halogen, preferably iodine.

In another embodiment, in step b) each modified analyte is labelled with a mass label from a set of two or more mass labels, wherein each mass label in the set has a common integer mass and an exact mass different to all other mass labels in the set; and wherein all the mass labels in the set are distinguishable from each other by mass spectrometry. Preferably, the difference in exact mass between at least two of the mass labels is less than 100 millidaltons, preferably less than 50 millidaltons. Typically each mass label in the set is isochemic. Usually the difference in exact mass is provided by a different number or type of heavy isotope substitution(s). In a preferable embodiment the set comprises n mass labels, where the $x^{th}$ mass label comprises (n−x) atoms of a first heavy isotope and (x−1) atoms of second heavy isotope different from the first, wherein x has values from 1 to n. The heavy isotope may be $^{2}H$, $^{13}C$ or $^{15}N$. In another embodiment the $x^{th}$ mass label comprises (n−x) atoms of a first heavy isotope selected from $^{18}O$ or $^{34}S$ and (2x−2) atoms of second heavy isotope different from the first selected from $^{2}H$ or $^{13}C$ or $^{15}N$, wherein x has values from 1 to n.

The analytes are not especially limited but are usually biomolecules, preferably selected from amino acids, peptides, polypeptides, glycans, steroids, lipids and oligonucleotides.

In a preferred embodiment the analytes are peptides formed by the cleavage of a polypeptide or a mixture of polypeptides, typically a phosphoprotein or glycoprotein or a mixture of phosphoproteins and/or glycoproteins. In a preferred embodiment of the invention, cleaving the mixture of polypeptides into smaller peptides is carried out by contacting the polypeptides with a protease. In specific preferred embodiments, the protease comprises the endoprotease Trypsin or Lys-C but sequence specific chemical cleavage, e.g. by Cyanogen Bromide, is envisaged and the use of other endoproteases is also anticipated.

In a further aspect, the present invention provides a set of two or more bifunctional linkers for labelling a plurality of analytes as defined above, wherein each linker in the set has a different mass.

In an additional aspect, the present invention provides a kit for labelling a plurality of analytes comprising a set two or more bifunctional linkers as defined in any preceding claim, and a set of two or mass labels as defined in any preceding claim, and optionally a solid phase support as defined in any preceding claim.

In a preferred embodiment the kit comprises the following bifunctional linkers:

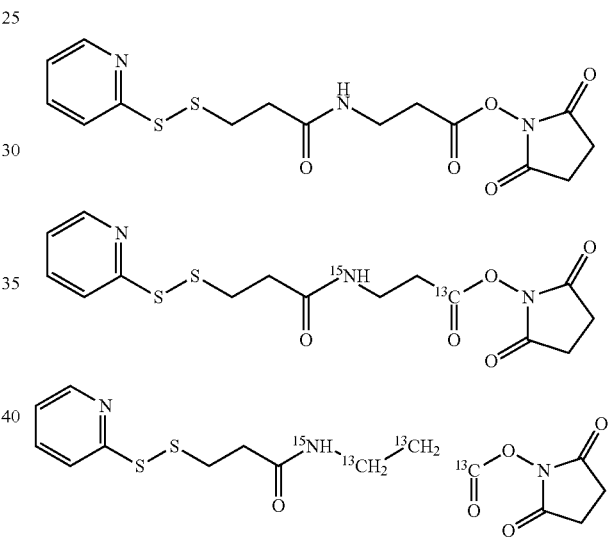

and the following mass labels:

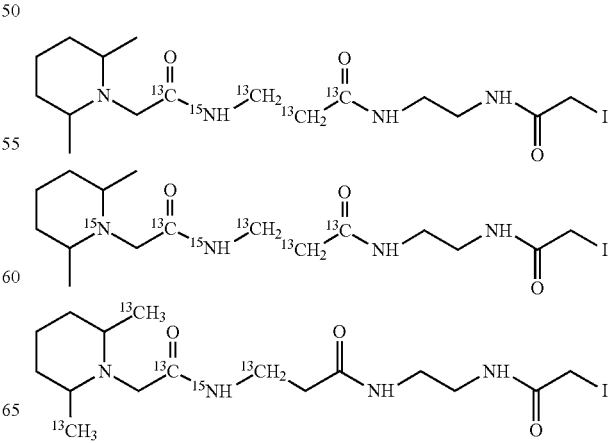

-continued

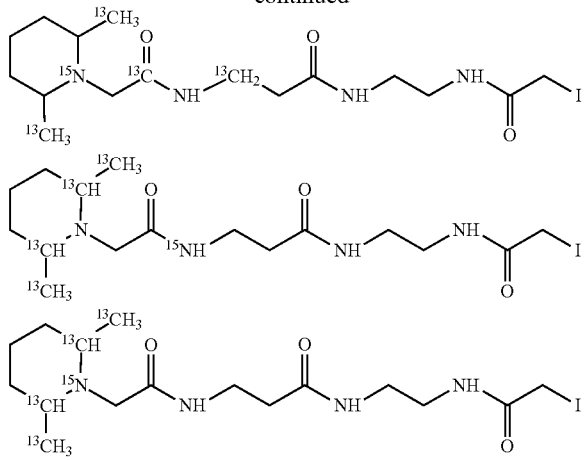

Step c) may comprise separating the analytes by chromatography prior to analysis in a mass spectrometer. Step c) typically comprises collision-induced dissociation in MS/MS or MS/MS/MS experiments.

DETAILED DESCRIPTION OF THE INVENTION

Figure 12:
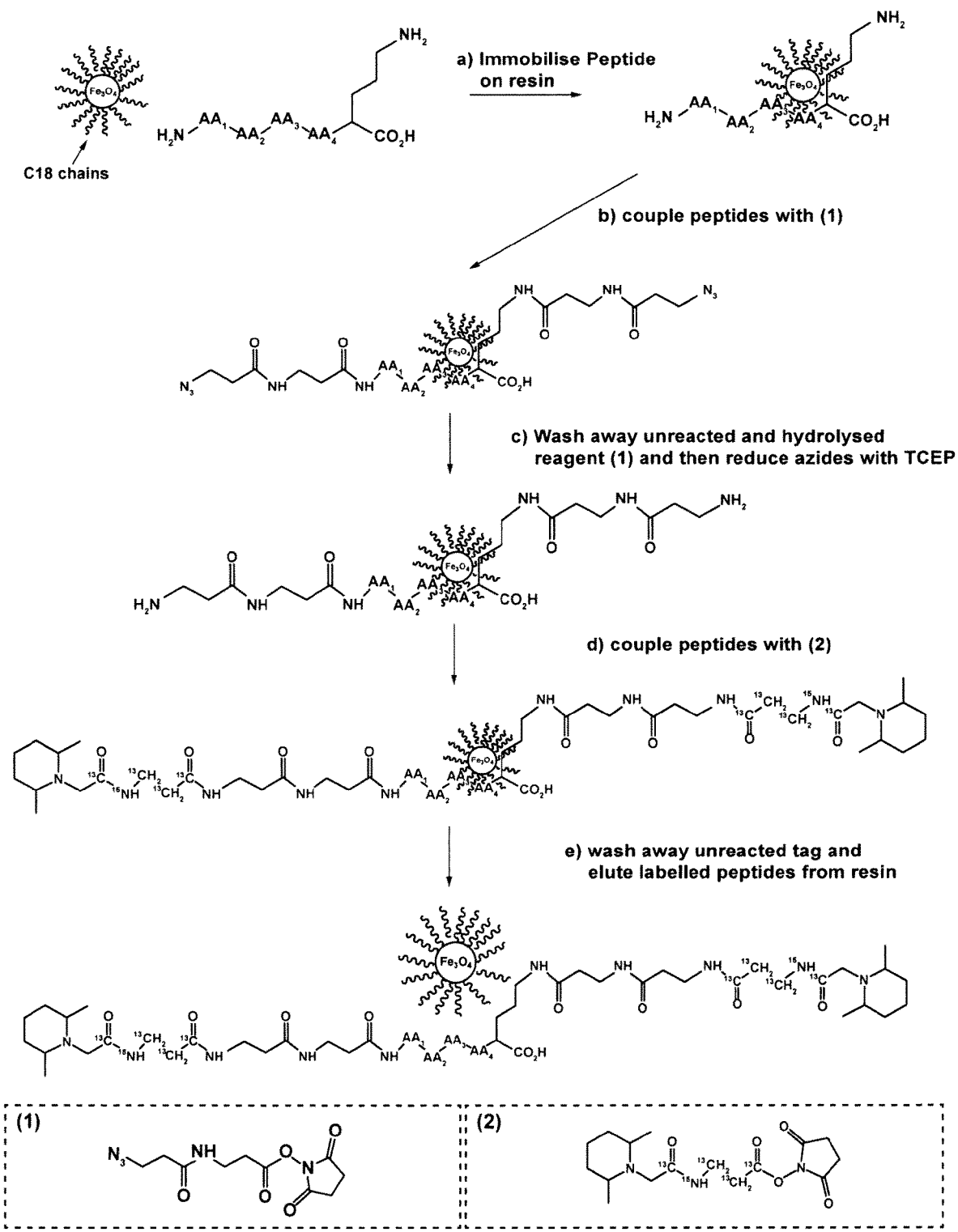
Figure 13:
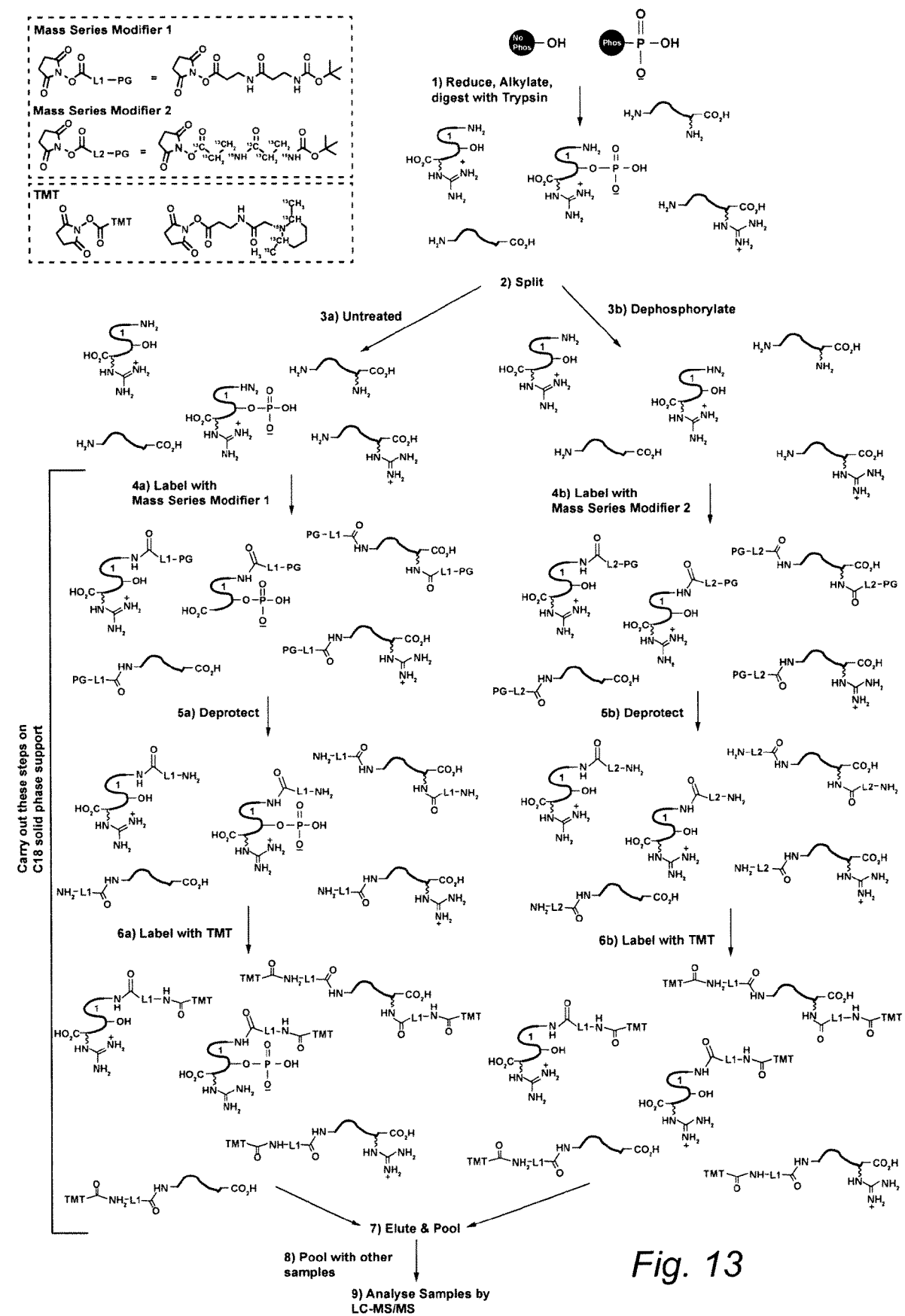

FIG. 12 shows an embodiment of the invention where peptides reversibly captured onto a solid phase support are reacted with an isotope-doped bifunctional linker where the doped bifunctional linker that acts as a mass series modifier comprises an NHS-ester to react with free amines in the immobilized peptides and an azide, which is used as a protected amine with which an NHS-ester activated mass tag can be reacted after reduction of the azide to an amine FIG. 13 shows an embodiment of the invention where a pair of aliquots of a phosphopeptide sample are reversibly captured onto a solid phase support and reacted with different isotope-doped bifunctional linkers where the doped bifunctional linker that acts as a mass series modifier comprises an NHS-ester to react with free amines in the immobilized peptides. The peptide aliquots are then labelled with the same Isobaric Mass Tags. In this way, the two phosphopeptide aliquots are identified by the Mass Series Modifier while the sample from which the phosphopeptide aliquots were taken are identified by the Isobaric Mass Tag.

Figure 14:
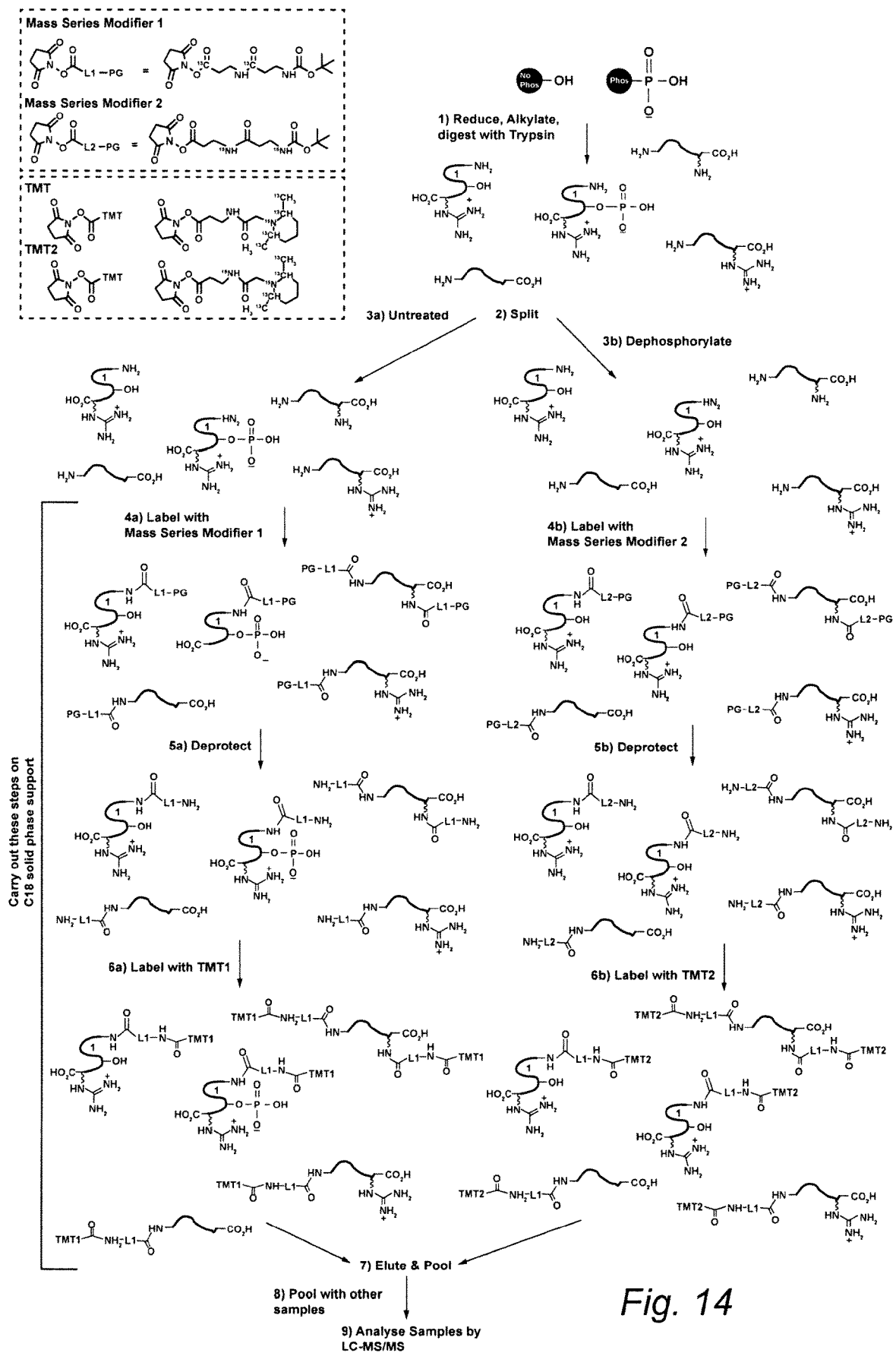

FIG. 14 shows an embodiment of the invention where a pair of aliquots of a phosphopeptide sample are reversibly captured onto a solid phase support and reacted with different isotope-doped bifunctional linkers where the doped bifunctional linker that acts as a mass series modifier comprises an NHS-ester to react with free amines in the immobilized peptides. The peptide aliquots are then labelled with different Isobaric Mass Tags. In this way, the two phosphopeptide aliquots are identified by both the Mass Series Modifier and by the Isobaric Mass Tag.

Figure 15:
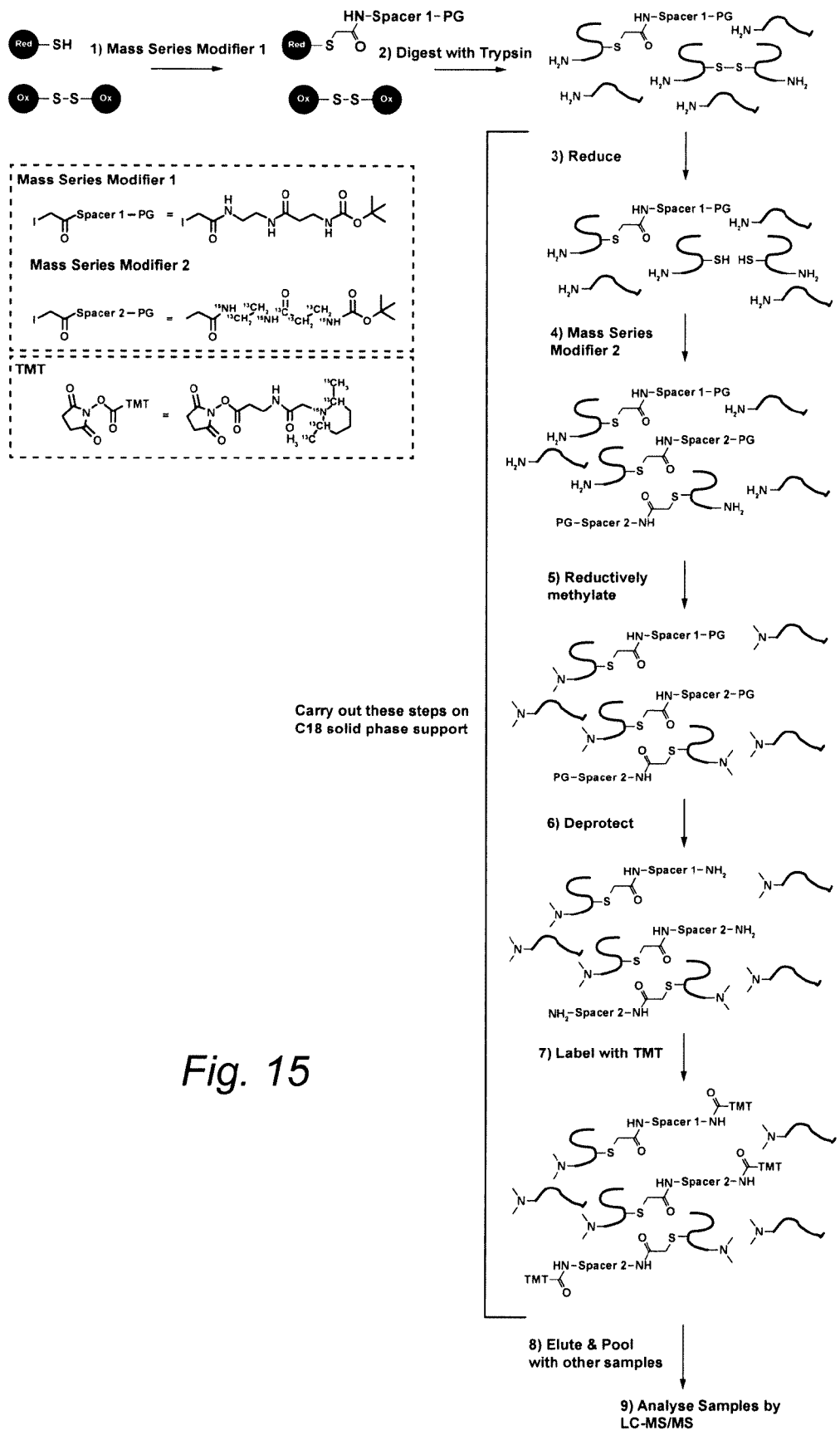

FIG. 15 shows an embodiment of the invention where a protein sample, in which some proteins are in different RedOx states. These are reversibly captured onto a solid phase support and free thiols are reacted with a first isotope-doped bifunctional linker. The sample is then treated with a reducing agent to reduce oxidised thiols which are then reacted with a second isotope-doped bifunctional linker where the doped bifunctional linker that acts as a mass series modifier comprises an iodoacetamide function to react with free thiols in the immobilized peptides. The peptide aliquots are then labelled with the same Isobaric Mass Tags. In this way, the redox state the thiols in the protein sample are identified by the Mass Series Modifier while the sample from which the proteins were taken are identified by the Isobaric Mass Tag.

Figure 16:
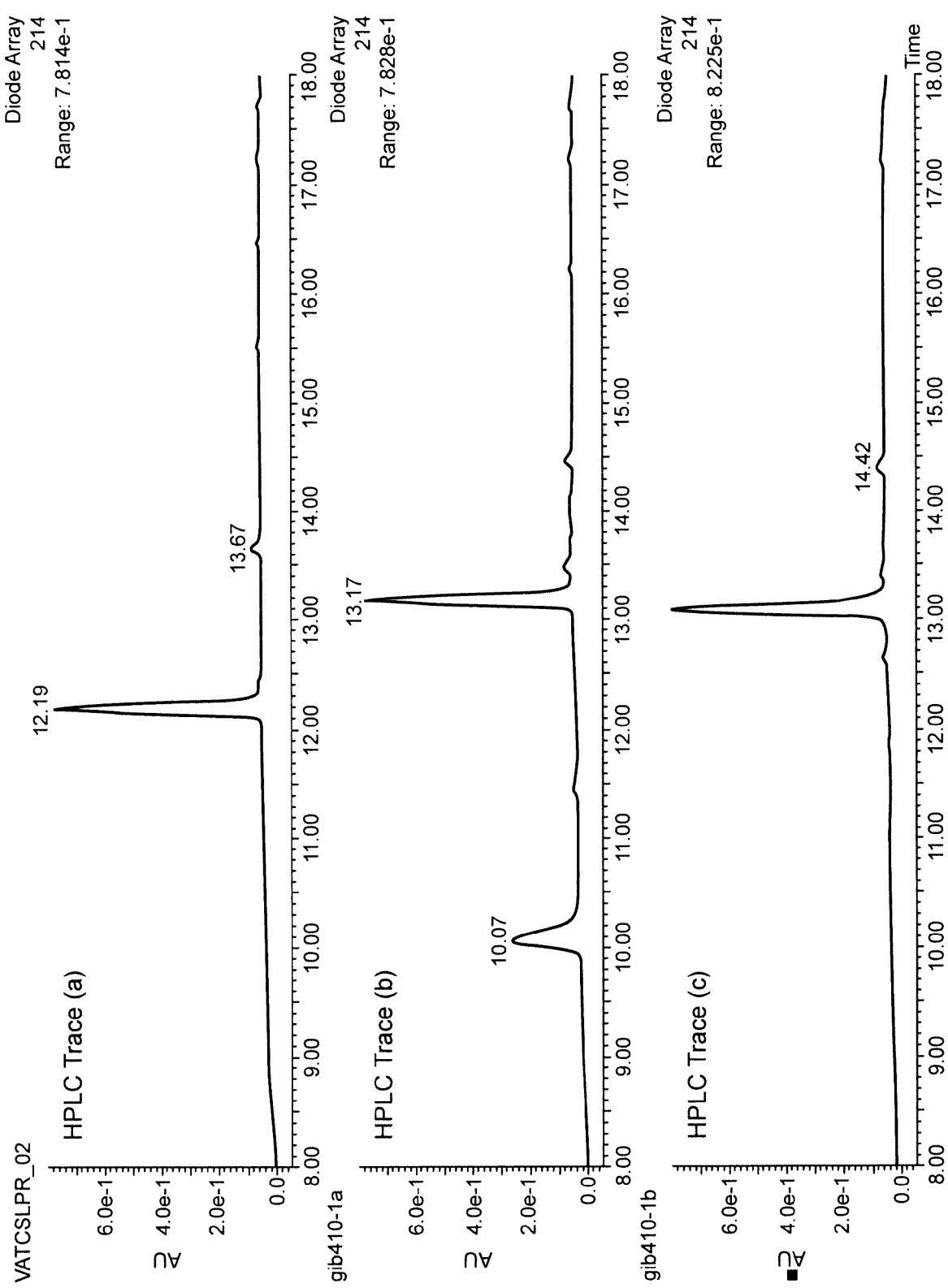

FIG. 16 shows three HPLC traces. HPLC trace (a) shows the unlabelled and unmodified synthetic peptide (VATVS-LPR) with a retention time of 12.2 minutes. HPLC trace (b) shows the product of the solution-phase labelling reaction of TMTzero with the synthetic peptide (VATVSLPR) without quenching by hydroxylamine. HPLC trace (c) shows the product of the solution-phase labelling reaction of TMTzero with the synthetic peptide (VATVSLPR) after quenching with hydroxylamine.

Figure 17:
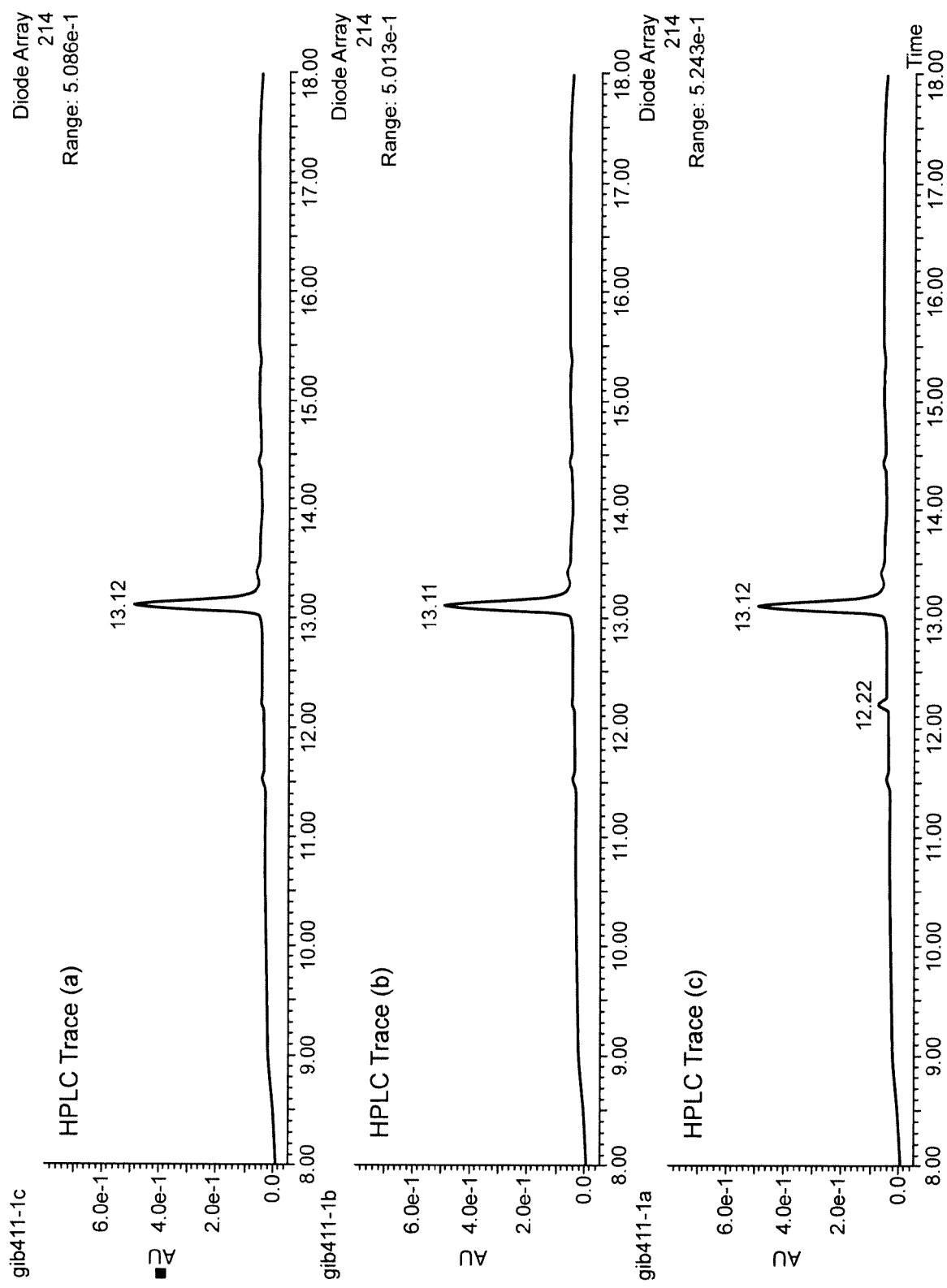

FIG. 17 shows three HPLC traces from the solid phase labelling of the synthetic peptide (VATVSLPR) using the Waters Oasis HLB cartridges. HPLC trace (a) shows the labelled synthetic peptide with a retention time of 13.1 minutes after an incubation time of 60 minutes on the cartridge. HPLC trace (b) shows the product of the solid-phase labelling reaction of TMTzero with the synthetic peptide after 30 minutes of incubation on the cartridge. HPLC trace (c) shows the product of the solid-phase labelling reaction of TMTzero with the synthetic peptide after an incubation time of 15 minutes.

Figure 18:
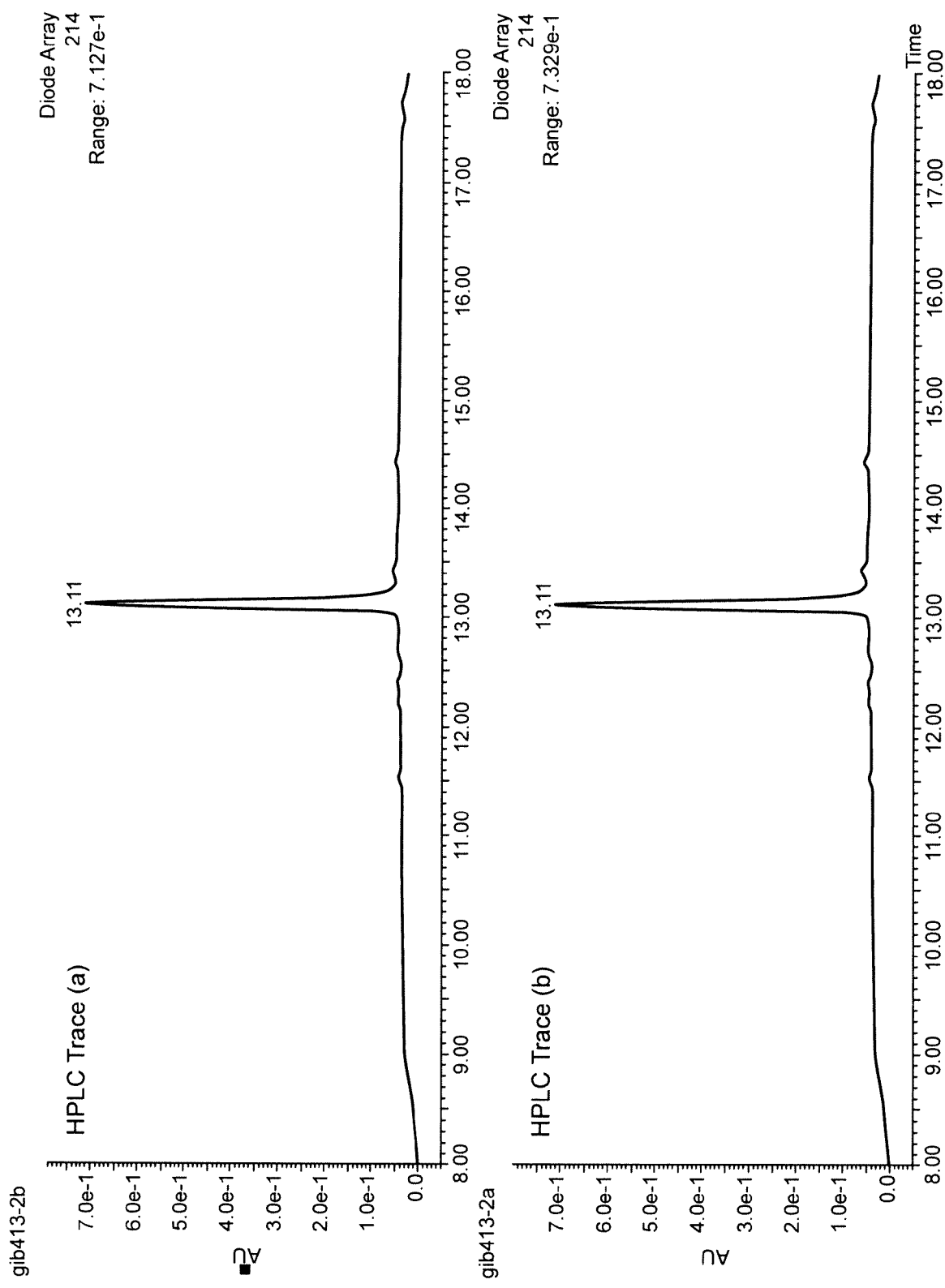

FIG. 18 shows two HPLC traces from two independent repetitions of the solid phase labelling of the synthetic peptide (VATVSLPR) using the Waters Oasis tC18 cartridges. HPLC trace (a) shows the labelled synthetic peptide with a retention time of 13.1 minutes after an incubation time of 60 minutes on the cartridge. Similarly, HPLC trace (b) shows the product of the solid-phase labelling reaction of TMTzero with the synthetic peptide using reagents and target peptide made up freshly again.

Figure 19:
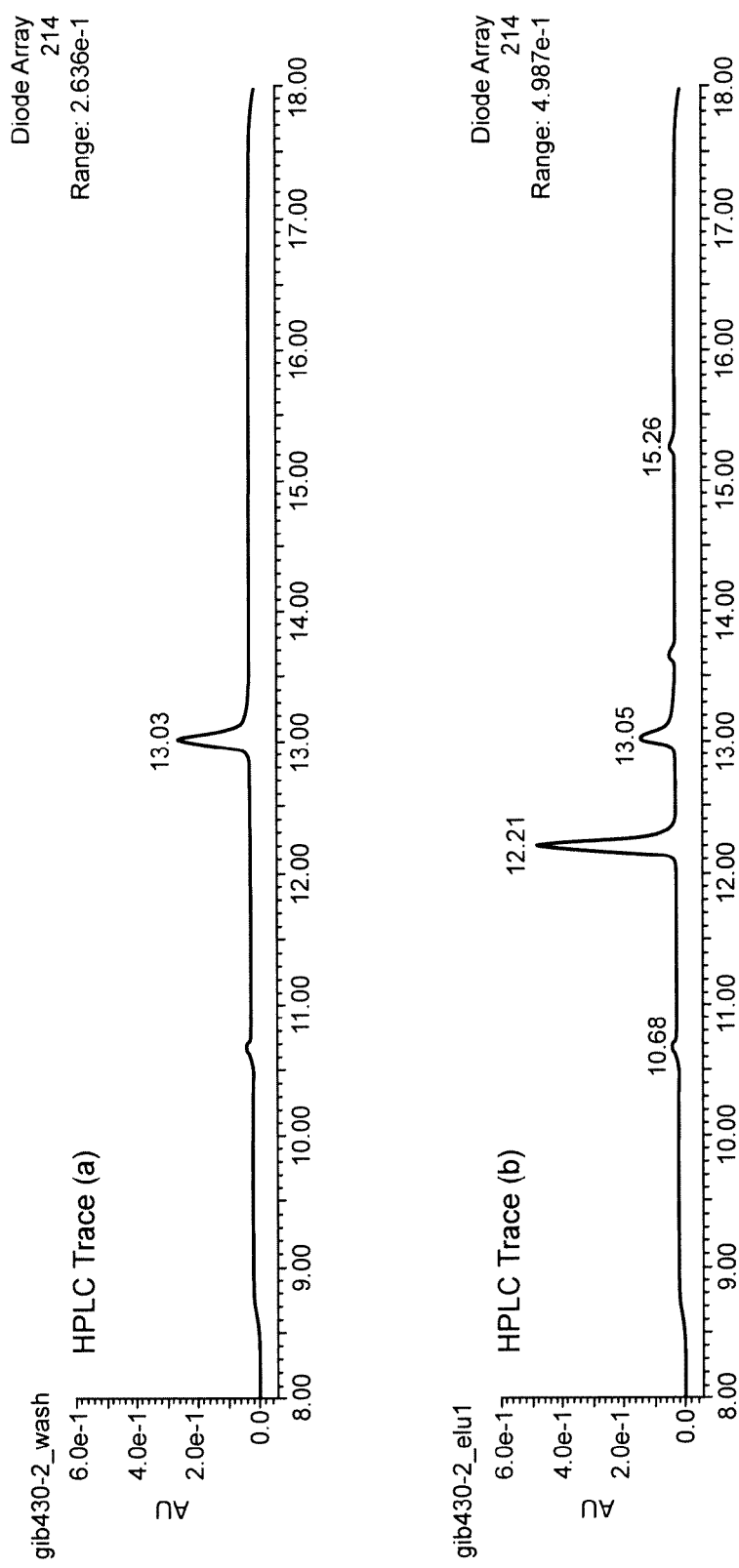

FIG. 19 HPLC trace (a) shows the combined flow-through of the loading buffer and the buffer exchange step while FIG.

19 HPLC trace (b) shows the final eluted peptide peptide after loading in Lysis buffer, buffer exchange with Phosphate buffer, washing twice with Wash Buffer and elution with Elution Buffer.

Figure 20:
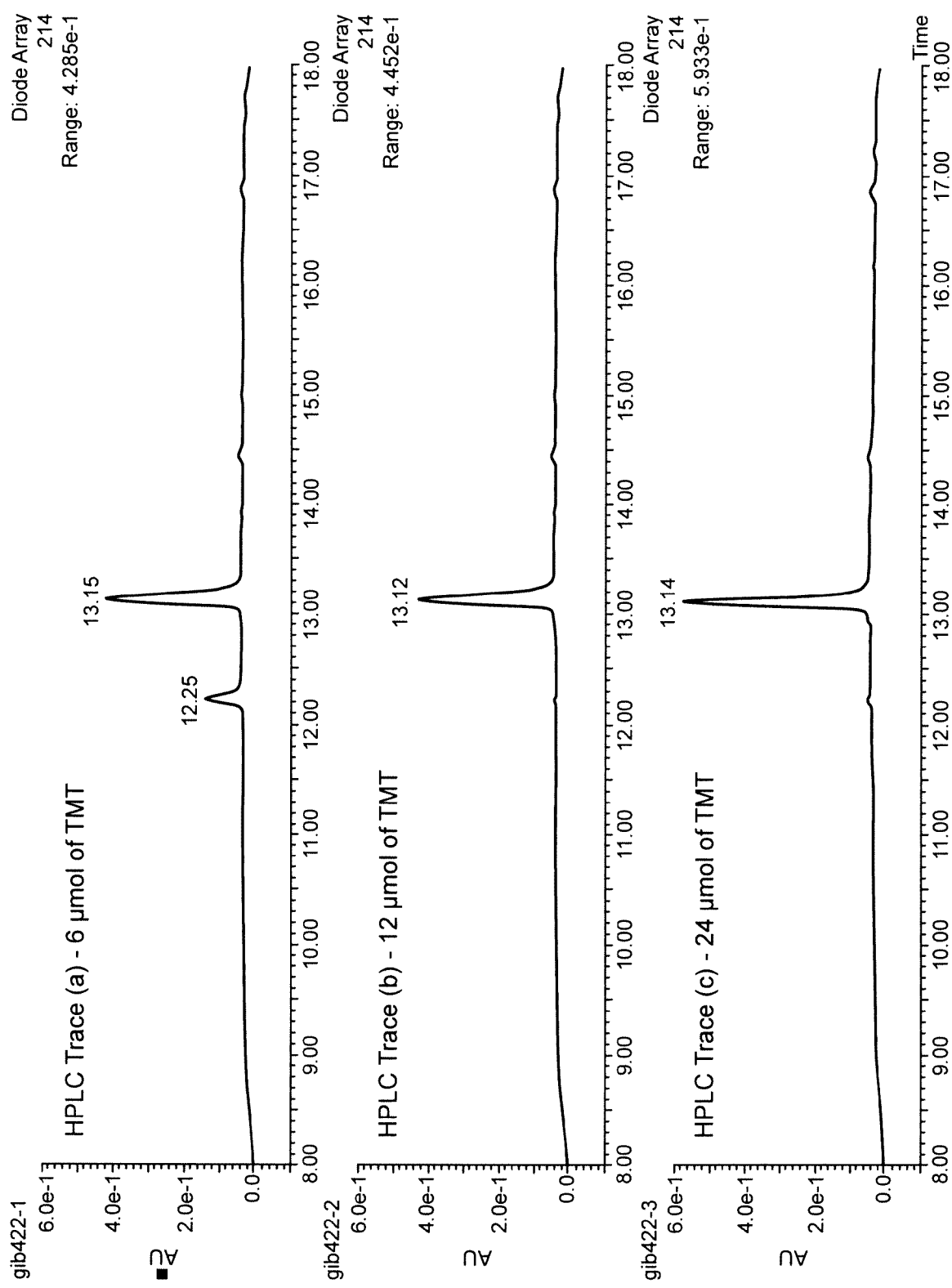

FIG. 20 shows HPLC traces of the eluted labelled peptide after incubation with different amounts of TMTzero reagent. HPLC Trace (a) in FIG. 20 shows the peptide after coupling with 6 μmol of TMTzero. HPLC Trace (b) in FIG. 20 shows the peptide after coupling with 12 μmol of TMTzero. HPLC Trace (c) in FIG. 20 shows the peptide after coupling with 24 μmol of TMTzero.

Figure 21:
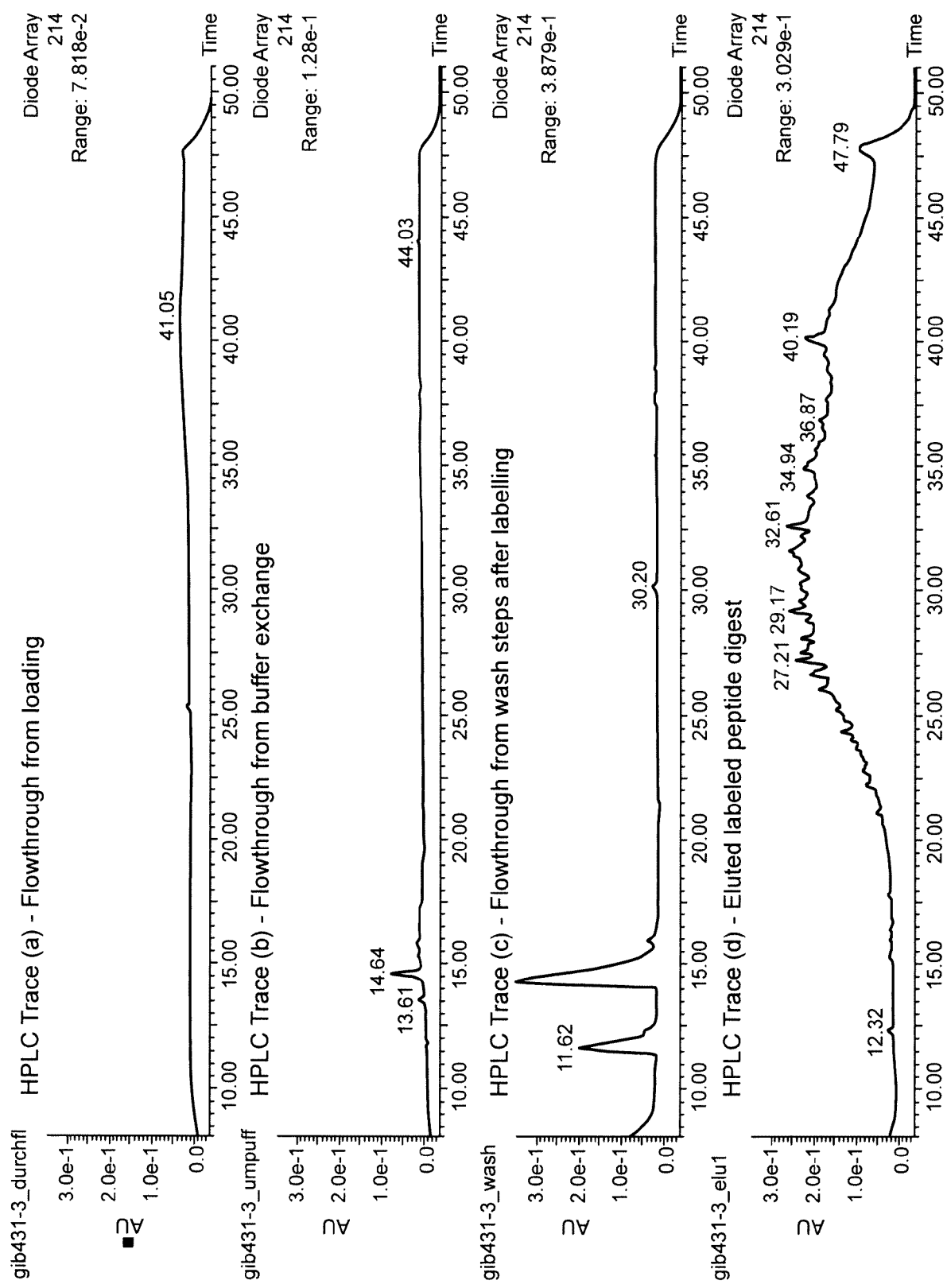

FIG. 21 shows HPLC traces from the solid phase labelling of Liver Protein Extract peptide digest after incubation with 15 μmol of TMTzero reagent.

Figure 22:
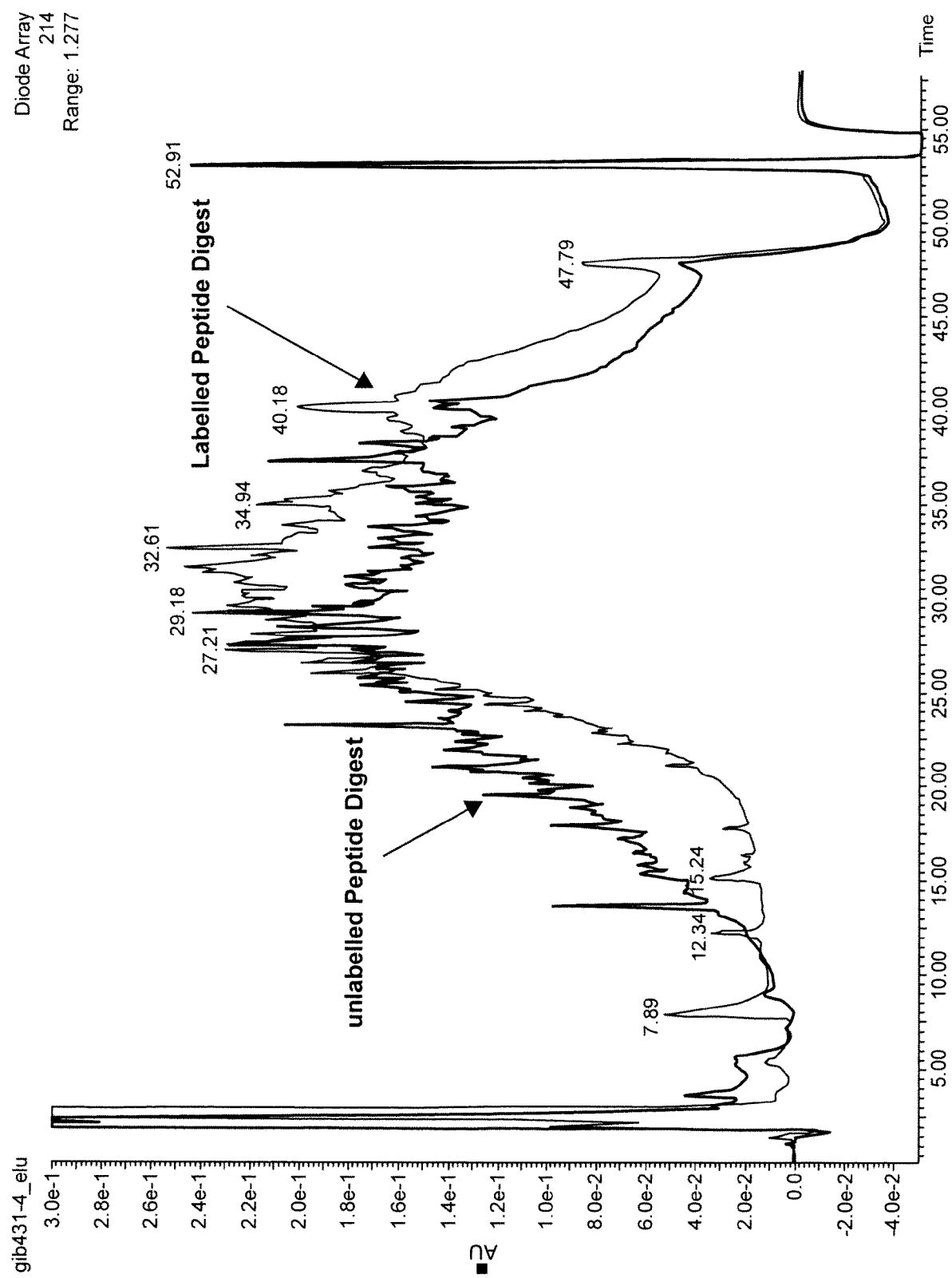

FIG. 22 shows overlaid HPLC traces comparing the unlabelled peptide digest with the labelled peptide digest.

Figure 23:
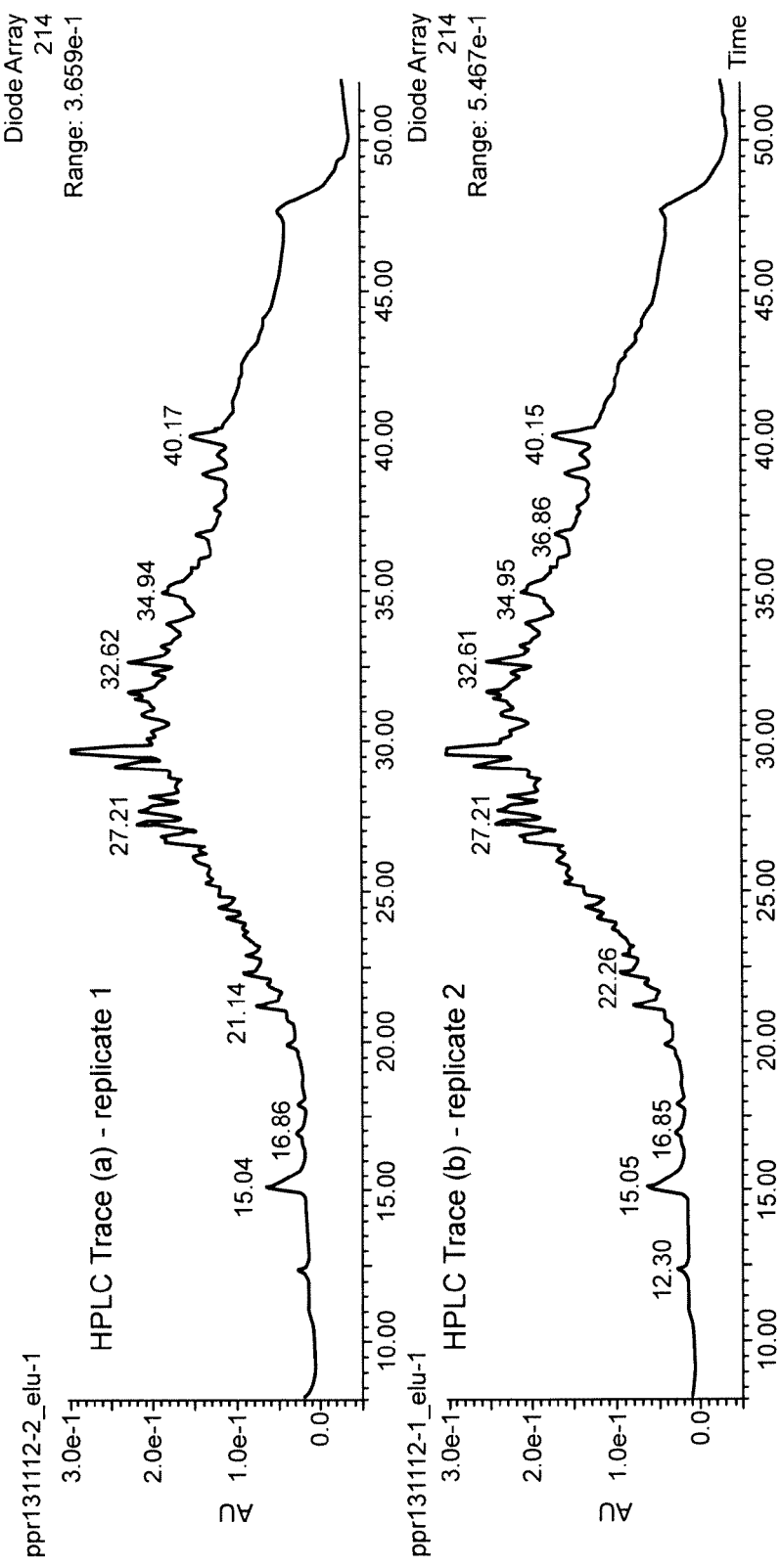

FIG. 23 shows HPLC traces of 2 further technical replicates of the labelled digest, showing that the same elution pattern occurs indicating a reproducible level of labelling in both samples.

Figure 24:
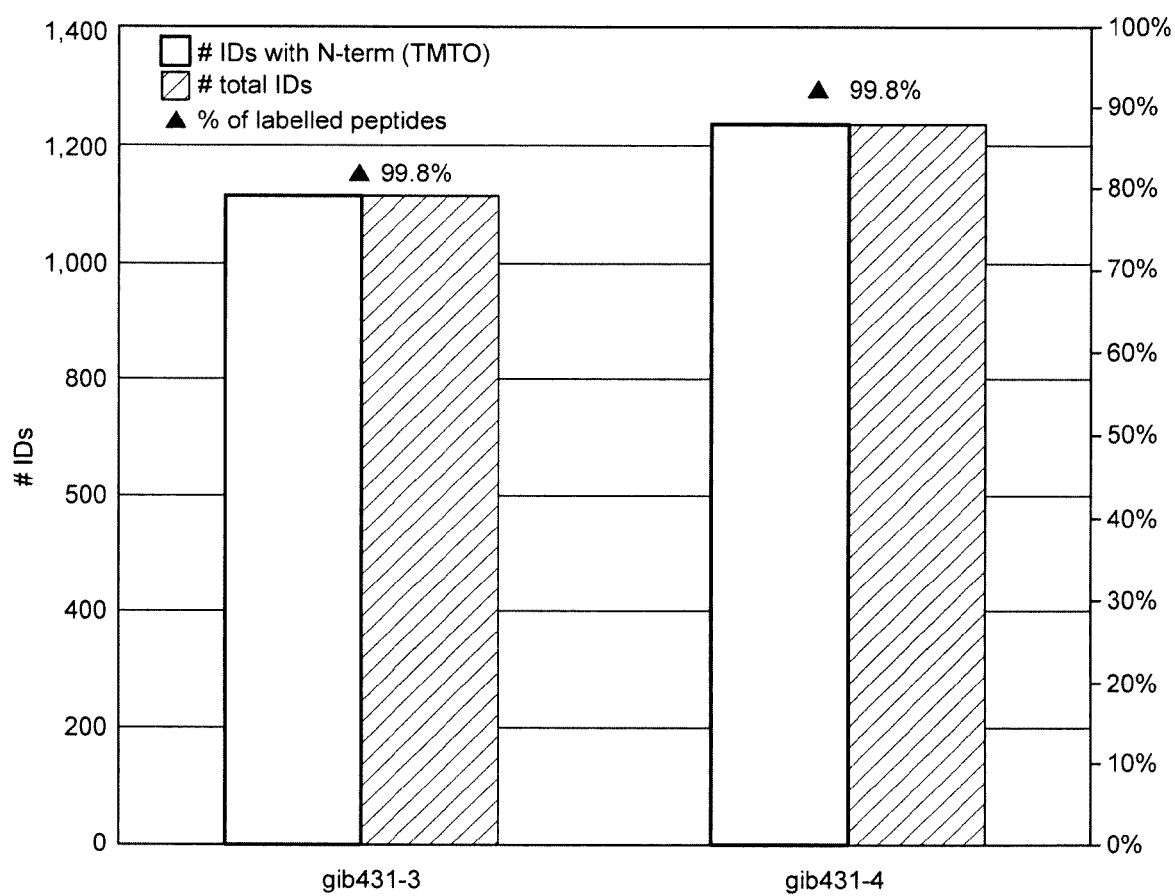

FIG. 24 shows a histogram of peptide identifications made using MASCOT software to analyse peptides from the two replicate digests in FIG. 19 that were sequenced in an Orbitrap Elite mass spectrometer after HPLC separation. The light bars indicate the number of peptides in each replicate that were sequenced that contained the TMTzero modification while the dark bars indicate the total number of peptides identified.

Figure 25:
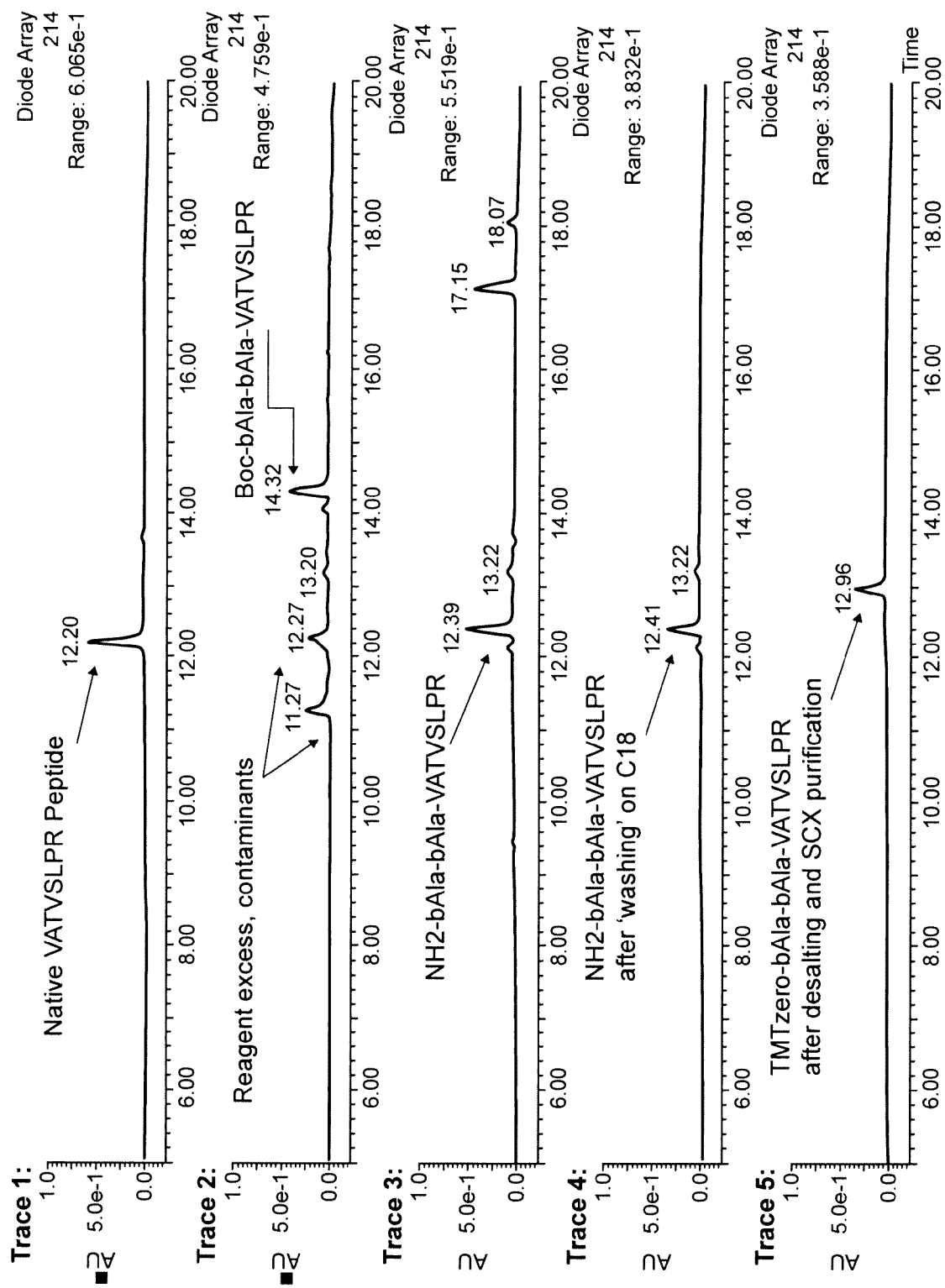

FIG. 25, Trace 1 shows an HPLC trace of the native VATVSLPR peptide before any labelling steps. FIG. 25, Trace 2 shows an HPLC trace of an analysis of the reaction mixture of the VATVSLPR peptide after coupling to the BOC-protected linker. FIG. 25, Trace 3 shows an HPLC trace of an analysis of the reaction mixture of the linker-coupled VATVSLPR peptide after removal of the Boc-protecting group from the peptide. FIG. 25, Trace 4 shows an HPLC trace of an analysis of the TMTzero linker-coupled VATVSLPR peptide after desalting on the C18 cartridge. FIG. 25, Trace 5 shows an HPLC trace of an analysis of the TMTzero linker-coupled VATVSLPR peptide after the second SCX purification step.

Figure 26:
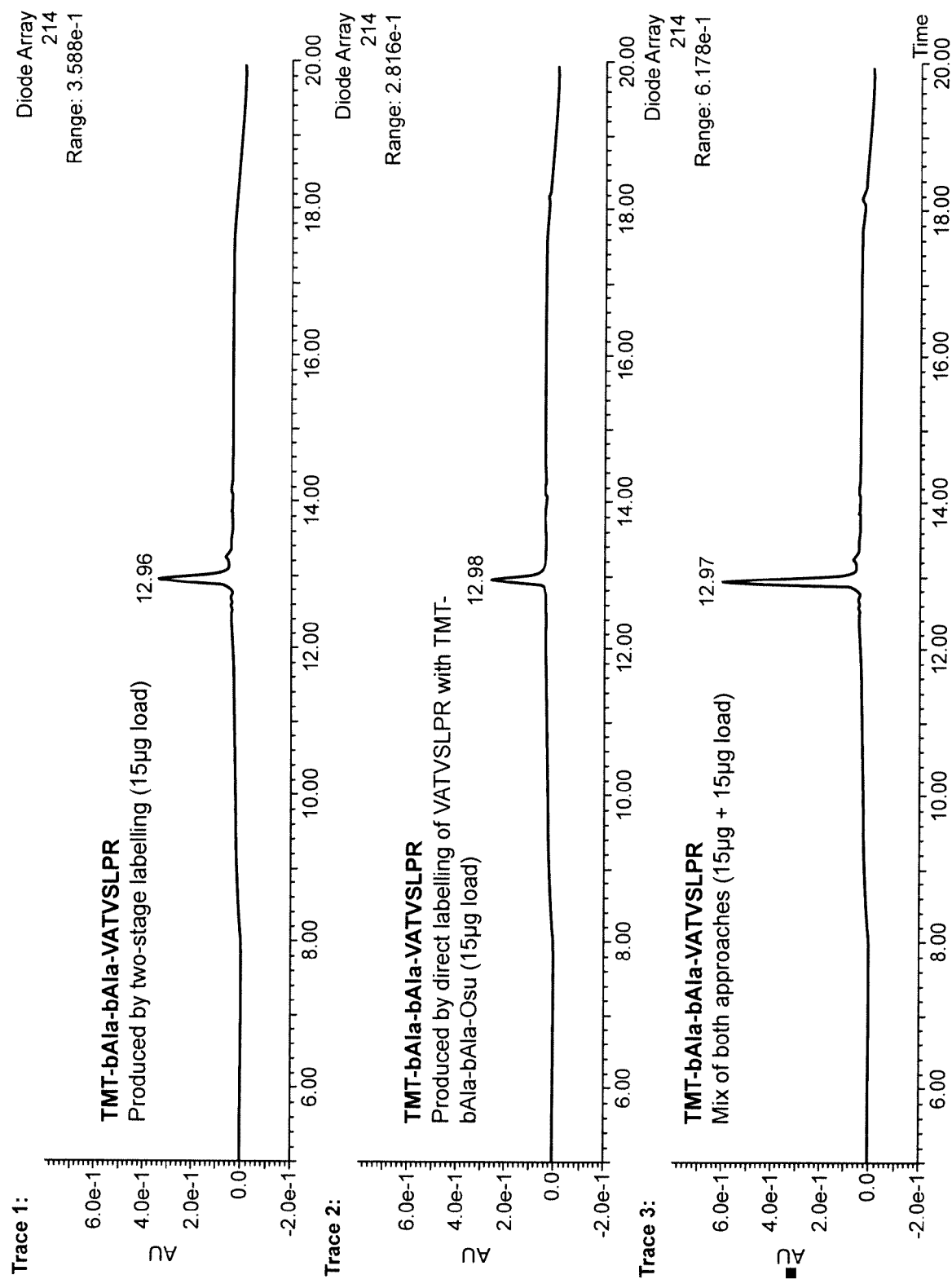

FIG. 26, Trace 1, shows an HPLC trace of the labelled species produced by the 2-step labelling reaction with an Intermediate Linker described in Example 5 below. FIG. 26, Trace 2, shows an HPLC trace of the labelled species produced by the 1-step labelling reaction carried out in this Example using the preformed TMTzero-bAla-bAla-OSu reagent. FIG. 26, Trace 3, show an HPLC trace of a mixture of equal amounts (15 μg) of the labelled species produced by the 1-step labelling reaction and 2-step labelling reactions.

FIG. 27a shows a mass spectrum of the labelled peptide produced by the 2-step labelling reaction with an Intermediate Linker described in Example 5 below. The expected mass of the labelled and doubly protonated peptide is 1209.74 Daltons giving an expected mass-to-charge ratio for the doubly-charged peptide of 604.87. An ion is present in the mass spectrum at 604.9.

FIG. 27b shows a zoom of this ion revealing the isotope peaks confirming that the ion is doubly-charged.

FIG. 28a shows a mass spectrum of the labelled peptide produced by the 1-step labelling reaction using the preformed TMTzero-bAla-bAla-OSu reagent described in Example 5. Again, an ion is present in the spectrum at 604.9. FIG. 28b shows a zoom of this ion revealing the isotope peaks confirming that the ion is doubly-charged.

Figure 29:
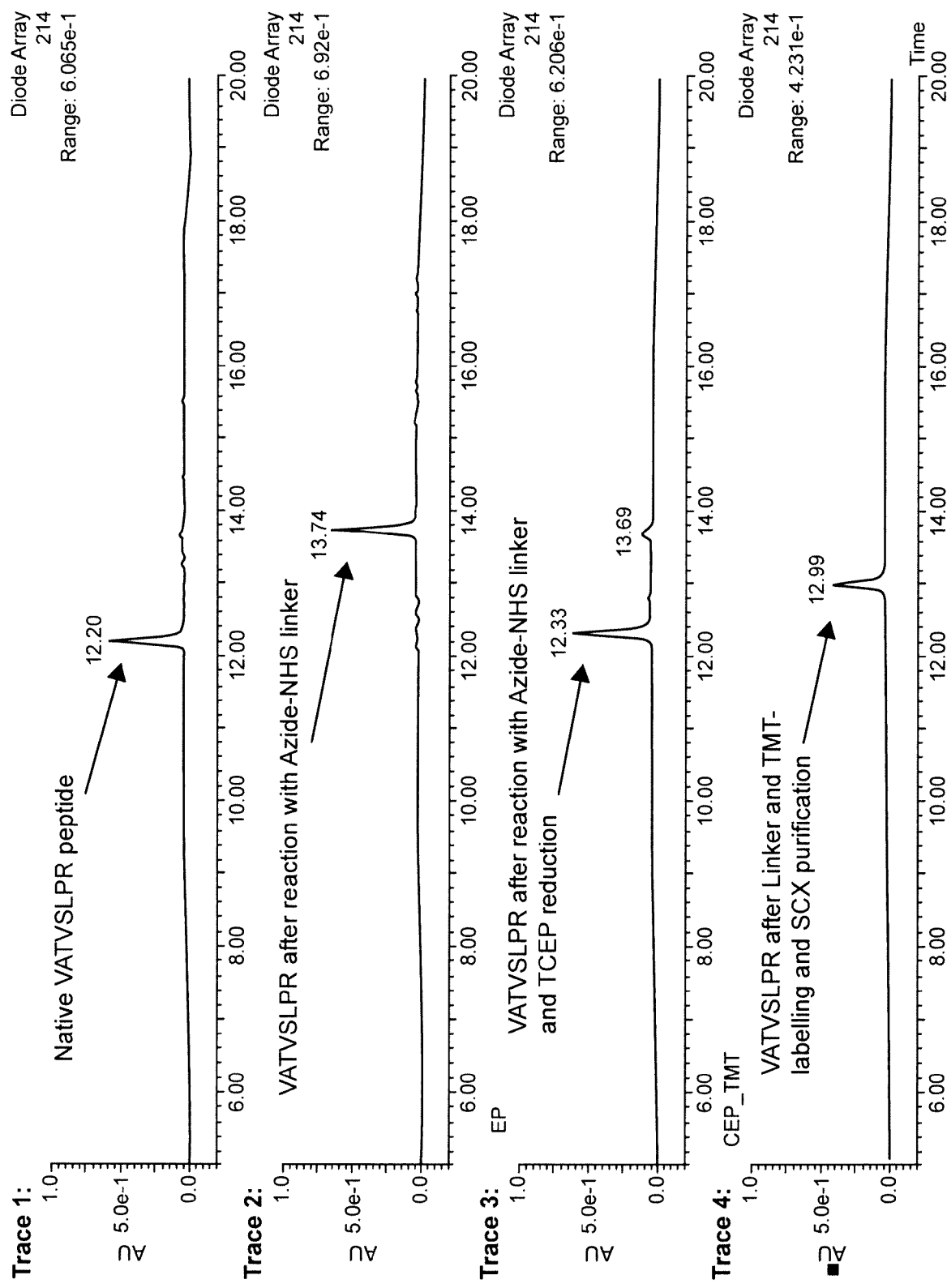

FIG. 29, Trace 1 shows an HPLC trace of the native VATVSLPR peptide before any labelling steps. FIG. 29, Trace 2 shows an HPLC trace of an analysis of the reaction mixture of the VATVSLPR peptide after coupling with the NHS-Azide linker. FIG. 29, Trace 3 shows an HPLC trace of an analysis of the reaction mixture of the VATVSLPR peptide after reduction/deprotection of the azide to give the glycine-extended peptide. FIG. 29, Trace 4 shows an HPLC trace of an analysis of the SCX-purified TMTzero-labelled and glycine-extended VATVSLPR peptide.

In some embodiments, the present invention provides reagents and methods for labelling peptides reversibly immobilized on solid phase supports. In particular, methods for introducing mass labels into peptides are provided that enhance protocols for characterizing peptides in complex mixtures. In addition, the methods of this invention are particularly helpful for characterising post-translational modifications of proteins. In particular, methods are provided for determining the phosphorylation state and/or level of a protein. In addition, methods are provided for characterising proteins that have been glycosylated.

In one embodiment of this invention, there is provided a method for labelling one or more peptides comprising:
1. optionally cleaving a complex mixture of polypeptides into smaller peptides
2. reversibly capturing the mixture of peptides onto a solid phase support
3. contacting the mixture of captured peptides on the hydrophobic solid support with one or more bifunctional linker reagents as defined above, wherein $Re^1$ reacts with a functional group in a peptide.
4. washing away unreacted bifunctional linker from the peptides on the solid support
5. contacting the modified captured peptides with one or more mass labels, wherein $Re^1$ of the bifunctional linker attached to the peptide reacts with a mass label to form a labelled analyte, wherein each mass label is relatable to an analyte.
6. eluting the labelled peptides from the solid phase support
7. analysing the eluted polypeptides or peptides by mass spectrometry The solid phase support may comprise a hydrophobic solid phase support. In specific preferred embodiment of the invention, the hydrophobic solid support employs a resin derivatized with an aliphatic hydrocarbon chain. For peptides, a saturated linear hydrocarbon with 18 carbon atoms in the chain (so-called C18 resins) are preferred. Alternatively, a resin derivatized with a tolyl group might be used. For polypeptides shorter linear aliphatic hydrocarbon chains can be used such as a C12 resin or even a C4 resin. In these embodiments, polypeptides or peptides are captured onto the hydrophobic resin by dissolving the polypeptides or peptides in a substantially aqueous solvent and contacting the resin with the dissolved polypeptides or peptides. The polypeptides or peptides will preferentially bind to the hydrophobic resin when applied to the resin in a substantially aqueous solvent.

In preferred embodiments of the invention, the solid supports used may be contained in a vessel that permits ready addition or removal of liquid phase materials to and from the support respectively. Alternatively, the solid support may be magnetic or paramagnetic so that the solid support may be easily moved between solutions by a magnetic particle carrier.

The step of analysing the eluted analytes, typically polypeptides or peptides, by mass spectrometry may comprise the steps of:
1. separating the analytes using one or chromatographic separations 2. subjecting the separated analytes to MS/MS or MS/MS/MS analysis The present invention provides a method to convert phosphate-bearing serine and threonine groups in a polypeptide into labelled serine and threonine sites comprising the steps of:
1. optionally cleaving a mixture of phosphate-bearing polypeptides into smaller peptides
2. reversibly capturing the mixture of phosphate-bearing polypeptides or phosphate-bearing peptides onto a hydrophobic solid phase support
3. contacting the mixture of captured phosphate-bearing polypeptides or phosphate-bearing peptides with a basic buffer to beta-eliminate the phosphate groups from phosphate-bearing serine and threonine residues in the polypeptides or peptides to leave Michael centres at the sites of beta-elimination in the polypeptides or peptides.
4. washing away the basic buffer from the solid phase support while the beta-eliminated polypeptides or peptides remain captured on the hydrophobic solid support
5. contacting the beta-eliminated polypeptides or peptides on the hydrophobic solid support with a bifunctional linker reagent as defined above comprising a nucleophilic $Re^1$ group that will react with the Michael centres in the beta-eliminated polypeptides or peptides to give modified polypeptides or peptides.
6. washing away unreacted bifunctional linker from the modified polypeptides or peptides on the hydrophobic solid support.
7. Contacting the reversibly immobilized modified peptides with one or more mass labels, wherein $Re^2$ of the bifunctional linker attached to the peptide reacts with a mass label to form a labelled peptide, wherein each mass label is relatable to a peptide, and then washing away unreacted mass labels
8. eluting the labelled polypeptides or peptides from the hydrophobic support
9. analysing the eluted polypeptides or peptides by mass spectrometry In a preferred phosphopeptide-labelling embodiment of the invention, the fourth step of washing away the basic buffer from the solid phase support while the beta-eliminated polypeptides or peptides remain captured on the hydrophobic solid support or the sixth step of washing away unreacted bifunctional linker is effected by contacting the solid support one or more times with a substantially aqueous solvent to wash away any unwanted salts and buffers.

In a preferred phosphopeptide-labelling embodiment of the invention, the fifth step of contacting the beta-eliminated polypeptides or peptides on the solid support with a bifunctional linker comprising a nucleophilic $Re^1$ group that will react with the Michael centres in the beta-eliminated polypeptides or peptides to give modified polypeptides or peptides, the nucleophile preferably comprises a thiol group or an amine group to react with the Michael centres.

In a preferred embodiment of the invention, the eighth step of eluting the labelled polypeptides or peptides from the hydrophobic support is effected by contacting the solid support with a substantially organic solvent. In preferred embodiments the eluting solvent is compatible with mass spectrometric analysis and more preferably is selected from methanol or acetonitrile. Alternatively, a different volatile organic solvent that can be readily removed from the eluted peptides may also be used.

In a specific O-linked Glycopeptide-labelling embodiment of the invention, there is provided a method to convert O-linked glycopeptides where the glycosylation function is linked to serine and threonine groups in a polypeptide into labelled serine and threonine sites comprising the steps of:
1. optionally cleaving a mixture of polypeptides comprising glycoproteins into smaller peptides.
2. reversibly capturing the mixture of glycopeptides onto a hydrophobic solid phase support.
3. contacting the mixture of captured glycopeptides with a basic buffer to beta-eliminate the phosphate groups from phosphate-bearing serine and threonine residues in the polypeptides or peptides to leave Michael centres at the sites of beta-elimination in the polypeptides or peptides.
4. washing away the basic buffer from the solid phase support while the beta-eliminated polypeptides or peptides remain captured on the hydrophobic solid support.
5. contacting the beta-eliminated polypeptides or peptides on the hydrophobic solid support with a bifunctional linker reagent as defined above comprising a nucleophilic $Re^1$ group that will react with the Michael centres in the beta-eliminated polypeptides or peptides to give modified polypeptides or peptides.
6. washing away unreacted bifunctional linker from the modified polypeptides or peptides on the hydrophobic solid support.
7. contacting the reversibly immobilized modified peptides or polypeptides with one or more mass labels, wherein $Re^2$ of the bifunctional linker attached to the peptide or polypeptide reacts with a mass label to form a labelled peptide or polypeptide, wherein each mass label is relatable to a peptide or polypeptide, and then washing away unreacted mass labels.
8. eluting the labelled polypeptides or peptides from the hydrophobic support.
9. analysing the eluted polypeptides or peptides by mass spectrometry.

In a further Glycopeptide-labelling embodiment of the invention, there is provided a method to convert glycopeptides into labelled glycopeptides comprising the steps of:
1. optionally cleaving a mixture of polypeptides comprising glycoproteins into smaller peptides.
2. reversibly capturing the mixture of glycopeptides onto a hydrophobic solid phase support.
3. contacting the mixture of captured glycopeptides with an oxidizing agent.
4. washing away the oxidizing agent from the solid phase support while the polypeptides or peptides remain captured on the hydrophobic solid support.
5. contacting the oxidized polypeptides or peptides on the hydrophobic solid support with a bifunctional linker comprising a hydrazide or aminooxy reactive group that will react with the aldehydes or ketones generated in polypeptides or peptides by the oxidizing agent to give modified polypeptides or peptides.
6. washing away unreacted bifunctional linker from the modified polypeptides or peptides on the hydrophobic solid support.
7. contacting the reversibly immobilized peptides with one or more mass labels, wherein $Re^2$ of the bifunctional linker attached to the peptide or polypeptide reacts with a mass label to form a labelled peptide or polypeptide, wherein each mass label is relatable to a peptide or polypeptide, and then washing away unreacted mass labels.
8. eluting the labelled polypeptides or peptides from the hydrophobic support.
9. analysing the eluted polypeptides or peptides by mass spectrometry.

In one embodiment of the invention, there is provided a method to convert phosphate-bearing serine and threonine groups in a polypeptide into labelled serine and threonine sites comprising the steps of:

1. optionally cleaving a mixture of phosphate-bearing polypeptides into smaller peptides.
2. reversibly capturing the mixture of phosphate-bearing polypeptides or phosphate-bearing peptides onto a hydrophobic solid phase support.
3. contacting the mixture of captured phosphate-bearing polypeptides or phosphate-bearing peptides with a basic buffer to beta-eliminate the phosphate groups from phosphate-bearing serine and threonine residues in the polypeptides or peptides to leave Michael centres at the sites of beta-elimination in the polypeptides or peptides.
4. washing away the basic buffer from the solid phase support while the beta-eliminated polypeptides or peptides remain captured on the hydrophobic solid support.
5. contacting the beta-eliminated polypeptides or peptides on the hydrophobic solid support with a first reactive modifier which is a bifunctional linker comprising a first reactive group that is a nucleophile that will react with the Michael centres in the beta-eliminated polypeptides or peptides to give linker-labelled polypeptides or peptides where the bifunctional linker comprises a second reactive group that remains available to react with other reactive modifiers.
6. washing away unreacted first reactive modifier from the labelled polypeptides or peptides on the solid support.
7. contacting the linker-labeled polypeptides or peptides on the solid support with a second reactive modifier which is a mass tag molecule that comprises a reactive group that is reactive to the second reactive group in the linker from step (5) to give tagged polypeptides or peptides.
8. washing away any unreacted second reactive modifier from the labelled polypeptides or peptides on the hydrophobic solid support.
9. Optionally contacting the reversibly immobilized peptides with further reactive modifiers and then washing away unreacted reactive modifiers as many times as desired to react further functional groups in the reversibly captured peptides.
10. eluting the tagged polypeptides or peptides from the hydrophobic support.
11. analysing the eluted polypeptides or peptides by mass spectrometry.

Preferred bifunctional linkers may be dithiols such as ethanedithiol, propanedithiol, dithiothreito or, dithioerythritol. Further preferred linkers include aminothiol reagents such as aminoethanethiol, aminopropanethiol. Still further preferred linkers include diamine reagents such as ethylenediamine, 4-(Aminomethyl)-piperidine or N-(2-Aminoethyl)-piperazine.

In an O-linked glycopeptide-labelling embodiment of the invention, there is provided a method to convert O-linked glycopeptides where serine and threonine groups bear sugar modifications in a polypeptide into labelled serine and threonine sites comprising the steps of:

1. optionally cleaving a mixture of polypeptides comprising glycoproteins into smaller peptides.
2. reversibly capturing the mixture of sugar-bearing polypeptides or sugar-bearing peptides onto a hydrophobic solid phase support.
3. contacting the mixture of captured sugar-bearing polypeptides or sugar-bearing peptides with a basic buffer to beta-eliminate the sugar groups from phosphate-bearing serine and threonine residues in the polypeptides or peptides to leave Michael centres at the sites of beta-elimination in the polypeptides or peptides.
4. washing away the basic buffer from the solid phase support while the beta-eliminated polypeptides or peptides remain captured on the hydrophobic solid support.
5. contacting the beta-eliminated polypeptides or peptides on the hydrophobic solid support with a first reactive modifier which is a bifunctional linker comprising a first reactive group that is a nucleophile that will react with the Michael centres in the beta-eliminated polypeptides or peptides to give linker-labelled polypeptides or peptides where the bifunctional linker comprises a second reactive group that remains available to react with other reactive modifiers.
6. washing away unreacted first reactive modifier from the labelled polypeptides or peptides on the solid support.
7. contacting the linker-labeled polypeptides or peptides on the solid support with a mass tag molecule that is reactive to the second reactive group in the linker from step (5) to give tagged polypeptides or peptides.
8. washing away unreacted tag molecule from the labelled polypeptides or peptides on the hydrophobic solid support.
9. eluting the tagged polypeptides or peptides from the hydrophobic support.
10. analysing the eluted polypeptides or peptides by mass spectrometry.

In a further glycopeptide-labelling embodiment of the this invention, there is provided a method to convert glycopeptides into labelled glycopeptides comprising the steps of:

1. optionally cleaving a mixture of polypeptides comprising glycoproteins into smaller peptides.
2. reversibly capturing the mixture of sugar-bearing polypeptides or sugar-bearing peptides onto a hydrophobic solid phase support.
3. contacting the mixture of captured sugar-bearing polypeptides or sugar-bearing peptides with an oxidizing agent.
4. washing away the oxidizing agent from the solid phase support while the beta-eliminated polypeptides or peptides remain captured on the hydrophobic solid support.
5. contacting the oxidized polypeptides or peptides on the hydrophobic solid support with a first reactive modifier where the first reactive modifier is a bifunctional linker comprising a first reactive group that is either a hydrazide reactive group or an aminooxy reactive group that will react with aldehydes or ketones generated in the immobilized peptides or polypeptides by the oxidizing agent where the second reactive group remains available for further reaction.
6. washing away unreacted first reactive modifier from the labelled polypeptides or peptides on the solid support.
7. contacting the linker-labeled polypeptides or peptides on the solid support with a second reactive modifier where the second reactive modifier is a mass tag molecule that is reactive to the second reactive group in the linker from step (5) to give tagged polypeptides or peptides.
8. washing away unreacted tag molecule from the labelled polypeptides or peptides on the hydrophobic solid support.
9. Optionally contacting the reversibly immobilized peptides with further reactive modifiers and then washing away unreacted reactive modifiers as many times as desired to react further functional groups in the reversibly captured peptides
10. eluting the tagged polypeptides or peptides from the hydrophobic support.
11. analysing the eluted polypeptides or peptides by mass spectrometry.

In an additional embodiment of this invention, there is provided a method to convert phosphate-bearing serine and threonine groups in a polypeptide into labelled serine and threonine sites comprising the steps of:

1. optionally cleaving a mixture of phosphate-bearing polypeptides into smaller peptides.
2. reversibly capturing the mixture of phosphate-bearing polypeptides or phosphate-bearing peptides onto a solid phase support that selectively binds phosphate bearing polypeptides or peptides via the phosphate groups.
3. contacting the mixture of captured phosphate-bearing polypeptides or phosphate-bearing peptides with a basic buffer to beta-eliminate the phosphate groups from phosphate-bearing serine and threonine residues in the polypeptides or peptides to leave Michael centres at the sites of beta-elimination in the polypeptides or peptides thus cleaving the phosphate bearing peptides or polypeptides from the solid phase support.
4. Isolating the beta-eliminated polypeptides or peptides that are released into the basic buffer from the support by the beta-elimination reaction.
5. Reversibly capturing the beta-eliminated polypeptides or peptides onto a hydrophobic solid support.
6. Contacting the beta-eliminated polypeptides or peptides on the hydrophobic solid support with a bifunctional linker wherein the $Re^1$ is a nucleophilic reactive group that will react with the Michael centres in the beta-eliminated polypeptides or peptides to give linker-labelled polypeptides or peptides.
7. washing away unreacted bifunctional linker from the linker-labelled polypeptides or peptides on the hydrophobic solid support.
8. contacting the reversibly immobilized linker-labelled peptides with one or more mass labels, wherein $Re^2$ of the bifunctional linker attached to the peptide or polypeptide reacts with a mass label to form a labelled peptide or polypeptide, wherein each mass label is relatable to a peptide or polypeptide, and then washing away unreacted mass labels.
9. eluting the labelled polypeptides or peptides from the hydrophobic support.
10. analysing the eluted polypeptides or peptides by mass spectrometry.

In a preferred embodiment of the invention, the second step of reversibly capturing the mixture of phosphate-bearing polypeptides or phosphate-bearing peptides onto a solid phase support that selectively binds phosphate bearing polypeptides or peptides via the phosphate groups preferably employs titanium dioxide solid supports or immobilized metal ion solid support. Preferred immobilized metal ion solid supports include Nitrilotriacetic acid (NTA) solid supports or Imino Diacetic Acid (IDA) solid supports or Phosphonic acid solid supports (PhA) where the NTA or IDA solid supports are preferably loaded with iron ions (Fe2+) or gallium ions (Ga2+) and the PhA solid supports are preferably loaded with Titanium ions (Ti4+). In other preferred embodiments, a biotinylated solid support may be used.

In a further embodiment of this invention, there is provided a method to convert phosphate-bearing serine and threonine groups in a polypeptide into labelled serine and threonine sites comprising the steps of:

1. optionally cleaving a mixture of phosphate-bearing polypeptides into smaller peptides.
2. reversibly capturing the mixture of phosphate-bearing polypeptides or phosphate-bearing peptides onto a solid phase support that selectively binds phosphate bearing polypeptides or peptides via the phosphate groups.
3. contacting the mixture of captured phosphate-bearing polypeptides or phosphate-bearing peptides with a basic buffer to beta-eliminate the phosphate groups from phosphate-bearing serine and threonine residues in the polypeptides or peptides to leave Michael centres at the sites of beta-elimination in the polypeptides or peptides thus cleaving the phosphate bearing peptides or polypeptides from the solid phase support.
4. Isolating the beta-eliminated polypeptides or peptides that are released into the basic buffer from the support by the beta-elimination reaction.
5. Reversibly capturing the beta-eliminated polypeptides or peptides onto a hydrophobic solid support.
6. contacting the beta-eliminated polypeptides or peptides on the hydrophobic solid support with a first reactive modifier which is a bifunctional linker comprising a first reactive group that is a nucleophile that will react with the Michael centres in the beta-eliminated polypeptides or peptides to give linker-labelled polypeptides or peptides where the bifunctional linker comprises a second reactive group that remains available to react with other reactive modifiers.
7. washing away unreacted first reactive modifier from the labelled polypeptides or peptides on the hydrophobic solid support.
8. contacting the linker-labeled polypeptides or peptides on the solid support with a second reactive modifier where the second reactive modifier is a mass tag molecule that is reactive to the second reactive group in the first reactive modifier from step (6) to give tagged polypeptides or peptides.
9. washing away unreacted second reactive modifier from the labelled polypeptides or peptides on the hydrophobic solid support.
10. Optionally contacting the reversibly immobilized peptides with further reactive modifiers and then washing away unreacted reactive modifiers as many times as desired to react further functional groups in the reversibly captured peptides.
11. eluting the tagged polypeptides or peptides from the hydrophobic support.
12. analysing the eluted polypeptides or peptides by mass spectrometry.

The mass labels of this invention are preferably isobaric mass labels or mass labels that are differentiated by very small mass differences as discussed below or in co-pending application GB1308765.5. However, other mass labels may also be used with this invention if that is desirable.

In preferred glycopeptide-labelling embodiments of this invention, complex polypeptide mixtures are enriched for glycoproteins or glycopeptides prior to further manipulations. Glycoproteins may be enriched using solid support bound affinity reagents such as lectins, or specific anti-carbohydrate antibodies. Alternatively, glycoproteins can be enzymatically or chemically cleaved before enrichment with solid support bound affinity reagents.

In glycopeptide-labelling embodiments of this invention, where beta-elimination of O-linked carbohydrate modifications takes place, it may be desirable to deplete the samples of phosphopeptides prior to attempting beta-elimination of carbohydrate modifications. Depletion of phosphopeptides would employ the same methods as enrichment of phosphopeptides for phosphopeptide-labelling embodiments of this invention, e.g. anti-phosphopeptide antibodies, Titanium Dioxide solid-phase capture, or Immobilized Metal ion Affinity Capture.

Thus, after samples have been contacted with solid-phase phosphopeptide affinity matrices to capture phosphopeptides for phosphopeptide-labelling embodiments of this invention, they are depleted for phosphopeptides and these can be analyzed for carbohydrate modifications using the glycopeptide-labelling embodiments of this invention.

Binding of Peptides or Polypeptides to Hydrophobic Solid Phase Supports:

In aspects of the invention, peptides or polypeptides in a complex mixture are reversibly immobilised onto solid phase supports for the purposes of carrying out chemical reactions. In preferred embodiments reversible immobilisation is effected by contacting peptides or polypeptides with a solid phase support derivatised with a hydrophobic or non-polar function. In preferred embodiments, reversible immobilisation onto a hydrophobic support is effected by dissolving the peptides or polypeptides in a polar, preferably aqueous, solvent and then contacting the polar solution with a hydrophobic solid phase support. As long as the peptides or polypeptides have a greater affinity for the immobilized hydrophobic phase, the peptides or polypeptides will adsorb onto the hydrophobic solid phase. While, adsorbed onto the hydrophobic solid phase, reagents can be applied to the immobilised peptides as long as they are applied in a polar solvent that does not result in any significant desorption of the peptides or polypeptides from the support. Obviously, the same solvent that is used to load the peptides onto the solid support can be used to deliver reagents to the solid support or to change pH or to wash the support. Once, the desired reactions and wash steps have taken place, the immobilised peptides can then be desorbed from the solid phase support. Typically this is effected by washing the support with a non-polar solvent into which the peptides will preferentially dissolve.

Typically a solid phase such as silica is derivatized with a linear aliphatic chain such as a saturated octadecyl hydrocarbon (so-called C-18 resin) to give a hydrophobic solid phase. A C-18 resin is typically loaded with peptide by applying the peptide in a substantially aqueous solvent such as pure water with 0.2% trifluoroacetic acid. Solvents are preferably acidified slightly, with a small percentage of organic acid, such as formic acid, acetic acid or trifluoroacetic acid. A small amount of polar organic solvent can be mixed with pure water too, although typically less than 20% organic solvent is used and preferably less than 10%. Polar organic solvents that can be mixed with water include methanol, ethanol, acetonitrile (ACN), Dimethylsulphoxide (DMSO) or Dimethylformamide (DMF). Other solvents may also be used and one of ordinary skill in the art would be able to select an appropriate polar organic solvent. Similar aqueous solvents can be used to wash the hydrophobic support between chemical reactions and to deliver reagents for reaction with the peptides on the solid phase support.

Desorption of the immobilised or adsorbed peptide is typically effected by contacting the hydrophobic support with an organic solvent, preferably a polar organic solvent and, if the sample is to be analysed immediately, then a solvent that is compatible with mass spectrometry should be used such as acetonitrile or methanol. Alternatively, any volatile organic solvent could be selected to desorb the peptides as a volatile solvent can be readily evaporated away from the peptides if that is desired.

Immobilised Metal Affinity Chromatography:

Immobilised Metal Affinity Chromatography (IMAC) is a useful method for isolation of charged molecules. IMAC has been extensively used for isolation of phosphopeptides (35, 43, 44) and may be used in various embodiments of this invention.

Immobilized metal ion solid supports include Nitrilotriacetic acid (NTA) solid supports or Imino Diacetic Acid (IDA) solid supports where the NTA or IDA solid supports are preferably loaded with iron ions (Fe2+) or gallium ions (Ga2+) to provide high affinity binding of phosphate bearing peptides (refs). The negatively charged phosphate groups in phosphorylated peptides or polypeptides bind readily to the positively charged immobilised metal ions. Typically, phosphorylated peptides or polypeptides are dissolved in a weakly acidic buffer such as 100 mM aqueous acetic acid or trifluoroacetic acid. Under these conditions the phosphorylated peptides or polypeptides will bind to immobilized iron or gallium ions, and any non-phosphopeptides are flushed away (or isolated separately) followed by repeated washes of the IMAC resin with 100 mM aqueous acetic acid. The bound phosphopeptides are typically eluted from the IMAC resin with a weakly basic buffer such as ammonium hydroxide ($NH_4OH$) solution.

More recently, Zr4+ and $Ti^{4+}$ IMAC has been developed in which phosphonate derivatised solid phase supports are used to coordinate Zirconium (IV) and Titanium (IV) ions (45-47). It is reported that Titanium (IV) affinity chromatography gives better performance than IDA and NTA supports with Iron (II) and Gallium (II) ions but these IMAC supports are used in a similar way to Iron (II) and Gallium (II) supports. Phosphopeptides are loaded under acidic conditions and eluted under basic conditions.

In embodiments of this invention, IMAC may be used prior to the reversible immobilization of a peptide or polypeptide mixture onto a hydrophobic solid phase support to enrich a complex peptide or polypeptide mixture for phosphorylated peptides or polypeptides. In these enrichment embodiments, phosphorylated peptides or polypeptides are loaded onto the IMAC resin in an acidic buffer as discussed above, while elution of phosphorylated peptides or polypeptides is effected by incubation of the resin with a weakly basic buffer such as ammonium hydroxide so as not to induce beta-elimination. In embodiments of the first and second aspects of this invention where IMAC is used to pre-enrich a complex mixture of peptides or polypeptides for phosphorylated peptides or polypeptides, the eluted phosphorylated peptides or polypeptides would typically be dried to down to evaporate off the volatile ammonium hydroxide buffer so that the sample can be resuspended in a suitable solvent to load the phosphorylated peptides or polypeptides onto a hydrophobic solid support.

In other embodiments of the invention, IMAC may be used to immobilise a phosphorylated peptide or polypeptide mixture for the purposes of carrying out a solid phase beta elimination of the phosphate groups from Serine and Threonine phosphates. In these beta-elimination embodiments of the invention, phosphorylated peptides or polypeptides are loaded onto the IMAC resin with a weakly acidic buffer as discussed above, while elution of phosphorylated peptides or polypeptides is effected by addition of a basic solution, preferably comprising Barium ions ($Ba^{2+}$), which will facilitate the beta-elimination of the phosphate groups from serine and threonine phosphates. In the beta-elimination aspects of this invention where IMAC is used, Tyrosine phosphate groups and any other phosphorylation sites will not be affected by beta-elimination and may be isolated separately, either by reapplication to an IMAC resin or by affinity capture using anti-phosphotyrosine antibodies or by Metal Oxide Affinity Chromatography as discussed below. Anti-phosphotyrosine antibodies may be applied to a sample to deplete the sample for phosphotyrosine before IMAC or Metal Oxide Affinity Chromatography is applied to the sample.

In further embodiments of this invention, an affinity capture reagent related to IMAC known as Phos-Tag may also be applied. In IMAC, the metal ion binding ligands, such as Nitrilotriacetic acid (NTA) or Imino Diacetic Acid (IDA), are linked to a solid phase support. The Phos-Tag technology provides a highly stable metal ion binding ligand that can be linked to a solid support such as magnetic beads (48) but a singly Phos-Tag ligand binds sufficiently strongly to a phosphate group that it can be linked to biotin and used free in solution to bind to phosphopeptides which may then be immobilized on a solid phase support through capture of the biotin by immobilized avidin (49). Phos-Tag reagents may be used in both pre-enrichment steps for the first and second aspects of this invention or the Phos-Tag reagents may be used in aspects of this invention where the beta-elimination of phosphate groups from peptides takes place from phosphopeptides captured by phosphopeptide affinity methods.

It is worth noting that there is a published protocol that combines calcium precipitation of phosphopeptides followed by IMAC enrichment that is reported to give broader phosphopeptide coverage than conventional IMAC alone (50). The authors report that this approach picks up peptides seen in TiO2 enrichment that are missed by conventional IMAC enrichment. In principle, Calcium precipitation can be combined with any of the enrichment methods described in this application.

Metal Oxide Affinity Chromatography:

Metal Oxide Affinity Chromatography (MOAC) is a useful method for isolation of phosphorylated molecules. MOAC has been extensively used for isolation of phosphopeptides and may be used in various embodiments of this invention.

MOAC works by a similar principle to IMAC. Metal oxides, particularly Titanium dioxide, provide immobilised positively charged metal ion centres to which negatively charged phosphate groups can bind. Like IMAC, phosphorylated peptides are dissolved in a weakly acidic buffer to load the phosphopeptides onto the resin. A suitable loading solvent would employ a mixture of acetonitrile (ACN) and water with a small amount of Trifluoroacetic Acid (TFA) to acidify the solvent, e.g. 80% ACN, 19.9% water and 0.1% TFA. Like IMAC, phosphopeptides may be eluted with a basic solvent or buffer, such as 200 mM aqueous ammonium bicarbonate. Alternatively, in preferred embodiments of this invention, phosphopeptides that are bound to the Metal Oxide solid phase can be eluted by barium-catalysed beta-elimination.

Handling of Solid Phase Media:

A key advantage of carrying out the methods of this invention using an insoluble solid phase support to reversibly immobilize or capture the peptides or polypeptides of interest is that the insoluble solid phase allows solution phase reagents to be added and removed from the solid support in a simple fashion that can be readily automated. Solid phases can be packed in to vessels that permit solution phase media to be passed over the resin very easily. Typically, columnar vessels are used which contain the solid phase support and any solution that is contacted with the solid support. In preferred embodiments, such columnar vessels may be loaded with solutions from the top. The bottom of the vessel may comprise a porous 'frit', which will retain the solid phase material but allow free passage of the solution phase material.

In some embodiments of the invention, samples in solution and solution phase reagents may freely flow through the columnar reaction vessel. The rate and completeness of the reaction can be controlled by varying the concentration of reagents in solution and the flow rate of reagents through the reaction vessel.

In some embodiments, the exit point of the columnar vessel may comprise a small exit aperture such that surface tension of a solution is sufficient to prevent any solution phase material from passively exiting the vessel. In other embodiments the columnar reaction vessel may comprise a valve at the exit aperture enabling mechanical control of fluids in the columnar reaction vessel.

In embodiments with valves or small apertures, removal of solution phase material may be effected by actively displacing the solution. This may be effected by increasing the gas pressure at the top of the column ('positive pressure displacement') or by decreasing the gas pressure at the bottom of the column ('vacuum displacement'). Vacuum manifolds and positive pressure displacement manifolds are commercially available for the purposes of actively displacing solutions from columnar supports. Such systems may be applied to individual columnar vessels or to multiple columnar vessels organized in planar arrays such as microtitre plate formats where 96 or 384 columnar reaction vessels may be processed in an 8 by 12 columnar array or in a 16 by 24 columnar array respectively. Microtitre plates packed with hydrophobic resins are commercially available (Chromtech). Similarly, SPE plates packed with metal oxide solid supports such as Titanium oxide are also commercially available (Glygen Corporation). Empty SPE plates for packing with resins are also commercially available and can be packed with immobilized metal ion solid supports include Nitrilotriacetic acid (NTA) solid supports or Imino Diacetic Acid (IDA) solid supports where the NTA or IDA solid supports are preferably loaded with iron ions (Fe2+) or gallium ions (Ga2+).

Conversely, pipette tips are commercially available (Harvard Apparatus, Merck Millipore) that are packed with small quantities of hydrophobic resins and metal oxide supports (Thermo Fisher Scientific). In these pipette tips, solutions are loaded onto the columns by negative pressure displacement by the pipettor and fluids are displaced off the column by positive pressure displacement by the pipettor. Microtitre plate formats are particularly preferred embodiments of this invention when large numbers of samples need to be processed in parallel. Columnar vessels organised into plate formats are known as Solid Phase Extraction (SPE) plates. Solution phase samples and reagents can be readily loaded into individual wells of SPE plates with liquid handling robots that are commercially available from various sources (Gilson, Hamilton, Qiagen). Similarly, solution phase reagents can be readily displaced from SPE plates with positive pressure displacement manifolds (Cerex) or by vacuum manifolds (Chromtech, Merck Millipore).

Centrifugation is also widely used to displace solutions from solid supports packed in columnar vessels. The centrifugal forces generated in a centrifuge will displace fluids from resin beds in columnar reaction vessels. So-called spin columns packed with solid phase supports of different kinds are widely available and would be suitable for use with this invention. Small columns packed with C18 resins are commercially available from various sources (Thermo Fisher Scientific, Harvard Apparatus, SigmaAldrich). Similarly, spin columns packed with IMAC resins and Titanium dioxide resins are available from various sources (ThermoFisher Scientific, SigmaAldrich). Individual columns may be loaded with solution phase materials using either manual or robotic pipettors. The solution phase can be readily displaced using centrifugation on a microcentrifuge, which can be readily obtained from commercial sources.

Similarly SPE plates can also be processed by centrifugation on a suitable sized centrifuge system that can cope with microtitre plates. Centrifuges for microtitre plates are widely available commercially (Eppendorf, Beckman Coulter, Agilent).

Magnetic particles are also extensively used to allow solid supports to be readily separated from solution phase reagents. For example, BcMag™ C-18 Magnetic Beads are available from BioClone Corporation. Similarly, Imino Diacetic Acid beads such as BcMag™ IDA-modified Magnetic Beads are available from BioClone Corporation while Nitrilotriacetic acid magnetic beads are commercially available from Micromod Partikeltechnologie GmbH. In addition, magnetic particles with metal oxide coatings such as titanium dioxide are also available commercially (Thermo Fisher Scientific; GE Healthcare Life Sciences, Little Chalfont, Bucks, UK; Phos-Trap from Perkin Elmer, Waltham, Mass.).

Magnetic particles can be physically retained in conventional reaction vessels such as small plastic vials or microtitre plates by application of a magnetic field. The particles will be attracted to the magnetic field allowing solutions to be added or removed from the solid support using pipettes while the beads are immobilized. In the absence of the magnetic field, the beads can be resuspended in solution. Magnetic beads are advantageous as they do not need to be packed into columns in the same way that conventional solid supports are packed. This means that reactions can be conducted in a more solution-like environment with the beads in suspension with a greater surface area exposed to solution than conventional solid supports, which improves reaction kinetics. Thus, magnetic beads and particles are also a preferred solid support for use with this invention. Instrumentation for automated handling of magnetic particles are also commercially available, such as the Kingfisher Magnetic Particle Processor (Thermo Fisher Scientific, Inc).

The quantities of solid phase support used for any given specific embodiment of the invention should match the amount of peptides or polypeptides in the sample to be analysed. Many solid phase supports that can be used with this invention are commercially available, and typically the manufacturer will provide data on the amount of peptide or polypeptide that a given amount of resin will bind. The necessary amounts can be readily worked out. Alternatively, for a novel resin, the binding capacity can be assayed before undertaking experiments. Binding capacity can be assayed by contacting a known quantity of resin with increasing quantities of a labelled peptide in loading buffer or solvent and determining the amount of peptide at which there is significant amounts of labelled peptide remaining in the loading after loading the resin. For example, with a fluorescently labelled peptide, it would be expected that as the amount of peptide in the loading solvent or buffer is increased for a given amount of resin, there would reach a point at which fluorescent label would be left in the loading solvent after contacting the dissolved peptide with the resin. This amount would be the upper limit of the binding capacity of the resin and as long as less peptide is loaded then the capacity of the resin will not be exceeded.

Mass Labels

The term mass label used in the present context is intended to refer to a moiety suitable to label an analyte for determination by mass spectrometry. The term label is synonymous with the term tag.

While it is preferred that Isobaric Mass labels are applied with this invention, numerous mass marker or mass tag designs are compatible with the coupling methods of this invention as long as the tags contain suitable reactive groups to allow the mass tags to be linked to modified peptides or polypeptides according to this invention.

Other useful mass tags according to this invention include WO 97/27327, WO 97/27325, WO 97/27331 and WO 03/025576. These publications disclose tags that comprise polyamide compounds, essentially peptides or peptide-like tags, which means that these tags can be prepared using a number of peptide synthesis methods that are well known in the art (see for example Jones, 1991, "The chemical synthesis of peptides", Oxford University Press; Fields & Noble, 1990, Int J Pept Protein Res 35(3): 161-214; Albericio, 2000, Biopolymers 55(2):123-139). Methods for conjugating peptides to biomolecules such as oligonucleotides via thiol groups at the termini of the oligonucleotides are disclosed in Arar et al. (1995, Bioconjug Chem. 6(5): 573-577).

Other mass tags for use with invention include trityl tags (Ustinov A V et al., Org Biomol Chem. 6(24):4593-608, "Reactive trityl derivatives: stabilised carbocation mass-tags for life sciences applications." 2008; Shchepinov M S et al., Nucleic Acids Symp Ser. 42:107-8, "Trityl mass-tags for encoding in combinatorial oligonucleotide synthesis." 1999), pixyl tags (Bernad P L Jr. et al, Chem Commun (Camb). 27:3466-8, "S(O)-pixyl protecting group as efficient mass-tag." 2005), electrophores (Shao G, Giese R W., Anal Chem. 76(11):3049-54, "Trace detection of glycolic acid by electrophore labeling gas chromatography-electron capture mass spectrometry." 2004; Zhang X, et al., Bioconjug Chem. 13(5):1002-12, "Synthesis of releasable electrophore tags for applications in mass spectrometry." 2002; Giese R W, J Chromatogr A. 892(1-2):329-46, Electron-capture mass spectrometry: recent advances." 2000) and metal atom isotope conjugates (Arlinghaus H F et al., Anal Chem. 69(8): 1510-7, "Multiplexed DNA sequencing and diagnostics by hybridization with enriched stable isotope labels." 1997; Sachleben R A et al., Genet Anal Tech Appl. 8(6):167-70, "Resonance ionization spectroscopy for multiplex sequencing of tin-labeled DNA." 1991).

In other embodiments, Mass Markers employing Neutral loss may be used as disclosed in US patent with number U.S. Pat. No. 7,556,969 and international patent with number WO2009153577. U.S. Pat. No. 7,556,969 discloses so-called intensified neutral loss tags in which the mass tag is designed to undergo a neutral loss upon collision and after neutral loss, the tag is left with a stabilized, typically delocalized charge on the neutral loss residue of the tag. Similarly, WO2009153577 discloses a variety of mass tags that are designed to undergo a neutral loss resulting in the labelled precursor ion undergoing a shift in mass-to-charge ratio as a result of the neutral loss.

Isobaric Mass Labels:

A variety of mass labels can be used with this invention although one particularly preferred class of mass labels are isobaric mass labels. The skilled artisan will understand that the nature of the isobaric mass label is not particularly limiting. Various suitable isobaric mass labels are known in the art such as Tandem Mass Tags (Thompson et al., 2003, Anal. Chem. 75(8): 1895-1904 (incorporated herein by reference) disclosed in WO 01/68664 (incorporated herein by reference), WO 03/025576 (incorporated herein by reference) and WO 07/012849 (incorporated herein by reference), iPROT tags disclosed in U.S. Pat. No. 6,824,981 (incorporated herein by reference) and iTRAQ tags (Pappin et al., 2004, Methods in Clinical Proteomics Manuscript M400129-MCP200 (incorporated herein by reference)). Any of these isobaric mass labels are suitable for performing the methods of the present invention.

Although the structure of the mass labels used in the present invention is not especially limited, preferably they are isobaric and have mass spectrometrically distinct mass marker groups (moieties), in preferred embodiments the mass label comprises the following structure:

$$V-L^2M$$

wherein V is a mass marker or reporter moiety, $L^2$ is a cleavable linker and M is a mass normalisation moiety. $L^2$ may be a single bond, or part of V, or part of M. The mass label reacts with $Re^2$ of the bifunctional linker.

This is effected by including a reactive functionality $Re^3$ in the mass label to allow it to bind to the analyte, e.g.:

$$V-L^2-M-Re^3$$

The reactive group $Re^3$ for attaching the mass label to the bifunctional linker (attached to the analyte) is not especially limited provided it comprises a moiety capable of reacting with $Re^2$.

The term mass marker moiety used in the present context is intended to refer to a moiety that is to be detected by mass spectrometry. The term mass marker moiety is synonymous with the term mass marker group or the term reporter group. The components of the mass marker moiety of this invention are preferably fragmentation resistant so that the site of fragmentation of the markers can be controlled by the introduction of a linkage that is easily broken by Collision Induced Dissociation (CID), Surface Induced Dissociation, Electron Capture Dissociation (ECD), Electron Transfer Dissociation (ETD), or Fast Atom Bombardment. In the most preferred embodiment, the linkage is easily broken by CID.

The term mass normalisation moiety used in the present context is intended to refer to a moiety that is not necessarily to be detected by mass spectrometry, but is present to ensure that a mass label has a desired aggregate mass. The mass normalisation moiety is not particularly limited structurally, but merely serves to vary the overall mass of the mass label.

In a preferred embodiment the aggregate molecular weight of the mass label is 600 Daltons or less, more preferably 500 Daltons or less, still more preferably 400 Daltons or less, most preferably from 300 to 400 Daltons. Particularly preferred molecular weights of the mass labels are 324, 338, 339 and 380 Daltons. These preferred embodiments are particularly advantageous because the small size of the mass labels means that the size of the peptide to be detected is minimally increased when labelled with the mass label.

In a preferred embodiment, the molecular weight of the mass marker moiety is 300 Daltons or less, preferably 250 Daltons or less, more preferably 100 to 250 Daltons, most preferably 100-200 Daltons. These preferred embodiments are particularly advantageous because the small size of the mass marker moiety means that it produces a peak in the silent region of a mass spectrum, which allows the mass marker to be easily identified from the mass spectrum and also allows sensitive quantification.

Particularly preferred molecular weights of the mass marker moiety are 125, 126, 153 and 154 Daltons, or weights in which one or more or all of the $^{12}C$ atoms are replaced by $^{13}C$ atoms, e.g. for a non-substituted mass marker moiety having a weight of 125, masses for its substituted counterparts would be 126, 127, 128, 129, 130 and 131 Daltons for substitution with 1, 2, 3, 4, 5 and 6 13C atoms respectively and/or one or more or all of the 14N atoms are replaced by 15N atoms.

The term silent region of a mass spectrum used in the present context is intended to refer to the region of a mass spectrum with low background "noise" caused by peaks relating to the presence of fragments generated by fragmentation of the labelled peptides. Thus, the term silent region is intended to refer to the region of the mass spectrum with low "noise" caused by peaks relating to the peptide to be detected. For a peptide or protein, the silent region of the mass spectrum is less than 200 Daltons.

The present inventors have also discovered that the reactive mass labels defined above are easily and quickly reacted with a protein to form a labelled protein.

In the present invention a set of two or more mass labels is preferably employed. The labels in the sets are preferably isobaric mass labels each having a mass marker of a different mass. Thus, each label in the set is as defined above and wherein each mass normalisation moiety ensures that a mass label has a desired aggregate mass, and wherein the set comprises mass labels having a mass marker moiety, each mass marker moiety having a mass different from that of all other mass marker groups in the set, and each label in the set having a common aggregate mass; and wherein all the mass labels in the set are distinguishable from each other by mass spectroscopy.

The term "isobaric" means that the mass labels have substantially the same aggregate mass as determined by mass spectrometry. Typically, the average molecular masses of the isobaric mass labels will fall within a range of ±0.5 Da of each other. The term "labels" shall be synonymous with the term "tags". In the context of the present invention, the skilled addressee will understand that the term "mass marker moiety" and the term "reporter group" can be used interchangeably.

The number of labels in the set is not especially limited, provided that the set comprises a plurality of labels. However, it is preferred if the set comprises two or more, three or more, four or more, or five or more labels, more preferably six or more labels, most preferably eight or more labels.

The term aggregate mass in the present context refers to the total mass of the mass label, i.e. the sum of the masses of the mass marker moiety, the cleavable linker, the mass normalisation moiety, $Re^3$ and any other components of the mass label.

The mass of the mass normalisation moiety will be different in each mass label in the set. The mass of the mass normalisation moiety in each individual mass label will be equal to the common aggregate mass minus the mass of the particular mass marker moiety in that mass label and minus the mass of the cleavable linker.

All mass labels in the set are distinguishable from each other by mass spectroscopy. Therefore, a mass spectrometer can discriminate between the mass labels, i.e. the peaks derived from individual mass labels can be clearly separated from one another. The difference in mass between the mass marker groups means that a mass spectrometer can discriminate between ions derived from different mass labels or mass marker groups.

The present invention may also employ an array of mass labels, comprising two or more sets of mass labels as defined above, wherein the aggregate mass of each of the mass labels in any one set is different from the aggregate mass of each of the mass labels in every other set in the array.

In preferred embodiments of the invention, the array of mass labels are preferably all chemically identical (substantially chemically identical). The term "substantially chemically identical" means that the mass labels have the same chemical structure, into which particular isotopic substitutions may be introduced or to which particular substituents may be attached.

In further preferred embodiments of this invention, the mass labels may comprise a sensitivity enhancing group. The mass labels are preferably of the form:

sensitivity enhancing group—V-L-M-Re$^3$

In this example the sensitivity enhancing group is usually attached to the mass marker moiety, since it is intended to increase the sensitivity of the detection of this moiety in the mass spectrometer. The reactive group Re$^3$ is shown as being present and attached to a different moiety than the sensitivity enhancing group. However, the mass labels need not be limited in this way and in some cases the sensitivity enhancing group may be attached to the same moiety as the reactive functionality.

Preferred structures of mass labels employed to tag the analytes in the present invention will now be described in more detail.

In preferred Isobaric Mass Tag (IMT) embodiments V is a mass marker moiety comprising the following group:

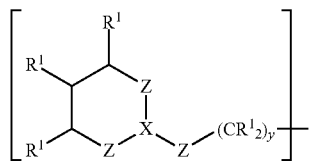

wherein the cyclic unit is aromatic or aliphatic and comprises from 0-3 double bonds independently between any two adjacent atoms; each Z is independently N, N(R$^1$), C(R$^1$), CO, CO(R$^1$) (i.e. —O—C(R$^1$)— or —C(R$^1$)—O—), C(R$^1$)$_2$, O or S; X is N, C or C(R$^1$); each R$^1$ is independently H, a substituted or unsubstituted straight or branched C$_1$-C$_6$ alkyl group, a substituted or unsubstituted aliphatic cyclic group, a substituted or unsubstituted aromatic group or a substituted or unsubstituted heterocyclic group; and y is an integer from 0-10.

In the above general formula, when Z is C(R$^1$)$_2$, each R$^1$ on the carbon atom may be the same or different (i.e. each R$^1$ is independent). Thus the C(R$^1$)$_2$ group includes groups such as CH(R$^1$), wherein one R$^1$ is H and the other R$^1$ is another group selected from the above definition of R$^1$.

In the above general formula, the bond between X and the non-cyclic Z may be single bond or a double bond depending upon the selected X and Z groups in this position. For example, when X is N or C(R$^1$) the bond from X to the non-cyclic Z must be a single bond. When X is C, the bond from X to the non-cyclic Z may be a single bond or a double bond depending upon the selected non-cyclic Z group and cyclic Z groups. When the non-cyclic Z group is N or C(R$^1$) the bond from non-cyclic Z to X is a single bond or if y is 0 may be a double bond depending on the selected X group and the group to which the non-cyclic Z is attached. When the non-cyclic Z is N(R$^1$), CO(R$^1$), CO, C(R$^1$)$_2$, O or S the bond to X must be a single bond. The person skilled in the art may easily select suitable X, Z and (CR$^1$$_2$)$_y$ groups with the correct valencies (single or double bond links) according to the above formula.

The substituents of the mass marker moiety are not particularly limited and may comprise any organic group and/or one or more atoms from any of groups IIIA, IVA, VA, VIA or VIIA of the Periodic Table, such as a B, Si, N, P, O, or S atom or a halogen atom (e.g. F, Cl, Br or I).

When the substituent comprises an organic group, the organic group preferably comprises a hydrocarbon group. The hydrocarbon group may comprise a straight chain, a branched chain or a cyclic group. Independently, the hydrocarbon group may comprise an aliphatic or an aromatic group. Also independently, the hydrocarbon group may comprise a saturated or unsaturated group.

When the hydrocarbon comprises an unsaturated group, it may comprise one or more alkene functionalities and/or one or more alkyne functionalities. When the hydrocarbon comprises a straight or branched chain group, it may comprise one or more primary, secondary and/or tertiary alkyl groups. When the hydrocarbon comprises a cyclic group it may comprise an aromatic ring, an aliphatic ring, a heterocyclic group, and/or fused ring derivatives of these groups. The cyclic group may thus comprise a benzene, naphthalene, anthracene, indene, fluorene, pyridine, quinoline, thiophene, benzothiophene, furan, benzofuran, pyrrole, indole, imidazole, thiazole, and/or an oxazole group, as well as regioisomers of the above groups.

The number of carbon atoms in the hydrocarbon group is not especially limited, but preferably the hydrocarbon group comprises from 1-40 C atoms. The hydrocarbon group may thus be a lower hydrocarbon (1-6 C atoms) or a higher hydrocarbon (7 C atoms or more, e.g. 7-40 C atoms). The number of atoms in the ring of the cyclic group is not especially limited, but preferably the ring of the cyclic group comprises from 3-10 atoms, such as 3, 4, 5, 6 or 7 atoms.

The groups comprising heteroatoms described above, as well as any of the other groups defined above, may comprise one or more heteroatoms from any of groups IIIA, IVA, VA, VIA or VIIA of the Periodic Table, such as a B, Si, N, P, O, or S atom or a halogen atom (e.g. F, Cl, Br or I). Thus the substituent may comprise one or more of any of the common functional groups in organic chemistry, such as hydroxy groups, carboxylic acid groups, ester groups, ether groups, aldehyde groups, ketone groups, amine groups, amide groups, imine groups, thiol groups, thioether groups, sulphate groups, sulphonic acid groups, and phosphate groups etc. The substituent may also comprise derivatives of these groups, such as carboxylic acid anhydrides and carboxylic acid halides.

In addition, any substituent may comprise a combination of two or more of the substituents and/or functional groups defined above.

The cleavable linker of the mass label used in the present invention is not especially limited. Preferably, the cleavable linker is a linker cleavable by Collision Induced Dissociation, Surface Induced Dissociation, Electron Capture Dissociation (ECD), Electron Transfer Dissociation (ETD), or Fast Atom Bombardment. In the most preferred embodiment, the linkage is cleavable by CID. The linker may comprise an amide bond.

A variety of known cleavable linker groups may be used in conjunction with the compounds employed in this invention, such as photocleavable linkers. Ortho-nitrobenzyl groups are known as photocleavable linkers, particularly 2-nitrobenzyl esters and 2-nitrobenzylamines, which cleave at the benzylamine bond. For a review on cleavable linkers see Lloyd-Williams et al., Tetrahedron 49, 11065-11133, 1993, which covers a variety of photocleavable and chemically cleavable linkers.

WO 00/02895 discloses the vinyl sulphone compounds as cleavable linkers, which are also applicable for use with this invention, particularly in applications involving the labelling of polypeptides, peptides and amino acids. The content of this application is incorporated by reference.

WO 00/02895 discloses the use of silicon compounds as linkers that are cleavable by base in the gas phase. These linkers are also applicable for use with this invention, particularly in applications involving the labelling of oligonucleotides. The content of this application is incorporated by reference.

The structure of the mass normalization moiety of the mass label used in the present invention is not particularly limited provided that it is suitable for ensuring that the mass label has a desired aggregate mass. However, the mass normalization moiety preferably comprises a straight or branched $C_1$-$C_{20}$ substituted or unsubstituted aliphatic group and/or one or more substituted or unsubstituted amino acids.

Preferably, the mass normalisation moiety comprises a $C_1$-$C_6$ substituted or unsubstituted aliphatic group, more preferably a $C_1$, $C_2$, $C_3$, $C_4$, $C_5$ substituted or unsubstituted aliphatic group, still more preferably a $C_1$, $C_2$, or $C_5$ substituted or unsubstituted aliphatic group or a $C_1$ methyl substituted group.

The one or more substituted or unsubstituted amino acids may be any essential or non-essential naturally occurring amino acids or non-naturally occurring amino acids. Preferred amino acids are alanine, μ-alanine and glycine.

The substituents of the mass normalisation moiety are not particularly limited and may comprise any organic group and/or one or more atoms from any of groups IIIA, IVA, VA, VIA or VIIA of the Periodic Table, such as a B, Si, N, P, O, or S atom or a halogen atom (e.g. F, Cl, Br or I).

When the substituent comprises an organic group, the organic group preferably comprises a hydrocarbon group. The hydrocarbon group may comprise a straight chain, a branched chain or a cyclic group. Independently, the hydrocarbon group may comprise an aliphatic or an aromatic group. Also independently, the hydrocarbon group may comprise a saturated or unsaturated group.

When the hydrocarbon comprises an unsaturated group, it may comprise one or more alkene functionalities and/or one or more alkyne functionalities. When the hydrocarbon comprises a straight or branched chain group, it may comprise one or more primary, secondary and/or tertiary alkyl groups. When the hydrocarbon comprises a cyclic group it may comprise an aromatic ring, an aliphatic ring, a heterocyclic group, and/or fused ring derivatives of these groups. The cyclic group may thus comprise a benzene, naphthalene, anthracene, indene, fluorene, pyridine, quinoline, thiophene, benzothiophene, furan, benzofuran, pyrrole, indole, imidazole, thiazole, and/or an oxazole group, as well as regioisomers of the above groups.

The number of carbon atoms in the hydrocarbon group is not especially limited, but preferably the hydrocarbon group comprises from 1-40 C atoms. The hydrocarbon group may thus be a lower hydrocarbon (1-6 C atoms) or a higher hydrocarbon (7 C atoms or more, e.g. 7-40 C atoms). The number of atoms in the ring of the cyclic group is not especially limited, but preferably the ring of the cyclic group comprises from 3-10 atoms, such as 3, 4, 5, 6 or 7 atoms.

The groups comprising heteroatoms described above, as well as any of the other groups defined above, may comprise one or more heteroatoms from any of groups IIIA, IVA, VA, VIA or VIIA of the Periodic Table, such as a B, Si, N, P, O, or S atom or a halogen atom (e.g. F, Cl, Br or I). Thus the substituent may comprise one or more of any of the common functional groups in organic chemistry, such as hydroxy groups, carboxylic acid groups, ester groups, ether groups, aldehyde groups, ketone groups, amine groups, amide groups, imine groups, thiol groups, thioether groups, sulphate groups, sulphonic acid groups, and phosphate groups etc. The substituent may also comprise derivatives of these groups, such as carboxylic acid anhydrides and carboxylic acid halides.

In addition, any substituent may comprise a combination of two or more of the substituents and/or functional groups defined above.

Isotopologue Millidalton Differentiated Mass Labels:

In alternative embodiments of the present invention, a different type of mass label is preferred. Co-pending application GB1308765.5 discloses sets of isotopologue mass tags that are differentiated by very small differences in mass that arise from appropriate substitutions of heavy nuclei into a mass tag structure. Co-pending application GB1308765.5 provides a set of two or more mass tag reagents, wherein each mass tag reagent in the set has a common integer mass and an exact mass different to all other mass tag reagents in the set; and wherein all the mass tag reagents in the set are distinguishable from each other by mass spectroscopy. The sets of 2 or more reactive isotopologue mass tags have the same integer mass but are differentiated from each other by very small differences in mass such that individual tags are differentiated from the nearest tags by less than 100 millidaltons and comprise the formula:

$$T\text{-}Re^3$$

Where T is a Mass Tag (mass label) and Re is a reactive functionality to allow the mass tag to be conjugated to a biomolecule. Where at least one of, and sometimes both of, T and $Re^3$ is or are modified with heavy isotopes to create isotopic tags of different masses. In the discussion that follows, mass tags of this structure will be referred to as Millidalton Mass Tags (MMTs) In preferred Millidalton Mass Tag embodiments, an isotopologue tag set for use with this invention comprises n tags, where the $x^{th}$ tag comprises (n-x) atoms of a first heavy isotope and (x-1) atoms of second heavy isotope different from the first. In this preferred embodiment x has values from 1 to n and preferred heavy isotopes include $^2H$ or $^{13}C$ or $^{15}N$ In other preferred embodiments, an isotopologue tag set of this invention comprises n tags, where the $x^{th}$ tag comprises (n−x) atoms of a first heavy isotope selected from $^{18}O$ or $^{34}S$ and (2x−2) atoms of second heavy isotope different from the first selected from $^2H$ or $^{13}C$ or $^{15}N$. In this preferred embodiment x has values from 1 to n.

In preferred embodiments of this invention, mass tags in an isotopologue set are differentiated by less than 50 millidaltons.

In preferred embodiments the Millidalton Mass Tag, T, comprises the formula $$V\text{-}M$$

Where V is a mass marker moiety, M is a mass normalisation moiety, although both the V and M groups may be modified with heavy isotopes to adjust the mass of the Mass Tag, T.

In some embodiments the Reactive group, $Re^3$, may be linked through the V group while in other embodiments the Reactive group, $Re^3$, may be linked through the M group as follows:

$$V\text{-}M\text{-}Re^3 \text{ or } M\text{-}V\text{---}Re^3$$

In further embodiments the Reactive group, the V group and the M group may be connected with linkers, L3, as follows:

V-(L3)$_n$-M-(L3)$_m$-Re$^3$ or M-(L3)$_n$-V-(L3)$_m$-Re$^3$

Where n and m are independently integers between 0 and 10. The linker groups, L3, may also be modified with heavy isotopes.

In some embodiments, an array of 2 or more sets of isotopic mass tags are used together where each set comprises n tags per set, where n is as defined above and may have independent values for each set in the array and each set of tags has a different integer mass from the other sets in the array through the addition of p further heavy nuclei to the isotopic structure in addition to the n-1 nuclei that are used to create the small mass shifts in the tags as defined above, where p may have independent values for each set in the array.

In some embodiments, an array of 2 or more sets of mass tags are used together where the members of each set of tags is isotopic with other members of the set but are not isotopic with other sets in the array. This may be achieved by varying the number of linker groups, L3, as defined above, between different sets of mass tags.

Preferred Tag Chemistries:

Preferably a set of mass labels for use with this invention has the one of the following general structures:

In embodiments of this invention, where sets of tags are designed to be truly isobaric with each other, the Mass Marker Moiety (V) as defined earlier and the rest of the tag which functions as the mass normalizer, are substituted so that the whole tag has the same total number of heavy isotope substitutions but each Mass Marker Moiety (V), which cleaves to give a reporter ion is substituted so that the cleaved reporters for each member of a set of tags is uniquely resolvable by mass spectrometry and wherein the cyclic unit is aromatic or aliphatic and comprises from 0-3 double bonds independently between any two adjacent atoms; each Z is independently N, N(R$^1$), C(R$^1$), CO, CO(R$^1$) (i.e. —O—C(R$^1$)— or —C(R)—O—), C(R$^1$)$_2$, O or S; X is N, C or C(R$^1$); each R$^1$ is independently H, a substituted or unsubstituted straight or branched C$_1$-C$_6$ alkyl group, a substituted or unsubstituted aliphatic cyclic group, a substituted or unsubstituted aromatic group or a substituted or unsubstituted heterocyclic group or an amino acid side chain; and a is an integer from 0-10; and b is at least 1, and wherein c is at least 1; and Re is a reactive functionality for attaching the mass label to a bifunctional linker (Re$^3$).

In the above general formula, when Z is C(R$^1$)$_2$, each R$^1$ on the carbon atom may be the same or different (i.e. each R$^1$ is independent). Thus the C(R$^1$)$_2$ group includes groups such as CH(R$^1$), wherein one R$^1$ is H and the other R$^1$ is another group selected from the above definition of R$^1$.

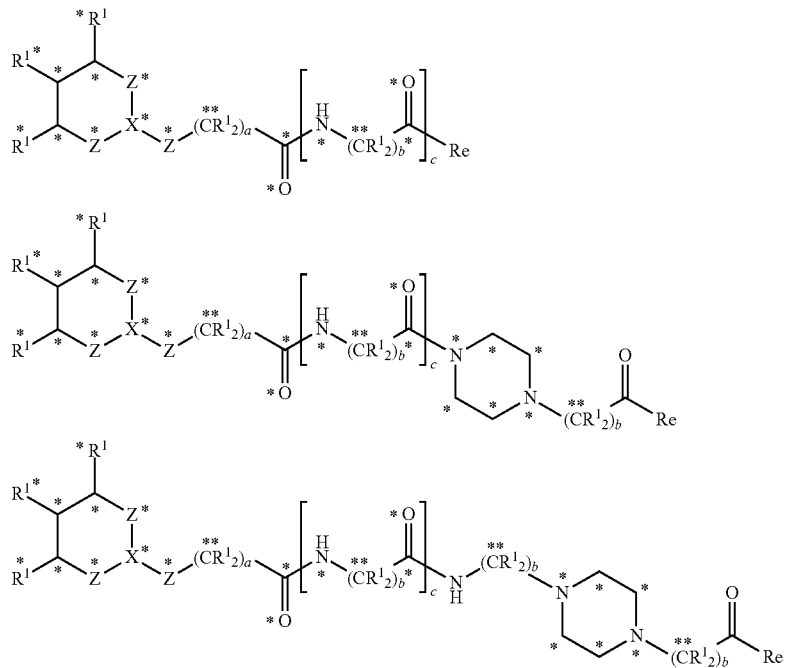

wherein * is an isotopic mass adjuster moiety and * represents that oxygen is $^{18}$O, carbon is $^{13}$C or nitrogen is $^{15}$N or at sites where the hydrogen is present, * may represent $^2$H.

In embodiments of this invention, where sets of tags are designed to have millidalton mass differences, i.e. Millidalton Mass Tag embodiments, each label in a set comprises one or more * such that in the set of n tags, the m$^{th}$ tag comprises (n-m) atoms of a first heavy isotope and (m−1) atoms of second heavy isotope different from the first. In this preferred embodiment m has values from 1 to n and n is 2 or more;

In the above general formula, the bond between X and the non-cyclic Z may be single bond or a double bond depending upon the selected X and Z groups in this position. For example, when X is N or C(R$^1$) the bond from X to the non-cyclic Z must be a single bond. When X is C, the bond from X to the non-cyclic Z may be a single bond or a double bond depending upon the selected non-cyclic Z group and cyclic Z groups. When the non-cyclic Z group is N or C(R$^1$) the bond from non-cyclic Z to X is a single bond or if y is 0 may be a double bond depending on the selected X group and the group to which the non-cyclic Z is attached. When the non-cyclic Z is $N(R^1)$, $CO(R^1)$, CO, $C(R^1)_2$, O or S the bond to X must be a single bond. The person skilled in the art may easily select suitable X, Z and $(CR^1_2)_a$ groups with the correct valencies (single or double bond links) according to the above formula.

The substituents of the mass marker moiety are not particularly limited and may comprise any organic group and/or one or more atoms from any of groups IIIA, IVA, VA, VIA or VIIA of the Periodic Table, such as a B, Si, N, P, O, or S atom or a halogen atom (e.g. F, Cl, Br or I).

When the substituent comprises an organic group, the organic group preferably comprises a hydrocarbon group. The hydrocarbon group may comprise a straight chain, a branched chain or a cyclic group. Independently, the hydrocarbon group may comprise an aliphatic or an aromatic group. Also independently, the hydrocarbon group may comprise a saturated or unsaturated group.

When the hydrocarbon comprises an unsaturated group, it may comprise one or more alkene functionalities and/or one or more alkyne functionalities. When the hydrocarbon comprises a straight or branched chain group, it may comprise one or more primary, secondary and/or tertiary alkyl groups. When the hydrocarbon comprises a cyclic group it may comprise an aromatic ring, an aliphatic ring, a heterocyclic group, and/or fused ring derivatives of these groups. The cyclic group may thus comprise a benzene, naphthalene, anthracene, indene, fluorene, pyridine, quinoline, thiophene, benzothiophene, furan, benzofuran, pyrrole, indole, imidazole, thiazole, and/or an oxazole group, as well as regioisomers of the above groups.

The number of carbon atoms in the hydrocarbon group is not especially limited, but preferably the hydrocarbon group comprises from 1-40 C atoms. The hydrocarbon group may thus be a lower hydrocarbon (1-6 C atoms) or a higher hydrocarbon (7 C atoms or more, e.g. 7-40 C atoms). The number of atoms in the ring of the cyclic group is not especially limited, but preferably the ring of the cyclic group comprises from 3-10 atoms, such as 3, 4, 5, 6 or 7 atoms.

The groups comprising heteroatoms described above, as well as any of the other groups defined above, may comprise one or more heteroatoms from any of groups IIIA, IVA, VA, VIA or VIIA of the Periodic Table, such as a B, Si, N, P, O, or S atom or a halogen atom (e.g. F, Cl, Br or I). Thus the substituent may comprise one or more of any of the common functional groups in organic chemistry, such as hydroxy groups, carboxylic acid groups, ester groups, ether groups, aldehyde groups, ketone groups, amine groups, amide groups, imine groups, thiol groups, thioether groups, sulphate groups, sulphonic acid groups, and phosphate groups etc. The substituent may also comprise derivatives of these groups, such as carboxylic acid anhydrides and carboxylic acid halides.

In addition, any substituent may comprise a combination of two or more of the substituents and/or functional groups defined above.

Reactive Functionalities:

The mass labels typically used in the present invention for labelling and detecting a biological molecule by mass spectroscopy comprise a reactive functionality $Re^3$ for facilitating attachment of or for attaching the mass label to a bifunctional linker (the linker attached to a biological molecule).

A variety of reactive functionalities may be introduced into the mass labels used in this invention. The structure of the reactive functionality $Re^3$ is not particularly limited provided that it is capable of reacting with $Re^2$ on the bifunctional linker. The reactive functionality is preferably a nucleophile or an electrophile.

Table 1 below lists some reactive functionalities that may be reacted with nucleophilic functionalities which are found in bifunctional linkers to generate a covalent linkage between the two entities. Any of the functionalities listed below could be introduced into the compounds of this invention to permit the mass markers to be attached to a bifunctional linker. A reactive functionality can be used to introduce a further linker groups with a further reactive functionality if that is desired. Table 1 is not intended to be exhaustive and the present invention is not limited to the use of only the listed functionalities.

TABLE 1

| Nucleophilic Functionality | Reactive Functionality | Resultant Linking Group |
|---|---|---|
| —SH | —SO$_2$—CH=CR$_2$ | —S—CR$_2$—CH$_2$—SO$_2$— |
| —NH$_2$ | —SO$_2$—CH=CR$_2$ | —N(CR$_2$—CH$_2$—SO$_2$—)$_2$ or —NH—CR$_2$—CH$_2$—SO$_2$— |
| —NH$_2$ | 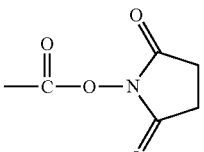 | —CO—NH— |
| —NH$_2$ | 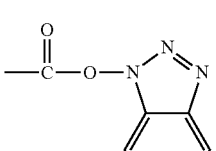 | —CO—NH— |
| —NH$_2$ | —NCO | —NH—CO—NH— |
| —NH$_2$ | —NCS | —NH—CS—NH— |
| —NH$_2$ | —CHO | —CH$_2$—NH— |
| —NH$_2$ | —SO$_2$Cl | —SO$_2$—NH— |
| —NH$_2$ | —CH=CH— | —NH—CH$_2$—CH$_2$— |
| —OH | —OP(NCH(CH$_3$)$_2$)$_2$ | —OP(=O)(O)O— |

TABLE 1-continued

| Nucleophilic Functionality | Reactive Functionality | Resultant Linking Group |
|---|---|---|
| —N=N=N | —≡— | 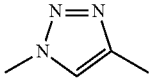 |

In the structures above the reactive group $Re^3$ is preferably selected from:

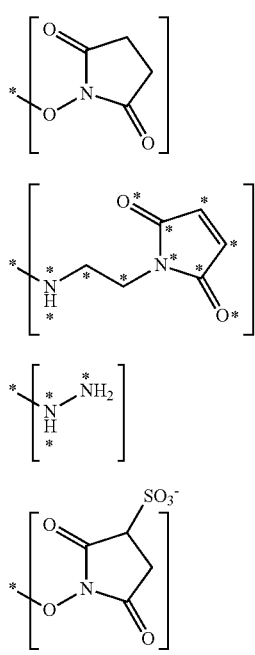

a)

b)

c)

d)

e)

f)

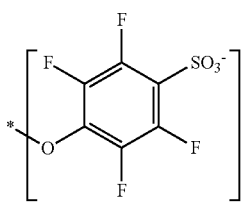 g)

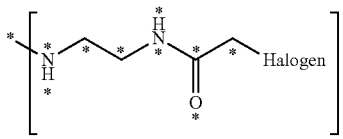 h)

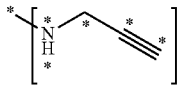 i)

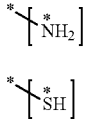 j)

 k)

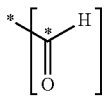 l)

 m)

wherein * represents that the oxygen is $^{18}O$, carbon is $^{13}C$ or nitrogen is $^{15}N$ of at sites where the heteroatom is hydrogenated, * may represent $^2H$.

Preferably, a set of reactive isotopic mass tags comprising n mass labels is selected from any one of the following structures:

a)

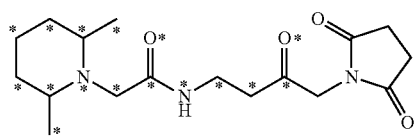

NHS—TMT b)

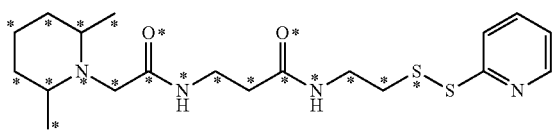

Pyridyldithio-TMT

-continued c)
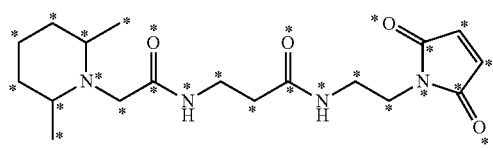
Maleimide-TMT d)
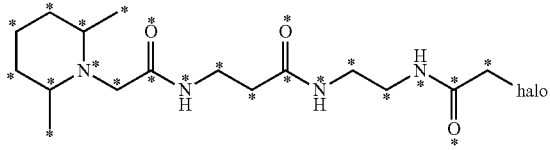
Haloacetyl-TMT e)
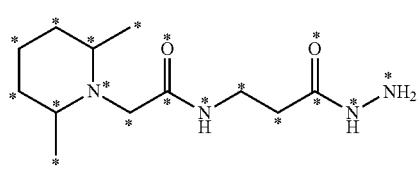
Hydrazide-TMT f)
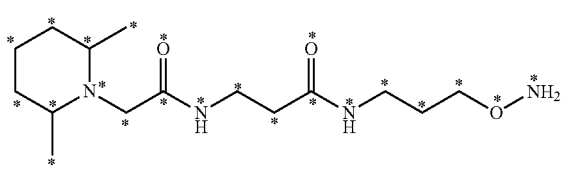
Aminooxy-TMT g)
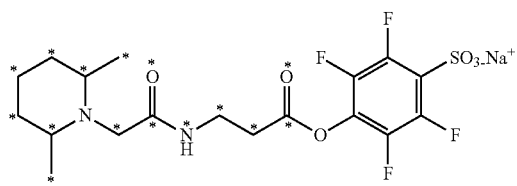

h)
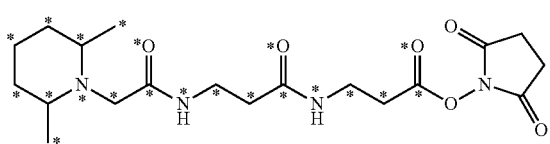

i)
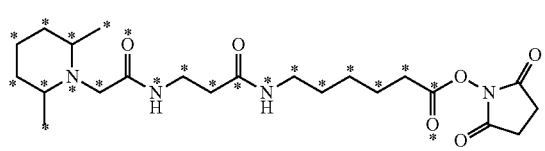

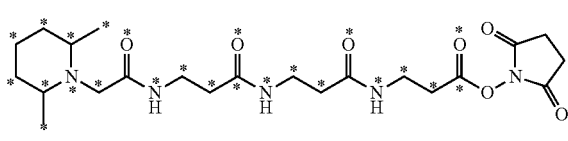

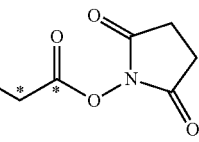

k)
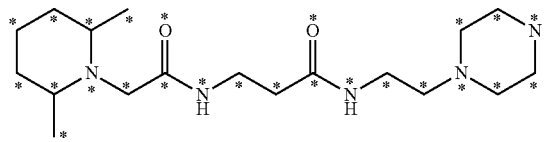

l)
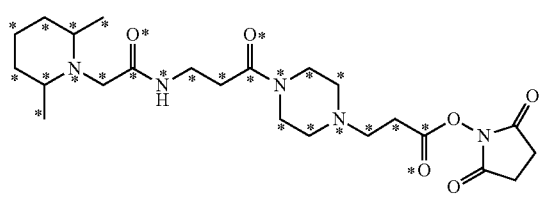

m)
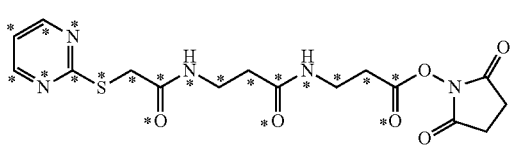

n)
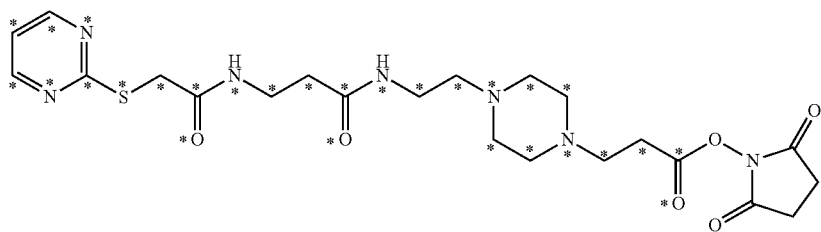

wherein * represents that the oxygen is $^{18}O$, carbon is $^{13}C$ or the nitrogen is $^{15}N$ or at sites where the heteroatom is hydrogenated, * may represent $^2H$.

In embodiments of this invention, where sets of tags are designed to have millidalton mass differences, i.e. Millidalton Mass Tag embodiments, each label in a set comprises one or more * such that in the set of n tags, the $m^{th}$ tag comprises (n-m) atoms of a first heavy isotope and (m-1) atoms of second heavy isotope different from the first. In this preferred embodiment m has values from 1 to n and n is 2 or more;

In embodiments of this invention, where sets of tags are designed to be truly isobaric with each other, the Mass Marker Moiety (Rep) as defined earlier and the rest of the tag which functions as the mass normalizer, are substituted so that the whole mass tag has the same total number of heavy isotope substitutions but each Mass Marker Moiety (Rep), which cleaves to give a reporter ion is substituted so that the cleaved reporters for each member of a set of tags is uniquely resolvable by mass spectrometry.

Reactive Functionalities and Methods for Labelling of Beta-Eliminated Peptides:

In embodiments of this invention where it is desirable to use mass label with a thiol as a reactive group, it may be preferable to provide the thiol as a protected thiol. Thiols are very reactive and, in particular, are readily oxidised, which renders the thiol unreactive. For the purposes of preparing a commercially useful thiol-functionalised reagent that may be kept for long periods, it is preferable to prepare the thiol mass tag with a protecting group on the thiol. Preferred protecting groups are groups, which can be readily removed prior to use of the reagent such as the pyridyldithio group, methyldithio group or thioacetyl group. The pyridyldithio group is readily introduced to a free thiol by reaction of the free thiol with 2,2'-dithiopyridine. Similarly, the methyldithio group is readily added to a free thiol by contacting the free thiol with Methyl methanethiosulfonate. The pyridylthio-protecting is a particularly preferred protecting group as it is stable to aqueous conditions and it may be readily removed by contacting the pyridylthio-protected mass tag with a suitable reducing agent such as Tris-(2-Carboxy-Ethyl)Phosphine (TCEP). TCEP will reduce the pyridyldithio linkage to give the mass tag as a free thiol and free pyridine-2-thione, which will not interfere with the coupling of the thiol mass tag with the Michael acceptor at a phosphosite. Similarly, the methyldithio group may be converted to the free thiol by contacting it with TCEP while the thioacetyl group is deprotected with hydroxylamine (typically 50 mM hydroxylamine) or hydrazine at near-neutral pH.

In some aspects of this invention a mass label with a nucleophilic reactive group is used. In preferred embodiment of the present invention the nucleophilic reactive functionality comprises one of the following groups:

—NH$_2$

—SH

In a preferred embodiment of the present invention the reactive mass label comprising a nucleophile has one of the following structures:

a) Amino-TMT:

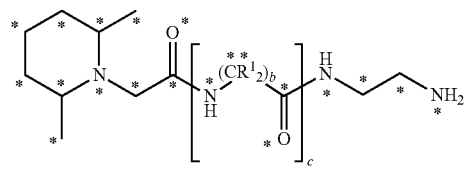

b) Thiol-TMT:

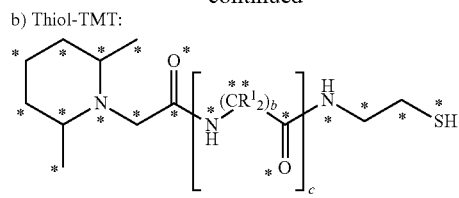

wherein one $R^1$ is independently H or and one $R^1$ is independently H or CH$_3$, and b is independently 1 or more for each integer value of c; and c is 1 or more; wherein * represents that the oxygen is $^{18}$O, carbon is $^{13}$C or the nitrogen is $^{15}$N or at sites where the heteroatom is hydrogenated, * may represent $^2$H.

In preferred embodiments, c=1, b=2, both $R^1$ is H and the reactive mass label comprising a nucleophile has one of the following structures:

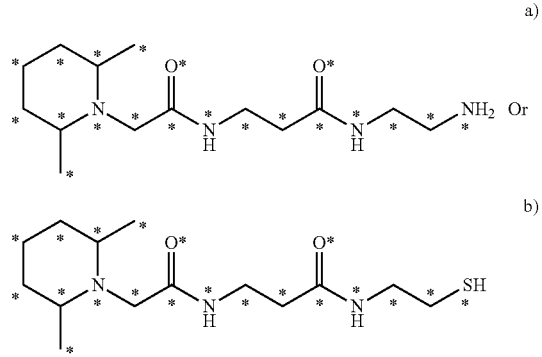

wherein * represents that the oxygen is $^{18}$O, carbon is $^{13}$C or the nitrogen is $^{15}$N or at sites where the heteroatom is hydrogenated, * may represent $^2$H.

In some embodiments of this invention where a thiol-functionalised mass tag is used, a preferred embodiment of the present invention uses a mass tag with a protected thiol where the protected thiol comprises the following group:

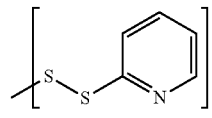

In a preferred embodiment of the present invention the reactive mass label with a protected thiol has one of the following structures:

Pyridyldithio-TMT:

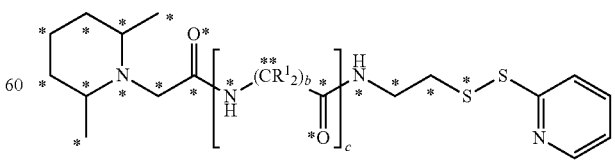

wherein one $R^1$ is independently H or and one $R^1$ is independently H or CH$_3$, and b is independently 1 or more for each integer value of c; and c is 1 or more; wherein * represents that the oxygen is $^{18}O$, carbon is $^{13}C$ or the nitrogen is $^{15}N$ or at sites where the heteroatom is hydrogenated, * may represent $^2H$.

In preferred embodiments, c=1, b=2, both $R^1$ is H and the reactive mass label comprising a nucleophile has one of the following structures:

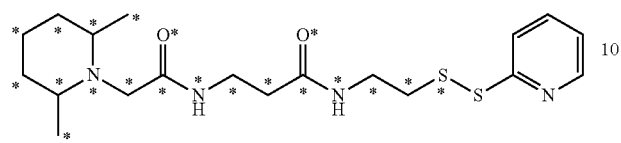

wherein * represents that the sulphur is $^{34}S$, oxygen is $^{18}O$, carbon is $^{13}C$ or the nitrogen is $^{15}N$ or at sites where the heteroatom is hydrogenated, * may represent $^2H$.

Synthesis of Amino-TMT and Pyridyldithio-TMT reagents as above is disclosed in WO11/036059. Thiol-TMT reagents may be generated from Pyridyldithio-TMT by reduction with TCEP as discussed above.

In embodiments of the invention, the Michael acceptor created by beta-elimination of a phosphate from a phosphoserine or phosphothreonine or a carbohydrate from an O-linked glycopeptide is reacted with a bifunctional linker with which the mass tag is then reacted. In embodiments of these aspects of the invention, the bifunctional linker must comprise a nucleophile that will react with the phosphosite Michael acceptor and again the preferred nucleophiles are amino groups or thiol groups. The bifunctional linker must then also comprise a reactive group with which the mass tag can be reacted. In the some embodiments a diamino linker may be used where one amino group will react with the Michael acceptor and one will be free to react with the mass tag. Similarly, an amino-thiol linker may be used. Since the linker is reacted with the phosphosite or glycosite first, in this embodiment, the thiol from the linker will react with the Michael acceptor again leaving an amino group for reaction with the mass tag. In embodiments of this invention where a bifunctional linker provides an amino group for reaction with the mass tag, the mass tag must therefore be amine-reactive. In preferred embodiments the amine-reactive group may be an active ester, preferably an N-hydroxysuccinimide ester.

In other preferred embodiments where a bifunctional linker is used to couple a mass tag to a phosphosite or glycosite Michael Acceptor, the bifunctional linker is a dithiol, preferably a symmetric dithiol so that it does not matter which thiol reacts to the Michael acceptor. If a large excess of the dithiol is used the linker will be very unlikely to cross-link peptides to each other. Similarly, since the methods of this invention reversibly immobilise peptides on a solid support, cross-linking is also sterically less favoured. In dithiol embodiments, the mass tag must comprise a thiol reactive functionality, such as an iodoacetamidyl group or a Michael acceptor, such as a maleimide or vinyl sulphone reactive group.

Other bifunctional linkers include propargylamine, where the amine will react with the Michael acceptor at the phosphosite while the alkyne function can be reacted with an azide functionalized mass tag using copper catalyzed azide/alkyne cycloaddition. Conversely, a bifunctional linker comprising an amino group and an azide group can be coupled to an alkyne functionalized mass tag.

Preferred bifunctional linkers for reaction to Michael Acceptors formed from beta-elimination of phosphate groups in phosphoserine or phosphothreonine or from beta-elimination of O-linked carbohydrate functions are listed below:

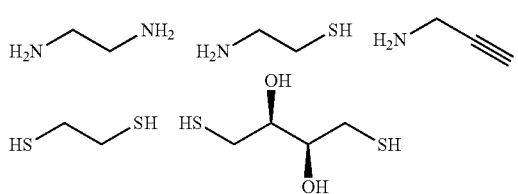

Affinity Ligands:

In a further embodiment, the mass labels used in the method further comprise an affinity capture ligand. The affinity capture ligand of the mass label binds to a counter-ligand so as to separate the isobarically labeled analytes from the unlabelled analytes prior to step (a), after step (a) but before step (b) or during step (b). The affinity capture ligand provides a means of enrichment of the analytes of interest, thereby increasing analytical sensitivity.

Affinity capture ligands are ligands which have highly specific binding partners. These binding partners allow molecules tagged with the ligand to be selectively captured by the binding partner.

Preferably a solid support is derivitised with the binding partner so that affinity ligand tagged molecules can be selectively captured onto the solid phase support. A preferred affinity capture ligand is biotin, which can be introduced into the mass labels of this invention by standard methods known in the art. In particular a lysine residue may be incorporated after the mass marker moiety or mass normalization moiety through which an amine-reactive biotin can be linked to the mass labels (see for example Geahlen R. L. et al., Anal Biochem 202(1): 68-67, "A general method for preparation of peptides biotinylated at the carboxy terminus." 1992; Sawutz D. G. et al., Peptides 12(5): 1019-1012, "Synthesis and molecular characterization of a biotinylated analogue of [Lys]bradykinin." 1991; Natarajan S. et al., Int J Pept Protein Res 40(6): 567-567, "Site-specific biotinylation. A novel approach and its application to endothelin-1 analogues and PTH-analogue.", 1992). Imino-biotin is also applicable. A variety of avidin counter-ligands for biotin are available, which include monomeric and tetrameric avidin and streptavidin, all of which are available on a number of solid supports.

Other affinity capture ligands include digoxigenin, fluorescein, nitrophenyl moieties and a number of peptide epitopes, such as the c-myc epitope, for which selective monoclonal antibodies exist as counter-ligands. Alternatively, an antibody or other binding agent with specificity for the mass label structure may be produced by methods known to one skilled in the art. An affinity matrix may then be constructed by attaching such binding agent onto a solid support such as a bead, well, or planar surface in a lateral flow device. Labelled analytes are then purified by contacting them with the affinity matrix in conditions whereby the mass labeled analytes are bound by the binding agents and retained whilst all unlabeled materials are removed, e.g. by washing. Finally, the captured analytes may be recovered by adjusting the conditions to those favouring release of the captured mass labeled analyte such as low pH or high salt. Preferably, conditions of low pH are used to avoid the need for subsequent removal of salt ions that may interfere with MS. As a further alternative, an affinity capture functionality may be selectively reactive with an appropriately derivatised solid phase support. Boronic acid, for example, is known to selectively react with vicinal cis-diols and chemically similar ligands, such as salicylhydroxamic acid.

It is worth noting that an antibody is commercially available (Anti-TMT Antibody, Thermo Scientific's Pierce Biotechnology division, Rockford, Ill., USA) that binds to the Dimethylpiperazine-beta alanine structure that is the core of most of the preferred tags for use with this invention, thus most of the TMT tags for use with this invention are already affinity capture reagents. In many embodiments of this invention it may be desirable, as a final step prior to mass spec analysis, to capture labelled peptides using the Anti-TMT Antibody to enrich samples for labelled species. Affinity capture can also concentrate dilute samples if that is desirable.

Figure 1:
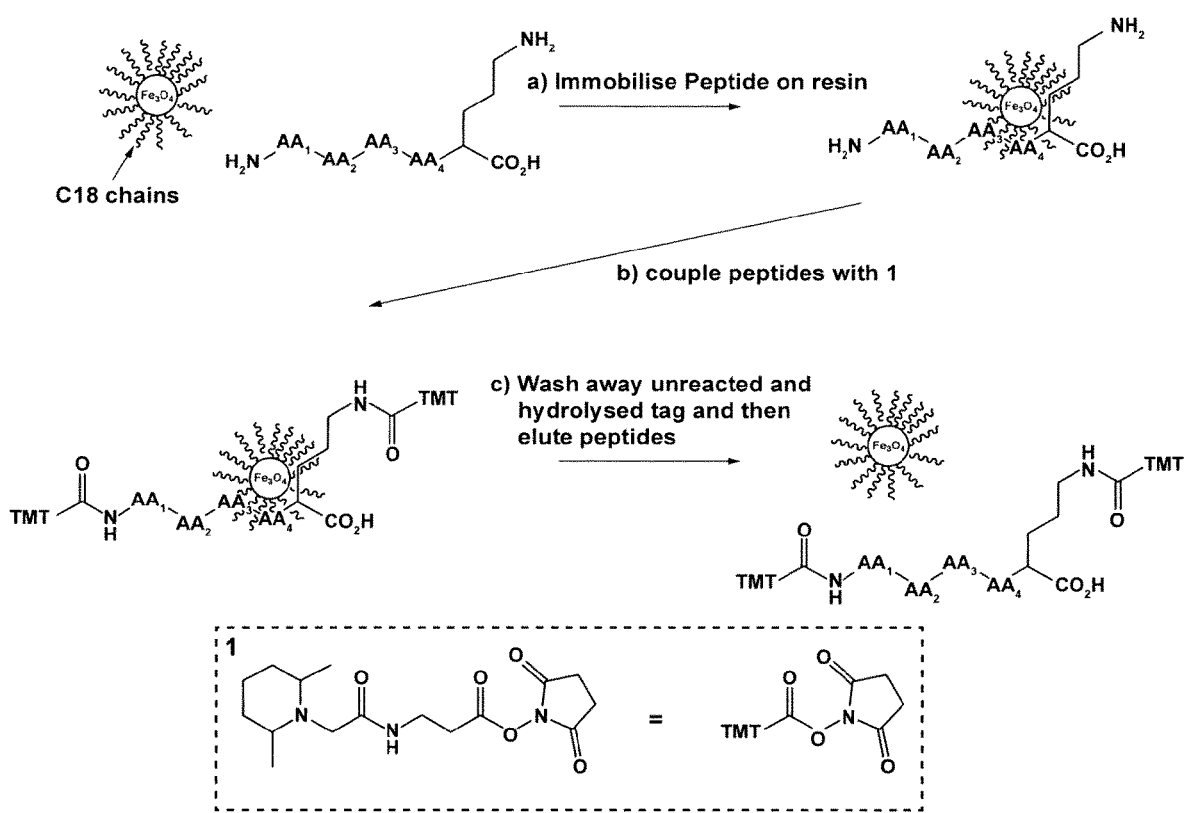
FIG. 1 illustrates the labelling of amino groups in peptides that have been reversibly immobilised on a solid phase support.

Labelling of Amino Groups in Peptides on Solid Phase Supports:

FIG. 1 illustrates schematically the labelling of amino groups in peptides that have been reversibly immobilised on a solid phase support according to the present invention. In FIG. 1, in step (a), peptides are dissolved in an acidified aqueous buffer, as discussed above, and are loaded onto a pre-conditioned C18 solid support, where they bind via hydrophobic interactions. The peptides can then be washed with aqueous solvents to remove any reagents left from the digestion and alkylation of the peptides. After washing, the peptides are contacted with an NHS-TMT as defined in the section on mass tags above.

After the coupling of the NHS-TMT has been allowed to run to completion, unreacted TMT reagent can then be washed away as well as any buffer salts, detergents or other reagents.

Finally in step (c), the peptides are eluted from the solid support by contacting the peptides with an elution buffer comprising a high proportion of an organic solvent. Preferably, the peptides are eluted with Acetonitrile.

In FIG. 1, the solid phase support is shown to be composed of Iron Oxide particles, which are amenable to manipulation in magnetic fields. Magnetic particles can be readily retained in a reaction vessel by contacting the outside of the reaction vessel with a magnet. While the particles are immobilised by the magnetic it is easy to change solvents, buffers and reagents as discussed above, facilitating automation of reaction steps.

Any mixture of peptides can be loaded onto the C18 resin. Typically, a biological sample will be treated to extract proteins, for example by precipitation of the proteins with acetonitrile or acetone. The precipitate may then be resuspended in an aqueous buffer for subsequent sample handling. The protein sample may be enriched for particular features and this step may take place before or after proteolytic digestion and alkylation of cysteine. In some embodiments, the protein sample may be enriched for glycoproteins by affinity methods prior to proteolytic digestion and alkylation. In other embodiments, the sample may be digested and alkylated followed by affinity enrichment of glycopeptides. Similarly, the sample can be enriched for phosphoproteins or phosphopeptides. Alternatively, cysteine-containing peptides can be isolated. The methods of this invention are not particularly limited by the nature of the peptide population to be labelled. In fact, the purpose of this invention, is to make it convenient to clean-up samples that have detergents, affinity reagents, salts or other reagents prior to labelling and to facilitate the clean-up of the sample after labelling so that the sample is ready for analysis by mass spectrometry after elution of the peptides from the C18 solid phase support. Affinity purification methods and chemical isolation methods for enriching peptides for different post-translational modifications are discussed in more detail in following sections of this document.

Some of the TMT reagents, including the NHS-TMT are only moderately soluble in aqueous solutions and typically these are dissolved in an organic solvent such as acetonitrile (ACN) followed by dilution with an aqueous buffer such as 100 mm TriEthylAmmonium Bicarbonate (TEAB) at pH 8.5. In the standard published protocol, NHS-TMT is made up to a concentration of 60 mM in ACN followed by dilution by 3 parts 100 mM TEAB to 1 part ACN solution to give a final concentration of 15 mM TMT with 25% ACN in the buffer (51). TMT reagent can be made up to 300 mM in Acetonitrile followed by dilution to 1 part in 20 in 100 mM TEAB giving a final concentration of 15 mM TMT with 5% ACN in the buffer. Peptides bound on a C18 solid phase will tolerate 5% ACN in the TEAB buffer without significant solvation of peptide off the solid phase.

In addition, after the coupling reaction is complete, the sample can be diluted to a lower concentration of ACN in the buffer by addition of further TEAB to facilitate re-binding of the peptides back onto the C18 solid phase support. If necessary, higher concentrations of NHS-TMT can be used by having a higher concentration of ACN in the buffer as long as the ACN is diluted down again prior to removal of the reaction solution from the C18 resin, i.e. the coupling reaction can be carried out under conditions which might solvate peptides on the C18 resin as long as those conditions are reversed with additional aqueous solvent after coupling and before removal of the reaction buffer.

Beta-Elimination Michael Addition Labelling of Phosphopeptides:

Phosphorylation in cellular systems occurs most frequently at serine (~90% of phosphorylation sites) followed by threonine (<10%), with tyrosine phosphorylation being the least abundant (~1%). The beta-elimination labelling methods of this invention are not applicable to Tyrosine phosphates but removal of serine and threonine phosphopeptides is helpful for Tyrosine phosphate analysis as the presence of a higher abundance of serine and threonine phosphorylation will no longer interfere with detection or enrichment of tyrosine phosphates, which will be discussed below. Since the majority of phosphorylation events in a cell are serine or threonine phosphorylations, the methods of this invention will be highly applicable to global analysis of phosphorylation in tissues.

In some embodiments of the invention, solid-phase beta elimination of serine and threonine phosphate groups from peptides or polypeptides in a complex mixture is followed by Michael addition with a nucleophile to introduce functional groups into the phosphopeptide that are advantageous.

The labelling methods of this invention are possible because the structure of the phosphorylation sites at serine and threonine are susceptible to beta-elimination under basic conditions. It has been found that addition of Barium ions greatly accelerates the beta-elimination reaction (22). Similarly, it has been found that the Michael addition is efficiently achieved using amino or thiol groups as the nucleophile (24).

The Beta-Elimination and Michael Addition reaction can be conducted consecutively or concurrently. In the consecutive reaction, the barium hydroxide for Beta-Elimination is added first and the reaction is allowed to go to completion before removing the barium hydroxide and then adding the nucleophile for the Michael Addition. In the concurrent reaction, the barium hydroxide for Beta-Elimination and the nucleophile for the Michael Addition are added simultaneously. Although the concurrent protocol is faster, this approach does, however, give less control over the concentration of thiol used in the Michael Addition and can cause issues with reaction times. The concurrent reaction is of greater benefit for a solution phase protocol as it is not necessary to get rid of the Barium Hydroxide before the Michael Addition. For the solid phase reaction, it is preferable, but not necessary, to do the steps consecutively. The reason for preferring a consecutive reaction is that peptides are susceptible to hydrolysis under the basic conditions needed for the beta-elimination reaction and many resins for the immobilisation of the peptides are also somewhat susceptible to degradation under basic conditions. In addition, beta-elimination can also take place at unmodified serine and threonine and cysteine although this takes place at a much lower rate than phosphate beta-elimination (52). Fortunately, the barium catalyzed phosphate beta-elimination reaction is rapid and to reduce the risk of peptide hydrolysis, side-reactions or resin degradation it is preferable to carry out the beta-elimination as quickly as possible. Since exchanging reagents with a solid phase reaction is trivial, the Beta-elimination can thus be done for the minimum amount of time necessary (52) and then the reagents can be washed away. The Michael addition can then be done at a lower pH than the beta-elimination and can thus be allowed to proceed for longer without risk of hydrolysis of the peptides or the degradation of the hydrophobic resin at the high pH of the Barium Hydroxide reaction.

For the Beta-Elimination reaction, Barium Hydroxide at concentrations ranging from 50 mM to a saturated solution may be used, preferably 66 to 100 mM (11, 16, 24, 29). A saturated solution is approximately 120 mM for BaOH (octahydrate) at RT although higher concentrations can be achieved at higher temperatures. In an alternative approach Sodium Hydroxide and Barium Nitrate may be used together (with preferred concentrations of 65 mM and 100 mM respectively). Barium Nitrate is much more soluble than Barium Hydroxide and so use of Sodium hydroxide and barium nitrate is reported to allow the control of the hydroxyl ion concentration independently of $Ba^{2+}$ concentration (53).

Both the Barium catalysed Beta Elimination and the Michael Addition reactions will take place at room temperature but they are both accelerated by increasing the temperature although elevated temperatures can increase the risk of side-reactions at unmodified serine. Reactions are preferably conducted at a temperature between 37 degrees Celcius and 60 degrees Celcius, preferably between 50 and 55 degrees Celsius.

It has been reported that reaction rate for phosphothreonine peptides and phosphoserine adjacent to proline is increased by reaction at the higher temperature but their paper does not give a complete report of optimal conditions for phosphothreonine. They state that these results will be published in a further article, which is as yet unpublished. Other publications using solution phase reactions report reactions at temperatures from RT to 50 degrees Celcius.

The Michael addition at methyldehydroalanine (beta-eliminated phosphothreonine) will react to produce stereoisomers. It has been reported that this causes peak splitting in LC separations (17,32). This could reduce sensitivity, although it has been reported that there is up to a 10-fold gain in sensitivity for some peptides depending on the peptide and derivatisation reagent (24) and it has been separately reported that the peak splitting actually increased identification of threonine phosphates by placing the same peptide in 2 different mass spectrometry contexts, i.e. different elution times, increasing the chance of favourable detection in shotgun analysis (17).

When carrying out the methods of this invention on solid supports, it is essential to ensure that sufficient time is allowed for reactions to go to completion. In general, reactions at 50 to 55 degrees Celsius are substantially complete after using reagent concentration as discussed above but it is reported in the literature that completeness of reactions for phosphothreonine peptides and phosphoserine adjacent to proline is increased by reaction for longer times in conventional solution phase reactions but in the concurrent protocols this increases the risk of hydrolysis and side-reactions—unmodified serine can form dehydroalanine if reaction is allowed to proceed too long. 2 hours at 50 degrees for Beta-Elimination followed by a further 2 hours at 50 degrees with the nucleophile is reported to result in complete labelling of phosphothreonine peptides (24) but in the same publication they report (data not shown) that 1 hour is sufficient at 50 degrees Celsius which is in agreement with Nika et al. (29) who suggest 1 hour at 55 degrees Celsius is sufficient.

In some embodiments of this invention, the Michael centre, resulting for beta-elimination of a phosphate, is reacted with a nucleophile that introduces properties that are useful for subsequent analysis of the peptide.

In preferred embodiments of this invention, the SP-BEMA reaction is used to introduce a mass tag into the beta-eliminated phosphopeptides. Introduction of a mass tag may be achieved by reacting the Michael centre with a bifunctional linker, which may comprise two nucleophilic centres such as a dithiol linker or an aminothiol linker.

Figure 2:
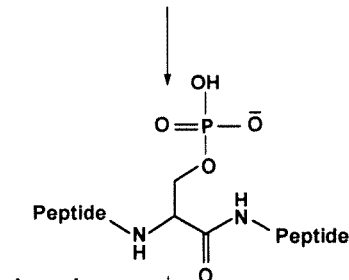
FIGS. 2 and 3 illustrate two variants of a Solid-Phase Beta-Elimination Michael Addition (SP-BEMA) protocol where phosphopeptides are labelled directly with mass tags after Beta-Elimination of Phosphate.
Figure 2:
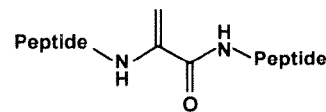
Figure 2:
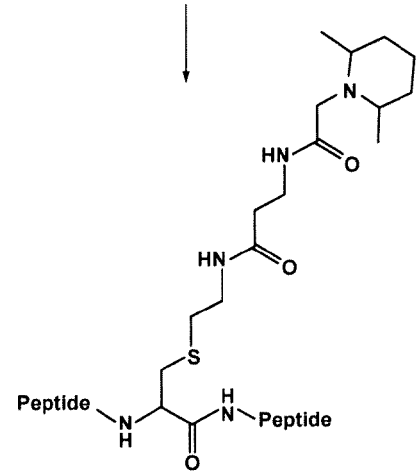
Figure 2:
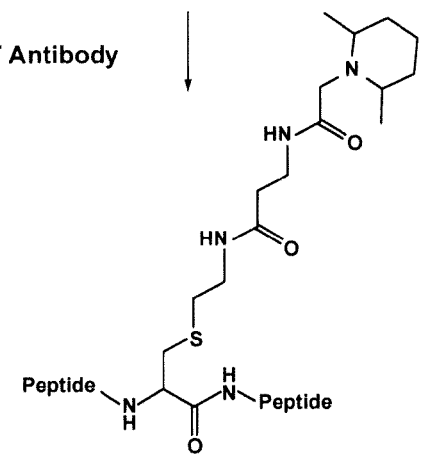
Figure 2:
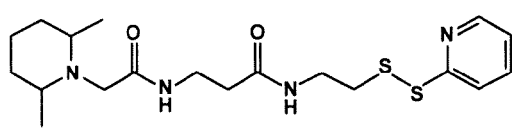
Figure 3:
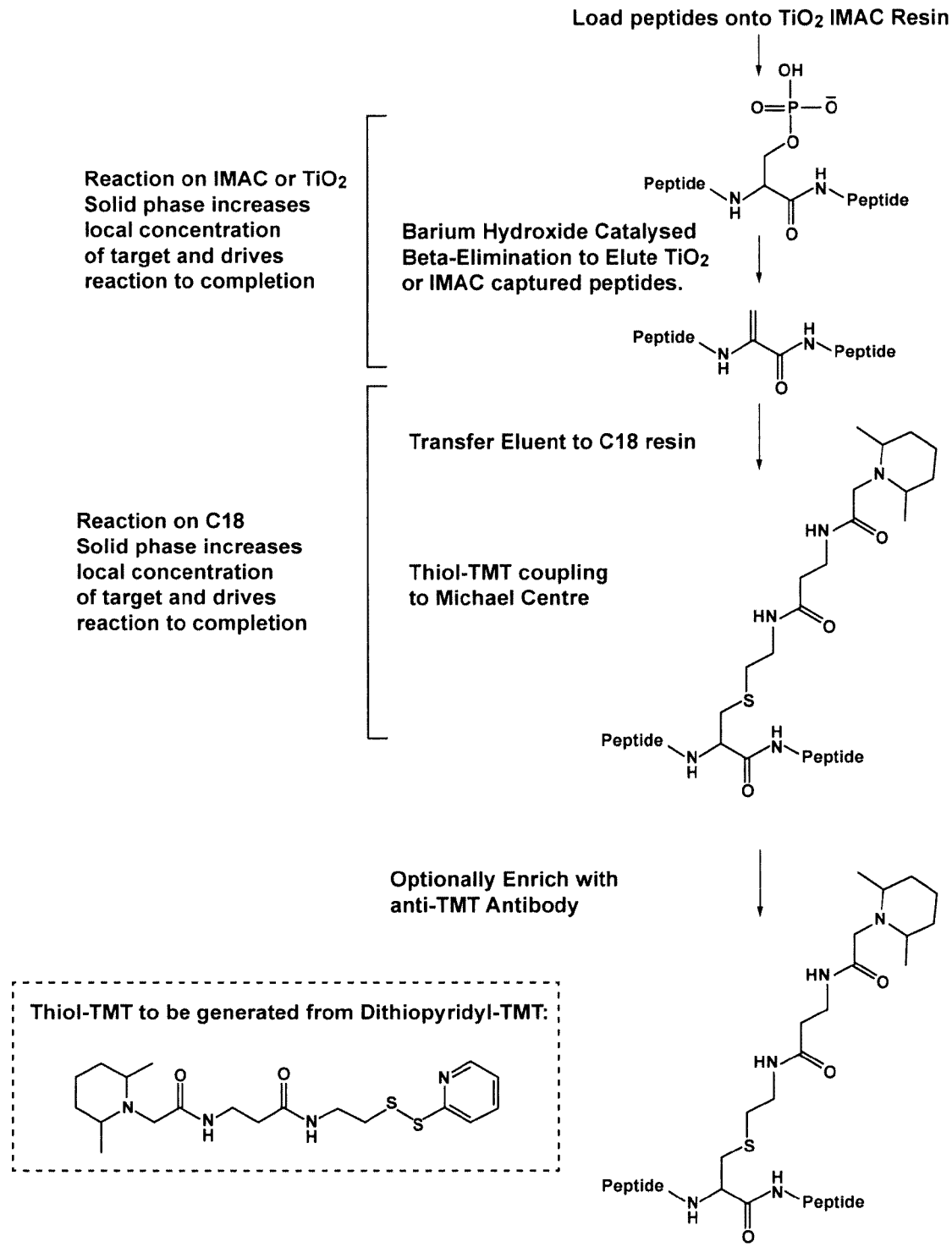

FIGS. 2 and 3 illustrate two variants of the SP-BEMA protocol. FIG. 2 shows a schematic of a protocol where phosphopeptides (after proteolytic digestion and alkylation of cysteine) dissolved in acidified aqueous buffer, as discussed above, are loaded onto a C18 solid support, where they reversibly bind via hydrophobic interactions. The peptides can then be washed with aqueous solvents. After washing, the peptides are contacted with a basic buffer comprising $Ba^{2+}$ ions, as discussed above, to catalyze beta-elimination of phosphate groups leaving a reactive Michael acceptor at the serine residue shown in the figure. A similar reaction would take place at phosphothreonine. The Michael acceptor is then reacted directly with a thiol-functionalised TMT mass tag according to the first aspect of this invention. In FIG. 2, the tag shown is referred to as a 'Thiol-TMT'. This tag would not typically be provided in the free thiol form as this tends to oxidise rapidly. As shown at the bottom of FIG. 2, the Thiol-TMT would be supplied as the pyridyldithio-protected form of the tag which would be deprotected by making up the tag in an aqueous buffer comprising a reducing agent such as TCEP, as discussed above. In FIG. 2, the Pyridyldithio-TMT tag is shown undoped but a 6-plex set of isotope-doped isobaric versions of this 'Pyridyldithio-TMT' molecule can be made and methods of synthesis of these tags are disclosed in WO11/036059. Unreacted tag may be washed away along with any unwanted buffer components leaving the peptides ready for mass spectrometric analysis. The peptides on the resin can then be eluted with an organic solvent such as neat acetonitrile or 80% acetonitrile/19% water/1% formic acid, which would leave the peptides ready for analysis by mass spectrometry.

Alternatively, after elution, the peptides may be dried down and resuspended in an neutral aqueous buffer to allow the TMT-labelled peptides to be enriched by contacting them with a solid support derivatised with an anti-TMT antibody (available from Pierce Biotechnology, Inc., Rockford, Ill., USA) as shown in FIG. 2a.

FIG. 3 shows a schematic of a protocol where phosphopeptides (after proteolytic digestion and alkylation of cysteine) dissolved in a suitable aqueous buffer, as discussed above, are loaded onto a solid phase support with a high affinity for phosphopeptides, such as a Titanium dioxide solid support or an Immobilized Metal ion Affinity Capture support. The phosphopeptides will bind to the support through the phosphate group. The peptides can then be washed with aqueous solvents. After washing, the peptides are contacted with a basic buffer comprising $Ba^{2+}$ ions, as discussed above, to catalyze beta-elimination of phosphate groups leaving a reactive Michael acceptor at the serine residue shown in FIG. 3. A similar reaction would take place at phosphothreonine. The beta-elimination reaction will effectively cleave peptides from the phosphate affinity capture support leaving peptides free in solution. The buffer with the eluted peptides should be acidified slightly, e.g. with Trifluoroacetic acid, after which the peptide solution can be contacted with a C18 solid support, where they will reversibly bind via hydrophobic interactions. The Michael acceptor is then reacted with a thiol-functionalised TMT reagent. In FIG. 3, the mass tag is a Thiol-TMT as in FIG. 2 derived from a pyridyldithio-TMT. Unreacted tag may be washed away along with any unwanted buffer components leaving the peptides ready for mass spectrometric analysis. The peptides on the resin can then be eluted with an organic solvent such as neat acetonitrile or 80% acetonitrile/19% water/1% formic acid, which would leave the peptides ready for analysis by mass spectrometry.

As with the scheme shown in FIG. 2, TMT-labelled peptides can be enriched by contacting them with a solid support derivatised with an anti-TMT antibody although the use of IMAC or MOAC would probably render this step unnecessary.

In one preferred embodiment of this invention, dehydroalanine (DHA) residues and methyldehydroalanine (MDHA) residues resulting from beta-elimination of the phosphate group are reacted with a dithiol reagent such as ethanedithiol or L-dithiothreitol (L-DTT). Coupling of a large excess of a dithiol should leave a free thiol available for reaction with a thiol-reactive mass tag such as an Iodoacetamide-TMT discussed below. The Iodoacetamide-TMT labeling of the thiolated DHA and MDHA residues should be effected in a substantially aqueous buffer to avoid eluting the captured analyte peptides from the resin.

Figure 4:
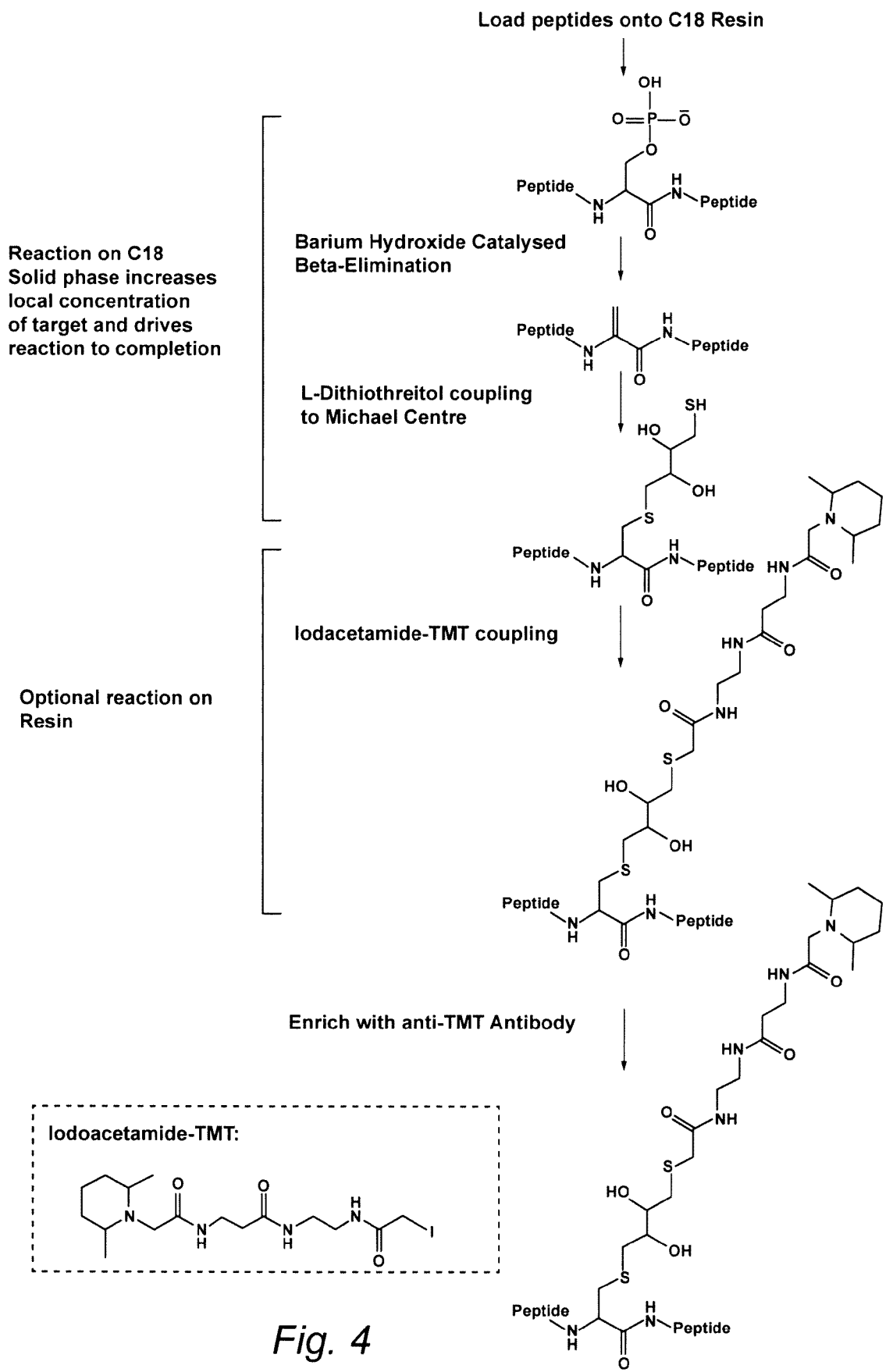
FIGS. 4 and 5 illustrate two further variants of the SP-BEMA protocol according to the invention where phosphopeptides are labelled with bifunctional linkers after Beta-Elimination of Phosphate prior to labelling with mass tags.
Figure 5:
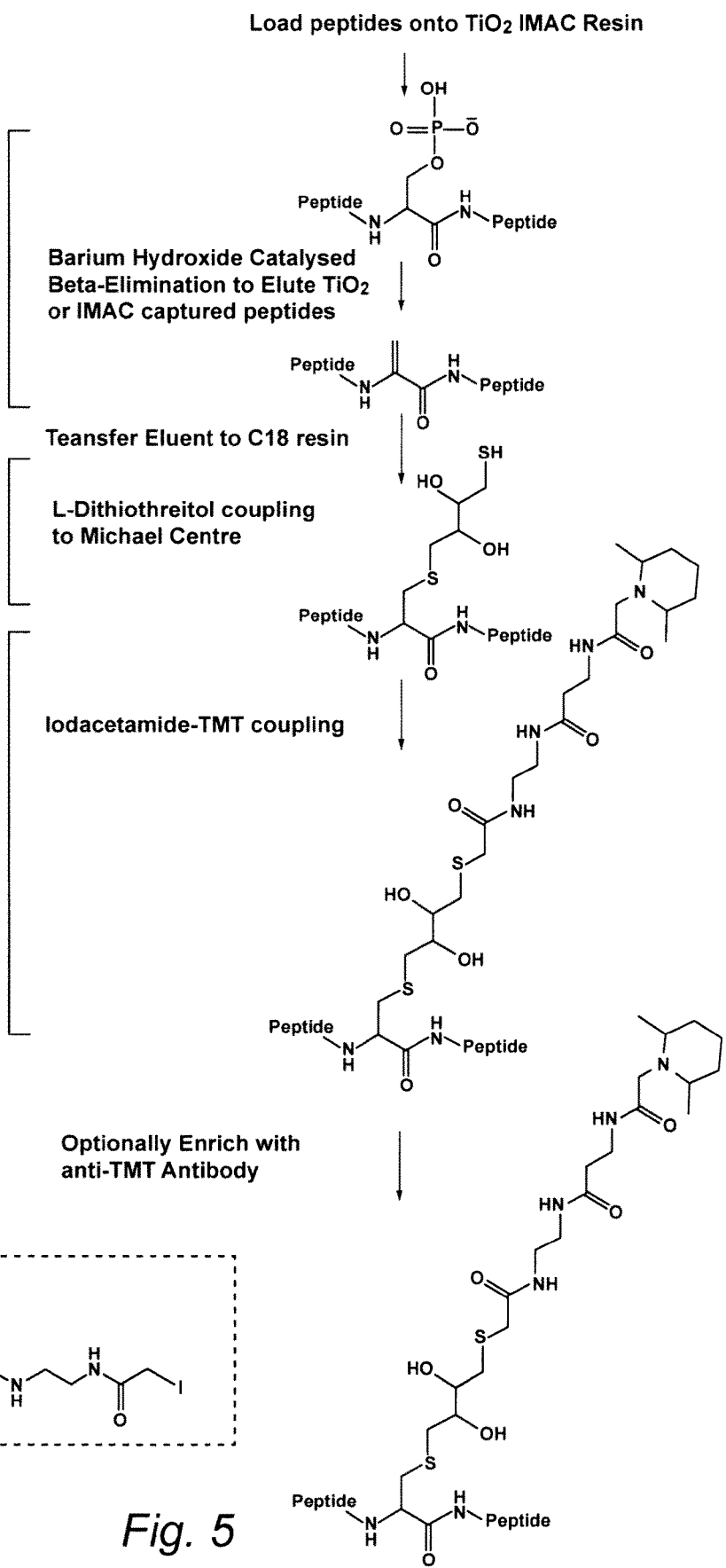

FIGS. 4 and 5 illustrate two further variants of the SP-BEMA protocol. FIG. 4 shows a schematic of a protocol according to the second aspect of this invention where phosphopeptides (after proteolytic digestion and alkylation of cysteine) dissolved in acidified aqueous buffer, as discussed above, are loaded onto a C18 solid support, where they reversibly bind via hydrophobic interactions. The peptides can then be washed with aqueous solvents. After washing, the peptides are contacted with a basic buffer comprising $Ba^{2+}$ ions, as discussed above, to catalyze beta-elimination of phosphate groups leaving a reactive Michael acceptor at the serine residue shown in the figure. A similar reaction would take place at phosphothreonine. The Michael acceptor is then reacted with a bifunctional linker. In FIG. 4, the bifunctional linker is L-Dithiothreitol (L-DTT), which is a symmetrical linker comprising two thiol functions that will act as nucleophiles. If a sufficiently large excess of L-DTT is used there will negligible cross-linking of peptides and one thiol function from each L-DTT molecule will react with a Michael acceptor in beta-eliminated peptides leaving a free thiol for reaction with a mass tag. Any excess of L-DTT linker is then washed away. The remaining thiolated peptides are then contacted with a thiol reactive mass tag.

The tag shown is referred to as an 'Iodoacetamide-TMT' and is shown undoped but a 6-plex set of isotope-doped isobaric versions of this 'Iodoacetamide-TMT' molecule are commercially available (available from Pierce Biotechnology, Inc., Rockford, Ill., USA) and methods of synthesis of this reagent are disclosed in WO11/036059. This thiol-reactive tag is coupled to the free thiols in L-DTT linkers coupled to immobilised peptides thus introducing a mass tag into peptides at sites that were phosphorylated. Unreacted tag may be washed away along with any unwanted buffer components leaving the peptides ready for mass spectrometric analysis. The peptides on the resin can then be eluted with an organic solvent such as neat acetonitrile or 80% acetonitrile/19% water/1% formic acid, which would leave the peptides ready for analysis by mass spectrometry.

Alternatively, after elution, the peptides may be dried down and resuspended in an neutral aqueous buffer to allow the TMT-labelled peptides to be enriched by contacting them with a solid support derivatised with an anti-TMT antibody (available from Pierce Biotechnology, Inc., Rockford, Ill., USA) as shown in FIG. 3a.

FIG. 5 shows a schematic of a protocol according to the fourth aspect of this invention where phosphopeptides (after proteolytic digestion and alkylation of cysteine) dissolved in a suitable aqueous buffer, as discussed above, are loaded onto a solid phase support with a high affinity for phosphopeptides, such as a Titanium dioxide solid support or an Immobilized Metal ion Affinity Capture support. The phosphopeptides will bind to the support through the phosphate group. The peptides can then be washed with aqueous solvents. After washing, the peptides are contacted with a basic buffer comprising $Ba^{2+}$ ions, as discussed above, to catalyze beta-elimination of phosphate groups leaving a reactive Michael acceptor at the serine residue shown in FIG. 5. A similar reaction would take place at phosphothreonine. The beta-elimination reaction will effectively cleave peptides from the phosphate affinity capture support leaving peptides free in solution. The buffer with the eluted peptides should be acidified slightly, e.g. with Trifluoroacetic acid, after which the peptide solution can be contacted with a C18 solid support, where they will reversibly bind via hydrophobic interactions. The Michael acceptor is then reacted with a bifunctional linker according to the fourth aspect of this invention.

In FIG. 5, the bifunctional linker is again L-Dithiothreitol (L-DTT). Reaction of the peptides with a sufficiently large excess of L-DTT will ensure that one thiol function from each L-DTT molecule will react with a Michael acceptor in beta-eliminated peptides leaving a free thiol for reaction with a mass tag. Any excess of L-DTT linker is then washed away. The remaining thiolated peptides are then contacted with the Iodoacetamide TMT. This thiol-reactive tag is coupled to the free thiols in L-DTT linkers coupled to immobilised peptides thus introducing a mass tag into peptides at sites that were phosphorylated. Unreacted tag may be washed away along with any unwanted buffer components leaving the peptides ready for mass spectrometric analysis. The peptides on the resin can then be eluted with an organic solvent such as neat acetonitrile or 80% acetonitrile/19% water/1% formic acid, which would leave the peptides ready for analysis by mass spectrometry.

In another embodiment of the invention, an aminothiol reagent may be used to label the Michael centres in beta-eliminated phosphopeptides rather than L-DTT as discussed above. For example, the modified amino acids resulting from the reaction of the Michael centre in serine or threonine with 2-aminoethanethiol are analogues of Lysine and are thus susceptible to tryptic hydrolysis.

The free amino group can also be labeled with a secondary label such as an N-hydroxysuccinimide ester TMT, disclosed in WO07/012849 and WO11/036059, although to ensure selective labeling at the modified phosphosite, any other amino groups in the peptide (epsilon and alpha) would need to be blocked. Blocking of other amino groups could be effected by reductive amination with formaldehyde after tryptic digestion of a complex polypeptide mixture. For reductive methylation of peptides with formaldehyde, cysteine-alkylated peptides are contacted with a suitable aqueous buffer, e.g. 300 mM triethanolamine buffer pH 7.5. A reducing agent is present, such as Sodium Cyanoborohydride (54) or Pyridine Borane (55) at a concentration of 30 mM with formaldehyde present at concentration of 20 mM. Reactions are typically allowed to react at room temperature for 2 hours or more. Sodium Cyanoborohydride is typically prepared as an aqueous solution and so reductive methylation with Sodium Cyanoborohydride can take place on a C18 solid support or prior to reversible capture if preferred. It would be preferred that reductive methylation take place on the solid support to facilitate removal of reagents after the reductive methylation is completed in accordance with the methods of this invention.

Pyridine Borane is typically made up in a high concentration of methanol and should therefore be used to reductively methylate peptides prior to immobilisation of the peptides on a C18 support and the methylated peptides should be dried down to remove methanol and then resuspended in aqueous solvent to enable loading of the peptides onto a C18 support for any subsequent reactions.

In a further embodiment of this invention, phosphopeptides may be captured onto an IMAC or MOAC solid phase support. After washing away unbound, unphosphorylated peptides, the captured peptides may then be labelled on alpha-amino groups or epsilon-amino groups using an NHS-TMT reagent. The unreacted tag may be washed away and then the peptides can be eluted for analysis by beta-elimination of the peptides. The amino-labelled peptides may then be analysed without further derivatisation of the Michael acceptors at the beta-elimination site. If the labelled peptides are analysed immediately, there will be negligible hydrolysis or further reaction of the Michael centres. Alternatively, the eluted peptides can be captured onto C18 resin and the Michael centres can be reacted with a blocking reagent such as 2-aminoethanethiol which would leave a primary amine at the elimination site. The captured peptides can then be washed and eluted for mass spectrometry analysis. A similar approach can be taken for O-linked glycopeptides after beta-elimination, discussed below.

Analysis of Glycopeptides:

Glycoproteins are characterized by the presence of oligosaccharides linked to the peptide backbone primarily through N- or O-glycosidic bonds at asparagine or serine/threonine residues, respectively (11). N- and mucin-type O-glycosylations are widely accepted as the most common and structurally diverse post-translational modifications found on secreted proteins and on the extracellular parts of membrane-bound proteins (12). Given that protein glycosylation is involved in various cellular processes (13-16), the site-specific characterization of N- and O-linked glycosylations and identification of the modified proteins is becoming increasingly important Numerous techniques for the analysis of glycopeptides have been developed in the prior art and several can adapted to the methods and labels of this invention as will be discussed below. In particular, many glycosyl-functions are susceptible to oxidation, which results in the formation of aldehyde and ketone functions. In addition, sugar analogues with reactive handles such as ketones, aldehydes, azides and alkyne functions are known in the literature and can be labelled with the methods and labels of this invention.

There are two approaches general approaches to carbohydrate analysis that can be considered in the context of this invention. The first approach is labelling of amino groups in peptides derived from glycoproteins by tryptic or other sequence specific cleavage methods with the mass tags of this invention using solid phase capture for the labelling step combined with enrichment or affinity purification of the glycopeptides.

The second approach is direct labelling of carbohydrate functions in glycopeptides or direct labelling of modification sites where carbohydrates were present in the biological sample.

Methods of labelling amino groups in peptide populations on a solid phase support have been discussed earlier in this manuscript. Methods of affinity purification of glycopeptides are discussed below and these can be used to isolate a population of peptides or amino-labelling.

Similarly, methods for direct labelling of carbohydrate functions or carbohydrate-modified site are discussed below.

Mass Tags with Reactive Groups and Bifunctional Linkers for Coupling with Ketones and Aldehydes Hydrazide- and aminooxy-functionalized mass tag reagents will couple with aldehydes and ketones. The synthesis of preferred hydrazide- and aminooxy-functionalized Tandem Mass Tag reagents has been described fully in a previous patent application (WO11/036059). General structures for individual examples of these tags are shown below:

Hydrazide-TMT:

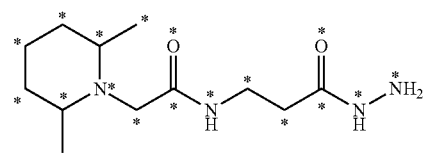

Aminooxy-TMT:

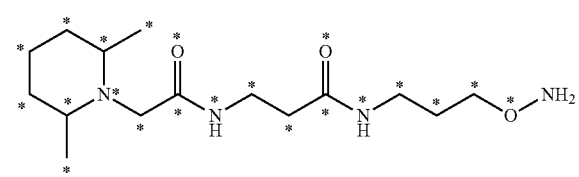

wherein * represents that the oxygen is $O^{18}$, carbon is $C^{13}$ or the nitrogen is $N^{15}$ or at sites where the heteroatom is hydrogenated, * may represent $H^2$.

Hydrazide and aminooxy functionalized reagents behave in a very similar fashion to each other in terms of reaction conditions. Coupling of reagents with hydrazide and aminooxy functions should take place in conditions that avoid primary amine-containing buffers, e.g. tris(hydroxymethyl)aminomethane (TRIS), in the oxidation and biotinylation steps as these buffers react with aldehydes and will quench the reaction with alkoxyamines. Hydrazide and aminooxy functionalized reagents will react with carbonyls most efficiently in amine-free, neutral conditions (pH 6.5-7.5).

If peptides are immobilized on a hydrophobic solid phase support for the coupling with an aminooxy or hydrazide reagent, the reagent should be applied in an aqueous solution. If it is necessary to dissolve the reagent in an organic solvent first then the dissolved reagent should be diluted so that the organic component is present at 5% or less in the buffer to be used with the hydrophobic support. If the reagent must be dissolved in an organic solvent, it could be with dimethylsulfoxide or acetonitrile and then diluted into an aqueous reaction mixture. A suitable aqueous buffer would be phosphate buffered saline for example (PBS; 100 mM Sodium Phosphate, 150 mM Sodium Chloride; pH 7.2). A final reagent concentration of 5 to 10 mM should be sufficient although this should be optimized if necessary by checking the completeness of any labelling reactions by HPLC and/or mass spectrometry. A typical coupling reaction with an aminooxy or hydrazide reagent should be complete in about 2 hours at room temperature. The coupling of hydrazides and aminooxy-functionalized reagents can be catalyzed by the presence of aniline in the reaction buffer (56-58). The use of solid phase coupling means additional reaction components such as aniline, which might interfere with mass spectrometry can be readily washed away.

The optimal aminooxy or hydrazide reagent concentration and reaction conditions depend on the specific peptides to be labelled. For best results, the molar ratio of reagent and glycoprotein should be empirically optimized.

Bifunctional Linkers for Labelling of Ketones and Aldehydes:

In some preferred embodiments of this invention, mass tags may be reacted indirectly with aldehydes or ketones in glycopeptides by the use of an intermediate bifunctional linker. In these embodiments of the invention, the bifunctional linker comprises either a hydrazide or an aminooxy function as $Re^1$ of the bifunctional linker. The second bifunctional group $Re^2$ is preferably selected to have 'orthogonal' properties to the first reactive group, i.e. it will not react with aldehydes or ketones and will react selectively with a third reactive group $Re^3$ present in a mass tag.

The second reactive group on the bifunctional linker may be an alkyne group, which can be reacted with an azide function on a mass tag via copper catalyzed azide alkyne cycloaddition. The second reactive group may alternatively comprise a protected thiol, such as a pyridyldithio reagent. Preferred bifunctional linkers for use with this invention are illustrated below:

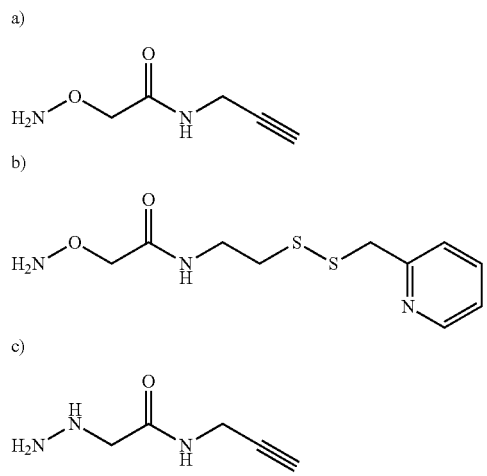

d)

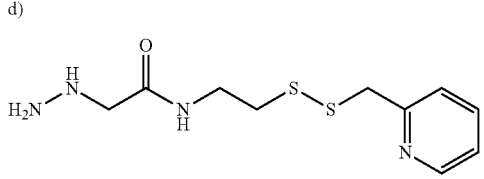

Bifunctional linkers b) and d) can be reacted with iodoacetamide-functionalised mass tags after deprotection of the thiol group. Deprotection may be effected with 1 to 10 mM Tris(2-CarboxyEthyl)Phosphine (TCEP) in aqueous buffer (50 mM TriEthylAmmonium Bicarbonate (TEAB) pH 8.0).

Bifunctional Linkers a) and c) can be reacted with azide-functionalized mass tags using copper catalyzed azide/alkyne cycloaddition (CUAAC) (59). The methods of this invention are well suited to the use of so called 'Click Coupling' with the CUAAC method. One issue with click coupling for biological applications is the contamination by residual copper after the coupling—removing the copper ions can be tedious. Since the peptides for labelling are reversibly immobilised on a solid phase support, copper ions can be washed away from the solid support relatively easily following click coupling.

Beta-Elimination Michael Addition Labelling of Glycopeptides:

O-linked Glycosylation in cellular systems occurs most frequently at serine followed by threonine, with less frequent glycosylation at tyrosine, hydroxylysine, hydroxyproline and even at some phosphoserine sites, i.e. with phosphate still present.

O-linked carbohydrates at serine and threonine are susceptible to beta-elimination under basic conditions as discussed above, allowing the beta-elimination site to be labelled. Thus, in some aspects of the invention, solid-phase beta elimination of serine and threonine carbohydrate groups from peptides or polypeptides in a complex mixture is followed by Michael addition with a nucleophile to introduce functional groups into the glycopeptide that are advantageous, particularly mass tags.

Figure 6:
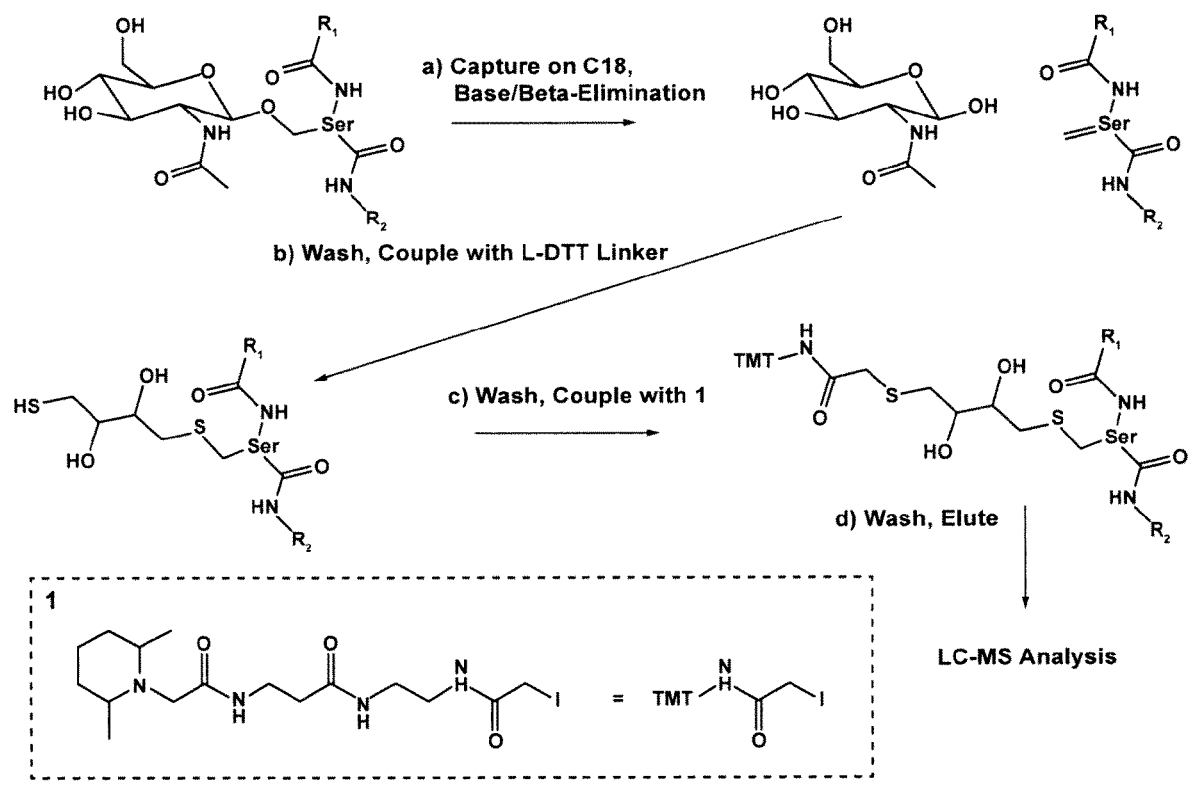
FIG. 6 illustrates a schematic of a Beta-Elimination Michael Addition protocol for labelling of O-linked glycopeptides with TMT reagents.

FIG. 6 illustrates schematically an embodiment of this invention with Beta-Elimination of an O-linked N-acetylglucosamine residue from a serine. Essentially the same reaction would take place at threonine. In step (a), a peptide population is immobilised on a C18 solid support and then beta-elimination takes place under basic conditions to produce the dehydroalanine function at the elimination site, which is a Michael Acceptor. In step (b) the beta-elimination reagents are removed, the resin washed and then L-DTT is reacted with the Michael Acceptor thus introducing a free thiol into the Beta-Elimination site. In step (c), unreacted L-DTT linker is washed away, and an Iodoacetamide-TMT is coupled to the free thiol in the L-DTT. Finally, in step (d) the resin is washed to remove unreacted TMT reagents and the labelled peptides are eluted in high organic solvent for liquid chromatography mass spectrometry analysis (LC-MS). In FIG. 6, the glycan is N-acetylglucosamine and, typically, this residue would not be analysed further but in the context of more complex glycans, the beta elimination solution could be subjected to further analysis to recover the glycans. In some instances, it may be desirable to label the glycans themselves, which could take place on the solid phase support in reactions that precede the beta-elimination step. Oxidation of sugars or chemoenzymatic labelling as discussed below would allow the O-linked glycans to be labelled with aminooxy-TMTs prior to beta-elimination allowing the O-linked glycans to be analysed separately in quantitative studies to compare different samples with each other, if different TMTs are used to label each sample. Thus, the methods of this invention make it relatively easy to consecutively label, recover and analyse both the peptide and the glycan components of O-linked glycopeptides.

The labelling methods of this invention are possible because the structure of the glycosylation sites at serine and threonine are susceptible to beta-elimination under basic conditions. In contrast to phosphopeptides, however, Barium ions do not accelerate the beta-elimination of carbohydrates and carbohydrate beta-elimination is typically much slower than phosphate beta-elimination (34). However, since the resulting Michael acceptor is the same as that generated at phosphate sites, Michael addition at carbohydrate beta-eliminated sites is essentially the same as for phosphopeptides using amino or thiol groups as the nucleophile (24).

Care must be taken in the analysis of both phosphopeptides and glycopeptides when using beta-elimination reactions to ensure that the populations of peptides that are being analyzed are composed of the peptides with the post-translational modification of interest. Phosphopeptides can be readily enriched with solid supports with a high affinity for phosphopeptides, as discussed above. In principle, glycopeptides can also be enriched with appropriate lectins or specific anti-carbohydrate antibodies or through reactions with biotin. A variety of such reagents are commercially available. However, specificity and binding affinity of these reagents is currently not as high as the corresponding phosphate affinity-capture reagents for phosphopeptide analysis so chemical capture of the glycopeptides may be preferable. This is discussed in more detail below.

Labelling of Glycopeptides after Oxidation:

Various procedures for labeling glycoconjugates have been described in academic literature. In particular, many glyco-functions are susceptible to oxidation. Oxidation of sugar functions may be effected by either chemical oxidation (periodate-induced) or enzymatic (via galactose oxidase) oxidation of glycoconjugates. The resultant aldehyde or ketone groups can then be labeled with hydrazide-functionalized or aminooxy-functionalized reagents. It should be noted that different sugar functions may require different procedures to effect complete oxidation, which means global analysis of sugar functions in proteins is very challenging. To achieve complete labelling of all available sugars requires multiple different procedures to be applied to the same samples. In addition, these individual procedures are multi-step protocols, requiring oxidation, removal of oxidation reagents, labelling and removal of labelling reagents.

Thus in a glycopeptide-labelling embodiment according to the invention, there is provided methods for labelling glycopeptides derived from complex polypeptide mixtures where the glycopeptides are reversibly immobilized on solid phase supports wherein the methods comprising the following steps:
1) Extracting polypeptides from biological samples
2) Reducing, alkylating and digesting the polypeptide mixture to produce a mixture of peptides.
3) Optionally, contacting the peptide mixture with reagents that will oxidize sugar functions to produce aldehydes or ketones
4) Reversibly immobilizing the peptides on a solid phase support
5) contacting the reversibly immobilized peptide mixture with reagents that will oxidize sugar functions to produce aldehydes or ketones
6) washing away the oxidizing agent from the solid phase support while the polypeptides or peptides remain captured on the hydrophobic solid support
7) contacting the oxidized polypeptides or peptides on the hydrophobic solid support with one or more bifunctional linker reagents as defined above, wherein $Re^1$ comprise a hydrazide or aminooxy reactive group that will react with the aldehydes or ketones generated in polypeptides or peptides by the oxidizing agent to give linker-labelled polypeptides or peptides
8) washing away unreacted bifunctional linker from the linker-labelled polypeptides or peptides on the hydrophobic solid support
9) contacting the reversibly immobilized peptides with one or more mass labels, wherein $Re^2$ of the bifunctional linker attached to the analyte reacts with the mass label to form a labelled analyte, and then optionally washing away unreacted mass labels
10) Eluting the immobilized peptide mixture
11) Analysing the eluted peptide mixture by mass spectrometry In a further glycopeptide-labelling embodiment according to the invention, there is provided a method to convert glycopeptides into labelled glycopeptides comprising the steps of:
1. optionally cleaving a mixture of polypeptides comprising glycoproteins into smaller peptides.
2. reversibly capturing the mixture of sugar-bearing polypeptides or sugar-bearing peptides onto a hydrophobic solid phase support.
3. contacting the mixture of captured sugar-bearing polypeptides or sugar-bearing peptides with an oxidizing agent.
4. washing away the oxidizing agent from the solid phase support while the beta-eliminated polypeptides or peptides remain captured on the hydrophobic solid support.
5. contacting the oxidized polypeptides or peptides on the hydrophobic solid support with a first reactive modifier where the first reactive modifier is a bifunctional linker comprising a first reactive group that is either a hydrazide reactive group or an aminooxy reactive group that will react with aldehydes or ketones generated in the immobilized peptides or polypeptides by the oxidizing agent where the second reactive group remains available for further reaction.
6. washing away unreacted first reactive modifier from the labelled polypeptides or peptides on the solid support.
7. contacting the linker-labeled polypeptides or peptides on the solid support with a second reactive modifier where the second reactive modifier is a mass tag molecule that is reactive to the second reactive group in the linker from step (5) to give tagged polypeptides or peptides.
8. washing away unreacted tag molecule from the labelled polypeptides or peptides on the hydrophobic solid support.
9. Optionally contacting the reversibly immobilized peptides with further reactive modifiers and then washing away unreacted reactive modifiers as many times as desired to react further functional groups in the reversibly captured peptides.
10. eluting the tagged polypeptides or peptides from the hydrophobic support.
11. analysing the eluted polypeptides or peptides by mass spectrometry.

In preferred glycopeptide-labeling embodiments of the invention, peptides are reversibly captured by immobilisation onto a C18 resin through hydrophobic interactions as discussed elsewhere in this disclosure.

In preferred glycopeptide-labeling embodiments of the invention, peptides are typically digested with Trypsin or LysC but sequence specific chemical cleavage by Cyanogen Bromide may also be envisaged and the use of other endoproteases is also anticipated.

In preferred glycopeptide-labeling embodiments of the invention, peptides may be oxidized prior to reversible immobilization on a solid support. Enzymatic oxidation of galactose via galactose oxidase may be carried out in solution after digestion of peptides. Periodate oxidation may also be carried out prior to immobilization on a solid support. It may also be carried out on the solid support if that is desirable.

Periodate Oxidation of Glycopeptides:

Glycopeptides may be oxidized using sodium periodate in a suitable aqueous buffer. The use of an aqueous buffer means that the periodate oxidation can be carried out on resin when using C18 resins for reversible immobilization of peptides if that is desirable although oxidation with periodate can be carried out before immobilisation too.

Sodium periodate is a relatively mild oxidizing agent that will oxidise vicinal diols in exocyclic sugars and cis-diols in cyclic sugars to yield reactive aldehyde groups. The carbon-carbon bond is cleaved between adjacent hydroxyl groups. By altering the amount of periodate used, aldehydes can be produced on a smaller or larger selection of sugar types. For example, treatment of glycoproteins with 1 mM periodate primarily affects sialic acid residues, which frequently occur at the ends of polysaccharide chains. At concentrations of 6 to 10 mM periodate, other sugar groups in proteins will be affected such as internal mannose residues. At a concentration of 20 mM, periodate will even oxidise N-acetylglucosamine functions but reaction for extended periods is required (6 hours or overnight) (60).

A typical buffer for periodate oxidation comprises 20 mM Sodium Acetate and 150 mM Sodium Chloride at pH 5.0, with between 1 and 15 mM sodium meta-periodate (NaIO4) depending on the desired degree of carbohydrate oxidation. The reaction can be left at room temperature (RT) for one hour with stirring, agitation or shaking of the samples. Samples should be protected from light as periodate is light-sensitive. After oxidation, the excess sodium periodate is removed. In the context of this invention this is effected by reversibly immobilising the sample on a solid phase support, if the sample is not already on the solid support, and washing the sample on the support with a suitable aqueous buffer.

Figure 7:
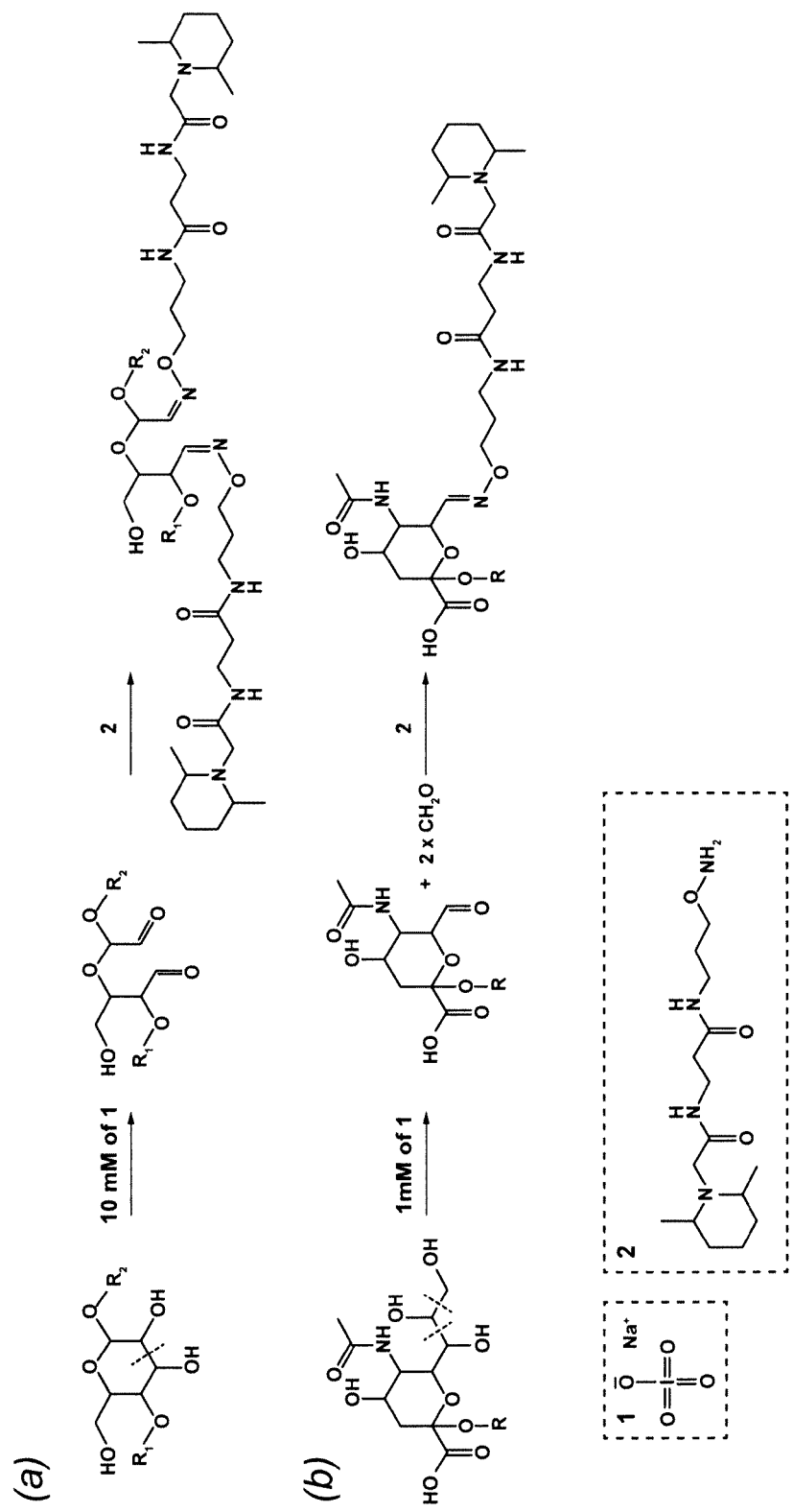
FIG. 7 illustrates a schematic of the oxidation of two different carbohydrate moieties using sodium periodate followed by labelling with an aminooxy-TMT reagent

FIG. 7 illustrates a schematic of the oxidation of two different carbohydrate moieties using sodium periodate followed by labelling with an aminooxy-TMT reagent.

Galactose Oxidase Oxidation of Glycopeptides:

Glycopeptides may also be oxidized using the enzyme Galactose Oxidase (Worthington Biochemical Corporation, Lakewood, N.J., USA) in a suitable aqueous buffer. The use of an aqueous buffer means that the Galactose Oxidase oxidation can be carried out on resin when using C18 resins for reversible immobilization of peptides if that is desirable although oxidation with Galactose Oxidase can be carried out before immobilisation too. A typical buffer for Galactose Oxidase oxidation is Phosphate Buffered Saline (PBS; 100 mM Sodium Phosphate, 150 mM Sodium Chloride; pH 7.4) with the addition of 1 mM Calcium Chloride and 1 mM Magnesium Chloride. Galactose Oxidase is added in PBS, typically to give a final reaction concentration of 0.2 to 0.5 units of activity per ml of solution with target protein at a concentration of up to 1 mg/ml.

Galactose Oxidase will oxidize galactose sugar residues to Galacto-hexodialdose. FIG. 6 illustrates Chemoenzymatic Labelling of Glycopeptides:

In further preferred embodiments of this invention, glycopeptides may be characterised by so-called chemoenzymatic labelling. The detection of O-linked N-acetylglucosamine functions in particular by this method has been described in the academic literature (61) and in patents (see for example U.S. Pat. No. 7,332,355). The chemoenzymatic method uses the ability of mutant beta 1,4-galactosyltransferase to transfer galactose analogues bearing reactive handles onto N-acetylglucosamine functions on proteins or peptides. This reactive handle then allows the subsequent introduction of further labelling agents.

Figure 8:
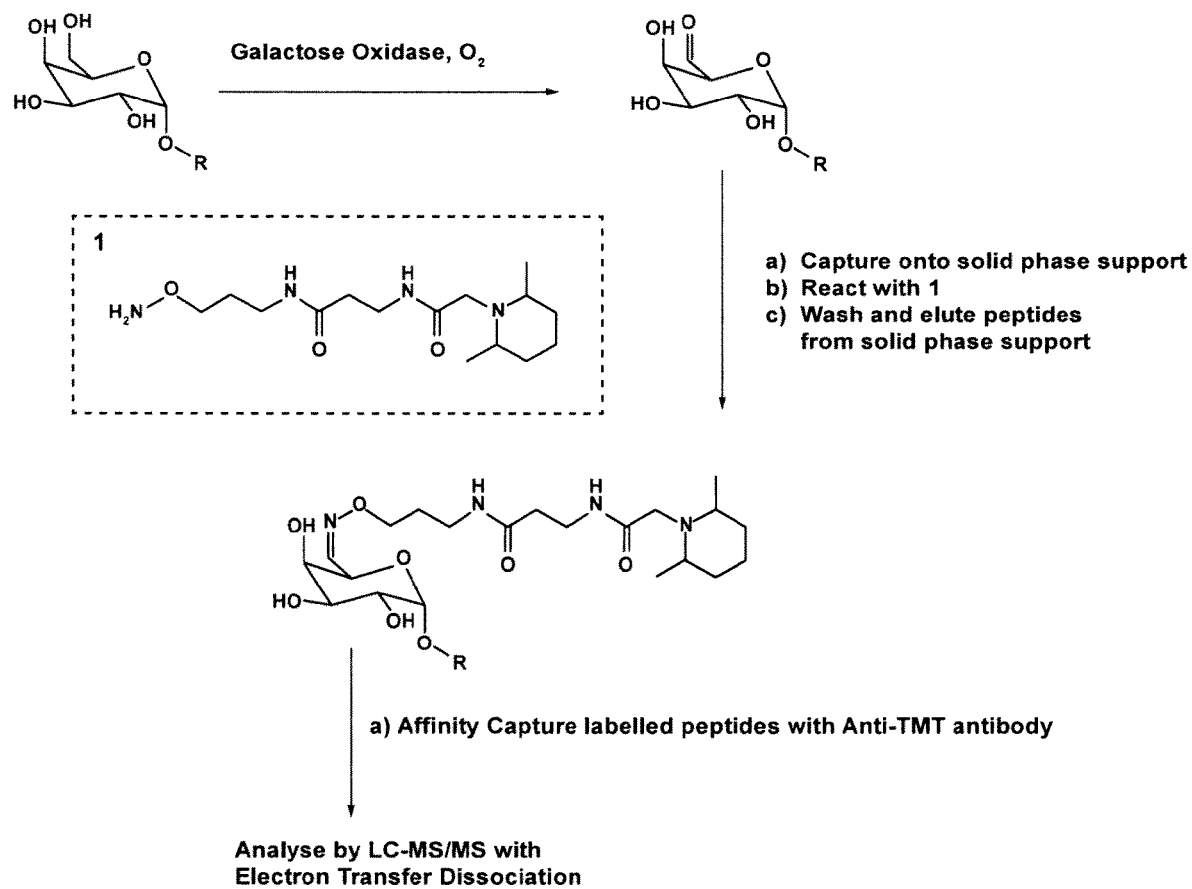
FIG. 8 illustrates a schematic of the oxidation a carbohydrate moiety comprising a terminal galactose residue using Galactose Oxidase followed by labelling with an aminooxy-TMT reagent.

In a method shown schematically in FIG. 8, N-acetylglucosamine functions are labelled with a ketone-functionalised UDP-galactose analogue, reagent 1 shown outlined in the figure. A peptide population comprising N-acetylglucosamine-modified peptides is captured onto a C18 resin in step (a) of the protocol. The ketone-galactose analogue is transferred from the corresponding UDP-galactose analogue by mutant beta 1,4-galactosyltransferase in step (b) of the reaction. In step (c), the spent enzyme and reagents from step (b) are washed away. Any N-acetylglucosamine peptides are now ketone-functionalised and are then reacted, in step (d), with an aminooxy-TMT reagent (Reagent 2 outlined in FIG. 7). In step (e), unreacted TMT and buffer is washed away and then the labelled peptides can be eluted in step (e). In step (f), the labelled peptides can be selectively enriched by contacting the eluted peptides a solid support bound anti-TMT antibody. The enriched peptides can then be eluted again for analysis by LC-MS.

Where glycopeptides are labelled on the carbohydrate residue and where the whole labelled glycopeptide is analysed, it may be desirable to analyse the peptides using Electron Transfer Dissociation (ETD) or Electron Capture Dissociation (ECD) rather than CID as illustrated in the final step of FIG. 8. In CID, the glycan functions, particularly of O-linked glycopeptides, fragment preferentially (by beta-elimination in O-linked glycopeptides). If labelled glycopeptides are analysed by CID with the TMT label on the glycan, the labelled glycan will eliminate as a protonated residue without significant fragmentation of the TMT but the labelled glycan fragment can be analysed further by $MS^3$ along with separate $MS^3$ analysis of the peptide fragment by CID. However, ETD or ECD will typically produce fragmentations in all of the peptide, sugar and TMT tag components of the labelled glycopeptide simultaneously enabling complete analysis of the labelled glycopeptide by $MS^2$ analysis, which is likely to be more sensitive and more rapid than $MS^3$ analysis (62,63). Glycopeptides can also be analysed by alternating CID and ETD to get complementary fragmentation data if desired (64).

Affinity Capture and Other Enrichment Methods for Glycopeptide Isolation:

As discussed above, glycopeptides can be analyzed by direct labelling of carbohydrates or by affinity capture or chemical capture of glycopeptides to isolate a pure population followed by labelling of amino groups on peptides.

Various natural carbohydrate-binding affinity agents exist and some are commercially available. Lectins are a family of carbohydrate-binding proteins with varying specificities for carbohydrate functions on proteins and peptides. For example, Concanavalin A (ConA) is a lectin that binds mainly to internal and non-reducing terminal α-D-mannosyl and terminal α-D-glucosyl residues. Similarly, Wheat Germ Agglutinin (WGA) selectively binds to N-Acetyl glucosamine (GlcNAc) groups and to sialic acid functions. Both ConA and WGA are available as affinity reagents for carbohydrate and glycoprotein affinity purification (Thermo Scientific, Pierce, Rockford, Ill., USA). Glycoproteins can be enriched from complex biological samples by use of commercially available affinity purification products such as spin columns and these enriched populations of proteins can then subjected to analysis using amine-reactive labels according to this invention.

However, specificity and binding affinity of these reagents is currently not as high as the corresponding phosphate affinity-capture reagents for phosphopeptide analysis.

Oxidized glycoproteins, treated using the oxidation methods discussed above (Periodate and Galactose Oxidase) can be reacted with aminoxy-functionalized or hydrazide-functionalized biotin reagents allowing affinity purification using avidin. Preferably, cleavable biotinylation reagents should be used to facilitate recovery of the peptides from avidin as elution of biotin from avidin requires harsh conditions due to the strong bind of biotin to avidin. Cleavable disulphide linked aminoxy-functionalized biotin is commercially available under the name EZ-Link Alkoxyamine-PEG4-SS-PEG4-Biotin (Thermo Scientific, Pierce, Rockford, Ill., USA). Avidin-captured peptides are recovered from avidin by reduction of the disulphide bond, which can be blocked with iodoacetamide or can be reacted with Iodoacetamide-TMTs, discussed above.

Oxidized glycoproteins, glycopeptides or free glycans, treated using the oxidation methods discussed above (Periodate and Galactose Oxidase) can be reacted with amine-functionalized, aminoxy-functionalized or hydrazide-functionalized solid phase supports (65,66). Amine-functionalized supports and hydrazide-functionalized supports enable reversible capture of carbonyl-functionalized molecules. Aniline catalysed reaction of carbonyls with an amine or hydrazide-support under basic conditions will promote capture of oxidised glycoproteins or glycopeptides or free glycans while acidic conditions will facilitate release of glycopeptides, glycoproteins and glycans. Basic conditions will keep glycopeptides, glycoproteins and glycans on the solid support allowing washing of the support to remove unmodified peptides, detergents and other unwanted reagents as long as basic wash buffers are used. On-resin labelling of free amino groups can be effected on captured glycopeptides using NHS-TMT reagents. Hydroxylamine can also be used to facilitate cleavage of oxidized glycopeptides or glycans captured on hydrazide resins.

Alternatively, the peptide portion of N-linked glycopeptides can be enzymatically cleaved from conjugates captured via avidin supports or reactive solid supports using the enzyme peptide-N-glycosidase F (PNGaseF). PNGaseF cleaves the amide bond between asparagine and a variety of carbohydrate functions in N-linked glycopeptides producing free peptide and glycan.

Mass Series Modifiers:

As mentioned above, in patents WO 01/68664, WO 03/25576, WO 07/012849 and WO 11/036059 the concept of 'mass series modifiers', is discussed. In these patents, different chemistries are described by which sets of isobaric tags may be modified. A mass-series modifier is a linker that changes the overall mass of each of the members in a set of isobaric tags to give a new set of isobaric mass tags. In patents WO 01/68664, WO 03/25576, WO 07/012849 and WO 11/036059, a mass-series modifier is introduced as a linker between the mass tag and the reactive function used to couple to tag to a molecule of interest:

Mass Tag-Mass Series Modifier-Reactive Function

This means that starting from a set of 10 mass tags and 3 Mass Series Modifiers, 30 tags (3×10) can be constructed in three offset isobaric sets. For example, consider the amine-reactive isobaric tag pair below:

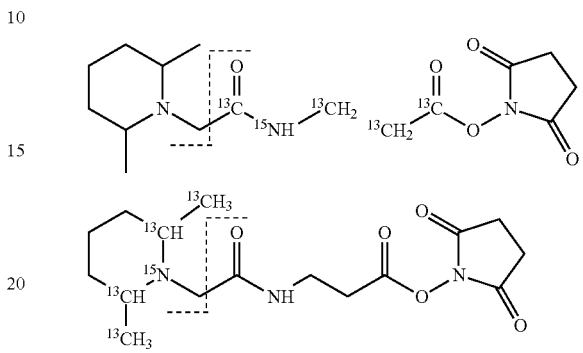

With three mass series modifiers comprising isotopes of beta-alanine, 3 pairs of isobaric tags can be created as shown below:

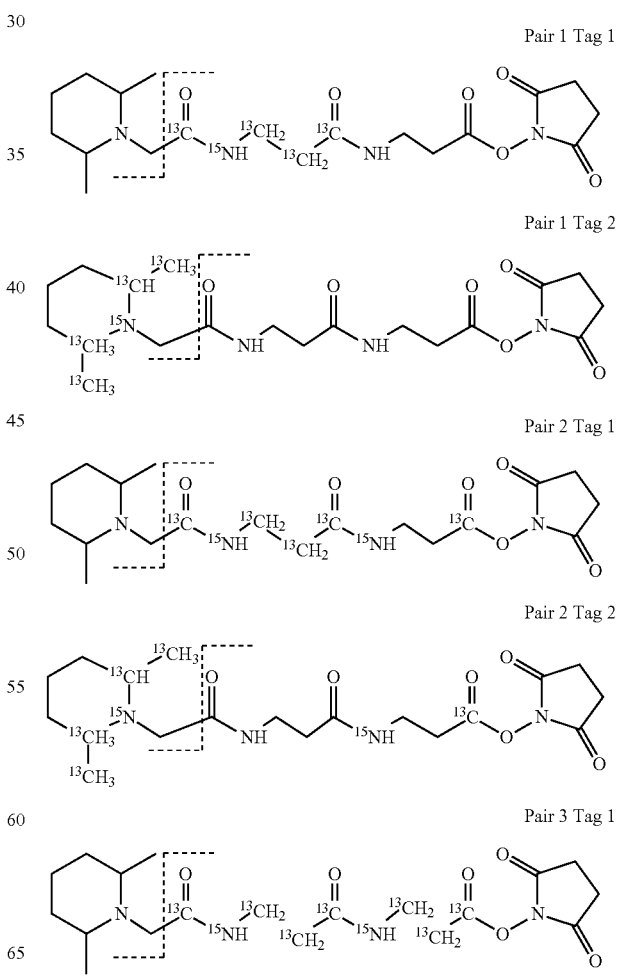

Pair 3 Tag 2

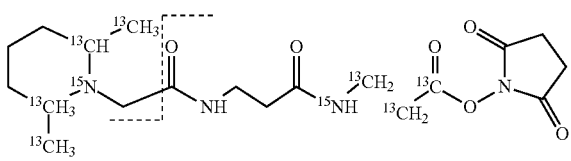

Note in the 6 tags above that the beta-alanine linker is introduced between the tag structure and the N-hydroxysuccinimide ester amine-reactive group. Pair 2 is approximately 2 daltons heavier than Pair 1. Similarly, Pair 3 is 4 approximately daltons heavier than Pair 1 and approximately 2 daltons heavier than Pair 2.

While this approach works well, it does mean that each of the 6 tags shown above must be synthesised individually prior to use. Similarly with 10 tags in an isobaric tag set (or in a set of isotopologue tags with millidalton mass differences) and 3 mass series modifiers, all 30 tags would have to be synthesized individually.

It would however be more convenient if the mass series modifiers could be synthesized separately and then coupled to a target biomolecule prior to coupling of Isobaric Mass Tags or Millidalton Mass Tags.

Accordingly, in some preferred aspects of the invention, peptides reversibly captured onto a solid phase support are reacted with an isotope-doped bifunctional linker with which the mass tag is then reacted. In these preferred embodiments, the isotope-doped bifunctional linker act as mass series modifiers.

For example a series of three mass-differentiated isotopic bifunctional linkers comprising an amine-reactive N-hydroxysuccinimide ester, a beta-alanine linker to act as a mass series modifier and a protected thiol (pyridyldithio-group) are shown below:

Example Mass Series Modifier Set 1:

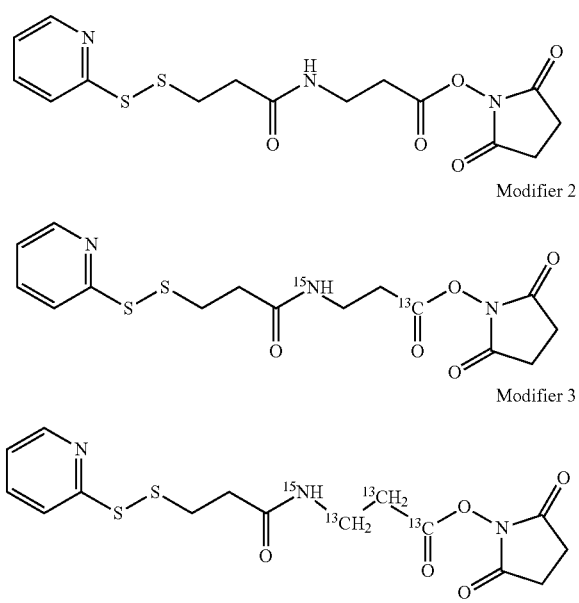

The three bifunctional mass series modifiers shown above can be combined with a series of thiol-reactive iodoacetamide modified isobaric mass tags as shown below:

Example Isobaric Mass Tag Set 1:

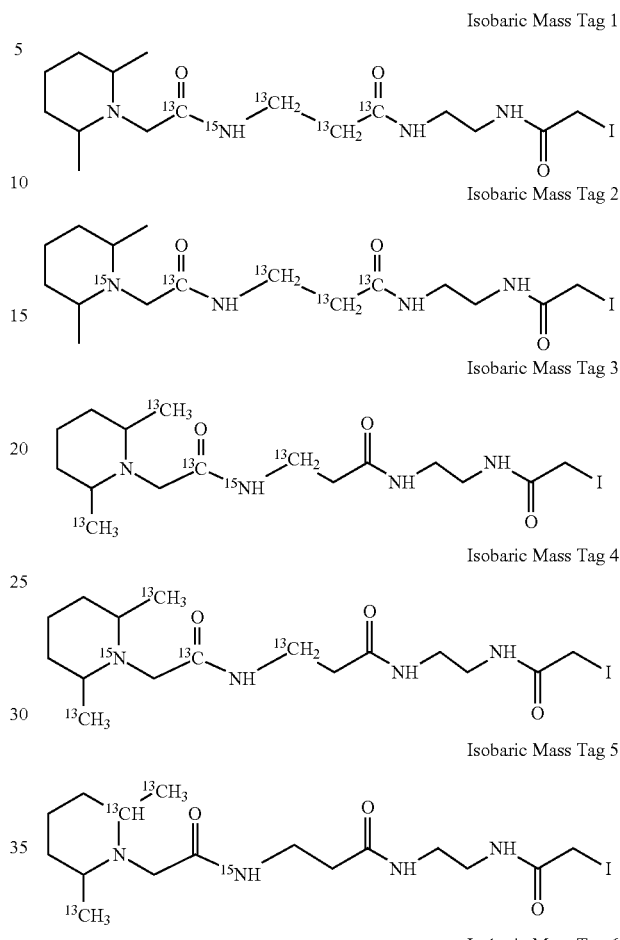

Figure 9:
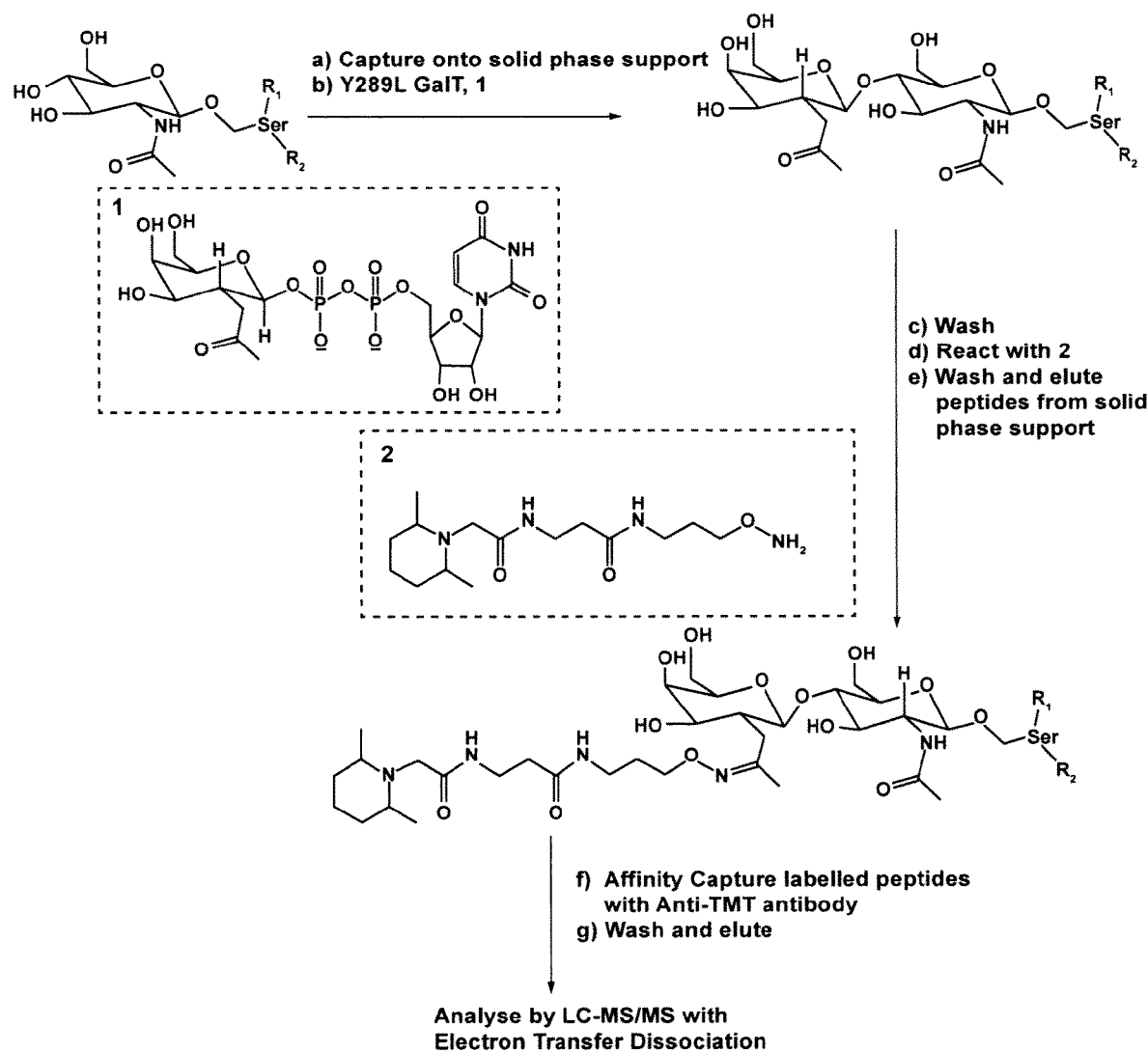
FIG. 9 illustrates a schematic of a chemoenzymatic labelling protocol in which mutant Beta 1,4-Galactosyltransferase is used to introduce a chemical handle (ketone) into an O-linked N-acetylglucosamine residue followed by labelling with an aminooxy-TMT reagent.
Figure 10:
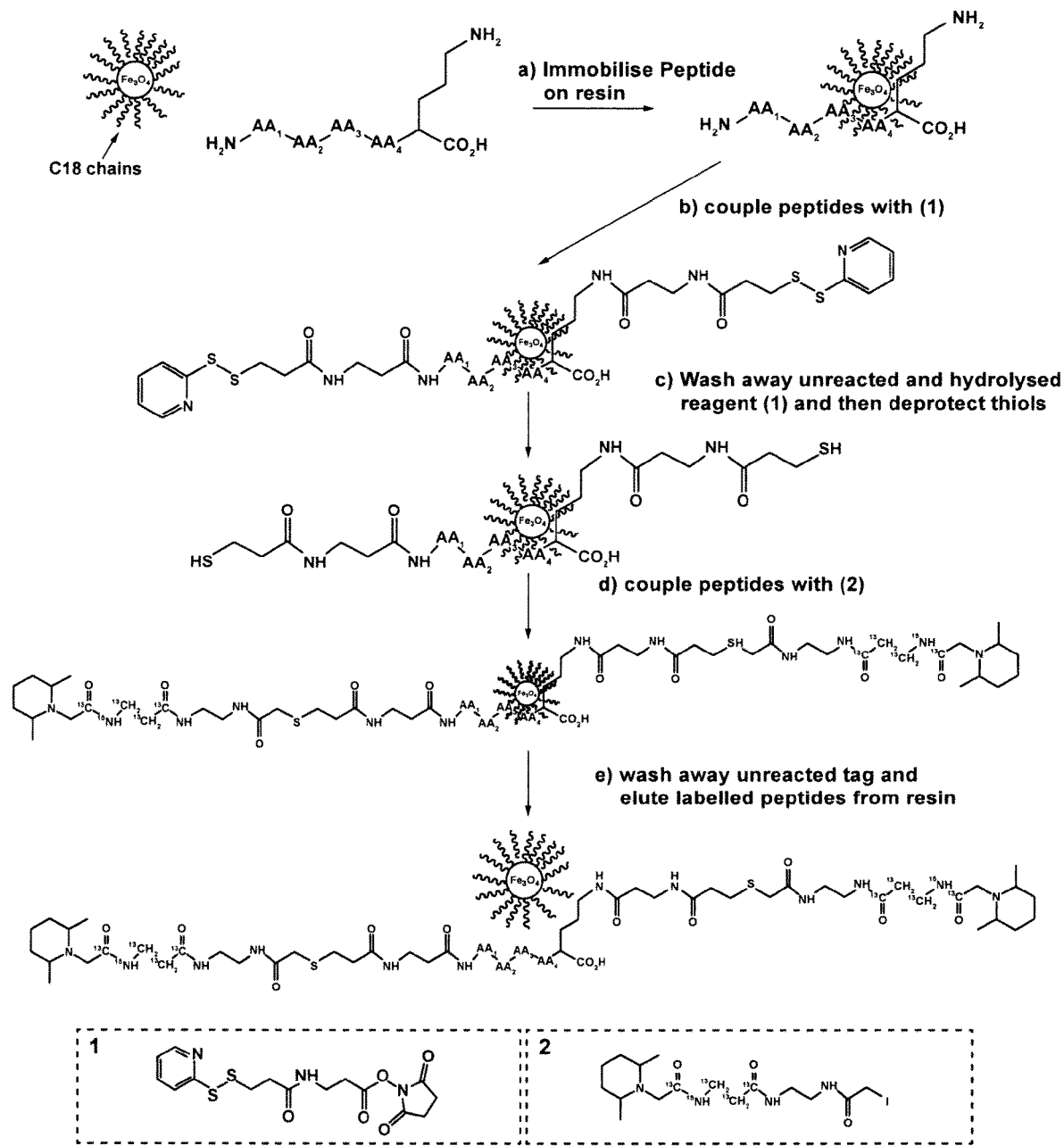
FIG. 10 shows a labelling protocol according to an embodiment of the invention.

The thiol-reactive iodoacetamide-activated 6-plex isobaric tag set shown above can be combined with the Example Mass Series Modifier Set 1 as shown in FIG. 9. In FIG. 10, step (a), a peptide is reversibly immobilised on C18-functionalized hydrophobic magnetic particles, which are preferably nanoparticles although non-magnetic particles could be used either as a slurry or in a column format. In this example, the peptide would be reduced, e.g. with dithiothreitol (DTT) or Tris-(carboxyethyl)phosphine (TCEP), and then it would be reacted with iodoacetamide to block any free thiols. This thiol-capping reaction may take place prior to immobilization or after immobilization but prior to step (b), and the C18 particles would be washed to remove any unreacted reagents. The peptide is then contacted, in step (b), with Modifier 1 from Example Mass Series Modifier Set 1, but the peptide could be coupled with any of the three modifiers. Different samples of the peptide could be coupled with different modifiers. In fact, 18 different samples of the peptide could be labelled in sets of 6 with each of the three modifiers. After coupling of the Modifier as shown in FIG. 10, any unreacted modifier can be washed away and the pyridyldithio group is reduced with a suitable reducing agent (DTT or TCEP) to expose a thiol group. The exposed thiols are then reacted with Mass Tag 1 from Example Isobaric Mass Tag Set 1, which is an iodoacetamide-functionalised mass tag, marked as (2) in FIG. 9. Reagent (2) reacts with any free thiols in the reversibly immobilized peptides. Any of the mass tags from Example Isobaric Mass Tag Set 1 could be used in this step. If the protocol shown in FIG. 10 is reacted making every combination of every modifier from Example Mass Series Modifier Set 1 with every mass tag from Example Isobaric Mass Tag Set 1, 18 samples of the immobilized peptide can be produced with a mass spectrometrically resolvable mass tag/mass series modifier combination. After labelling with (2), unreacted tag is washed away with aqueous wash solvent and the peptide is then eluted in a buffer comprising mostly organic solvent such as acetonitrile for analysis by mass spectrometry.

Compared with previous approaches, where it would be necessary to make 18 different reagents prior to labelling a peptide sample, with the approach described above, only 9 reagents are necessary (3 mass series modifiers and 6 tags) although a two-step labelling protocol is required. However, the methods of this invention make it convenient to carry out multi-step process in a readily automatable format. Higher level multiplexing can be achieved by producing more mass tags and mass series modifiers but the total number of reagents necessary is greatly reduced making high-level multiplexing much more cost-effective.

It should be clear to one of ordinary skill in the art that although FIG. 10 shows only a single peptide, the method can be applied to complex mixtures of peptides. Similarly, the same method can be applied to label other types of biomolecules including glycans, steroids, lipids and oligonucleotides.

In previously described embodiments of this invention which employ bifunctional linkers such as labelling of beta-eliminated phosphate sites or beta-eliminated O-linked sugar sites or oxidized carbohydrates, it is possible to make isotopes of the bifunctional linkers used in accordance with this aspect of the invention. Thus, as discussed previously, a linker for reacting with a biological Michael acceptor must comprise a nucleophile that will react with the Michael acceptor and again the preferred nucleophiles for these applications are amino groups or thiol groups. The bifunctional linker must then also comprise a reactive group with which the mass tag can be reacted. In the some embodiments a diamino linker may be used where one amino group will react with the Michael acceptor and one will be free to react with the mass tag. If a diamine-linker is used, preferably a symmetric diamine is used so that it does not matter which amine reacts to the Michael acceptor, although it does not matter if heavy isotopes are distributed within the molecule in an asymmetric fashion. Similarly, an amino-thiol linker may be used. Since the linker is reacted with the phosphosite or glycosite first, in this embodiment, the thiol from the linker will react with the Michael acceptor again leaving an amino group for reaction with the mass tag. In embodiments of this invention where a bifunctional linker provides an amino group for reaction with the mass tag, the mass tag must therefore be amine-reactive. In preferred embodiments the amine-reactive group may be an active ester, preferably an N-hydroxysuccinimide ester.

In other preferred embodiments where a bifunctional linker is used to couple a mass tag to a phosphosite or glycosite Michael Acceptor for example, the bifunctional linker is a dithiol, preferably a symmetric dithiol so that it does not matter which thiol reacts to the Michael acceptor. If a large excess of the dithiol is used the linker will be very unlikely to cross-link peptides to each other. Similarly, since the methods of this invention, reversibly immobilise peptides on a solid support, cross-linking is also sterically less favoured. In dithiol embodiments, the mass tag must comprise a thiol reactive functionality, such as an iodoacetamidyl group or a Michael acceptor, such as a maleimide or vinyl sulphone reactive group.

While isotopes of all of the bifunctional linkers discussed previously are likely to be applicable in this mass series modifier aspect of the invention, it may be desirable to have longer linkers to allow for introduction of more heavy isotope nuclei into linker structures.

It should be clear to one of ordinary skill in the art that although FIG. 10 and Example Mass Series Modifier Set 1 shown above shows one particular bifunctional linker, different possible structures for the bifunctional linker could be used. Some different examples are shown below:

Example Mass Series Modifier 2:

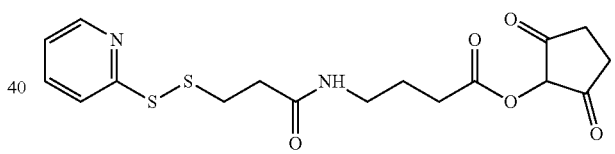

Example Mass Series Modifier 3:

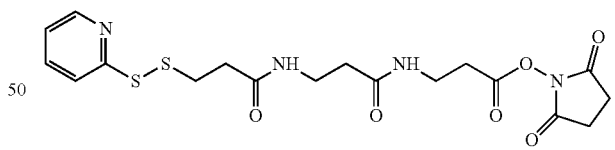

Example Mass Series Modifier 4:

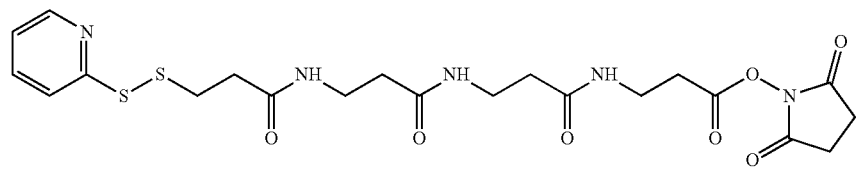 [SMILES: O=C(CCNC(=O)CCSSc1ccccn1)NCCC(=O)NCCC(=O)ON1C(=O)CCC1=O]

In Example Mass Series Modifier 2, a gamma-aminobutyric acid (GABA) linker has replaced the beta-alanine linker used in the structure shown in FIG. 9 and in Example Mass Series Modifier Set 1. Similarly, the single beta-alanine linker used in the structure shown in FIG. 10 and in Example Mass Series Modifier Set 1 has been replaced with two beta-alanine linkers in Example Mass Series Modifier 2 and with three beta-alanine linkers in Example Mass Series Modifier 3.

In general embodiments of these mass series modifier aspects of the invention, the bifunctional linker that acts as a mass series modifier preferably comprises the general formula as shown below:

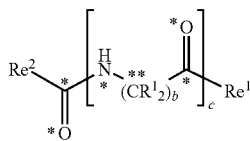

Where $Re^1$ comprises a first reactive group that is selected to be reactive to a functional group in the target molecule, $Re^2$ comprises a second reactive group that is selected to be reactive to a functional group in a mass tag reagent and where each $R^1$ is independently H, a substituted or unsubstituted straight or branched $C_1$-$C_6$ alkyl group, a substituted or unsubstituted aliphatic cyclic group, a substituted or unsubstituted aromatic group or a substituted or unsubstituted heterocyclic group or an amino acid side chain; and b is an integer from 1-10 and c is an integer from 1 to 10; and wherein * is an isotopic mass adjuster moiety and * represents that oxygen is $^{18}O$, carbon is $^{13}C$ or nitrogen is $^{15}N$ or at sites where hydrogen is present, * may represent $^{2}H$.

In some embodiments, $Re^2$ may comprise a protected reactive group that is deprotected prior to reaction with a mass tag. In FIG. 9 and in Example Mass Series Modifier Set 1, the mass series modifier linker comprises a pyridyldithio group at the $Re^2$ position, which can be reduced to expose a free thiol.

In embodiments of these mass series modifier aspects of the invention, the mass tag that is coupled to each mass series modifier preferably comprises the general formula below:

MT-$Re^3$

Where MT is a mass tag and preferably MT is a tag that is part of an isobaric set or MT is part of a set of Millidalton Mass Tags and $Re^3$ is reactive with $Re^2$ or with a deprotected form of $Re^2$.

Various combinations of $Re^1$ and $Re^2$ are shown in the table 2 below:

TABLE 2

| $Re^2$ | $Re^1$ |
|---|---|
|  | |

TABLE 2-continued

| Re² | Re¹ |
| --- | --- |

TABLE 2-continued

| Re² | Re¹ |
|---|---|

TABLE 2-continued

| Re² | Re¹ |
|---|---|

TABLE 2-continued

| Re² | Re¹ |
| --- | --- |

TABLE 2-continued

| Re² | Re¹ |
|---|---|

TABLE 2-continued

| Re² | Re¹ |
|---|---|
| (chemical structures shown) | |

In several preferred embodiments, the Mass Series Modifier reagents of this invention comprise a first reactive group that is amine-reactive and second reactive group that comprises a protected amino group which can be deprotected, after coupling of the Mass Series Modifier reagent with amino groups in the target molecule, for later modification with an amine-reactive tag. The examples listed in Table 2 above are not comprehensive and further amino-protecting reagents are known in the art that could be applied with this invention however, preferred protecting groups should be removable in substantially aqueous conditions, using 5% or less of organic solvent. Boc-protected amino groups are useful. Those modifiers are relatively simple to introduce into amino groups, and aqueous Boc-deprotection has been reported (67). Furthermore, a Boc group is relatively hydrophobic, which means that it will adhere well to a hydrophobic solid phase support. Similarly, the AZOC protecting group is relatively hydrophobic and may be removed under aqueous conditions (68).

It should be understood that Table 2 is for the purposes of illustration and that one of ordinary skill in the art would be aware of variations. For example, the amine-reactive N-hydroxysuccinimide ester could be changed for different active esters, such as a Sulfo-N-hydroxysuccinimidyl ester, a pentafluorophenyl ester, a tetrafluorophenyl ester or a (4-sulfo-2,3,5,6-tetrafluorophenyl) ester. Similarly, the maleimidyl function could be changed for a different Michael acceptor, such as a vinylsulphone or a propenylsulphone.

Various combinations of $Re^2$ and $Re^3$ are shown in the table 3 below:

In Table 3, the structure of MT is as follows:

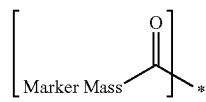

Where the mass marker is preferably an Isobaric Mass Tag or an Isotopologue Millidalton Mass Tag as discussed above.

It should be understood that Table 3 is for the purposes of illustration and that one of ordinary skill in the art would be aware of variations as discussed for Table 2. Pairs 3 and 4 illustrate Mass Tags and Mass Series Modifiers that employ azides and alkynes, which will react by azide/alkyne cycloaddition to form a triazole linkage as discussed earlier. Pairs 5 and 6 illustrate examples of the reagents that can undergo traceless Staudinger ligation, where the Mass tag (MT) entities are activated with Phosphines that will react with azides to leave the MT and Mass Series Modifier linked by an amide bond.

Similarly, the Mass Series Modifiers and Mass Tags according to this aspect of the invention are applied according to the methods of this invention, where analytes are labelled according to the following method:
a. reversibly capturing the one or more analytes onto a solid phase support
b. contacting the captured analyte(s) with a first reactive modifier which comprises a mass series modifier which reacts with a first functional group of the analyte(s) thereby introducing a new functional group into the analytes;
c. contacting the modified analyte(s) of step b) with a second reactive modifier which comprises a mass label that reacts with the new functional group introduced into the analytes by the first reactive modifier.
d. Optionally repeating step b) and step c) to react further functional groups in the analyte with further reactive modifiers; and
e. optionally eluting the sample from the solid phase support;
wherein the mass series modifier preferably comprises the general formula:

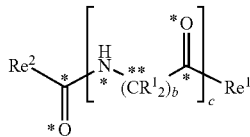

Where $Re^1$ comprises a first reactive group that is selected to be reactive to a functional group in the target molecule, $Re^2$ comprises a second reactive group that is selected to be reactive to a functional group in a mass tag reagent and where each $R^1$ is independently H, a substituted or unsubstituted straight or branched $C_1$-$C_6$ alkyl group, a substituted or unsubstituted aliphatic cyclic group, a substituted or unsubstituted aromatic group or a substituted or unsubstituted heterocyclic group or an amino acid side chain; and b is an integer from 1-10 and c is an integer from 1 to 10; and wherein * is an isotopic mass adjuster moiety and * represents that oxygen is $^{18}O$, carbon is $^{3}C$ or nitrogen is $^{15}N$ or at sites where hydrogen is present, * may represent $^{2}H$; and wherein the mass label is an Isobaric Mass Tag as defined previously and has the general formula:

V-L-M-Re³ wherein V is a mass marker moiety, L is a linker cleavable by dissociation in a mass spectrometer and M is a mass normalisation moiety which ensures that the mass label has a desired aggregate mass, and $Re^3$ comprises a reactive functionality which reacts with $Re^2$ in the mass series modifiers;
or wherein the mass label is a Millidalton Mass Tag and has the general formula:

T-Re³

Where T is a Mass Tag as defined previously for Millidalton Mass Tags and $Re^3$ comprises a reactive functionality which reacts with $Re^2$ in the mass series modifiers. Where at least one of, and sometimes both of, T and $Re^3$ is or are modified with heavy isotopes to create isotopic tags of different masses.

In another preferred embodiment of the mass series modifier aspect of the invention, peptides reversibly captured onto a solid phase support are reacted with an isotope-doped bifunctional linker where the doped bifunctional linker that acts as a mass series modifier comprises an NHS-ester to react with free amines in the immobilized peptides and an azide, which is used as a protected amine with which an NHS-ester activated mass tag can be reacted after reduction of the azide to an amine as shown in FIG. 12.

For example a series of three mass-differentiated isotopic bifunctional linkers comprising an amine-reactive N-hydroxysuccinimide ester, two beta-alanine linkers that act as mass series modifiers and an azide are shown below:

Example Mass Series Modifier Set 5:

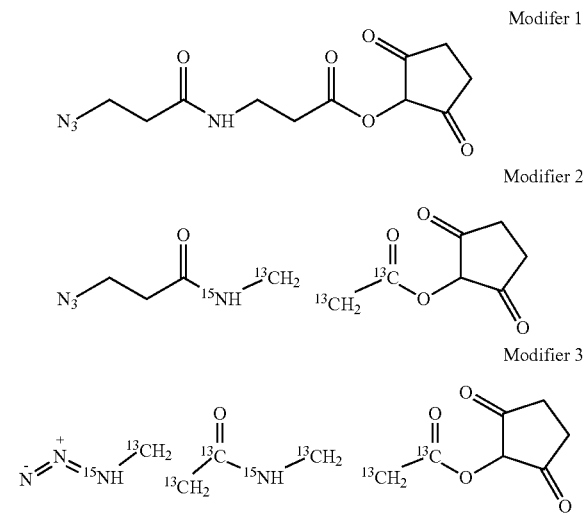

Figure 11:
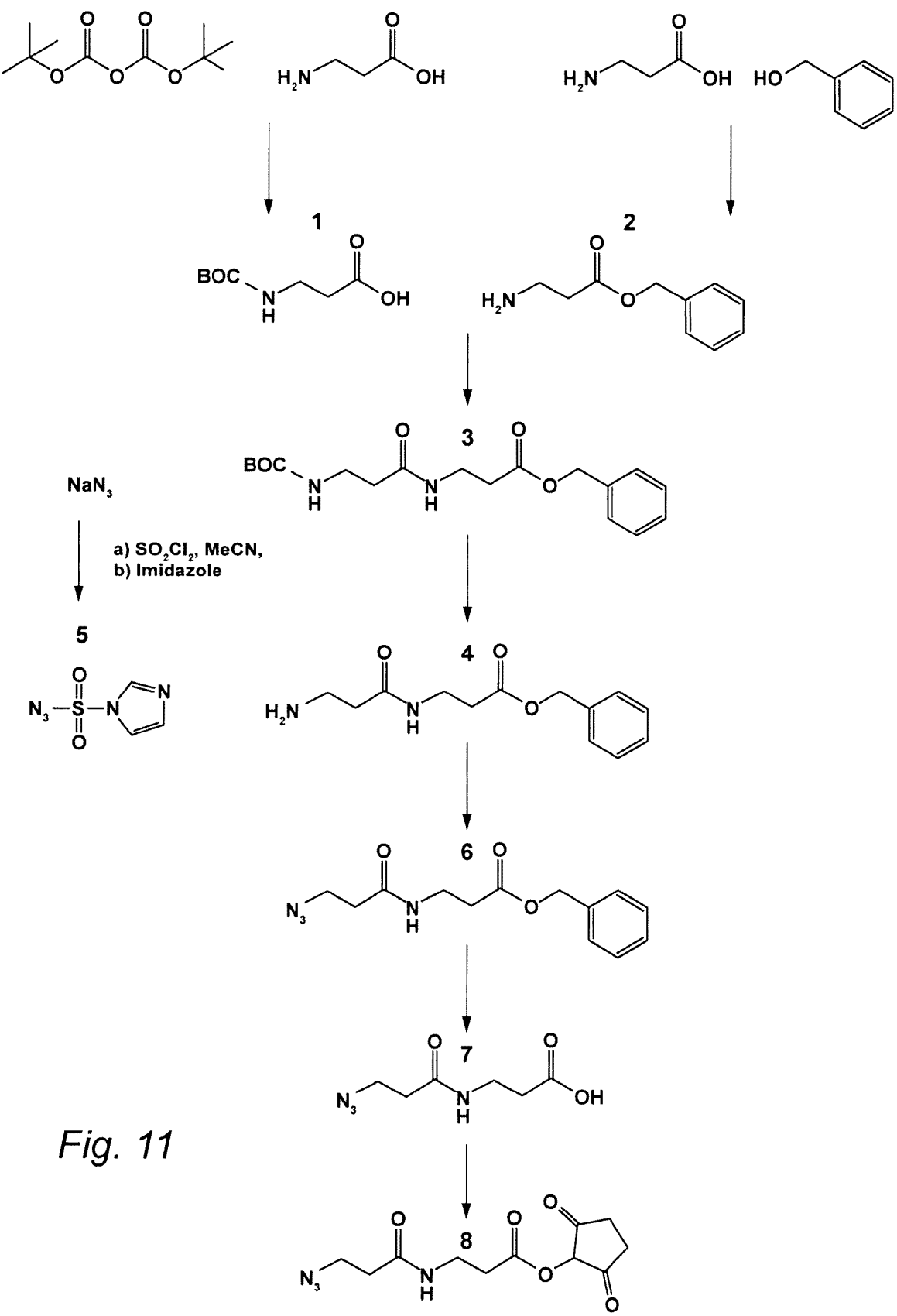
FIG. 11 shows a synthesis route for the production of the linkers shown in Example Mass Series Modifier Set 5.

FIG. 11 shows a synthesis route for the production of the bifunctional linkers shown in Example Mass Series Modifier Set 5. The synthesis starts with beta-alanine, which may comprise heavy isotopes. Two different protected forms of beta-alanine are prepared. In the first reaction, beta-alanine is reacted with Di-tert-butyl dicarbonate (BOC-anhydride) to give beta-alanine that is protected at the amino group with a BOC protecting group (1). In the second step beta-alanine is esterified to give a benzyl ester protecting the carboxyl group (2). The BOC-protected beta-alanine (1) is then coupled with the benzyl-protected beta alanine (2) to give a double beta-alanine linker (3). Various isotopes of beta-alanine are commercially available allowing the synthesis of a large number of different isotopes of this linker enabling the production of a large number of isotopic mass series modifiers. Product (3) is then treated to deprotect the BOC-amine giving the free amine (5). Aqueous phosphoric acid is a mild reagent for the deprotection of tert-butyl carbamates (67). In parallel, the azidification reagent imidazole-1-sulfonyl azide (4) is prepared by treating sulfuryl chloride with sodium azide in acetonitrile, followed by the addition of excess imidazole (69). The amine product (5) is then contacted with the reagent (4) to give the azide product (6). Product (6) is then deprotected to give the free acid (7), which is in turn activated with a carbodiimide in the presence of N-hydroxysuccinimide to give the corresponding N-hydroxysuccinimide ester (8).

The three bifunctional mass series modifiers shown above can be combined with a series of amine-reactive NHS-activated isobaric mass tags as shown below:

Example Isobaric Mass Tag Set 2:

Isobaric Mass Tag 1 (TMT6-126):

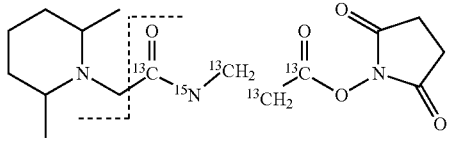

Isobaric Mass Tag 2 (TMT6-127):

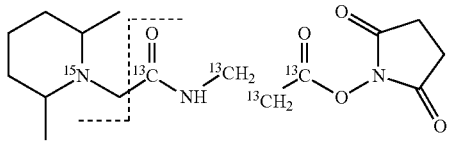

Isobaric Mass Tag 3 (TMT6-128):

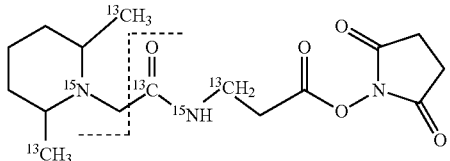

Isobaric Mass Tag 4 (TMT6-129):

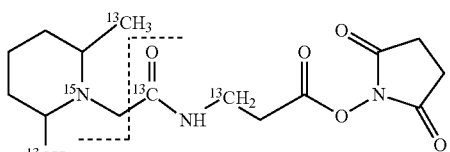

Isobaric Mass Tag 5 (TMT6-130):

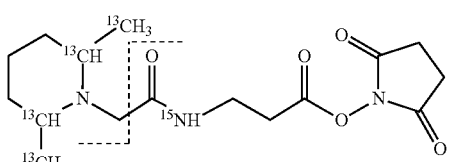

Isobaric Mass Tag 6 (TMT6-131):

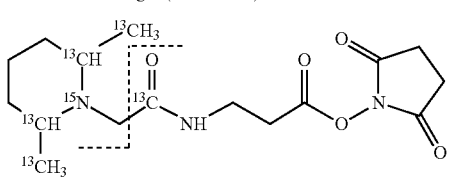

The amine-reactive NHS ester-activated 6-plex isobaric tag set shown above can be combined with the Example Mass Series Modifier Set 5 as shown in FIG. 12. In FIG. 12, step (a), a peptide is reversibly immobilised on C18-functionalized hydrophobic magnetic particles, which are preferably nanoparticles although non-magnetic particles could be used either as a slurry or in a column format. In this example, the peptide would be reduced, e.g. with dithiothreitol (DTT) or Tris-(carboxyethyl)phosphine (TCEP), and then it would be reacted with iodoacetamide to block any free thiols. This thiol-capping reaction may take place prior to immobilization or after immobilization but prior to step (b), and the C18 particles would be washed to remove any unreacted reagents. The peptide is then contacted, in step (b), with Modifier 1 from Example Mass Series Modifier Set 2, but the peptide could be coupled with any of the three modifiers.

Different samples of the peptide could be coupled with different modifiers. In fact, 18 different samples of the peptide could be labelled in sets of 6 with each of the three modifiers. After coupling of the Modifier as shown in FIG. 12, any unreacted modifier can be washed away and the azide group is reduced with a suitable reducing agent (DTT or TCEP) to expose a free amino group. The exposed amines are then reacted with Mass Tag 1 from Example Isobaric Mass Tag Set 2, which is an NHS ester-functionalised mass tag, marked as (2) in FIG. 12. Reagent (2) reacts with any free amines in the reversibly immobilized peptides. Any of the mass tags from Example Isobaric Mass Tag Set 2 could be used in this step. If the protocol shown in FIG. 12 is reacted making every combination of every modifier from Example Mass Series Modifier Set 5 with every mass tag from Example Isobaric Mass Tag Set 2, 18 samples of the immobilized peptide can be produced with a mass spectrometrically resolvable mass tag/mass series modifier combination. After labelling with (2), unreacted tag is washed away with aqueous wash solvent and the peptide is then eluted in a buffer comprising mostly organic solvent such as acetonitrile for analysis by mass spectrometry.

Compared with previous approaches, where it would be necessary to make 18 different reagents prior to labelling a peptide sample, with the approach described above, only 9 reagents are necessary (3 mass series modifiers and 6 tags) although a two-step labelling protocol is required. However, the methods of this invention make it convenient to carry out multi-step process in a readily automatable format. Higher level multiplexing can be achieved by producing more mass tags and mass series modifiers but the total number of reagents necessary is greatly reduced making high-level multiplexing much more cost-effective.

It should be clear to one of ordinary skill in the art that although FIG. 12 shows only a single peptide, the method can be applied to complex mixtures of peptides. Similarly, the same method can be applied to label other types of biomolecules including glycans, steroids, lipids and oligonucleotides. Similarly, the linkers comprising the Mass series modifiers in Example Mass Series Modifier Set 5 can also be varied considerably to produce different isotope spacings and/or larger numbers of linkers if that is desirable.

In the examples above, the Mass series modifiers have been isotopes of each other but non-isotopic mass series modifiers can be used together as well. For example, Mass Series Modifiers 2, 3 and 4 can all be used as mass series modifiers along with Modifier 1 from Examples Mass Series Modifier Set 1 to distinguish sets of samples from each other as the resulting labelled samples would all have different masses. Thus 4 different sets of samples could be produced by labelling with these 4 linkers and in combination with Example Isobaric Mass Tag Set 1 this would enable 6×4 or 24 individual samples to be multiplexed together. Similarly, isotopes of Mass Series Modifiers 2, 3 and 4 can all be prepared and as long as the individual masses differ from each other and all of these could be used together. Thus if 3 isotopes of each of the Mass Series Modifiers 2, 3 and 4 are prepared and combined with Example Mass Series Modifier Set 1, 12 different Mass Series Modifiers would be available and in combination with Example Isobaric Mass Tag Set 1, this would allow 6×12 or 72 individual samples to be multiplexed together.

Methods for analysing samples with high levels of multiplexing using isotopic mass series modifier offsets are discussed in the literature by Dephoure & Gygi (70). Similarly, methods for analysing peptides label with isobaric tags comprising non-isotopic mass modifier offsets are discussed by Everley et al. (71).

Further Applications of Mass Series Modifiers for the Analysis of Phosphopeptides:

It has been reported in the literature that phosphopeptides may be analysed using phosphatase treatment. In this approach, a sample containing phosphopeptides is split into two equal aliquots where a first aliquot is labelled with a first isotopic mass tag and the second aliquot is labelled with a second isotopic mass tag. The second aliquot of phosphopeptides is then also treated to remove the phosphate groups from the phosphopeptides in the sample. This is typically effected with alkaline phosphatase (72) but more recently, it has been reported that incubation of the sample with Cerium Oxide nanoparticles will remove the phosphate groups more completely (73,74). The second aliquot which is now labelled and dephosphorylated is then mixed back with the first aliquot and analyzed by Reverse Phase High Performance Liquid Chromatography Mass Spectrometry. Since the two aliquots of the sample containing phosphopeptides are identical except for the dephosphorylation in the second aliquot of any phosphopeptides, corresponding peptides in each aliquot, which are now labelled with different isotopic tags, will co-elute and appear in the recorded spectra as pairs of peaks shifted relative to each other according to the charge state of the ionized peptides and the mass of the isotopic label. Since the samples were split into two equal aliquots, the intensity of the ion peaks of the peptides that are not phosphorylated should be equal. However, any peptides that are phosphorylated should be dephosphorylated in the second aliquot and the dephosphorylated peptides will elute at a different time resulting in a difference in intensity compared with the corresponding ion in the first aliquot allowing phosphorylated peptides to be identified (75).

FIG. 13 illustrates a further embodiment of this invention where Mass Series Modifiers are used to label peptides from phosphopeptide samples that have been dephosphorylated. Two forms of the same Protein are shown at the top of the figure—one form is phosphorylated while the other form is not. In step 1) of analysis the proteins are reduced (e.g. with TCEP), alkylated (e.g. with Iodoacetamide) and digested with trypsin to form smaller peptides. Note that the corresponding digest peptide that is phosphorylated in one form of the protein and dephosphorylated in the other form of the protein is marked as peptide 1 in FIG. 13.

In step 2), the tryptic digest is split into two equal aliquots. In step 3a, the first aliquot is left unmodified while in step 3b) the second aliquot of tryptic digest is treated to dephosphorylate the phosphopeptides present in the sample. Dephosphorylation may be effected by contacting the peptide digest with Cerium Oxide nanoparticles as published (73) or the peptides may be treated with alkaline phosphatase. Each aliquot is then reversibly loaded onto separate solid phase supports, e.g. C18 supports.

In step 4a) the first aliquot of peptide digest is contacted with a first Mass Series Modifier reagent while in step 4b) the second aliquot of peptide digest is contacted with a second Mass Series Modifier reagent. Any unreacted Mass Series Modifier is then washed from the support or it is deactivated. In the case of the amino-reactive mass series modifiers shown in FIG. 13, deactivation can be effected by addition of 5% aqueous hydroxylamine solution. Deactivation solution, if used, must also be washed away. In step 5a) and 5b) the protecting group present on the Mass Series Modifier (if present) is removed. In FIG. 13, the protecting group shown is a BOC protecting group and can be removed by thermolysis with hot water (>80 degrees celsius) or with aqueous phosphoric acid as published (67). The two aliquots are then washed.

In steps 6a) and 6b), both aliquots of peptide digest are coupled to the same isobaric mass tag. Isobaric Mass Tag 6 (TMT6-131) from Example Isobaric Mass Tag Set 2 is shown in FIG. 13, but other isobaric tags would be appropriate, such as iTRAQ reagents. After labelling, in step 7), the aliquots are washed and then eluted from the solid support with a suitable solvent such as 80% acetonitrile in water and pooled together. Using the tags in Example Isobaric Mass Tag Set 2, this process could be repeated for six different samples of proteins replacing Isobaric Mass Tag 6 as shown in FIG. 13 with a different mass tag in each sample. These differently labelled samples could then pooled in step 8) for subsequent analysis by Liquid Chromatography-Tandem Mass Spectrometry (LC-MS/MS). It should be understood that although FIG. 13 shows, for the purposes of illustration, only two forms of a single protein, it is expected that this method would be applied to complex protein samples with thousands of phosphorylated proteins present. This method would be suitable for the analysis of a series of related samples where changes in phosphorylation might be expected in the different samples, for example a time course analysis of a cell line treated with a kinase inhibitor where each time point is subjected to the process shown in FIG. 13 but using a different TMT reagent for each time point.

One of ordinary skill in the art would be aware that many variations on this method are possible. The Mass series modifier reagent could be substituted with many of the examples discussed in the text above. For example, the mass series modifiers could be selected from Example Mass Series Modifier Set 1, in which case the TMT reagents would be selected from Example Isobaric Mass Tag Set 1. In this instance de-protection (step 5a) and step 5b)) would require addition of aqueous 50 mM TCEP to the aliquots on the C18 resin. Alternatively, the BOC protecting group in the mass series modifiers shown in FIG. 13 could be substituted for a more acid-labile amine-protecting group such as BPOC (2-(4-biphenyl)isopropoxycarbonyl) or HDOC (Hexadienyloxycarbonyl) (76).

FIG. 14 illustrates a further variation of the method shown in FIG. 13 of this invention. In this embodiment of the invention, Mass Series Modifiers with millidalton mass differences are used to label peptides from phosphopeptide samples that have been dephosphorylated. Two forms of the same Protein are shown at the top of the figure—one form is phosphorylated while the other form is not.

In step 1) of analysis the proteins are reduced (e.g. with TCEP), alkylated (e.g. with Iodoacetamide) and digested with trypsin to form smaller peptides. Note that the corresponding digest peptide that is phosphorylated in one form of the protein and dephosphorylated in the other form of the protein is marked as peptide 1 in FIG. 14.

In step 2), the tryptic digest is split into two equal aliquots. In step 3a, the first aliquot is left unmodified while in step 3b) the second aliquot of tryptic digest is treated to dephosphorylate the phosphopeptides present in the sample. Dephosphorylation may be effected by contacting the peptide digest with Cerium Oxide nanoparticles or the peptides may be treated with alkaline phosphatase. Each aliquot is then reversibly loaded onto separate solid phase supports, e.g. C18 supports. In step 4a) the first aliquot of peptide digest is contacted with the Mass Series Modifier 1 reagent while in step 4b) the second aliquot of peptide digest is contacted with the Mass Series Modifier 2 reagent.

Note that Mass Series Modifier 1 and Mass Series Modifier 2 now differ by approximately 12.6 Millidaltons. Any unreacted Mass Series Modifier is then washed from the support or it is deactivated. In the case of the amino-reactive mass series modifiers shown in FIG. 14, deactivation can be effected by addition of 5% aqueous hydroxylamine solution. Deactivation solution, if used, must also be washed away. In step 5a) and 5b) the protecting group present on the Mass Series Modifier (if present) is removed. In FIG. 14, the protecting group shown is a BOC protecting group and can be removed by thermolysis with hot water (>80 degrees celsius) or with aqueous phosphoric acid as published (67). The two aliquots are then washed. In step 6a), the first aliquot of peptide digest is coupled to a first isobaric mass tag (TMT1) while in step 6b), the first aliquot of peptide digest is coupled to a second isobaric mass tag (TMT2).

It is necessary to use two different isobaric mass tags in this embodiment of the invention because the mass series modifiers only differ by 12.6 millidaltons and so any peptides labelled with these mass series modifiers will be co-selected for CID analysis to detect the Isobaric Mass Tags. This means that it is necessary to have different mass tags for the first and second aliquots of the tryptic digest to allow the two samples to be distinguished. Hence, in FIG. 14, TMT1 is Isobaric Mass Tag 6 (TMT6-131) from Example Isobaric Mass Tag Set 2 while TMT2 is Isobaric Mass Tag 5 (TMT6-130) from Example Isobaric Mass Tag Set 2. After labelling, in step 7), the aliquots are washed and then eluted from the solid support with a suitable solvent such as 80% acetonitrile in water and pooled together. Using the tags in Example Isobaric Mass Tag Set 2, this process could be repeated for 3 different samples of proteins replacing Isobaric Mass Tags 5 and 6 as shown in FIG. 14 with a different pairs of mass tag in each sample. These differently labelled samples could then pooled in step 8) for subsequent analysis by Liquid Chromatography-Tandem Mass Spectrometry (LC-MS/MS). This method is potentially advantageous over the method shown in FIG. 13, as corresponding peptides in the method in FIG. 14 all appear in the mass spectrum within the same ion cluster and will be selected as a single ion for sequencing in contrast to the method in FIG. 13 where the dephosphorylated peptides will appear in the mass spectrum as a separate ion cluster from the untreated peptides meaning that both ion clusters would have to be sequenced to quantify the changes in phosphorylation. In this way the method illustrated in FIG. 14 should increase the throughput of the sequence analysis allowing deeper analysis of a complex sample for the same amount of instrument time.

Further Applications of Mass Series Modifiers for the Analysis of Protein RedOx States:

Studies of oxidative stress in yeast has been reported to change the oxidation state of cysteine thiols in large numbers of proteins in the organism (77). Similar observations have been made in C. elegans (78) and similar molecular events take place in mammalian systems too (79). Thus it is of great interest to have tools to investigate modifications of cysteine. FIG. 15 illustrates a method to distinguish between endogenously reduced cysteine thiols and cysteine thiols that have been oxidised to form disulphides. In step 1) of this method, the free thiols in a protein mixture (illustrated in FIG. 15 by a single protein in an oxidized and reduced state), are reacted with a first thiol reactive mass series modifier (Mass Series Modifier 1). Ideally, the cell sample that is to be analysed is treated with trichloroacetic acid to quench any further disulphide exchange reactions in the sample (80). Proteins are extracted and then labelled on free thiols with Mass Series Modifier 1. In step 2) of the method in FIG. 15, the protein samples is digested with Trypsin (without the usual reduction and alkylation step).

In some variants of this method, Trypsin digestion could take place before labelling with Mass Series Modifier 1 but in general it is preferable to block any free thiols as early in the process as possible before they can undergo any side-reactions. The resulting digested peptide mixture is then loaded reversibly onto a solid phase support such as a C18 resin. The captured peptides are then reduced in step 3) of FIG. 15, e.g. with TCEP, followed by labelling of the exposed free thiols with Mass Series Modifier 2 shown in FIG. 15 in step 4). Unreacted reagent is washed away and then free amines in the peptides are blocked by reductive methylation in step 5) (81). In step 6), the protecting groups, if present, on the Mass Series Modifiers are then removed exposing free amino groups. The C18 support is then washed again and the peptides are then labelled in step 7) on the exposed amino groups of the Mass Series Modifiers with the amine-reactive TMT reagent shown in FIG. 15. Finally, in step 8) the peptides are washed and eluted. Using the tags in Example Isobaric Mass Tag Set 2, the process shown in FIG. 15 could be repeated for six different samples of proteins replacing Isobaric Mass Tag 6 used in FIG. 15 with a different mass tag in each sample. These differently labelled samples could then pooled in step 8) for subsequent analysis by Liquid Chromatography-Tandem Mass Spectrometry (LC-MS/MS).

It should be understood that although FIG. 13 shows, for the purposes of illustration, only two forms of a single protein, it is expected that this method would be applied to complex protein samples with thousands of proteins present of which hundreds might be present in different states of oxidation. It is worth noting that FIG. 15 shows only one possible change in oxidation (from a free thiol in a monomer of a protein to a dimer with an inter-protein disulphide bond). Other possibilities, include intra-protein disulphide bond formation, which could also be analyzed by this method. Free thiols can also be oxidized by reaction with nitrous oxide. To analyse S-nitrosylated peptides, the reducing agent in step 3) of FIG. 15 can be replaced with 2M aqueous ascorbic acid, which will reduce the nitroso group to give the free thiol again as described previously (82). Similarly, some peptides become modified with glutathione after oxidation. Glutathionylated peptides can be analysed by the process shown in FIG. 15 by using mutant E. coli glutaredoxin as the reducing agent in step 3) of FIG. 15 to expose free thiols blocked by glutathione as described previously (83). Vicinal dithiols are also of interest as redox regulation sites in proteins. Vicinal dithiols can be trapped by including additional steps in the method shown in FIG. 15. At any stage where free thiols are exposed, vicinal dithiols can be capped with the vicinal dithiol specific capping agent, PhenylArsine Oxide (PAO) before reaction with a mass series modifier (84).

After reacting free thiols with the Mass Series Modifier, the dithiols can be reduced again with the specific reducing agent 2,3-dimercapto-1-propanesulfonic acid (DMPS) for reaction with a different mass series modifier or mass tag. In some embodiments, multiple different oxidation states of cysteine could be analyzed by applying the different reducing agents sequentially, using a different Mass Series Modifier to block the exposed thiols in each case. In this way, multiple different modifications of cysteines could be identified by multiple different mass series modifiers. Since the peptides are immobilised on a solid phase support, the addition and removal of each reducing agent and corresponding Mass Series Modifier is relatively trivial thus enabling complex biology to analyzed in a single sample.

There are other cysteine modifications of interest such as formation of sulfenic acid, which will react with dimedone-based probes. Thus, it is anticipated that a Mass Series Modifier where the $R^1$ group comprises a dimedone reactive functionality would be useful for detection of Sulfenic acid modified peptides.

EXAMPLES

The following examples illustrate the reagents and practice of this invention.

The amine-reactive mass tag with the structure below was used for the following labelling experiments:

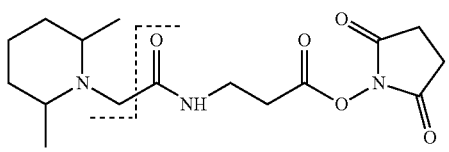

The synthesis of this reagent, which is referred to as TMTzero, has been described previously (WO2007012849) and is commercially available (Thermo Fisher Scientific, Pierce division, Rockford, Ill., USA).

For solid phase labelling, a TMTzero Stock Solution was made up at a concentration of 300 mM in Acetonitrile (ACN). For solid phase labelling experiments, the TMTzero stock solution was then diluted with 50 mM aqueous potassium dihydrogen phosphate buffer ($KH_2PO_4$; pH~4.5) giving a final ACN concentration of ~5%, to avoid elution of target peptide during loading. Aqueous solutions of TMTzero were made and used immediately.

In the following examples various buffers are used with the solid phase cartridges:
Conditioning Buffer: 95% ACN, 4.9% water and 0.1% TriFluoroacetic Acid (TFA)
Wash Buffer: 5% ACN in water with 0.1% TFA
Elution Buffer: 50% ACN in water with 0.1% TFA

Example 1—Labelling of a Synthetic Peptide Reversibly Immobilized on C18 and Hydrophilic/Lipophilic Solid Phase Supports The following example illustrates the labelling of a synthetic peptide with an amine-reactive mass tag where the peptide has been reversibly immobilized on a solid phase support To provide a comparison for the solid phase labelling, solution phase labelling was carried out as follows using a standard published protocol (51):

50 µg of a synthetic peptide with the sequence VATVSLPR was dissolved in 100 µl of 100 mM Triethylammonium Bicarbonate (TEAB) buffer followed by addition of 34 µl of a 60 mM stock solution of TMTzero in ACN. The reaction was allowed to run for 1 hour as previously determined in the published protocol. The reactions were quenched by addition of 8 µl of 5% hydroxylamine solution. The labelled peptide was then analyzed directly by Reverse Phase High Performance Liquid Chromatography (RP-HPLC) with UV detection of the labelled peptide at 214 nm.

FIG. 16 shows three HPLC traces. HPLC trace (a) shows the unlabelled and unmodified synthetic peptide (VATVSLPR) with a retention time of 12.2 minutes. HPLC trace (b) shows the product of the solution-phase labelling reaction of TMTzero with the synthetic peptide (VATVSLPR) without quenching by hydroxylamine. It can be seen in the HPLC trace (b) that the labelled form of the synthetic peptide elutes with a retention time of 13.1 minutes and a very small peak can be seen eluting at approximately 13.5 minutes, which corresponds to the over-labelled product. No unlabelled peptide remains but some unreacted TMTzero reagent can be seen eluting with a retention time of 10.1 minutes. HPLC trace (c) shows the product of the solution-phase labelling reaction of TMTzero with the synthetic peptide (VATVSLPR) after quenching with hydroxylamine. It can be seen in the HPLC trace (c) that the labelled form of the synthetic peptide still elutes with a retention time of 13.1 minutes but the very small peak resulting from over-labelling no longer elutes at 13.5 minutes.

For solid phase labelling, both Waters Oasis HLB cartridges and Waters Sep-Pak tC18 were tested. For the Oasis HLB experiments, 1 ml cartridges were used with 30 mg of HLB substrate and for the Sep-Pak tC18 experiments, 1 ml cartridges with 50 mg of tC18 substrate were used.

In the following experiments the cartridges were flushed after each step using a vacuum manifold. For both cartridges, the substrate was 'activated' by wetting with a single 1 ml aliquot of Conditioning Buffer and then flushed. The resin was then equilibrated with 2 washes of 1 ml of 50 mM $KH_2PO_4$ buffer with 5% ACN (pH~4.5). The synthetic peptide was then loaded in 50 mM $KH_2PO_4$ buffer (no ACN) and the buffer flushed after a minute.

Once loaded the cartridges were incubated with 105 µl of ~12 mM TMTzero in 50 mM $KH_2PO_4$ buffer with ~5% ACN (4 µl of 300 mM stock solution was added to 100 µl of 50 mM $KH_2PO_4$ buffer giving a total of 1.2 micromoles of TMT) Note, that the 104 µl of TMTzero solution were loaded by flushing the solvent through the column slowly. The TMTzero reagent binds to the solid phase resin under these loading conditions much the same as the peptide and does not appear to flush through with the solvent. The resin was not run dry although all the solvent was allowed to pass through and the TMTzero was left to incubate in the cartridge for various durations. After incubation of TMTzero, the cartridges were washed twice with 1 mL aliquots of Wash Buffer. No quenching of the reaction on the cartridges with hydroxylamine was necessary in these experiments. The labelled peptide was then eluted in two aliquots of 0.7 mL of Elution Buffer into a clean collection tube.

The samples were then dried down followed by redissolution in 350 µL of 5% ACN in water with 0.1% TFA. Finally, 105 µL was loaded onto the HPLC column for subsequent analysis by Reverse Phase High Performance Liquid Chromatography (RP-HPLC) with UV detection of the labelled peptide at 214 nm.

It is worth noting that essentially the same labelling experiment was carried out on the HLB cartridges but using the TEAB buffer that was used for solution phase labelling initially rather than 50 mM $KH_2PO_4$ but it was found that the reactions did not go to completion in a reasonable time and there was significant over-labelling (reactions of the TMTzero with serine and threonine and other side-reactions specific to the peptide that was used—data not shown). This was corrected by using a buffer with a lower pH: 50 mM KH$_2$PO$_4$ (pH 4.5). It is expected that other reagents without free amines that buffer at about pH 4.5 would be suitable to use as well.

FIG. 17 shows three HPLC traces from the solid phase labelling of the synthetic peptide (VATVSLPR) using the Waters Oasis HLB cartridges. HPLC trace (a) shows the labelled synthetic peptide with a retention time of 13.1 minutes after an incubation time of 60 minutes on the cartridge. It can be seen that the labelling reaction is substantially complete. HPLC trace (b) shows the product of the solid-phase labelling reaction of TMTzero with the synthetic peptide after 30 minutes of incubation on the cartridge. It can be seen in the HPLC trace (b) that there is a very small peak from the unlabelled form of the synthetic peptide still present at a retention time of 12.1 minutes and but the reaction is almost complete with a substantial peak at 13.1 minutes. HPLC trace (c) shows the product of the solid-phase labelling reaction of TMTzero with the synthetic peptide after an incubation time of 15 minutes, which can be seen to be less complete than the 30 minute incubation with a reasonably significant peak still present at a retention time of 12.1 minutes. In all three traces there is almost no detectable over-labelling peak and so it was determined that quenching of the reaction with hydroxylamine was unnecessary in these experiments.

FIG. 18 shows two HPLC traces from two independent repetitions of the solid phase labelling of the synthetic peptide (VATVSLPR) using the Waters Oasis tC18 cartridges. HPLC trace (a) shows the labelled synthetic peptide with a retention time of 13.1 minutes after an incubation time of 60 minutes on the cartridge. It can be seen that the labelling reaction is substantially complete. Similarly, HPLC trace (b) shows the product of the solid-phase labelling reaction of TMTzero with the synthetic peptide using reagents and target peptide made up freshly again. The reaction time is again 60 minutes of incubation on the cartridge. It can be seen that HPLC trace (b) is almost identical to HPLC trace (a) and that the reaction appears to be very reproducible. In both traces, again, there is almost no detectable over-labelling peak as for the Oasis HLB cartridges and quenching with hydroxylamine was omitted. It was thus determined that 1 hour of coupling time was sufficient for complete labelling on a solid support.

It can therefore, be seen that a peptide can be completely and reproducibly labelled on a solid phase support using the methods of this invention.

Example 2—Labelling of a Large Quantity of a Synthetic Peptide Reversibly Immobilized on a C18 Solid Phase Support The following example illustrates the labelling of a large amount of synthetic peptide with an amine-reactive mass tag where the peptide has been reversibly immobilized on a C18 solid phase support. Loading of the peptide was carried out in a buffer that is normally used for tryptic digestion to simulate the loading conditions for a normal biological sample. Solution phase labelling assays were also carried out in parallel.

The TMTzero amine-reactive mass tag that was used in example 1 was also used

3000 µg of the synthetic peptide (VATVSLPR) was dissolved in 13 ml µl of the following buffer (referred to as Lysis Buffer): 8 M urea, 75 mM NaCl, 50 mM Tris, pH 8.2, one tablet of protease inhibitors cocktail (cOmplete Protease Inhibitors Cocktail Tablets, Roche) and one tablet of phosphatase inhibitor cocktail (Roche) per 10 mL of Lysis Buffer.

For solid phase labelling, Waters Sep-Pak tC18 cartridges were used. For the Sep-Pak tC18 experiments, 3 ml cartridges with 200 mg of tC18 substrate were used. 100 mg cartridges were also tested but shown to bind inconsistently to samples at this scale suggesting the loading capacity was being exceeded (data not shown).

In the following experiments the cartridges were flushed after each step using a vacuum manifold. The C18 substrate was 'activated' by wetting with a single 3 ml aliquot of Conditioning Buffer and then flushed. The C18 resin was then equilibrated with 2 washes of 3 ml of Wash buffer. Then aliquots of 3000 µg of synthetic peptide (VATVSLPR) dissolved in 13 ml of Lysis Buffer were then loaded onto the cartridge by allowing the solution to flow through the cartridge slowly, keeping the flow rate to about 1 mL per minute.

After loading, buffer exchange on the cartridge was carried out in a single wash of the cartridge with 3 ml of 50 mM KH$_2$PO$_4$ buffer (pH 4.5; Phosphate Buffer) with ~5% ACN.

After buffer exchange, the cartridges were incubated with different amounts of TMTzero reagent to determine how much was necessary for complete labelling of the peptide on resin. The desired amounts of TMTzero were made by diluting stock solution of TMTzero (300 mM in ACN) with 50 mM KH$_2$PO$_4$ buffer to give a final concentration of ~5% ACN (pH 4.5), i.e. 6 µmol was made up by adding 20 µl of Stock solution to 400 µl of Phosphate buffer, 12 µmol was made up by adding 40 µl of Stock solution to 800 µl of Phosphate buffer and 24 µmol was made up by adding 80 µl to 1600 µl of Phosphate buffer. As in example 1, the TMTzero reagent is loaded by flushing the solution over the bed allowing the TMTzero reagent to bind to the C18. Again, the reagent is left to react for 1 hour at room temperature. After incubation of TMTzero, the cartridges were washed twice after incubation with 3 mL aliquots of Wash Buffer (see Example 1). Again, no quenching of the reaction on the cartridges with hydroxylamine was necessary in these experiments. The labelled peptide was then eluted with 1.5 ml of Elution Buffer. The eluted samples were then dried down followed by re-dissolution in 1000 µL of 5% ACN in water with 0.1% TFA. Finally, 5 µL was loaded (corresponding to an amount of 15 µg of synthetic peptide) onto the HPLC column for subsequent analysis by Reverse Phase High Performance Liquid Chromatography (RP-HPLC) with UV detection of the labelled peptide at 214 nm.

In a first experiment, the TMTzero reagent was not added. The sample was simply loaded in Lysis buffer, buffer exchange was applied and the cartridges were washed with Wash Buffer and then eluted with Elution Buffer. FIG. 19 HPLC trace (a) shows the combined flow-through of the loading buffer and the buffer exchange step while FIG. 19 HPLC trace (b) shows the final eluted peptide peptide after loading in Lysis buffer, buffer exchange with Phosphate buffer, washing twice with Wash Buffer and elution with Elution Buffer. It can be seen that there is no peak at 12.2 min, which would indicate the presence of the native peptide in the HPLC trace in the combined Loading buffer and Buffer Exchange flow-through. Similarly, the peptide clearly elutes in the Elution Buffer (indicated by the presence of the peak at 12.2 min), showing that the 200 mg tC18 SepPak cartridges can bind 3000 µg of the synthetic peptide and keep the peptide bound during buffer exchange.

FIG. 20 shows HPLC traces of the eluted labelled peptide after incubation with different amounts of TMTzero reagent. HPLC Trace (a) in FIG. 16 shows the peptide after coupling with 6 µmol of TMTzero. HPLC Trace (b) in FIG. 16 shows the peptide after coupling with 12 µmol of TMTzero. HPLC Trace (c) in FIG. 16 shows the peptide after coupling with 24 µmol of TMTzero. It can be seen that labelling is substantially complete with loading of both 12 µmol and 24 µmol of TMTzero reagent. Although the labelling was complete with 12 µmol of reagent, it was decided for the experiments that follow to use 15 µmol of reagent for consistency with the solution phase protocol.

It can therefore, be seen that even a substantial quantity of peptide can be completely labelled on a solid phase support using the methods of this invention.

Example 3—Labelling of a Large Quantity of a Peptide Digest Reversibly Immobilized on a C18 Solid Phase Support The following example illustrates the labelling of a large amount of peptide digest with an amine-reactive mass tag where the peptide digest is reversibly immobilized on a C18 solid phase support. Large amounts of peptide digest are often required for analysis of post-translational modifications, which are present at sub-stoichiometric levels in most biological samples and therefore these modified peptides need enrichment from large samples of protein to become detectable. The peptide digest was prepared from homogenized rat liver. Pieces of rat liver were were ground up with a disintegrator (Mikro-Dismembrator S, B. Braun Biotech International) under regular cooling with liquid nitrogen. To extract the proteins, the resulting powder was taken up in Lysis buffer and treated with a W-450D sonifier tip (Branson). The homogenized sample was centrifuged (20,000 g for 10 min at 4° C.) to remove cell debris. Supernatent was transferred to clean tubes and the pellet was discarded. Protein concentration was determined using the Bradford assay and the protein concentration was adjusted to 5 µg/µl by addition of further Lysis Buffer (Liver Protein Extract).

For each experiment 600 µl of Liver Protein Extract (equivalent to 3000 µg of protein) was used.

Aliquots of Liver Protein Extract were reduced, alkylated and digested as follows: 6 µl of 0.5M dithiothreitol (DTT stock) in water was added to 600 µl of the Liver Protein Extract, which was then incubated in a shaker for 25 min at 56° C. to reduce disulfide bonds. The reduced protein mixture was allowed to cool to room temperature and then 17 µl of 0.5M iodoacetamide (IAA stock) was added to give a final concentration of ~14 mM. After vortexing briefly, each aliquot of protein was left to incubate for 30 min at room temperature and in the dark to alkylate cysteines. After incubation, unreacted IAA was quenched by addition of a further 6 µl of DTT stock.

2441 µl of 25 mM Tris-HCl (pH 8.2) was added to each aliquot of Liver Protein Extract reducing the concentration of urea to 1.6M. 32 µl of 0.1M $CaCl_2$ was added to each aliquot to give a concentration of ~1 mM. 32 µg of Trypsin (Promega) was added to the aliquots to give a final trypsin concentration of 10 ng/µl. After adding Trypsin and $CaCl_2$, each aliquot of protein was incubated at 37° C. overnight (~15-18 hours). After digestion, the aliquots of digested Liver Protein Extract were allowed to cool to room temperature and the digestion was stopped by acidification with TFA to 0.4% (vol/vol). If the pH was >2.0 more acid was added. Finally, the digested Liver Protein Extracts were centrifuged at 2,500 g for 10 min at room temperature, the supernatant was transferred to a clean tube and the pellet was discarded.

For solid phase labelling, Waters Sep-Pak tC18 cartridges were used again. For the Sep-Pak tC18 experiments, 3 ml cartridges with 200 mg of tC18 substrate were used. As before, the cartridges were flushed after each step using a vacuum manifold. The C18 substrate was 'activated' by wetting with a single 3 ml wash of Conditioning Buffer and then flushed. The C18 resin was then equilibrated with 2 washes of 3 ml of Wash buffer. Each aliquot of digested Liver Protein Extract was slightly more than 3 ml and this was loaded onto the cartridge by allowing the solution to flow through the cartridge slowly, keeping the flow rate to about 1 mL per minute or less?.

Buffer exchange on the cartridge was carried out in a single wash of the cartridge with 3 ml of Phosphate buffer with ~5% ACN.

After buffer exchange, the cartridges were incubated with 15 µmol of TMTzero reagent. The 300 mM Stock solution was used again and 50 µl of this stock solution was added to 1000 µl of 50 mM $KH_2PO_4$ buffer to give a final ACN concentration of ~5% (pH 4.5). As in example 1, the TMTzero reagent is loaded by flushing the solution over the bed allowing the TMTzero reagent to bind to the C18. Again, the reagent is left to react for 1 hour at room temperature. After incubation of TMTzero, the cartridges were washed twice with 3 ml aliquots of Wash buffer (5% ACN in water with 0.1% TFA). Again, no quenching of the reaction on the cartridges with hydroxylamine was carried out in these experiments. The labelled peptides were then eluted with 1.5 mL of Elution Buffer of 50% ACN in water with 0.1% TFA. The eluted samples were then dried down followed by re-dissolution in 1000 µL of 5% ACN in water with 0.1% TFA. Finally, 250 µL (corresponding to 750 µg of labelled peptide digest) to HPLC for subsequent analysis by Reverse Phase High Performance Liquid Chromatography (RP-HPLC) with UV detection of the labelled peptide at 214 nm.

FIG. 21 shows HPLC traces from the solid phase labelling of Liver Protein Extract peptide digest after incubation with 15 µmol of TMTzero reagent. HPLC Trace (a) in FIG. 17 shows the collected flowthrough of loading buffer showing that the peptide digest has bound to the C18 column. HPLC Trace (b) in FIG. 17 shows the flowthrough of Phosphate Buffer used for the buffer exchange step and again there is no digest washing through. HPLC Trace (c) in FIG. 17 shows the flowthrough of the wash buffer post-labelling. The two major peaks observed in Trace (c) are hydrolysis products of excess labelling reagent which are washed away at this stage. HPLC Trace (d) in FIG. 17 shows the eluted labelled peptide after coupling with 15 µmol of TMTzero. It can be seen that peptide digest is being eluted after labelling.

FIG. 22 shows overlaid HPLC traces comparing the unlabelled peptide digest with the labelled peptide digest. It can be seen that the labelled digest is eluting overall at a later time indicating that labelling has taken place since the introduction of the TMTzero tag into peptides generally results in a later elution of the peptide compared to the unlabelled form. FIG. 23 shows HPLC traces of 2 further technical replicates of the labelled digest, showing that the same elution pattern occurs indicating a reproducible level of labelling in both samples. Finally, FIG. 24 shows a histogram of peptide identifications made using SEQUEST software to analyse peptides from the two replicate digests in FIG. 19 that were sequenced in an Orbitrap Velos Pro mass spectrometer after HPLC separation. The light bars indicate the number of peptides in each replicate that were sequenced that contained the TMTzero modification while the dark bars indicate the total number of peptides identified.

In both replicates, 0.2% of peptides were identified without a TMTzero label indicating a very high level of labelling that is similar to the levels of labelling expected from solution phase labelling protocols.

It can therefore, be seen that even a substantial quantity of a complex tryptic peptide digest can be completely and reproducibly labelled on a solid phase support using the methods of this invention.

Example 4—Synthesis of an Amine-Reactive BOC-Protected Intermediate Linker (Bifunctional Linker Reagent)

The linker shown below comprising 2 beta-alanine residues protected at the N-terminus with a BOC protecting group and activated at the C-terminus with an N-hydroxysuccinimide ester (Boc-bAla-bAla-OSu) was synthesized:

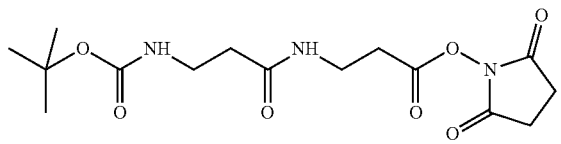 [SMILES: CC(C)(C)OC(=O)NCCC(=O)NCCC(=O)ON1C(=O)CCC1=O]

N—BOC protected beta-alanine is commercially available from a number of suppliers (e.g. Sigma-Aldrich Corp., St Louis, Mo., USA, Product Number: Aldrich 15382). Similarly, Benzyl-ester protected beta-alanine is commercially available from a number of suppliers (e.g. Sigma-Aldrich Corp., St Louis, Mo., USA, Product Number: Sigma A1139). 95 g N—BOC protected beta-alanine (0.5 mol) were dissolved in 800 mL THF and 170 mL diisopropylethylamine (DIEA) have been added to give a clear solution. Then, 108 g 1-Hydroxybenzotriazole hydrate and 135 g Dicyclohexylcarbodiimide (DCC) were added and stirred for 30 min. Finally, 176 g (0.5 mol) beta-alanine benzylester hydrotosylate have been added and stirred 4 h. The precipitated urea has been filtered off and the solvent has been evaporated. The residue has been dissolved in ethyl acetate, then the organic layer was washed twice with saturated sodium bicarbonate solution, once with brine and then dried over sodium sulphate. After evaporation, the residue has been crystallised from diethyl ether to give 162 g of the doubly protected dipeptide as white powder (0.45 mol, 90%).

1.83 g (5.22 mmol) of the protected dipeptide was dissolved in 20 ml of methanol. The benzyl ester group was removed from the C-terminus of the dipeptide by addition of 100 mg of 5%-Pd/C catalyst to the solution, which was then hydrogenated with hydrogen (120 mL usage under consideration of ideal conditions) at room temperature. The reaction mixture was filtered and the solvent was evaporated to yield 1.05 g (4.03 mmol, 77%) of the C-terminally deprotected dipeptide.

390 mg (1.51 mmol) of the free carboxylic acid of the BOC-protected dipeptide were dissolved in 5 mL THF, and 179 mg of N-hydroxysuccinimide and 300 mg of DCC were added. The reaction mixture stirred for 2 hours at room temperature. The precipitated urea was filtered off, and the solvent was evaporated. The residue was purified by crystallisation from ethyl acetate/diethylether to yield 520 mg of the BOC-protected NHS-activated beta-alanine dipeptide (Boc-bAla-bAla-OSu) shown above (1.45 mol, 93%).

Various isotopes of beta-alanine are commercially available and it would be clear to one of ordinary skill in the art that it would be possible to prepare numerous different isotopes of the linker above by using different combinations of these commercially available isotopes.

Example 5—Labelling of a Synthetic Peptide with a BOC-Protected Intermediate Linker 100 µg of a synthetic model peptide with the amino acid sequence VATVSLPR was dissolved in 100 µL TEAB buffer (100 mM). The peptide was labelled with the BOC-linker (Boc-bAla-bAla-OSu) according to the TMT labelling approach. Briefly, a 60 mM stock solution of Boc-bAla-bAla-OSu in acetonitrile was prepared, and 33 µL of the stock solution were added to the peptide solution to achieve a reagent concentration of 15 mM and an acetonitrile (ACN) content of 25%. After incubation for 1 hour at room temperature, 8 µL of aqueous hydroxylamine solution (5% by volume) were added to quench reagent excess. The quenching reaction was left to incubate for 15 minutes. Then, 16 µL of trifluoroacetic acid (TFA) were added to achieve a concentration of 10% TFA. The Boc group was cleaved by incubation of the solution at 50° C. for 4 hours. FIG. 25, Trace 1 shows an HPLC trace of the native VATVSLPR peptide before any labelling steps. It can be seen that the peptide elutes with the peak at 12.20 minutes. FIG. 25, Trace 2 shows an HPLC trace of an analysis of the reaction mixture of the VATVSLPR peptide after coupling with the Boc-bAla-bAla-OSu reagent. It can be seen that the BOC-linker coupled peptide elutes with the peak at 14.32 minutes. Some other peaks can also be seen, which may be produced by residual unreacted linker and other contaminants.

Subsequently, the peptide solution was diluted with 3 mL of water to decrease the TFA concentration to 0.5%. A Waters SepPak tC18 cartridge (50 mg, 1 cc) was activated with a wash of 1 mL of 95% ACN+0.1% TFA and then equilibrated with 2 mL of 5% ACN+0.1% TFA. The diluted peptide solution was then loaded onto the SepPak cartridge. The trapped peptides were washed with 3 mL of 50 mM $KH_2PO_4$+5% ACN to achieve the labelling conditions for the Solid Phase Amino Labelling (SPAL) approach. FIG. 25, Trace 3 shows an HPLC trace of an analysis of the reaction mixture of the linker-coupled VATVSLPR peptide after removal of the Boc-protecting group from the peptide. It can be seen that the linker-coupled peptide with the free amine now elutes with a peak at 12.39 minutes.

A solution of TMTzero reagent (Pierce Biotechnology, Inc., Rockford, Ill., USA; product number: 90060) for SPAL labelling was prepared immediately before use by adding 5 µL of a 300 mM TMT stock in ACN to 100 µL 50 mM $KH_2PO_4$. This solution was loaded onto the trapped peptide, and the cartridge was incubated for 1 hour at room temperature to achieve complete labelling. Then, the trapped peptides were washed with 3 mL of 5% ACN+0.1% TFA, and then eluted with 800 µL 50% ACN+0.1% TFA. A sample of the eluent was analysed by HPLC and FIG. 25, Trace 4 shows an HPLC trace of an analysis of the TMTzero linker-coupled VATVSLPR peptide after desalting on the C18 cartridge. It can be seen that the TMTzero linker-coupled peptide now elutes with a peak at 12.96 minutes. A contaminant eluting at 13.22 minutes can also be seen in the HPLC trace.

The eluate was further purified by SCX cartridges as follows: the eluate was directly loaded onto self-made SCX cartridges (CHROMABOND empty columns 15 mL, Macherey-Nagel, filled with 650 µL SP Sepharose Fast Flow, Sigma) and, after washing with 4 mL of 50% ACN+ 0.1% TFA, the peptides were eluted with 2 mL of 25% ACN in 400 mM ammonium acetate. After lyophilisation to dryness, the labeled peptides were analysed by RP-HPLC and by mass spectrometry to confirm purity and identity. FIG. 25, Trace 5 shows an HPLC trace of an analysis of the TMTzero linker-coupled VATVSLPR peptide after the second SCX purification step. It can be seen that the labelled peptide at 12.96 minutes is now substantially free of contaminants.

The mass spectra will be discussed in Example 6.

Example 6—Labelling of a Synthetic Peptide with TMTzero-bAla-bAla-OSu

The tag reagent (TMTzero-bAla-bAla-OSu) shown below, comprising 2 beta-alanine residues coupled to a TMTzero reagent, was synthesised as described previously (WO002011036059, FIG. 12):

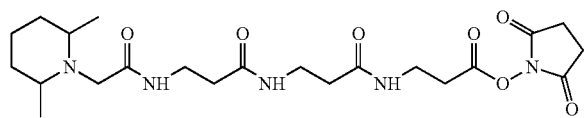 [SMILES: CC1CCCC(C)N1CC(=O)NCCC(=O)NCCC(=O)NCCC(=O)ON1C(=O)CCC1=O]

100 µg of a synthetic model peptide with the amino acid sequence VATVSLPR was dissolved in 100 µL TEAB buffer (100 mM). The peptide was labelled with the TMTzero-bAla-bAla-OSu reagent. Briefly, a 120 mM stock solution of TMTzero-bAla-bAla-OSu in acetonitrile was prepared, and 33 µL of the stock solution were added to the peptide solution to achieve a reagent concentration of 30 mM and an acetonitrile (ACN) content of 25%. After incubation for 1 hour at room temperature, 8 µL of aqueous hydroxylamine solution (5% by volume) were added to quench reagent excess. The quenching reaction was left to incubate for 15 minutes.

Subsequently, the labelled peptide solution was diluted with 1 mL of 0.1% TFA. A Waters Oasis HLB cartridge (30 mg, 1 cc) was activated with a wash of 1 mL of 95% ACN+0.1% TFA and then equilibrated with 2 mL of 5% ACN+0.1% TFA. The diluted peptide solution was then loaded onto the SepPak cartridge. The trapped peptides were washed with 3 mL of 5% ACN+0.1% TFA, and then eluted with 800 µL 50% ACN+0.1% TFA.

The eluate was further purified by SCX cartridges as follows: the eluate was directly loaded onto self-made SCX cartridges (CHROMABOND empty columns 15 mL, Macherey-Nagel, filled with 650 µL SP Sepharose Fast Flow, Sigma) and, after washing with 4 mL of 50% ACN+0.1% TFA, the peptides were eluted with 2 mL of 25% ACN in 400 mM ammonium acetate. After lyophilisation to dryness, the labelled peptides were analysed by RP-HPLC and by mass spectrometry to confirm purity and identity.

FIG. 26, Trace 1, show an HPLC trace of the labelled species produced by the 2-step labelling reaction with an Intermediate Linker described in Example 5 above. It can be seen that the labelled peptide elutes at 12.96 minutes. FIG. 26, Trace 2, show an HPLC trace of the labelled species produced by the 1-step labelling reaction carried out in this Example using the preformed TMTzero-bAla-bAla-OSu reagent. It can be seen that the labelled peptide elutes at 12.98 minutes and is almost identical to Trace 1. FIG. 26, Trace 3, show an HPLC trace of a mixture of equal amounts (15 µg) of the labelled species produced by the 1-step labelling reaction and 2-step labelling reactions. It can be seen that the two products co-elute and are identical.

FIG. 27a shows a mass spectrum of the labelled peptide produced by the 2-step labelling reaction with an Intermediate Linker described in Example 5 above. The expected mass of the labelled and doubly protonated peptide is 1209.74 Daltons giving an expected mass-to-charge ratio for the doubly-charged peptide of 604.87. An ion is present in the mass spectrum at 604.9. FIG. 27b shows a zoom of this ion revealing the isotope peaks confirming that the ion is doubly-charged. This strongly indicates that the expected labelling product has been produced by the two-step labelling reaction.

Figure 27:
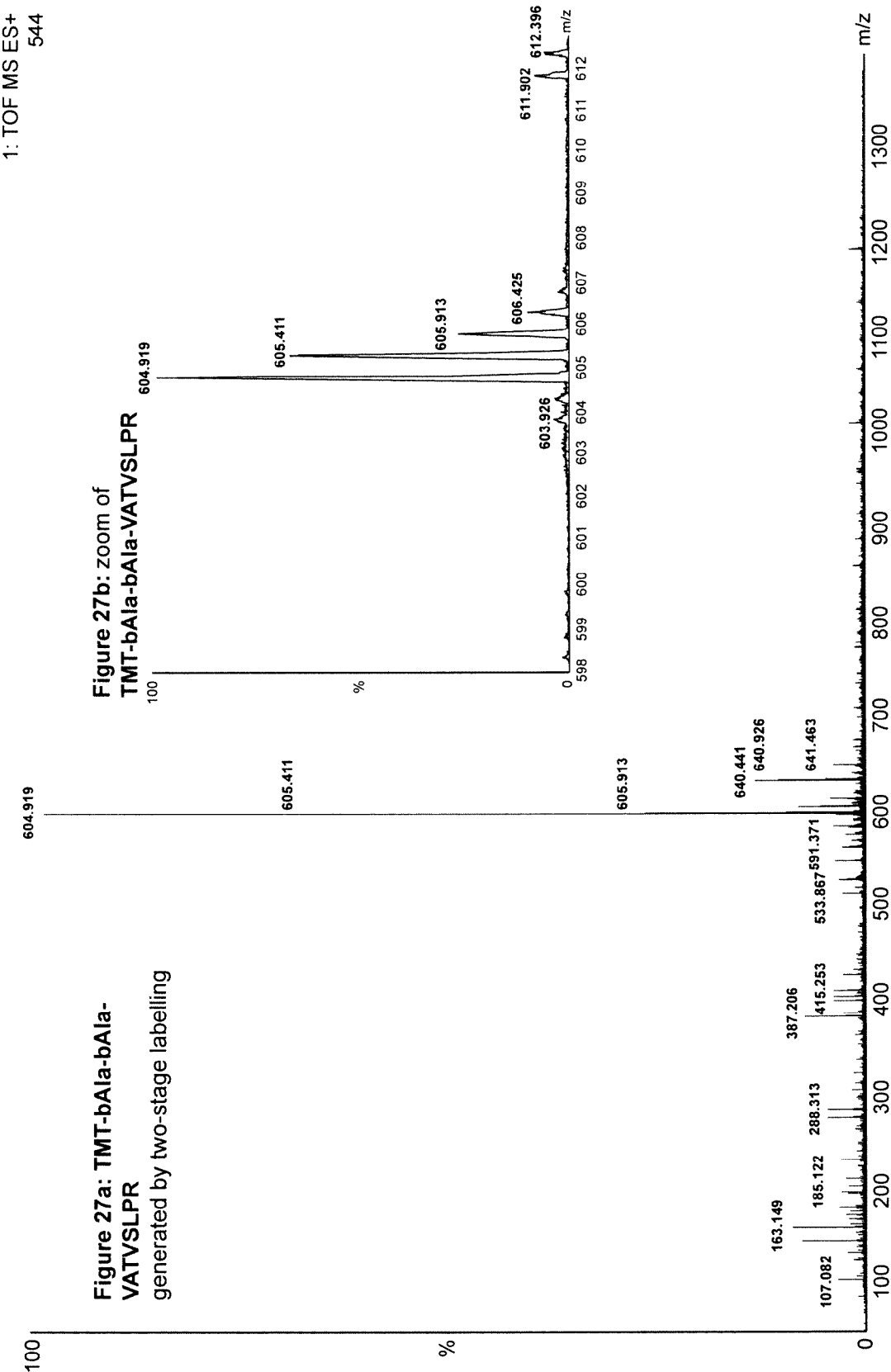
Figure 28:
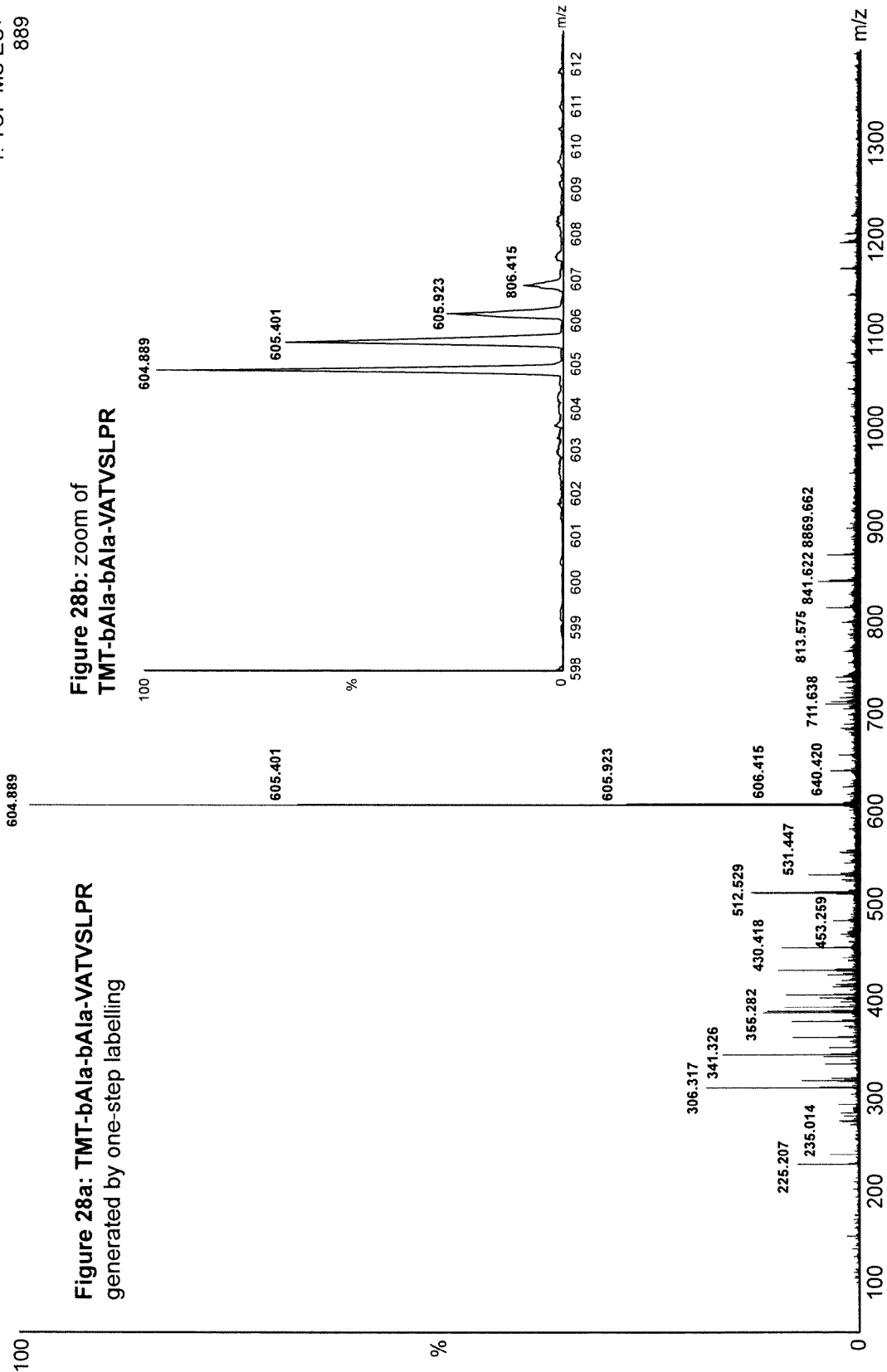

FIG. 28a shows a mass spectrum of the labelled peptide produced by the 1-step labelling reaction using the preformed TMTzero-bAla-bAla-OSu reagent described in this Example. Again, an ion is present in the spectrum at 604.9. FIG. 28b shows a zoom of this ion revealing the isotope peaks confirming that the ion is doubly-charged. FIGS. 27 and 28 both strongly indicate that the labelling products of the 1 and 2-step labelling protocols are identical and correct.

This indicates that the methods and bifunctional linkers of this invention can produce identical results to direct labelling with a single tag reagent and provide a useful way to reduce the number of reagents that need to be synthesized to produce highly multiplexed label sets.

Example 7—Labelling of a Synthetic Peptide with an Azide-Protected Intermediate Linker The NHS-Azide linker below is commercially available (Pierce Biotechnology, Inc., Rockford, Ill., USA; product number: 88902).

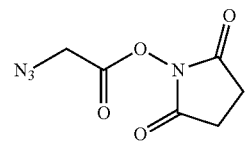 [SMILES: [N-]=[N+]=NCC(=O)ON1C(=O)CCC1=O]

100 µg of a synthetic model peptide with the amino acid sequence VATVSLPR was dissolved in 100 µL TEAB buffer (100 mM). The peptide was then labelled with the NHS-Azide linker. Briefly, a 60 mM stock solution of the NHS-Azide linker in acetonitrile was prepared, and 33 µL of the stock solution were added to the peptide solution to achieve a reagent concentration of 15 mM and an acetonitrile (ACN) content of 25%. After incubation for 1 hour at room temperature, 8 µL of aqueous hydroxylamine solution (5% by volume) were added to quench reagent excess. The quenching reaction was left to incubate for 15 minutes. The azide group was 'deprotected' by addition of 19 µl of a 200 mM stock solution of aqueous Tris(2-Carboxyethyl)phosphine (TCEP) with a concentration of to give a final TCEP concentration of 30 mM. The TCEP reduction reaction was left for 18 hours at room temperature.

FIG. 29, Trace 1 shows an HPLC trace of the native VATVSLPR peptide before any labelling steps. It can be seen that the peptide elutes with the peak at 12.20 minutes. FIG. 29, Trace 2 shows an HPLC trace of an analysis of the reaction mixture of the VATVSLPR peptide after coupling with the NHS-Azide linker. It can be seen that the azide-linker coupled peptide elutes with the peak at 13.74 minutes. The unreacted linker does not bind well to C18 so no other peaks can be seen in the HPLC trace indicating a very clean coupling reaction (this HPLC was carried out directly on the coupling reaction material without further purification).

FIG. 29, Trace 3 shows an HPLC trace of an analysis of the reaction mixture of the VATVSLPR peptide after reduction/deprotection of the azide to give the glycine-extended peptide. It can be seen that the glycine-extended peptide elutes with the peak at 12.33 minutes.

Subsequently, the peptide solution was diluted with 1 mL of water+0.5% TFA. A Waters SepPak tC18 cartridge (50 mg, 1 cc) was activated with a wash of 1 mL of 95% ACN+0.1% TFA and then equilibrated with 2 mL of 5% ACN+0.1% TFA. The diluted peptide solution was then loaded onto the SepPak cartridge. The trapped peptides were washed with 3 mL of 50 mM $KH_2PO_4$+5% ACN to achieve the labelling conditions for the Solid Phase Amino Labelling (SPAL) approach.

A solution of TMTzero reagent (Pierce Biotechnology, Inc., Rockford, Ill., USA; product number: 90060) for SPAL labelling was prepared immediately before use by adding 5 μL of a 300 mM TMT stock in ACN to 100 μL 50 mM $KH_2PO_4$. This solution was loaded onto the trapped peptide, and the cartridge was incubated for 1 hour at room temperature to achieve complete labelling. Then, the trapped peptides were washed with 3 mL of 5% ACN+0.1% TFA, and then eluted with 800 μL 50% ACN+0.1% TFA.

The eluate was further purified by SCX cartridges as follows: the eluate was directly loaded onto self-made SCX cartridges (CHROMABOND empty columns 15 mL, Macherey-Nagel, filled with 650 μL SP Sepharose Fast Flow, Sigma) and, after washing with 4 mL of 50% ACN+0.1% TFA, the peptides were eluted with 2 mL of 25% ACN in 400 mM ammonium acetate. After lyophilisation to dryness, the labeled peptide was analysed by RP-HPLC to confirm purity and identity. FIG. 29, Trace 4 shows an HPLC trace of an analysis of the SCX-purified TMTzero-labelled and glycine-extended VATVSLPR peptide. It can be seen that the TMTzero-labelled and azide-linker coupled peptide now elutes with the peak at 12.99 minutes and that the labelled peptide is substantially free of contaminants.

These results suggest that azide-based protecting groups can protect amino groups efficiently and that they can be used for preparation of bifunctional Intermediate Linkers that can be deprotected under very mild reaction conditions.

REFERENCES

1. Wasinger, V. C., Cordwell, S., Cerpa-Poljak, A., Yan, J. X., Gooley, A. A., Wilkins, M. R., Duncan, M. W., Harris, R., Williams, K. L. and Humphery-Smith, I. (1995) Progress with gene-product mapping of the Mollicutes: *Mycoplasma genitalium*. *Electrophoresis*, 16, 1090-1094.
2. Patterson, S. D. (2000) Proteomics: the industrialization of protein chemistry. *Curr Opin Biotechnol*, 11, 413-418.
3. Vanmechelen, E., Vanderstichele, H., Davidsson, P., Van Kerschaver, E., Van Der Perre, B., Sjogren, M., Andreasen, N. and Blennow, K. (2000) Quantification of tau phosphorylated at threonine 181 in human cerebrospinal fluid: a sandwich ELISA with a synthetic phosphopeptide for standardization. *Neurosci Lett*, 285, 49-52.
4. Nakayama, K., Yamada, Y., Koji, T., Hayashi, T., Tomonaga, M. and Kamihira, S. (2000) Expression and phosphorylation status of retinoblastoma protein in adult T-cell leukemia/lymphoma. *Leuk Res*, 24, 299-305.
5. Ignatoski, K. M. (2001) Immunoprecipitation and western blotting of phosphotyrosine-containing proteins. *Methods Mol Bio*, 124, 39-48.
6. Nakanishi, T., Ando, E., Furuta, M., Tsunasawa, S. and Nishimura, O. (2007) Direct on-membrane peptide mass fingerprinting with MALDI-MS of tyrosine-phosphorylated proteins detected by immunostaining. *J Chromatogr B Analyt Technol Biomed Life Sc*; 847, 24-29.
7. Cantin, G. T., Venable, J. D., Cociorva, D. and Yates, J. R., 3rd. (2006) Quantitative phosphoproteomic analysis of the tumor necrosis factor pathway. *J Proteome Res*, 5, 127-134.
8. Adamczyk, M., Gebler, I. C. and Wu, J. (2002) Identification of phosphopeptides by chemical modification with an isotopic tag and ion trap mass spectrometry. *Rapid Commun Mass Spectrom*, 16, 999-1001.
9. Adamczyk, M., Gebler, J. C. and Wu, J. (2001) Selective analysis of phosphopeptides within a protein mixture by chemical modification, reversible biotinylation and mass spectrometry. *Rapid Commun Mass Spectrom*, 15, 1481-1488.
10. Goshe, M. B., Conrads, T. P., Panisko, E. A., Angell, N. H., Veenstra, T. D. and Smith, R. D. (2001) Phosphoprotein isotope-coded affinity tag approach for isolating and quantitating phosphopeptides in proteome-wide analyses. *Anal Chem*, 73, 2578-2586.
11. Kota, U., Chien, K. Y. and Goshe, M. B. (2009) Isotope-labeling and affinity enrichment of phosphopeptides for proteomic analysis using liquid chromatography-tandem mass spectrometry. *Methods Mol Biol*, 564, 303-321.
12. Qian, W. J., Goshe, M. B., Camp, D. G., 2nd, Yu, L. R., Tang, K. and Smith, R. D. (2003) Phosphoprotein isotope-coded solid-phase tag approach for enrichment and quantitative analysis of phosphopeptides from complex mixtures. *Anal Chem*, 75, 5441-5450.
13. Gygi, S. P., Rist, B., Gerber, S. A., Turecek, F., Gelb, M. H. and Aebersold, R. (1999) Quantitative analysis of complex protein mixtures using isotope-coded affinity tags. *Nat Biotechnol*, 17, 994-999.
14. Zhou, H., Ranish, J. A., Watts, J. D. and Aebersold, R. (2002) Quantitative proteome analysis by solid-phase isotope tagging and mass spectrometry. *Nat Biotechnol*, 20, 512-515.
15. Wu, J., Warren, P., Shakey, Q., Sousa, E., Hill, A., Ryan, T. E. and He, T. (2010) Integrating titania enrichment, iTRAQ labeling, and Orbitrap CID-HCD for global identification and quantitative analysis of phosphopeptides. *Proteomics*, 10, 2224-2234.
16. Arrigoni, G., Resjo, S., Levander, F., Nilsson, R., Degerman, E., Quadroni, M., Pinna, L. A. and James, P. (2006) Chemical derivatization of phosphoserine and phosphothreonine containing peptides to increase sensitivity for MALDI-based analysis and for selectivity of MS/MS analysis. *Proteomics*, 6, 757-766.
17. Jaffe, H., Veeranna and Pant, H. (1998) Characterization of serine and threonine phosphorylation sites in beta-elimination/ethanethiol addition-modified proteins by electrospray tandem mass spectrometry and database searching. *Biochemistry*, 37, 16211-16224.
18. Beausoleil, S. A., Jedrychowski, M., Schwartz, D., Elias, J. E., Villen, J., Li, J., Cohn, M. A., Cantley, L. C. and Gygi, S. P. (2004) Large-scale characterization of HeLa cell nuclear phosphoproteins. *Proc Nat Acad Sci USA*, 101, 12130-12135.
19. Ficarro, S. B., Zhang, Y., Carrasco-Alfonso, M. J., Garg, B., Adelmant, G., Webber, J. T., Luckey, C. J. and Marto, J. A. Online nanoflow multidimensional fractionation for high efficiency phosphopeptide analysis. *Mol Cell Proteomics*, 10, O111 011064.
20. Hennrich, M. L., Groenewold, V., Kops, G. J., Heck, A. J. and Mohammed, S. Improving depth in phosphoproteomics by using a strong cation exchange-weak anion exchange-reversed phase multidimensional separation approach. *Anal Chem,* 83, 7137-7143.
21. McNulty, D. E. and Annan, R. S. (2008) Hydrophilic interaction chromatography reduces the complexity of the phosphoproteome and improves global phosphopeptide isolation and detection. *Mol Cell Proteomics,* 7, 971-980.
22. Byford, M. F. (1991) Rapid and selective modification of phosphoserine residues catalysed by Ba2+ ions for their detection during peptide microsequencing. *Biochem J,* 280 (Pt 1), 261-265.
23. Fadden, P. and Haystead, T. A. (1995) Quantitative and selective fluorophore labeling of phosphoserine on peptides and proteins: characterization at the attomole level by capillary electrophoresis and laser-induced fluorescence. *Anal Biochem,* 225, 81-88.
24. Klemm, C., Schroder, S., Gluckmann, M., Beyermann, M. and Krause, E. (2004) Derivatization of phosphorylated peptides with S- and N-nucleophiles for enhanced ionization efficiency in matrix-assisted laser desorption/ionization mass spectrometry. *Rapid Commun Mass Spectrom,* 18, 2697-2705.
25. Ahn, Y. H., Ji, E. S., Lee, J. Y., Cho, K. and Yoo, J. S. (2007) Arginine-mimic labeling with guanidinoethanethiol to increase mass sensitivity of lysine-terminated phosphopeptides by matrix-assisted laser desorption/ionization time-of-flight mass spectrometry. *Rapid Commun Mass Spectrom,* 21, 2204-2210.
26. Molloy, M. P. and Andrews, P. C. (2001) Phosphopeptide derivatization signatures to identify serine and threonine phosphorylated peptides by mass spectrometry. *Anal Chem,* 73, 5387-5394.
27. Cindric, M., Cepo, T., Skrlin, A., Vuletic, M. and Bindila, L. (2006) Accelerated on-column lysine derivatization and cysteine methylation by imidazole reaction in a deuterated environment for enhanced product ion analysis. *Rapid Commun Mass Spectrom,* 20, 694-702.
28. Conrotto, P. and Hellman, U. (2005) Sulfonation chemistry as a powerful tool for MALDI TOF/TOF de novo sequencing and post-translational modification analysis. *J Biomol Tech,* 16, 441-452.
29. Nika, H., Lee, J., Willis, L. M., Angeletti, R. H. and Hawke, D. H. (2012) Phosphopeptide characterization by mass spectrometry using reversed-phase supports for solid-phase beta-elimination/Michael addition. *J Biomol Tech,* 23, 51-68.
30. Pfleiderer, W., Matysiak, S., Bergmann, F. and Schnell, R. (1996) Recent progress in oligonucleotide synthesis. *Acta Biochim Pol,* 43, 37-44.
31. Stawikowski, M. and Fields, G. B. Introduction to peptide synthesis. *Curr Protoc Protein Sci,* Chapter 18, Unit 18 11.
32. Thompson, A. J., Hart, S. R., Franz, C., Barnouin, K., Ridley, A. and Cramer, R. (2003) Characterization of protein phosphorylation by mass spectrometry using immobilized metal ion affinity chromatography with on-resin beta-elimination and Michael addition. *Anal Chem,* 75, 3232-3243.
33. Lee, H. S., Osuga, D. T., Nashef, A. S., Ahmed, A. I., Whitaker, J. R. and Feeney, R. (1977) Effects of alkali on glycoproteins. beta-Elimination and nucleophilic addition reactions of substituted threonyl residues of antifreeze glycoprotein. *J Agric Food Chem,* 25, 1153-1158.
34. Mega, T., Nakamura, N. and Ikenaka. (1990) Modifications of substituted seryl and threonyl residues in phosphopeptides and a polysialoglycoprotein by beta-elimination and nucleophile additions. *J Biochem (Tokyo),* 107, 68-72.
35. Ndassa, Y. M., Orsi, C., Marto, J. A., Chen, S. and Ross, M. M. (2006) Improved immobilized metal affinity chromatography for large-scale phosphoproteomics applications. *J Proteome Res,* 5, 2789-2799.
36. Wells, L., Vosseller, K., Cole, R. N., Cronshaw, J. M., Matunis, M. J. and Hart, G. W. (2002) Mapping sites of O-GlcNAc modification using affinity tags for serine and threonine post-translational modifications. *Mol Cell Proteomics,* 1, 791-804.
37. Czeszak, X., Ricart, G., Tetaert, D., Michalski, J. C. and Lemoine, J. (2002) Identification of substituted sites on MUC5AC mucin motif peptides after enzymatic O-glycosylation combining beta-elimination and fixed-charge derivatization. *Rapid Commun Mass Spectrom,* 16, 27-34.
38. Czeszak, X., Morelle, W., Ricart, G., Tetaert, D. and Lemoine, J. (2004) Localization of the O-glycosylated sites in peptides by fixed-charge derivatization with a phosphonium group. *Anal Chem,* 76, 4320-4324.
39. Butkinaree, C., Park, K. and Hart, G. W. O-linked beta-N-acetylglucosamine (O-GlcNAc): Extensive crosstalk with phosphorylation to regulate signaling and transcription in response to nutrients and stress. *Biochim Biophys Acta,* 1800, 96-106.
40. Hu, P., Shimoji, S. and Hart, G. W. Site-specific interplay between O-GlcNAcylation and phosphorylation in cellular regulation. *FEBS Lett,* 584, 2526-2538.
41. Copeland, R. J., Bullen, J. W. and Hart, G. W. (2008) Cross-talk between GlcNAcylation and phosphorylation: roles in insulin resistance and glucose toxicity. *Am J Physiol Endocrinol Metab,* 295, E17-28.
42. Love, D. C. and Hanover, J. A. (2005) The hexosamine signaling pathway: deciphering the "O-GlcNAc code". *Sci STKE,* 2005, re13.
43. Ficarro, S. B., McCleland, M. L., Stukenberg, P. T., Burke, D. J., Ross, M. M., Shabanowitz, J., Hunt, D. F. and White, F. M. (2002) Phosphoproteome analysis by mass spectrometry and its application to *Saccharomyces cerevisiae. Nat Biotechnol,* 20, 301-305.
44. Kinoshita, E., Yamada, A., Takeda, H., Kinoshita-Kikuta, E. and Koike, T. (2005) Novel immobilized zinc(II) affinity chromatography for phosphopeptides and phosphorylated proteins. *J Sep Sci,* 28, 155-162.
45. Zhou, H., Low, T. Y., Hennrich, M. L., van der Toorn, H., Schwend, T., Zou, H., Mohammed, S. and Heck, A. J. Enhancing the identification of phosphopeptides from putative basophilic kinase substrates using Ti (IV) based IMAC enrichment. *Mol Cell Proteomics,* 10, 10, M110 006452.
46. Zhou, H., Xu, S., Ye, M., Feng, S., Pan, C., Jiang, X., Li, X., Han, G., Fu, Y. and Zou, H. (2006) Zirconium phosphonate-modified porous silicon for highly specific capture of phosphopeptides and MALDI-TOF MS analysis. *J Proteome Res,* 5, 2431-2437.
47. Zhou, H., Ye, M., Dong, J., Corradini, Cristobal, A., Heck, A. J., Zou, H. and Mohammed, S. Robust phosphoproteome enrichment using monodisperse microsphere-based immobilized titanium (IV) ion affinity chromatography. *Nat Protoc,* 8, 461-480.
48. Tsunehiro, M., Meki, Y., Matsuoka, K., Kinoshita-Kikuta, E., Kinoshita, E. and Koike, T. A Phos-tag-based magnetic-bead method for rapid and selective separation of phosphorylated biomolecules. *J Chromatogr B Analyt Technol Biomed Life Sci,* 925, 86-94.
49. Kinoshita, E., Kinoshita-Kikuta, E., Sugiyama, Y., Fukada, Y., Ozeki, T. and Koike, T. Highly sensitive detection of protein phosphorylation by using improved Phos-tag Biotin. *Proteomics,* 12, 932-937.

50. Zhang, X., Ye, J., Jensen, O. N. and Roepstorff, P. (2007) Highly Efficient Phosphopeptide Enrichment by Calcium Phosphate Precipitation Combined with Subsequent IMAC Enrichment. *Mol Cell Proteomics,* 6, 2032-2042.
51. Kuhn, K., Baumann, C., Tommassen, J. and Prinz, T. (2012) TMT labelling for the quantitative analysis of adaptive responses in the meningococcal proteome. *Methods Mol Biol,* 799, 127-141.
52. Li, W., Backlund, P. S., Boykins, R. A., Wang, G. and Chen, H. C. (2003) Susceptibility of the hydroxyl groups in serine and threonine to beta-elimination/Michael addition under commonly used moderately high-temperature conditions. *Anal Biochem,* 323, 94-102.
53. McLachlin, D. T. and Chait, B. T. (2003) Improved beta-elimination-based affinity purification strategy for enrichment of phosphopeptides. *Anal Chem,* 75, 6826-6836.
54. Jentoft, N. and Dearborn, D. G. (1979) Labeling of proteins by reductive methylation using sodium cyanoborohydride. *J Biol Chem,* 254, 4359-4365.
55. Wong, W. S., Osuga, D. T. and Feeney, R. E. (1984) Pyridine borane as a reducing agent for proteins. *Anal Biochem,* 139, 58-67.
56. Dirksen, A. and Dawson, P. E. (2008) Rapid oxime and hydrazone ligations with aromatic aldehydes for biomolecular labeling. *Bioconjug Chem,* 19, 2543-2548.
57. Dirksen, A., Dirksen, S., Hackeng, T. M. and Dawson, P. E. (2006) Nucleophilic catalysis of hydrazone formation and transimination: implications for dynamic covalent chemistry. *J Am Chem Soc,* 128, 15602-15603.
58. Byeon, J. Y., Limpoco, F. T. and Bailey, R. C. Efficient bioconjugation of protein capture agents to biosensor surfaces using aniline-catalyzed hydrazone ligation. *Langmuir,* 26, 15430-15435.
59. Li, X. Click to join peptides/proteins together. *Chem Asian J,* 6, 2606-2616.
60. Klement, E., Lipinszki, Z., Kupihar, Z., Udvardy, A. and Medzihradszky, K. F. Enrichment of O-GlcNAc modified proteins by the periodate oxidation-hydrazide resin capture approach. *J Proteome Res,* 9, 2200-2206.
61. Boeggeman, E., Ramakrishnan, B., Kilgore, C., Khidekel, N., Hsieh-Wilson, L. C., Simpson, J. T. and Qasba, P. K. (2007) Direct identification of nonreducing GlcNAc residues on N-glycans of glycoproteins using a novel chemoenzymatic method. *Bioconjug Chem,* 18, 806-814.
62. Sihlbom, C., van Dijk Hard, I., Lidell, M. E., Noll, T., Hansson, G. C. and Backstrom, M. (2009) Localization of O-glycans in MUC1 glycoproteins using electron-capture dissociation fragmentation mass spectrometry. *Glycobiology,* 19, 375-381.
63. Mechref, Y. Use of CID/ETD mass spectrometry to analyze glycopeptides. *Curr Protoc Protein Sci*; Chapter 12, Unit 12 11 11-11.
64. Han, H., Xia, Y., Yang, M. and McLuckey, S. A. (2008) Rapidly alternating transmission mode electron-transfer dissociation and collisional activation for the characterization of polypeptide ions. *Anal Chem,* 80, 3492-3497.
65. Yang, S. and Zhang, H. Solid-phase glycan isolation for glycomics analysis. *Proteomics Clin Appl,* 6, 596-608.
66. Yang, S. J. and Zhang, H. Glycan analysis by reversible reaction to hydrazide beads and mass spectrometry. *Anal Chem,* 84, 2232-2238.
67. Li, B., Berliner, M., Buzon, R., Chiu, C. K., Colgan, S. T., Kaneko, T., Keene, N., Kissel, W., Le, T., Leeman, K. R. et al. (2006) Aqueous phosphoric acid as a mild reagent for deprotection of tert-butyl carbamates, esters, and ethers. *J Org Chem,* 71, 9045-9050.
68. Pothukanuri, S. and Winssinger, N. (2007) A highly efficient azide-based protecting group for amines and alcohols. *Org Let,* 9, 2223-2225.
69. Goddard-Borger, E. D. and Stick, R. V. (2007) An efficient, inexpensive, and shelf-stable diazotransfer reagent: imidazole-1-sulfonyl azide hydrochloride. *Org Lett,* 9, 3797-3800.
70. Dephoure, N. and Gygi, S. P. (2012) Hyperplexing: a method for higher-order multiplexed quantitative proteomics provides a map of the dynamic response to rapamycin in yeast. *Sci Signal,* 5, rs2.
71. Everley, R. A., Kunz, R. C., McAllister, F. E. and Gygi, S. P. (2013) Increasing throughput in targeted proteomics assays: 54-plex quantitation in a single mass spectrometry run. *Anal Chem,* 85, 5340-5346.
72. Zhang, X., Jin, Q. K., Carr, S. A. and Annan, R. S. (2002) N-Terminal peptide labeling strategy for incorporation of isotopic tags: a method for the determination of site-specific absolute phosphorylation stoichiometry. *Rapid Commun Mass Spectrom,* 16, 2325-2332.
73. Tan, F., Zhang, Y., Wang, J., Wei, J., Cai, Y. and Qian, X. (2008) An efficient method for dephosphorylation of phosphopeptides by cerium oxide. *J Mass Spectrom,* 43, 628-632.
74. Jia, W., Andaya, A. and Leary, J. A. (2012) Novel mass spectrometric method for phosphorylation quantification using cerium oxide nanoparticles and tandem mass tags. *Anal Chem,* 84, 2466-2473.
75. Wu, H. Y., Tseng, V. S., Chen, L. C., Chang, Y. C., Ping, P., Liao, C. C., Tsay, Y. G., Yu, I. S. and Liao, P. C. (2009) Combining alkaline phosphatase treatment and hybrid linear ion trap/Orbitrap high mass accuracy liquid chromatography-mass spectrometry data for the efficient and confident identification of protein phosphorylation. *Anal Chem,* 81, 7778-7787.
76. Isidro-Llobet, A., Alvarez, M. and Albericio, F. (2009) Amino acid-protecting groups. *Chem Rev,* 109, 2455-2504.
77. Brandes, N., Reichmann, D., Tienson, H., Leichert, L. I. and Jakob, U. (2011) Using quantitative redox proteomics to dissect the yeast redoxome. *J Biol Chem,* 286, 41893-41903.
78. Kumsta, C., Thamsen, M. and Jakob, U. (2011) Effects of oxidative stress on behavior, physiology, and the redox thiol proteome of *Caenorhabditis elegans. Antioxid Redox Signal,* 14, 1023-1037.
79. Brennan, J. P., Wait, R., Begum, S., Bell, J. R., Dunn, M. J. and Eaton, P. (2004) Detection and mapping of widespread intermolecular protein disulfide formation during cardiac oxidative stress using proteomics with diagonal electrophoresis. *J Biol Chem,* 279, 41352-41360.
80. Leichert, L. I. and Jakob, U. (2004) Protein thiol modifications visualized in vivo. *PLoS Biol,* 2, e333.
81. Boersema, P. J., Raijmakers, R., Lemeer, S., Mohammed, S. and Heck, A. J. (2009) Multiplex peptide stable isotope dimethyl labeling for quantitative proteomics. *Nat Protoc,* 4, 484-494.
82. Derakhshan, B., Wille, P. C. and Gross, S. S. (2007) Unbiased identification of cysteine S-nitrosylation sites on proteins. *Nat Protoc,* 2, 1685-1691.
83. Lind, C., Gerdes, R., Hamnell, Y., Schuppe-Koistinen, I., von Lowenhielm, H. B., Holmgren, A. and Cotgreave, I. A. (2002) Identification of S-glutathionylated cellular proteins during oxidative stress and constitutive metabolism by affinity purification and proteomic analysis. *Arch Biochem Biophys,* 406, 229-240.

84. Requejo, R., Chouchani, E. T., James, A. M., Prime, T. A., Lilley, K. S., Fearnley, I. M. and Murphy, M. P. (2010) Quantification and identification of mitochondrial proteins containing vicinal dithiols. *Arch Biochem Biophys*, 504, 228-235.

The invention claimed is:

1. A method for the mass spectrometric analysis of one or more analytes in a sample, the method comprising:
   a) contacting the sample with two or more bifunctional linker reagents having the general formula $Re^1$-$L^1$-$Re^2$, wherein $Re^1$ is a first reactive group, $L^1$ is a linker moiety and $Re^2$ is a protected reactive group, wherein $Re^1$ reacts with an analyte to form a modified analyte;
   b) deprotecting $Re^2$ of the bifunctional linker to form a second reactive group;
   c) contacting the sample with two or more mass labels, wherein $Re^2$ of the bifunctional linker attached to the analyte reacts with a mass label to form a labelled analyte, wherein each mass label is relatable to an analyte by mass spectrometry; and
   d) analysing the labelled analytes by mass spectrometry;
   wherein in step a) each analyte is reacted with a bifunctional linker from a set of two or more bifunctional linkers, wherein each bifunctional linker in the set has a unique mass;
   wherein each mass label has the general formula:

V-$L^2$-M wherein V is a mass marker moiety, $L^2$ is a linker cleavable by dissociation in a mass spectrometer and M is a mass normalisation moiety which causes the mass label to have a selected aggregate mass, and the mass label further comprises a reactive group $Re^3$ which reacts with $Re^2$ of the bifunctional linker;
   wherein the one or more analytes in the sample are reversibly captured onto a solid phase support prior to step a), and the labelled analyte is eluted from the solid phase support after step c) and prior to step d); and
   wherein each reactive group to be coupled, $Re^1$ and $Re^2$, is an amino group or an active ester, and wherein a buffer solution having a pH of from 3.5 to 5 is contacted with the solid phase support bearing the one or more analytes to provide a pH for the coupling reaction.

2. The method of claim 1, comprising a step prior to step a) of:
   depleting the sample of analytes comprising saccharide groups by reacting the sample with affinity reagents bound to a solid phase support, such that analytes comprising saccharide groups are captured on the solid phase support, and eluting the sample from the solid phase support under conditions in which the analytes comprising saccharide groups remain bound on the solid phase support; or alternatively, comprising a step prior to step a) of:
   depleting the sample of analytes comprising phosphate groups by reacting the sample with immobilised antibodies against phosphopeptides, or using immobilized metal oxide chromatography or immobilised metal ion affinity chromatography, and eluting the sample from the solid phase support under conditions in which the analytes comprising phosphate groups remain bound on the solid phase support.

3. The method of claim 1, wherein prior to step a) the one or more analytes are attached to the solid phase support by means of a functional group, and beta elimination of the functional group cleaves the analyte(s) from the solid phase support; and in a further step the released analytes(s) are isolated and reversibly captured onto a further solid phase support.

4. The method of claim 1, wherein the analyte comprises an O-linked saccharide; and prior to step a) the O-linked saccharide is reacted with an oxidising agent to form an aldehyde or a ketone; and $Re^1$ of the bifunctional linker reacts with the aldehyde or ketone.

5. The method of claim 1, wherein each bifunctional linker in the set of two or more bifunctional linkers has the following structure:

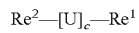
$Re^2$—[U]$_c$—$Re^1$ wherein $Re^1$ is a first reactive group, $Re^2$ is a second reactive group, U is a linker repeat unit and c is an integer from 1 to 10.

6. The method of claim 1, wherein $Re^1$ or $Re^2$ of the bifunctional linker further comprises at least one mass adjuster moiety selected from a $^2H$, $^{15}N$, $^{13}C$ or $^{18}O$ isotopic substituent.

7. The method of claim 1, wherein for each bifunctional linker $Re^1$ and $Re^2$ are each independently selected from:

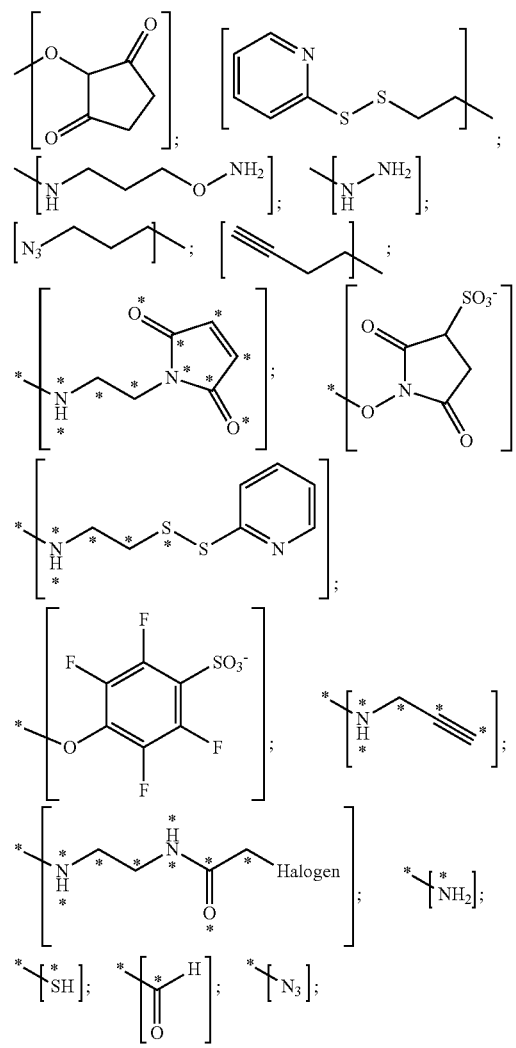

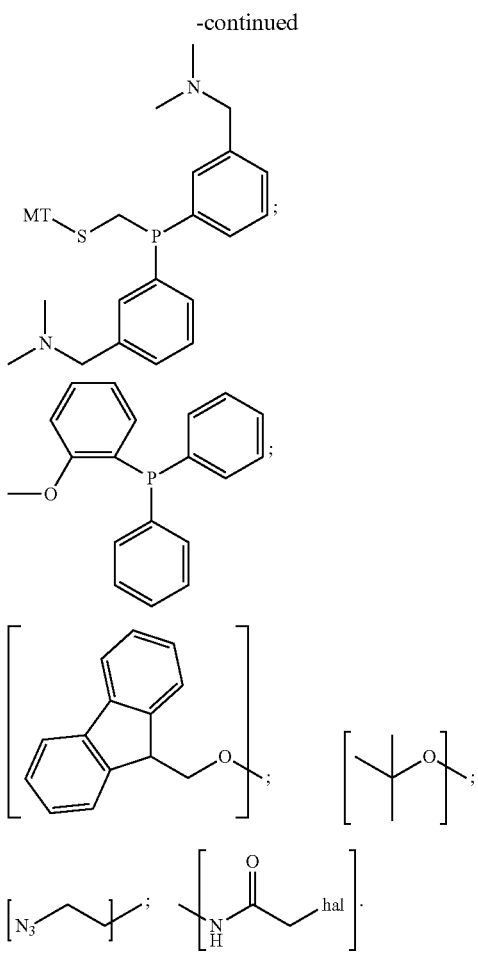

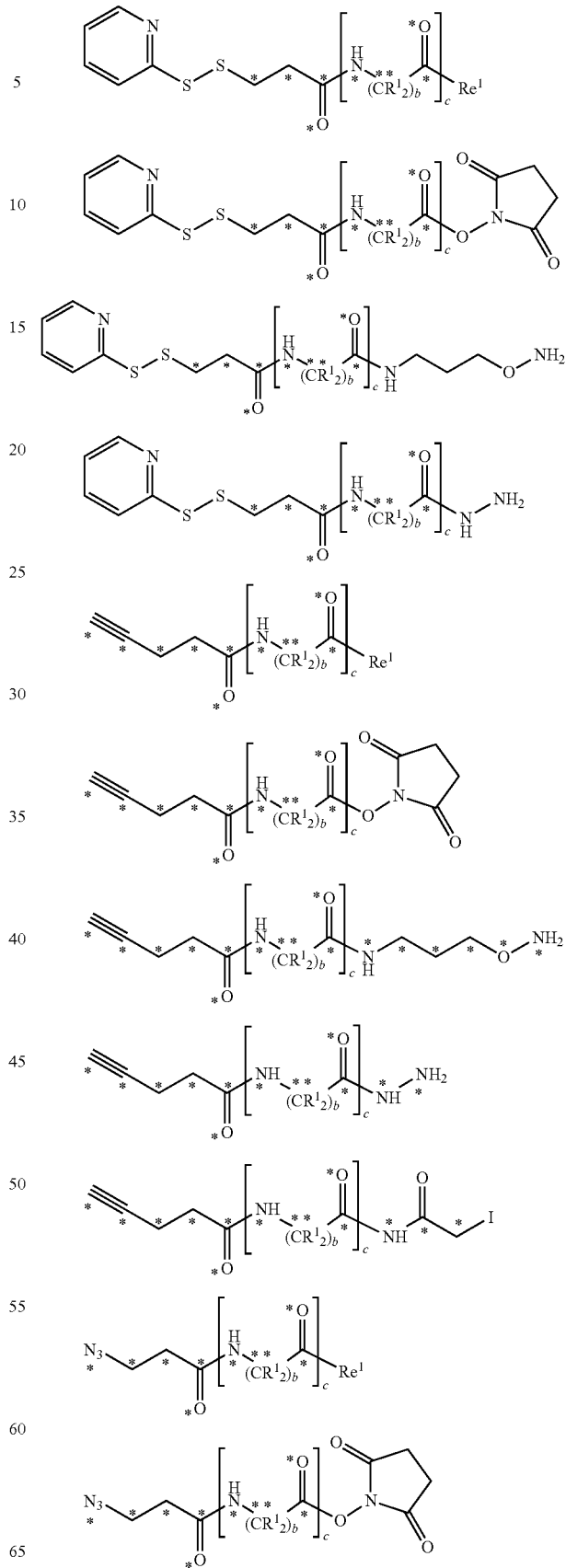

8. The method of claim 5, wherein each bifunctional linker has the general formula:

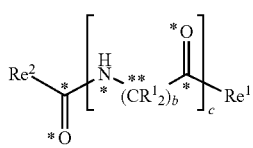

wherein Re$^1$ is the first reactive group,

Re$^2$ is the second reactive group, each R$^1$ is independently H, a substituted or unsubstituted straight or branched C$_1$-C$_6$ alkyl group, a substituted or unsubstituted aliphatic cyclic group, a substituted or unsubstituted aromatic group or a substituted or unsubstituted heterocyclic group or an amino acid side chain; and b is an integer from 1-10 and c is an integer from 1 to 10; and wherein each * is an isotopic mass adjuster moiety which may be present or absent and * represents that oxygen is $^{18}$O, carbon is $^{13}$C or nitrogen is $^{15}$N or hydrogen is 2H.

9. The method of claim 8, wherein each bifunctional linker is selected from the following compounds:

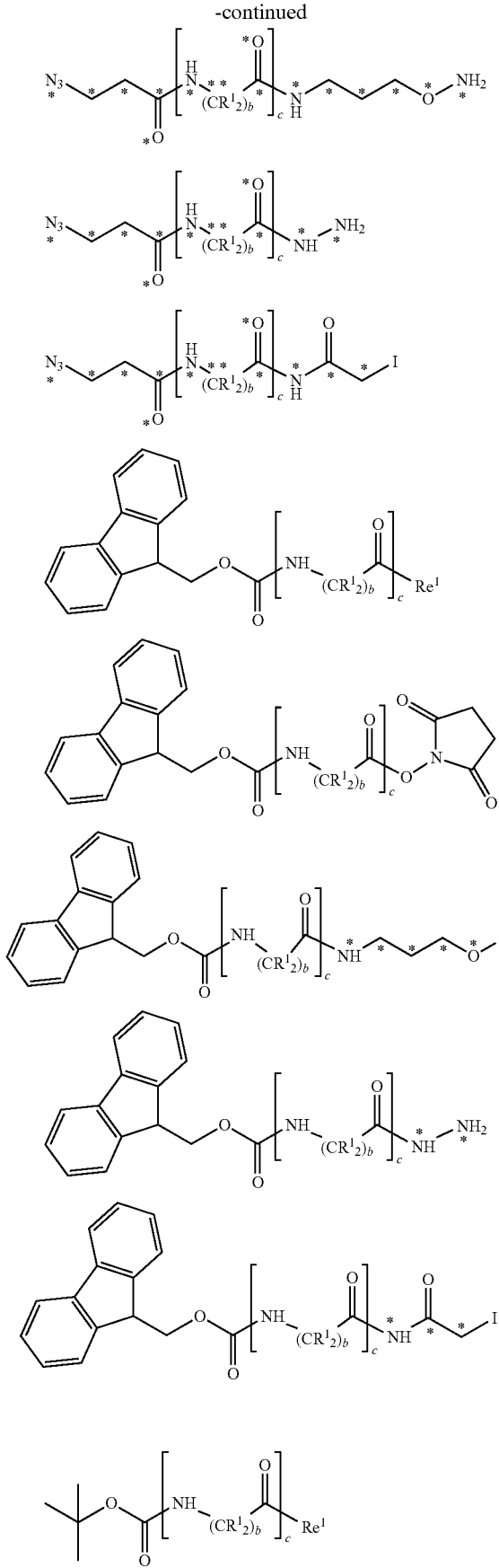

-continued

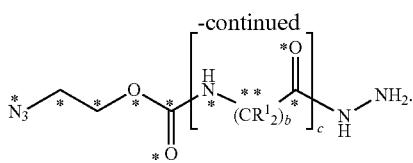

-continued

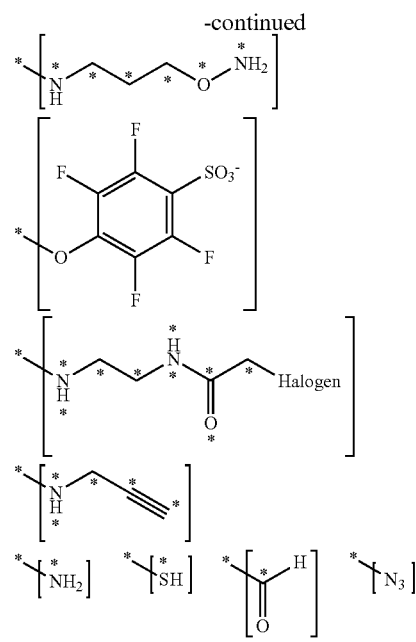

10. The method of claim 1, wherein in the step c), each modified analyte is labelled with a mass label selected from a set of two or more mass labels, and wherein the set comprises either:
(i) a group of mass labels that each has a mass marker moiety that has a common mass, wherein each mass label in the group has a unique aggregate mass; or
(ii) a group of mass labels that each has a mass marker moiety having a mass different from that of all of the other mass marker moieties in the group, and wherein each mass label in the group has a common aggregate mass; and
wherein all the mass labels in the set are distinguishable from each other by mass spectrometry.

11. The method of claim 1, wherein the mass marker moiety V comprises the following group:

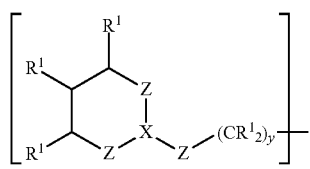

wherein the cyclic unit is aromatic or aliphatic and comprises from 0-3 double bonds independently between any two adjacent atoms;
each Z is independently N, N($R^1$), C($R^1$), CO, CO($R^1$), C($R^1$)$_2$, O or S; X is N, C or C($R^1$),
each $R^1$ is independently H, a substituted or unsubstituted straight or branched $C_1$-$C_6$ alkyl group, a substituted or unsubstituted aliphatic cyclic group, a substituted or unsubstituted aromatic group or a substituted or unsubstituted heterocyclic group; and
y is an integer from 0-10.

12. The method of claim 1, wherein $Re^3$ of each mass label is selected from the following:

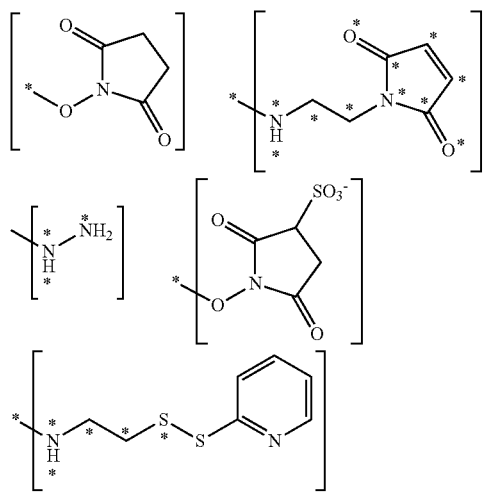

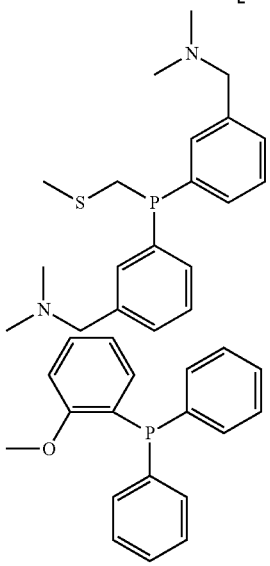

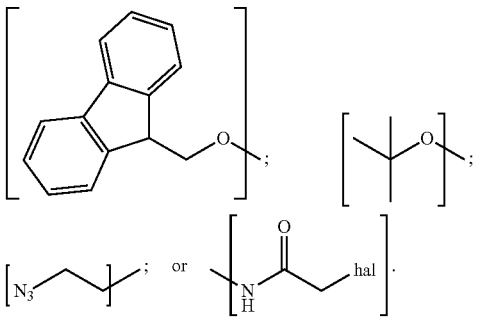

13. A method for the mass spectrometric analysis of one or more analytes in a sample, the method comprising:
a) contacting the sample with two or more bifunctional linker reagents having the general formula $Re^1$-$L^1$-$Re^2$, wherein $Re^1$ is a first reactive group, $L^1$ is a linker moiety and $Re^2$ is a protected reactive group, wherein $Re^1$ reacts with an analyte to form a modified analyte;
b) deprotecting $Re^2$ of the bifunctional linker to form a second reactive group;

c) contacting the sample with two or more mass labels, wherein $Re^2$ of the bifunctional linker attached to the analyte reacts with a mass label to form a labelled analyte, wherein each mass label is relatable to an analyte by mass spectrometry; and d) analysing the labelled analytes by mass spectrometry;

wherein in step a) each analyte is reacted with a bifunctional linker from a set of two or more bifunctional linkers, wherein each bifunctional linker in the set has a unique mass;

wherein each mass label has the general formula:

$V$-$L^2$-$M$ wherein V is a mass marker moiety, $L^2$ is a linker cleavable by dissociation in a mass spectrometer and M is a mass normalisation moiety which causes the mass label to have a selected aggregate mass, and the mass label further comprises a reactive group $Re^3$ which reacts with $Re^2$ of the bifunctional linker;

wherein prior to step a) the one or more analytes are attached to a solid phase support by means of a functional group, and beta elimination of the functional group cleaves the analyte(s) from the solid phase support; and in a further step the released analytes(s) are isolated and reversibly captured onto a further solid phase support.

14. The method of claim 13, comprising a step prior to step a) of:

depleting the sample of analytes comprising saccharide groups by reacting the sample with affinity reagents bound to a solid phase support, such that analytes comprising saccharide groups are captured on the solid phase support, and eluting the sample from the solid phase support under conditions in which the analytes comprising saccharide groups remain bound on the solid phase support; or alternatively, comprising a step prior to step a) of:

depleting the sample of analytes comprising phosphate groups by reacting the sample with immobilised antibodies against phosphopeptides, or using immobilized metal oxide chromatography or immobilised metal ion affinity chromatography, and eluting the sample from the solid phase support under conditions in which the analytes comprising phosphate groups remain bound on the solid phase support.

15. The method of claim 13, wherein prior to step a) the one or more analytes are attached to the solid phase support by means of a functional group, and beta elimination of the functional group cleaves the analyte(s) from the solid phase support; and in a further step the released analytes(s) are isolated and reversibly captured onto a further solid phase support.

16. The method of claim 13, wherein the analyte comprises an O-linked saccharide; and prior to step a) the O-linked saccharide is reacted with an oxidising agent to form an aldehyde or a ketone; and $Re^1$ of the bifunctional linker reacts with the aldehyde or ketone.

17. The method of claim 13, wherein each bifunctional linker in the set of two or more bifunctional linkers has the following structure:

$Re^2$—$[U]_c$—$Re^1$ wherein $Re^1$ is a first reactive group, $Re^2$ is a second reactive group, U is a linker repeat unit and c is an integer from 1 to 10.

18. A method for the mass spectrometric analysis of one or more analytes in a sample, the method comprising:

a) contacting the sample with two or more bifunctional linker reagents having the general formula $Re^1$-$L^1$-$Re^2$, wherein $Re^1$ is a first reactive group, $L^1$ is a linker moiety and $Re^2$ is a protected reactive group, wherein $Re^1$ reacts with an analyte to form a modified analyte;

b) deprotecting $Re^2$ of the bifunctional linker to form a second reactive group;

c) contacting the sample with two or more mass labels, wherein $Re^2$ of the bifunctional linker attached to the analyte reacts with a mass label to form a labelled analyte, wherein each mass label is relatable to an analyte by mass spectrometry; and d) analysing the labelled analytes by mass spectrometry;

wherein in step a) each analyte is reacted with a bifunctional linker from a set of two or more bifunctional linkers, wherein each bifunctional linker in the set has a unique mass;

wherein each mass label has the general formula:

$V$-$L^2$-$M$ wherein V is a mass marker moiety, $L^2$ is a linker cleavable by dissociation in a mass spectrometer and M is a mass normalisation moiety which causes the mass label to have a selected aggregate mass, and the mass label further comprises a reactive group $Re^3$ which reacts with $Re^2$ of the bifunctional linker; and wherein the analyte comprises an O-linked saccharide; and prior to step a) the O-linked saccharide is reacted with an oxidising agent to form an aldehyde or a ketone; and $Re^1$ of the bifunctional linker reacts with the aldehyde or ketone.

19. The method of claim 18, comprising a step prior to step a) of:

depleting the sample of analytes comprising saccharide groups by reacting the sample with affinity reagents bound to a solid phase support, such that analytes comprising saccharide groups are captured on the solid phase support, and eluting the sample from the solid phase support under conditions in which the analytes comprising saccharide groups remain bound on the solid phase support; or alternatively, comprising a step prior to step a) of:

depleting the sample of analytes comprising phosphate groups by reacting the sample with immobilised antibodies against phosphopeptides, or using immobilized metal oxide chromatography or immobilised metal ion affinity chromatography, and eluting the sample from the solid phase support under conditions in which the analytes comprising phosphate groups remain bound on the solid phase support.

20. The method of claim 18, wherein prior to step a) the one or more analytes are attached to the solid phase support by means of a functional group, and beta elimination of the functional group cleaves the analyte(s) from the solid phase support; and in a further step the released analytes(s) are isolated and reversibly captured onto a further solid phase support.

* * * * *